US009290749B2

(12) United States Patent
Rudenko et al.

(10) Patent No.: US 9,290,749 B2

(45) Date of Patent: Mar. 22, 2016

(54) THIOESTERASES AND CELLS FOR PRODUCTION OF TAILORED OILS

(71) Applicant: Solazyme, Inc., South San Francisco, CA (US)

(72) Inventors: George N. Rudenko, South San Francisco, CA (US); Jason Casolari, South San Francisco, CA (US); Scott Franklin, South San Francisco, CA (US)

(73) Assignee: Solazyme, Inc., South San Francisco, CA (US)

( * ) Notice: Subject to any disclaimer, the term of this patent is extended or adjusted under 35 U.S.C. 154(b) by 349 days.

(21) Appl. No.: 13/837,996

(22) Filed: Mar. 15, 2013

(65) Prior Publication Data

US 2014/0275586 A1 Sep. 18, 2014

(51) Int. Cl.

| | |
|---|---|
| ***C12N 15/82*** | (2006.01) |
| ***C12N 5/14*** | (2006.01) |
| ***C12N 9/18*** | (2006.01) |
| ***C07H 21/04*** | (2006.01) |
| ***C12N 9/16*** | (2006.01) |
| ***C12P 7/64*** | (2006.01) |

(52) U.S. Cl.

CPC ................. *C12N 9/16* (2013.01); *C12P 7/6463* (2013.01); *C12Y 301/02014* (2013.01)

(58) Field of Classification Search

None

See application file for complete search history.

(56) References Cited

U.S. PATENT DOCUMENTS

| | | | |
|---|---|---|---|
| 4,049,724 | A | 9/1977 | Sheng et al. |
| 4,288,378 | A | 9/1981 | Japikse et al. |
| 4,335,156 | A | 6/1982 | Kogan et al. |
| 4,584,139 | A | 4/1986 | Gray et al. |
| 4,603,188 | A | 7/1986 | Kusakawa et al. |
| 4,683,202 | A | 7/1987 | Mullis |
| 4,798,793 | A | 1/1989 | Eigtved |
| 4,940,835 | A | 7/1990 | Shah et al. |
| 4,940,845 | A | 7/1990 | Hirota et al. |
| 4,945,050 | A | 7/1990 | Sanford et al. |
| 4,992,189 | A | 2/1991 | Chen et al. |
| 5,080,848 | A | 1/1992 | Strauss et al. |
| 5,091,116 | A | 2/1992 | Krishnamurthy et al. |
| 5,156,963 | A | 10/1992 | Eigtved |
| 5,233,099 | A | 8/1993 | Tabata |
| 5,233,100 | A | 8/1993 | Tabata et al. |
| 5,258,197 | A | 11/1993 | Wheeler et al. |
| 5,268,192 | A | 12/1993 | Zook et al. |
| 5,298,421 | A | 3/1994 | Davies et al. |
| 5,298,637 | A | 3/1994 | Cooper |
| 5,304,481 | A | 4/1994 | Davies et al. |
| 5,304,664 | A | 4/1994 | Peppmoller et al. |
| 5,342,768 | A | 8/1994 | Pedersen et al. |
| 5,344,771 | A | 9/1994 | Davies et al. |
| 5,346,724 | A | 9/1994 | Ohgake et al. |
| 5,380,894 | A | 1/1995 | Burg et al. |
| 5,391,383 | A | 2/1995 | Sullivan et al. |
| 5,427,704 | A | 6/1995 | Lawate |
| 5,434,278 | A | 7/1995 | Pelloso et al. |
| 5,451,332 | A | 9/1995 | Lawate |
| 5,455,167 | A | 10/1995 | Voelker et al. |
| 5,458,795 | A | 10/1995 | Lawate |
| 5,475,160 | A | 12/1995 | Singleton et al. |
| 5,506,201 | A | 4/1996 | McDermott et al. |
| 5,512,482 | A | 4/1996 | Voelker et al. |
| 5,567,359 | A | 10/1996 | Cassidy et al. |
| 5,576,027 | A | 11/1996 | Friedman et al. |
| 5,639,790 | A | 6/1997 | Voelker et al. |
| 5,654,495 | A | 8/1997 | Voelker et al. |
| 5,667,997 | A | 9/1997 | Voelker et al. |
| 5,686,131 | A | 11/1997 | Sato et al. |
| 5,693,507 | A | 12/1997 | Daniell et al. |
| 5,723,761 | A | 3/1998 | Voelker et al. |
| 5,776,741 | A | 7/1998 | Pedersen et al. |
| 5,807,893 | A | 9/1998 | Voelker et al. |
| 5,833,999 | A | 11/1998 | Trinh et al. |
| 5,850,022 | A | 12/1998 | Dehesh et al. |
| 5,885,440 | A | 3/1999 | Hoehn et al. |
| 5,888,947 | A | 3/1999 | Lambert et al. |
| 5,928,696 | A | 7/1999 | Best et al. |
| 5,942,479 | A | 8/1999 | Frankenbach et al. |
| 5,945,585 | A | 8/1999 | Hitz et al. |
| 6,020,509 | A | 2/2000 | Weerasooriya et al. |
| 6,022,577 | A | 2/2000 | Chrysam et al. |
| 6,027,900 | A | 2/2000 | Allnutt et al. |
| 6,051,539 | A | 4/2000 | Kodali et al. |
| 6,057,375 | A | 5/2000 | Wollenweber et al. |

(Continued)

FOREIGN PATENT DOCUMENTS

| | | | |
|---|---|---|---|
| EP | 1 605 048 | A1 | 12/2005 |
| EP | 1 640 437 | A1 | 3/2006 |

(Continued)

OTHER PUBLICATIONS

Guo et al. (PNAS (2004) 101: 9205-9210).*

U.S. Appl. No. 14/808,361, filed Jul. 24, 2015, Davis et al.

US Office Action, dated Jul. 16, 2015, issued in U.S. Appl. No. 13/797,733.

PCT International Search Report and Written Opinion dated Jun. 24, 2014 issued in PCT/US2014/013676.

PCT International Preliminary Report on Patentability and Written Opinion dated Aug. 13, 2015 issued in PCT/US2014/013676.

(Continued)

*Primary Examiner* — Brent T Page

*Assistant Examiner* — Matthew Keogh

(74) *Attorney, Agent, or Firm* — Weaver Austin Villeneuve & Sampson LLP

(57) ABSTRACT

The invention features plant acyl-ACP thioesterase genes of the FatB class and proteins encoded by these genes. The genes are useful for constructing recombinant host cells having altered fatty acid profiles. Oleaginous microalga host cells with the new genes or previously identified FatB genes are disclosed. The microalgae cells produce triglycerides with useful fatty acid profiles.

8 Claims, No Drawings

(56) References Cited

U.S. PATENT DOCUMENTS

| | | | |
|---|---|---|---|
| 6,080,853 | A | 6/2000 | Corrigan et al. |
| 6,086,903 | A | 7/2000 | Trinh et al. |
| 6,113,971 | A | 9/2000 | Elmaleh |
| 6,140,302 | A | 10/2000 | Lueder et al. |
| 6,150,512 | A | 11/2000 | Yuan |
| 6,217,746 | B1 | 4/2001 | Thakkar et al. |
| 6,268,517 | B1 | 7/2001 | Filler et al. |
| 6,278,006 | B1 | 8/2001 | Kodali et al. |
| 6,320,101 | B1 | 11/2001 | Kaplan et al. |
| 6,331,664 | B1 | 12/2001 | Rubin-Wilson et al. |
| 6,342,208 | B1 | 1/2002 | Hyldgaard et al. |
| 6,380,410 | B1 | 4/2002 | Oftring et al. |
| 6,391,815 | B1 | 5/2002 | Weston et al. |
| 6,395,965 | B1 | 5/2002 | Xia |
| 6,398,707 | B1 | 6/2002 | Wu et al. |
| 6,407,044 | B2 | 6/2002 | Dixon |
| 6,465,642 | B1 | 10/2002 | Kenneally et al. |
| 6,468,955 | B1 | 10/2002 | Smets et al. |
| 6,538,169 | B1 | 3/2003 | Pittman et al. |
| 6,590,113 | B1 | 7/2003 | Sleeter |
| 6,596,155 | B1 | 7/2003 | Gates et al. |
| 6,596,768 | B2 | 7/2003 | Block et al. |
| 6,630,066 | B2 | 10/2003 | Cash et al. |
| 6,680,426 | B2 | 1/2004 | Daniell et al. |
| 6,692,730 | B2 | 2/2004 | Perron et al. |
| 6,750,048 | B2 | 6/2004 | Ruecker et al. |
| 6,770,104 | B2 | 8/2004 | Murphy |
| 6,808,737 | B2 | 10/2004 | Ullanoormadam |
| 6,869,597 | B2 | 3/2005 | Arnaud |
| 6,881,873 | B2 | 4/2005 | Gillespie et al. |
| 6,924,333 | B2 | 8/2005 | Bloom et al. |
| 6,946,430 | B2 | 9/2005 | Sakai et al. |
| 6,977,322 | B2 | 12/2005 | Gillespie |
| 7,041,866 | B1 | 5/2006 | Gillespie |
| 7,053,267 | B2 | 5/2006 | Knauf et al. |
| 7,081,567 | B2 | 7/2006 | Xue et al. |
| 7,115,173 | B2 | 10/2006 | Caswell et al. |
| 7,115,760 | B2 | 10/2006 | Sparso et al. |
| 7,118,773 | B2 | 10/2006 | Floeter et al. |
| 7,135,290 | B2 | 11/2006 | Dillon |
| 7,135,620 | B2 | 11/2006 | Daniell et al. |
| 7,196,124 | B2 | 3/2007 | Parker et al. |
| 7,232,935 | B2 | 6/2007 | Jakkula et al. |
| 7,238,277 | B2 | 7/2007 | Dahlberg et al. |
| 7,262,158 | B1 | 8/2007 | Lukenbach et al. |
| 7,264,886 | B2 | 9/2007 | Cui et al. |
| 7,268,276 | B2 | 9/2007 | Ruezinsky et al. |
| 7,288,278 | B2 | 10/2007 | Mellerup et al. |
| 7,288,685 | B2 | 10/2007 | Marker |
| 7,588,931 | B2 | 9/2009 | Damude et al. |
| 7,622,570 | B2 | 11/2009 | Oswald et al. |
| 8,029,579 | B2 | 10/2011 | Knuth et al. |
| 8,530,207 | B2 | 9/2013 | Watts et al. |
| 2002/0178467 | A1 | 11/2002 | Dehesh |
| 2003/0097686 | A1* | 5/2003 | Knauf et al. .................. 800/281 |
| 2003/0145350 | A1 | 7/2003 | Spener et al. |
| 2005/0005333 | A1 | 1/2005 | Ruezinsky et al. |
| 2005/0102716 | A1 | 5/2005 | Venkatramesh et al. |
| 2005/0262588 | A1 | 11/2005 | Dehesh et al. |
| 2007/0175091 | A1 | 8/2007 | Danzer et al. |
| 2007/0261138 | A1 | 11/2007 | Graham et al. |
| 2009/0176272 | A1 | 7/2009 | Champagne et al. |
| 2009/0317878 | A1 | 12/2009 | Champagne et al. |
| 2010/0058651 | A1 | 3/2010 | Knuth et al. |
| 2010/0105955 | A1 | 4/2010 | Alibhai et al. |
| 2010/0154293 | A1 | 6/2010 | Hom et al. |
| 2011/0072714 | A1 | 3/2011 | Gaertner et al. |
| 2011/0145944 | A1 | 6/2011 | Laga et al. |
| 2012/0009636 | A1 | 1/2012 | Berry et al. |
| 2012/0283460 | A1 | 11/2012 | Franklin et al. |
| 2012/0288930 | A1 | 11/2012 | Trimbur et al. |
| 2013/0031678 | A1 | 1/2013 | Zheng et al. |
| 2013/0034887 | A1 | 2/2013 | Franklin et al. |
| 2014/0215654 | A1 | 7/2014 | Davis |
| 2014/0234920 | A1 | 8/2014 | Davis |
| 2014/0288320 | A1 | 9/2014 | Rudenko et al. |

FOREIGN PATENT DOCUMENTS

| | | | |
|---|---|---|---|
| EP | 1 681 337 | A1 | 7/2006 |
| EP | 1 741 767 | A1 | 1/2007 |
| EP | 1 741 768 | A1 | 1/2007 |
| EP | 1 795 576 | A1 | 6/2007 |
| EP | 1 682 466 | B1 | 11/2008 |
| WO | WO 89/01032 | A1 | 2/1989 |
| WO | WO 92/11373 | A1 | 7/1992 |
| WO | WO 94/10288 | A2 | 5/1994 |
| WO | WO 95/13390 | A2 | 5/1995 |
| WO | WO 96/23892 | A2 | 8/1996 |
| WO | WO 00/61740 | A1 | 10/2000 |
| WO | WO 00/66750 | A2 | 11/2000 |
| WO | WO 02/08403 | A2 | 1/2002 |
| WO | WO 2005/047216 | A1 | 5/2005 |
| WO | WO 2006/055322 | A2 | 5/2006 |
| WO | WO 2007/106903 | A2 | 9/2007 |
| WO | WO 2008/002643 | A2 | 1/2008 |
| WO | WO 2008/151149 | A2 | 12/2008 |
| WO | WO 2010/019813 | A2 | 2/2010 |
| WO | WO 2010/063031 | A2 | 6/2010 |
| WO | WO 2010/063032 | A2 | 6/2010 |
| WO | WO 2010/120939 | A2 | 10/2010 |
| WO | WO 2011/008565 | A1 | 1/2011 |
| WO | WO 2011/127069 | A1 | 10/2011 |
| WO | WO 2011/150410 | A2 | 12/2011 |
| WO | WO 2011/150411 | A1 | 12/2011 |
| WO | WO 2012/061647 | A2 | 5/2012 |
| WO | WO 2012/106560 | A1 | 8/2012 |
| WO | WO 2012/154626 | A1 | 11/2012 |
| WO | WO 2013/158938 | A1 | 10/2013 |
| WO | WO 2014/120829 | A1 | 8/2014 |
| WO | WO 2014/151904 | A1 | 9/2014 |
| WO | WO 2015/051319 | A2 | 4/2015 |
| WO | PCT/US2015/42044 | | 7/2015 |

OTHER PUBLICATIONS

Database Geneseq [Online] (Jun. 6, 2000) “Bay C18:1 preferring acyl-ACP thioesterase protein from clone 3A-17.”, retrieved from EBI accession No. GSP:AAY80558 Database accession No. AAY80558; and Database Geneseq [Online] (Jun. 6, 2000) “Bay C18:1 preferring acyl-ACP thioesterase protein.”, retrieved from EBI accession No. GSP:AAY80559 Database accession No. AAY80559.

Database Geneseq [Online] (Nov. 2, 1995) “Camphor thioesterase.”, retrieved from EBI accession No. GSP:AAR74148 Database accession No. AAR74148.

Database Geneseq [Online] (Oct. 26, 1996) “Cuphea C14:0-ACP thioesterase.”, retrieved from EBI accession No. GSP:AAW02081 Database accession No. AAW02081.

Database Geneseq [Online] (Aug. 5, 2010) “U. californica fatty acyl-ACP thioesterase protein (without PTS), SEQ:139.”, retrieved from EBI accession No. GSP:AYC84249 Database accession No. AYC84249.

PCT Invitation to Pay Additional Fees and, Where Applicable, Protest Fee dated Jun. 18, 2014 issued in PCT/US2014/026644.

PCT International Search Report and Written Opinion dated Aug. 29, 2014 issued in PCT/US2014/026644.

PCT International Preliminary Report on Patentability dated Sep. 24, 2015 issued in PCT/US2014/026644.

GenBank Accession No. U17097, Umbellularia californica Uc FatB2 (FatB) mRNA, complete cds., Jun. 1, 1995, 2pp.

GenBank: Accession No. U39834.1, Cuphea hookeriana 8:0- and 10:0-ACP specific thioesterase (FatB2) mRNA, complete cds, May 21, 2014, 2pp.

GenBank Accession No. AAC49001, Uc FatB2 (FatB) Umbellularica californica, May 30, 1995, 2pp.

Apt et al., (1996) “Stable nuclear transformation of the diatom *Phaeodactylum tricornutum,” Molecular and General Genetics*, 252:572-579.

Barnes et al., (2005) “Contribution of 5'- and 3'-untranslated regions of plastid mRNAs to the expression of *Chlamydomonas reinhardtii* chloroplast genes,” *Mol Gen Genomics*274:625-636.

(56) References Cited

OTHER PUBLICATIONS

Blatti et al., (Sep. 2012) "Manipulating Fatty Acid Biosynthesis in Microalgae for Biofuel through Protein-Protein Interactions," *PLoS ONE* 7(9):e42949, 12pp.
Blowers et al., (Jan. 1989) "Studies on *Chlamydomonas* Chloroplast Transformation: Foreign DNA Can Be Stably Maintained in the Chromosome," *The Plant Cell*, 1:123-132.
Bonaventure et al., (Apr. 2003) "Disruption of the FATB Gene in Arabidopsis Dethonstrates an Essential Role of Saturated Fatty Acids in Plant Growth," *The Plant Cell* 15:1020-1033.
Boynton et al., (1988) "Chloroplast Transformation in *Chlamydomonas* with High Velocity Microprojectiles," *Science*, 240(4858):1534-1538.
Chasan, (Mar. 1995) "Engineering Fatty Acids—The Long and Short of It," *Plant Cell*, 7:235-237.
Chen et al.,(1988) "Recognition of prokaryotic transcription terminators by spinach chloroplast RNA polymerase," *Nucleic Acids Research*,16(17):8411-8431.
Chen et al., (2001) "Highly efficient expression of rabbit neutrophil peptide-1 gene in *Chlorella ellipsoidea* cells," *Current Genetics*, 39(5):365-370.
Chow et al., (1999) "Electrotransformation of *Chlorella vulgaris*," *Plant Cell Reports*, 18:778-780.
Cobley et al., (Sep. 1993) "Construction of Shuttle Plasmids Which Can Be Efficiently Mobilzed from *Escherichia coli* into the Chromatically Adapting Cyanobacterium, *Fremyella diplosiphon*," *Plasmid*, 30(2): 90-105.
Cobley et al., (2002) "CpeR is an activator required for expression of the phycoerythrin operon (*cpeBA*) in the cyanobacterium Fremyella diplosiphon and is encoded in the phycoerythrin linker-polypeptide operon (*cpeCDESTR*)," *Molecular Microbiololgy*,44(6):1517-1531.
Comai et al., (Oct. 15, 1988) "Chloroplast Transport of a Ribulose Bisphosphate Carboxylase Small Subunit-5-Enolpyruvyl 3-Phosphoshikimate Synthase Chimeric Protein Requires Part of the Mature Small Subunit in Addition to the Transit Peptide," *The Journal of Biological Chemistry*, 263(29):15104-15109.
Courchesne, Noémie Manuelle Dorval el al., (2009) "Enhancement of lipid production using biochemical, genetic and transcription factor engineering approaches," *Journal of Biotechnology*, 141(1):31-41.
Davies et al., (1992) "Expression of the arylsulfatase gene from the $\beta_2$-tubulin promoter in *Chlamydomonas reinhardtii*," *Nucleic Acids Res.*, 20(12):2959-2965.
Dawson et al., (1997) "Stable Transformation of *Chlorella*: Rescue of Nitrate Reductase-Deficient Mutants with the Nitrate Reductase Gene," *Current Microbiol.*, 35(6):356-362.
Debuchy et al., (1989) "The argininosuccinate lyase gene of *Chlamydomonas reinhardtii*: an important tool for nuclear transformation and for correlating the genetic and molecular maps of the ARG7 locus," *EMBO Journal*, 8(10):2803-2809.
Dehesh et al. (1996) "Production of high levels of 8:0 and 10:0 fatty acids in transgenic canola by overexpression of *Ch FatB2*, a thioesterase cDNA from *Cuphea hookeriana*," *The Plant Journal*, 9(2):167-172.
Dehesh et al., (1998) "KAS IV: a 3-ketoacyl-ACP synthase from *Cuphea* sp. is a medium chain specific condensing enzyme," *The Plant Journal*, 15:383-390.
Deshnium et al., (1995) "Transformation of *Synechococcus* with a gene for choline oxidase enhances tolerance to salt stress," *Plant Mol. Biol.*,29(5):897-907.
Dörmann et al., (Jan. 1995) "Cloning and Expression in *Escherichia coli* of a Novel Thioesterase from *Arabidopsis thaliana* Specific for Long-Chain Acyl-Acyl Carrier Proteins," *Archives of Biochemistry and Biophysics*, 316(1):612-618.
Eccleston et al., (1996) "Medium-chain fatty Acid biosynthesis and utilization in *Brassica napus* plants expressing lauroyl-acyl carrier protein thioesterase," *Planta*, 198:46-53.
El-Sheekh et al., (1999) "Stable transformation of the intact cells of *Chlorella kessleri* with high velocity microprojectiles," *Biologia Plantarium*, 42:(2):209-216.

Facciotti et al., (1998) "Molecular dissection of the plant acyl-acyl carrier protein thioesterases," *European Journal of Lipid Science and Technology*, 100(Nr. 4-5, S.):167-172.
Facciotti et al., (Jun. 1999) "Improved stearate phenotype in transgenic canola expressing a modified acyl-acyl carrier protein thioesterase," *Nat Biotechnol.*, 17(6):593-597.
Falciatore et al., (May 1999) "Transformation of Nonselectable Reporter Genes in Marine Diatoms," *Mar. Biotechnol.*, 1(3):239-251.
Frenz et al., (1989) "Hydrocarbon recovery by extraction with a biocompatible solvent from free and immobilized cultures of *Botryococcus braunii*," *Enzyme Microb. Technol.*, 11:717-724.
Fromm et al., (Sep. 1985) "Expression of genes transferred into monocot and dicot plant cells by electroporation," *Proc. Natl. Acad. Sci. USA*, 82:5824 5828.
Ginalski et al., (2003) "Detection of reliable and unexpected protein fold predictions using 3D-Jury," *Nucleic Acids Research*,31(13):3291-3292.
Giuffrida et al., (2004) "Formation and Hydrolysis of Triacylglycerol and Sterol Epdxides: Role of Unsaturated Triacylglycerol Peroxyl Radicals," *Free Radical Biology and & Medicine*, 37(1):104-114.
Gruber et al., (1991) "*Escherichia coli-Anacystis nidulans* Plasmid Shuttle Vectors Containing the $P_L$ Promoter from Bacteriophage Lambda," *Current Micro.* 22:15-19.
Gruber et al., (1996) "Expression of the *Volvox* gene encoding nitrate reductase: Mutation-dependent activation of cryptic splice sites and intron-enhanced gene expression from a cDNA," *Plant Molecular Biology*, 31(1):1-12.
Hall et al., (1993) "Expression of a foreign gene in *Chlamydomonas reinhardtii*," *Gene*, 124:75-81.
Hallmann et al., (Nov. 1994) "Reporter genes and highly regulated promoters as tools for transformation experiments in *Volvox carteri*," *Proc. Natl. Acad. Sci. USA*, 91:11562-11566.
Hanley-Bowdoin et al., (Feb. 1987) "Chloroplast promoters," *TIBS*, 12:67-70.
Hawkins et al., (1999) "Expression of Human Growth Hormone by the Eukaryotic Alga, *Chlorella*," *Current Microbiology*, 38:335-341.
Heise et al., (1994) "Factors Controlling Medium-Chain Fatty Acid Synthesis in Plastids From *Cuphea* Embryos," *Prog. Lipid Res.*, 33(1/2):87-95.
Hejazi et al., (Apr. 2004) "Milking of microalgae," *TRENDS in Biotechnology*, 22(4):189-194.
Hillen et al., (1982) "Hydrocracking of the Oils of *Botryococcus braunii* to Transport Fuels," *Biotechnology and Bioengineering*, XXIV:193-205.
Hitz et al., (1994) "Cloning of a Higher-Plant Plastid ω-6 Fatty Acid Desaturase cDNA and Its Expression in a Cyanobacterium," *Plant Physiol.*,105(2):635-641.
Huang et al. (2006) "Expression of mercuric reductase from *Bacillus megaterium* MB1 in eukaryotic microalga *Chlorella* sp. DT: an approach for mercury phytoremediation," *Appl. Microbiol. Biotechnol.* 72:197-205.
Inoue et al., (1993) "Analysis of Oil Derived From Liquefaction of *Botryococcus braunii*," *Biomass Bioenergy*, 6(4):269-274).
Isbell et al., (Feb. 1994) "Acid-Catalyzed Condensation of Oleic Acid into Estolides and Polyestolides," *JAOCS*, 71(2):169-174.
Jakobiak et al. (Dec. 2004) "The Bacterial Paromomycin Resistance Gene, *aphH*, as a Dominant Selectable Marker in *Volvox carteri*," *Protist*,155(4):381-393.
Jarvis et al. (1991) "Transient expression of firefly luciferase in protoplasts of the green alga *Chlorella elltpsoidea*," *Current Genetics*, 19:317-321.
Jha et al., (2006) "Cloning and functional expression of an acyl-ACP thioesterase FatB type from *Diploknema* (*Madhuca*) *butyracea* seeds in *Escherichia coli*," *Plant Physiology and Biochemistry*, 44:645-655.
Jiang et al., (Apr. 2005) "The Actin Gene Promoter-driven bar as a Dominant Selectable Marker for Nuclear Transformation of *Dunaliella salina*," *Acta Genetica Sinica*, 32(4):424-433.
Jones et al., (Mar. 1995) "Palmitoyl-Acyl Carrier Protein (ACP) Thioesterase and the Evolutionary Origin of Plant Acyl-ACP Thioesterases," *The Plant Cell*, 7:359-371.
Kalscheuer et al., (1999) "Establishment of a gene transfer system for *Rhodococcus opacus* PD630 based on electroporation and its appli-

(56) References Cited

OTHER PUBLICATIONS cation for recombinant biosynthesis of poly(3-hydroxyalkanoic acids)," *Applied and Environmental Microbiology*, 52:508-515.
Kang et al., (Jul. 2000) "The Regulation Activity of Chlorella Virus Gene 5' Upstream Sequence in *Escherichia coli* and Eucaryotic Algae," [English Abstract] *Chinese Journal of Biotechnology*, 16(4):6 pages.
Kang et al., (2004) "Genetic diversity in chlorella viruses flanking *kcv*, a gene that encodes a potassium ion channel protein," *Virology*, 326(1):150-159.
Kawasaki et al., (2004) "Immediate early genes expressed in chlorovirus infections," *Virology*,318(1):214-223.
Kim et al., (2002) Stable Integration and Functional Expression of Flounder Growth Hormone Gene in Transformed Microalga, *Chlorella ellipsoidea, Mar. Biotechnol*., 4(1):63-73.
Kindle, (Feb. 1990) "High-frequency nuclear transformation of *Chlamydomonas reinhardtii," Proc. Natl. Acad. Sci. USA*, 87(3):1228-1232.
Klein et al., (1987) "High-velocity microprojectiles for delivering nucleic acids into living cells," *Nature* London 327(7):70-73.
Knauf, (Feb. 1987) "The application of genetic engineering to oilseed crops," *TIBTECH*, 5:40-47.
Knutzon et al., (Jul. 1999) "Lysophosphatidic Acid Acyltransferase from Coconut Endosperm Mediates the Insertion of Laurate at the *sn-2* Position of Triacylglycerols in Lauric Rapeseed Oil and Can Increase Total Laurate Levels," *Plant Physiology*, 120:739-746.
Kojima et al., (1999) "Growth and Hydrocarbon Production of Microalga *Botryococcus braunii* in Bubble Column Photobioreactors," *Journal of Bioscience and Bioengineering*, 87(6): 811-815.
Koksharova et al., (Feb. 2002) "Genetic tools for cyanobacteria," *Appl Microbiol Biotechnol* 58(2):123-137.
Krebbers et al., (1982) "The maize chloroplast genes for the β and ϵ subunits of the photosynthetic coupling factor $CF_1$ are fused," *Nucleic Acids Research*, 10(16):4985-5002.
La Scala et al., (Jan. 2002) "The Effect of Fatty Acid Composition on the Acrylation Kinetics of Epoxidized Triacylglycerols", *Journal of the American Oil Chemists' Society*, 79(1):59-63.
Lapidot et al., (May 2002) "Stable Chloroplast Transformation of the Unicellular Red Alga *Porphyridium* Species," *Plant Physiol*., 129(1):7-12.
Larson et al., (2002) "Acyl CoA profilesof transgenic plants that accumulate medium-chain fatty acids indicate inefficient storage lipid synthesis in developing oilseeds," *The Plant Journal*, 32(4):519-527.
Lumbreras et al., (1998) "Efficient foreign gene expression in *Chlamydomonas reinhardtii* mediated by an endogenous intron," *Plant Journal*, 14(4):441-447.
Manuell et al., (2007) "Robust expression of a bioactive mammalian protein in *Chlamydomonas* chloroplast," *Plant Biotechnol Journal*, 5:402-412.
Mayer et al., (Feb. 4, 2005) "A Structural Model of the Plant Acyl-Acyl Carrier Protein Thioesterase FatB Comprises Two Helix/4-Stranded Sheet Domains, the N-terminal Domain Containing Residues That Affect Specificity and the C-terminal Domain Containing Catalytic Residues," *The Journal of Biological Chemistry*, 280(5):3621-3627.
Mayfield et al., (Jan. 21, 2003) "Expression and assembly of a fully active antibody in algae," *Proc. Natl. Acad. Sci. USA*, 100(2):438-442.
Mekhedov et al., (Feb. 2000) "Toward a Functional Catalog of the Plant Genome. A Survey of Genes for Lipid Biosynthesis," *Plant Physiology*, 122:389-401.
Mendes et al. (2003) "Supercritical carbon dioxide extraction of compounds with pharmaceutical importance from microalgae," *Inorganica Chimica Acta*, 356:328-334.
Metzger et al., (Jun. 2003) "Lycopanerols I-L, Four New Tetraterpenoid Ethers from *Botryococcus braunii," J Nat. Prod*. 66(6):772-778.
Metzger et al., (2005) "*Botryococcus braunii*: a rich source for hydrocarbons and related ether lipids," *Appl Microbiol Biotechnol* 66:486-496.
Miao et al., (2004) "High yield bio-oil production from fast pyrolysis by metabolic controlling of *Chlorella protothecoides," Journal of Biotechnology*, 110:85-93.
Miao et al., (2006) "Biodiesel production from heterotrophic microalgal oil," *Biosource Technology*, 97:841-846.
Minowa et al., (1995) "Oil production from algal cells of *Dunaliella tertiolecta* by direct thermochemical liquefaction," *Fuel*, 74(12):1735-1738.
Mitra et al., (Oct. 14, 1994) "A Chlorella Virus Gene Promoter Functions as a Strong Promoter Both in Plants and Bacteria," *Biochemical Biophysical Research Communication*, 204(1): 187-194.
Mitra et al., (Oct. 1994) "The *Chlorella* virus adenine methyltransferase gene promoter is a strong promoter in plants," *Plant Mol. Biol*., 26(1):85-93.
Moreno-Pérez et al., (2012) "Reduced expression of FatA thioesterases in Arabidopsis affects the oil content and fatty acid composition of the seeds," *Planta*, 235:629-639.
Mullet et al., (1985) "Multiple transcripts for higher plant *rbc*L and *atp*B genes and localization of the transcription initiation site of the *rbc*L gene," *Plant Molecular Biology*, 4:39-54.
Oda et al., (2000) "Degradation of Polylactide by Commercial Proteases," *Journal of Polymers and the Environment*, 8(1):29-32.
Onai et al., (2004) "Natural transformation of the thermophilic cyanobacterium *Thermosynechococcus elongatus* BP-1: a simple and efficient method for gene transfer," *Mol Genet Genomics*, 271(1):50-59.
Park et al., (2005) "Isolation and Characterization of Chlorella Virus from Fresh Water in Korea and Application in Chlorella Transformation System," *The Plant Patholology Journal*, 21(1): 13-20.
Pröschold et al., (Aug. 2005) "Portrait of a species: *Chlamydomonas reinhardtii," Genetics*,170:1601-1610.
Radakovits et al., (Apr. 2010) "Genetic Engineering of Algae for Enhanced Biofuel Production," *Eukaryotic Cell*, 9(4):486-501.
Rao et al., (2006) "Antioxidant Activity of *Botryococcus braunii* Extract Elucidated in Vitro Models," *J. Agric. Food Chem*., 54(13):4593-4599.
Rehm et al., (2001)"Heterologous expression of the acyl-acyl carrier protein thioesterase gene from the plant *Umbellularia californica* mediates polyhydroxyalkanoate biosynthesis in recombinant *Escherichia coli," Appl Microbiol Biotechnol*, 55:205-209.
Rismani-Yazdi et al., (2011) "Transcriptome sequencing and annotation of the microalgae *Dunaliella tertiolecta*: Pathway description and gene discovery for production of next-generation biofuels," *BMC Genomics*, 12:148, 17 pages; doi:10.1186/1471-2164-12-148.
Rosenberg, Julian N. et al., (2008) "A green light for engineered algae: redirecting metabolism to fuel a biotechnology revolution," *Current Opinion in Biotechnology*, 19(5):430-436.
Salas et al., (2002) "Characterization of substrate specificity of plant FatA and FatB acyl-ACP thioesterases," *Archives of Biochemistry and Biophysics*, 403:25-34.
Sanford, (Dec. 1988) "The biolistic process," *Trends in Biotech*. 6:299-302.
Sawayama et al. (1999) Possibility of renewable energy production and $CO_2$ mitigation by thermochemical liquefaction of microalgae *Biomass and Bioenergy*, 17:33-39.
Schreier et al., (1985) "The use of nuclear-encoded sequences to direct the light-regulated synthesis and transport of a foreign protein into plant chloroplasts," *EMBO J*. 4(1):25-32.
Schultz et al., (Apr. 2005) "A common core of secondary structure of the internal transcribed spacer 2 (ITS2) throughout the Eukaryota," *RNA*, 11(4):361-364.
Schütt et al., (1998) "The role of acyl carrier protein isoforms from *Cuphea lanceolata* seeds in the de-novo biosynthesis of medium-chain fatty acids," *Publication, Planta*, 205:263-268.
Shao et al., (2002) "Cloning and expression of metallothionein mutant α-KKS-α in *Anabaena* sp. PCC 7120," *Marine Pollution Bulletin*,45(1-12):163-167.
Sheehan, John; Dunahay, Terri; Benemann, John; Roessler, Paul; (Jul. 1998) "A Look Back at the U.S. Department of Energy's Aquatic Species Program: Biodiesel from Algae," Prepared for U.S. Depart-

(56) References Cited

OTHER PUBLICATIONS ment of Energy's Office of Fuels Development, Prepared by *National Renewable Energy Laboratory*, NREL/TP-580-24190, 328 pages.
Stemmer et al., (1995) "Single-step assembly of a gene and entire plasmid from large numbers of oligodeoxyribonucleotides," *Gene*, 164(1):49-53.
Tan et al., (Aug. 2005) "Establishment of a Micro-Particle Bombardment Transformation System for *Dunaliella salina," The Journal of Microbiology*, 43(4):361-365.
Tang et al., (Aug. 1995) "Insertion Mutagenesis of *Chlamydomonas reinhardtii* by Electroporation and Heterologous DNA," *Biochemistry and Molecular Biology International*, 36(5):1025-1035.
Tyystjärvi et al., (2005) "Mathematical modelling of the light response curve of photoinhibition of Photosystem II," *Photosynthesis Research*, 84(1-3):21-27.
Vázquez-Bermúdez et al., (Jan. 2000) "Uptake of 2-Oxoglutarate in *Synechococcus* Strains Transformed with the *Escherichia coli kgtP* Gene," *Journal of Bacteriology*, 182(1):211-215.
Vázquez-Bermúdez et al., (2003) "Carbon supply and 2-oxoglutarate ejects on expression of nitrate reductase and nitrogen-regulated genes in *Synechococcus* sp. strain PCC 7942," *FEMS Microbiology Letters*, 221(2):155-159.
Voelker, (1996) "Plant Acyl-ACP Thioesterases: Chain-Length Determining Enzymes in Plant Fatty Acid Biosynthesis," *Genetic Engineering*, Edited by: Setlow JK. Plenum Pres, New York, 18:111-133.
Voelker et al., (Dec. 1994) "Alteration of the Specificity and Regulation of Fatty Acid Synthesis of *Escherichia coli* by Expression of a Plant Medium Chain Acyl-Acyl Carrier Protein Thioesterase," *Journal of Bacteriology*, 176(23):7320-7327.
Voelker et al., (1997) "Broad-Range and Binary-Range Acyl-Acyl-Carrier-Protein Thioesterases Suggest an Alternative Mechanism for Medium-Chain Production in Seeds," *Plant Physiol.*, 114:669-677.
Voetz et al., (1994) "Three Different cDNAs Encoding Acyl Carrier Proteins from *Cuphea lanceolata," Plant Physiol.*, 106:785-786.
Walker et al., (2005) "Characterisation of the *Dunaliella tertiolecta RbcS* genes and their promoter activity in *Chlamydomonas reinhardtii," Plant Cell Rep.* 23(10-11):727-735.
Westphal et al., (Mar. 27, 2001) "*Vipp1* deletion mutant of *Synechocystis*: A connection between bacterial phage shock and thylakoid biogenesis?" *Proc. Natl. Acad. Sci. USA*, 98(7):4243-4248.
Wiberg et al., (2000) "The distribution of caprylate, caprate and laurate in lipids from developing and mature seeds of transgenic *Brassica napus* L.," *Planta*, 212:33-40.
Wirth et al., (1989) "Transformation of various species of gram-negative bacteria belonging to 11 different genera by electroporation," *Mol Gen Genet.* 216(1):175-177.
Wolk et al., (Mar. 1984) "Construction of shuttle vectors capable of conjugative transfer from *Escherichia coli* to nitrogen-fixing filamentous cyanobacteria," *Proc. Natl. Acad. Sci. USA*, 81(5):1561-1565.
Wong et al., (1992) "*Arabidopsis thaliana* small subunit leader and transit peptide enhance the expression of *Bacillus thuringiensis* proteins in transgenic plants," *Plant Molecular Biology*, 20:81-93.
Wu et al., (2001) "Identification of *Chlorella* spp. isolates using ribosomal DNA sequences," *Bot. Bull. Acad. Sin.*42:115-121.
Yu et al., (2011) "Modifications of the metabolic pathways of lipid and triacylglycerol production in microalgae," *Microbial Cell Factories*, 10:91 [Retrieved from the Internet Jul. 24, 2012: <URL:http://www.microbialcellfactories.com/content/10/1/91>], 11 pages.
Yuan et al., (Feb. 16, 1996) "The Catalytic Cysteine and Histidine in the Plant Acyl-Acyl Carrier Protein Thioesterases," *The Journal of Biological Chemistry*, 271(7):3417-3419.
Zurawski et al., (1981) "The structure of the gene for the large subunit of ribulose 1,5-bisphosphate carboxylase from spinach chloroplast DNA, " *Nucleic Acids Res.* 9(14):3251-3270.
Zurawski et al., (Dec. 1982) "Nucleotide sequence of the gene for the $M_r$ 32,000 thylakoid membrane protein from *Spinacia oleracea* and *Nicotiana debneyi* predicts a totally conserved primary translation product of $M_r$ 38,950," *Proc. Natl. Acad. Sci. USA*, 79:7699-7703.
Mayer, et al. 2007, "Identification of amino acid residues involved in substrate specificity of plant acyl-ACP thioesterases using a bioinformatics-guided approach," *BMC Plant Biology* 7(1):1-11.
Yuan, et al. 1995, "Modification of the substrate specificity of an acyl-acyl carrier protein thioesterase by protein engineering," Proc. Natl. Acad. Sci. USA 92:10639-10643.

* cited by examiner

THIOESTERASES AND CELLS FOR PRODUCTION OF TAILORED OILS

SEQUENCE LISTING

The instant application contains a Sequence Listing which has been submitted in ASCII format via EFS-Web and is hereby incorporated by reference in its entirety. Said ASCII copy, created on Jul. 3, 2013, is named SOLAP019US_SL.txt and is 318,250 bytes in size.

BACKGROUND

Certain organisms including plants and some microalgae use a type II fatty acid biosynthetic pathway, characterized by the use of discrete, monofunctional enzymes for fatty acid synthesis. In contrast, mammals and fungi use a single, large, multifunctional protein.

Type II fatty acid biosynthesis typically involves extension of a growing acyl-ACP (acyl-carrier protein) chain by two carbon units followed by cleavage by an acyl-ACP thioesterase. In plants, two main classes of acyl-ACP thioesterases have been identified: (i) those encoded by genes of the FatA class, which tend to hydrolyze oleoyl-ACP into oleate (an 18:1 fatty acid) and ACP, and (ii) those encoded by genes of the FatB class, which liberate C8-C16 fatty acids from corresponding acyl-ACP molecules.

Different FatB genes from various plants have specificities for different acyl chain lengths. As a result, different gene products will produce different fatty acid profiles in plant seeds. See, U.S. Pat. Nos. 5,850,022; 5,723,761; 5,639,790; 5,807,893; 5,455,167; 5,654,495; 5,512,482; 5,298,421; 5,667,997; and 5,344,771; 5,304,481. Recently, FatB genes have been cloned into oleaginous microalgae to produce triglycerides with altered fatty acid profiles. See, WO2010/063032, WO2011,150411, and WO2012/106560.

SUMMARY

In an embodiment of the invention, there is a nucleic acid having at least 80% sequence identity to any of SEQ ID NOS: 2, 3, 5, 6, 8, 9, 11, 12, 14, 15, 17, 18, 20, 21, 23, 24, 26, 27, 29, 30, 32, 33, 35, 36, 38, 39, 41, 42, 44, 45, 47, 48, 50, 51, 53, 54, 56, 57, 59, 60, 62, 63, 65, 66, 68, 69, 71, 72, 74, 76 or any equivalent sequences by virtue of the degeneracy of the genetic code.

In another embodiment of the invention, there is a nucleic acid sequence encoding a protein having at least 80% sequence identity to any of SEQ ID NOS: 1, 4, 7, 10, 13, 16, 19, 22, 25, 28, 31, 34, 37, 40, 43, 46, 49, 52, 55, 58, 61, 64, 67, 70, 73, 75, or 77, or a fragment thereof having acyl-ACP thioesterase activity. The protein can have acyl-ACP thioesterase activity operable to alter the fatty acid profile of an oil produced by a recombinant cell comprising that sequence.

In a further embodiment of the invention there is a method of producing a recombinant host cell that produces an altered fatty acid profile, the method comprising transforming the cell with any of the nucleic acids mentioned above. The host cell can be a plant cell, a microbial cell, or a microalgal cell. Another embodiment of the invention includes a host cell produced by this method.

In an embodiment, there is a method for producing an oil or oil-derived product, the method comprising cultivating the host cell and extracting the oil, optionally wherein the cultivation is heterotrophic growth on sugar. Optionally, a fatty acid, fuel, chemical, or other oil-derived product can be produced from the oil. Optionally, the oil can have a fatty acid profile comprising at least 20% C8, C10, C12, C14 or C16 fatty acids. Optionally, the oil is produced by a microalgae and can lack C24-alpha sterols.

DESCRIPTION OF ILLUSTRATIVE EMBODIMENTS OF THE INVENTION

Definitions

As used with respect to nucleic acids, the term "isolated" refers to a nucleic acid that is free of at least one other component that is typically present with the naturally occurring nucleic acid. Thus, a naturally occurring nucleic acid is isolated if it has been purified away from at least one other component that occurs naturally with the nucleic acid.

A "natural oil" or "natural fat" shall mean a predominantly triglyceride oil obtained from an organism, where the oil has not undergone blending with another natural or synthetic oil, or fractionation so as to substantially alter the fatty acid profile of the triglyceride. In connection with an oil comprising triglycerides of a particular regiospecificity, the natural oil or natural fat has not been subjected to interesterification or other synthetic process to obtain that regiospecific triglyceride profile, rather the regiospecificity is produced naturally, by a cell or population of cells. In connection with a natural oil or natural fat, and as used generally throughout the present disclosure, the terms oil and fat are used interchangeably, except where otherwise noted. Thus, an "oil" or a "fat" can be liquid, solid, or partially solid at room temperature, depending on the makeup of the substance and other conditions. Here, the term "fractionation" means removing material from the oil in a way that changes its fatty acid profile relative to the profile produced by the organism, however accomplished. The terms "natural oil" and "natural fat" encompass such oils obtained from an organism, where the oil has undergone minimal processing, including refining, bleaching and/or degumming, that does not substantially change its triglyceride profile. A natural oil can also be a "noninteresterified natural oil", which means that the natural oil has not undergone a process in which fatty acids have been redistributed in their acyl linkages to glycerol and remain essentially in the same configuration as when recovered from the organism.

"Exogenous gene" shall mean a nucleic acid that codes for the expression of an RNA and/or protein that has been introduced into a cell (e.g. by transformation/transfection), and is also referred to as a "transgene". A cell comprising an exogenous gene may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell as an insertion into the genome (nuclear or plastid) or as an episomal molecule.

"Fatty acids" shall mean free fatty acids, fatty acid salts, or fatty acyl moieties in a glycerolipid. It will be understood that fatty acyl groups of glycerolipids can be described in terms of the carboxylic acid or anion of a carboxylic acid that is produced when the triglyceride is hydrolyzed or saponified.

"Microalgae" are microbial organisms that contain a chloroplast or other plastid, and optionally that are capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, Volvox, which is a simple multicellular photosynthetic microbe of two distinct cell types. Microalgae include cells such as *Chlorella, Dunaliella*, and *Prototheca*. Microalgae also include other microbial photosynthetic organisms that exhibit cell-cell adhesion, such as *Agmenellum, Anabaena*, and *Pyrobotrys*. Microalgae also include obligate heterotrophic microorganisms that have lost the ability to perform photosynthesis, such as certain dinoflagellate algae species and species of the genus *Prototheca*.

An "oleaginous" cell is a cell capable of producing at least 20% lipid by dry cell weight, naturally or through recombinant or classical strain improvement. An "oleaginous microbe" or "oleaginous microorganism" is a microbe, including a microalga that is oleaginous.

In connection with a natural oil, a "profile" is the distribution of particular species or triglycerides or fatty acyl groups within the oil. A "fatty acid profile" is the distribution of fatty acyl groups in the triglycerides of the oil without reference to attachment to a glycerol backbone. Fatty acid profiles are typically determined by conversion to a fatty acid methyl ester (FAME), followed by gas chromatography (GC) analysis with flame ionization detection (FID). The fatty acid profile can be expressed as one or more percent of a fatty acid in the total fatty acid signal determined from the area under the curve for that fatty acid. FAME-GC-FID measurement approximate weight percentages of the fatty acids.

"Recombinant" is a cell, nucleic acid, protein or vector that has been modified due to the introduction of an exogenous nucleic acid or the alteration of a native nucleic acid. Thus, e.g., recombinant cells can express genes that are not found within the native (non-recombinant) form of the cell or express native genes differently than those genes are expressed by a non-recombinant cell. Recombinant cells can, without limitation, include recombinant nucleic acids that encode a gene product or suppression elements such as mutations, knockouts, antisense, interfering RNA (RNAi) or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, using chemical synthesis, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

Thioesterase Sequences

Additional FatB genes encoding thioesterases with varying substrate preferences have been identified from plant seeds. These genes or functional subsequences thereof can be used to engineer organisms to produce fatty acids having a chain-length distribution (fatty acid profile) that is altered from the wild type organism. Specifically, recombinant cells express one or more of the exogenous FatB genes. The fatty acids can be further converted to triglycerides, fatty aldehydes, fatty alcohols and other oleochemicals either synthetically or biosynthetically. In specific embodiments, triglycerides are produced by a host cell expressing the novel FatB gene. A triglyceride-containing natural oil can be recovered from the host cell. The natural oil can be refined, degummed, bleached and/or deodorized. The oil, in its natural or processed form, can be used for foods, chemicals, fuels, cosmetics, plastics, and other uses.

The genes can be used in a variety of genetic constructs including plasmids or other vectors for expression or recombination in a host cell. The genes can be codon optimized for expression in a target host cell. The proteins produced by the genes can be used in vivo or in purified form.

The gene sequences disclosed can also be used to prepare antisense, or inhibitory RNA (e.g., RNAi or hairpin RNA) to inhibit complementary genes in a plant or other organism.

FatB genes found to be useful in producing desired fatty acid profiles in a cell are summarized below in Table 1. Nucleic acids or proteins having the sequence of SEQ ID NOS: 1-78 can be used to alter the fatty acid profile of a recombinant cell. Variant nucleic acids can also be used; e.g, variants having at least 80, 85, 90, 95, 96, 97, 98, or 99% sequence identity to SEQ ID NOS: 2, 3, 5, 6, 8, 9, 11, 12, 14, 15, 17, 18, 20, 21, 23, 24, 26, 27, 29, 30, 32, 33, 35, 36, 38, 39, 41, 42, 44, 45, 47, 48, 50, 51, 53, 54, 56, 57, 59, 60, 62, 63, 65, 66, 68, 69, 71, 72, 74, 76, or 78. Codon optimization of the genes for a variety of host organisms is contemplated, as is the use of gene fragments. Preferred codons for *Prototheca* strains and for *Chlorella protothecoides* are shown below in Tables 2 and 3, respectively. In some embodiments, the first and/or second most preferred *Prototheca* codons are employed for codon optimization.

In embodiments of the invention, there is protein or a nucleic acid encoding a protein having any of SEQ ID NOS: 1, 4, 7, 10, 13, 16, 19, 22, 25, 28, 31, 34, 37, 40, 43, 46, 49, 52, 55, 58, 61, 64, 67, 70, 73, 75, or 77. In an embodiment, there is protein or a nucleic acid encoding a protein having at least 70, 75, 80, 85, 90, 91, 92, 93, 94, 95, 96, 97, 98, 99, or 100% sequence identity with any of SEQ ID NOS: 1, 4, 7, 10, 13, 16, 19, 22, 25, 28, 31, 34, 37, 40, 43, 46, 49, 52, 55, 58, 61, 64, 67, 70, 73, 75, or 77. In certain embodiments, the invention encompasses a fragment any of the above-described proteins or nucleic acids (including fragments of protein or nucleic acid variants), wherein the protein fragment has acyl-ACP thioesterase activity or the nucleic acid fragment encodes such a protein fragment. In other embodiments, the fragment includes a domain of an acyl-ACP thioesterase that mediates a particular function, e.g., a specificity-determining domain. Illustrative fragments can be produced by C-terminal and/or N-terminal truncations and include at least 50%, 55%, 60%, 65%, 70%, 75%, 80%, 85%, 90%, 95%, 96%, 97%, 98%, or 99% of the full-length sequences disclosed herein.

The term "percent sequence identity," in the context of two or more amino acid or nucleic acid sequences, refers to two or more sequences or subsequences that are the same or have a specified percentage of amino acid residues or nucleotides that are the same, when compared and aligned for maximum correspondence, as measured using a sequence comparison algorithm or by visual inspection. For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted using the NCBI BLAST software (ncbi.nlm.nih.gov/BLAST/) set to default parameters. For example, to compare two nucleic acid sequences, one may use blastn with the "BLAST 2 Sequences" tool Version 2.0.12 (Apr. 21, 2000) set at the following default parameters: Matrix: BLOSUM62; Reward for match: 1; Penalty for mismatch: −2; Open Gap: 5 and Extension Gap: 2 penalties; Gap×drop-off: 50; Expect: 10; Word Size: 11; Filter: on. For a pairwise comparison of two amino acid sequences, one may use the "BLAST 2 Sequences" tool Version 2.0.12 (Apr. 21, 2000) with blastp set, for example, at the following default parameters: Matrix: BLOSUM62; Open Gap: 11 and Extension Gap: 1 penalties; Gap×drop-off 50; Expect: 10; Word Size: 3; Filter: on.

In certain embodiments, percent sequence identity for variants of the nucleic acids or proteins discussed above can be calculated by using the full-length nucleic acid sequence (e.g., one of SEQ ID NOS: 2, 3, 5, 6, 8, 9, 11, 12, 14, 15, 17, 18, 20, 21, 23, 24, 26, 27, 29, 30, 32, 33, 35, 36, 38, 39, 41, 42, 44, 45, 47, 48, 50, 51, 53, 54, 56, 57, 59, 60, 62, 63, 65, 66, 68, 69, 71, 72, 74, 76, or 78) or full-length amino acid sequence (e.g., one of SEQ ID NOS: 1, 4, 7, 10, 13, 16, 19, 22, 25, 28, 31, 34, 37, 40, 43, 46, 49, 52, 55, 58, 61, 64, 67, 70, 73, 75, or 77) as the reference sequence and comparing the full-length test sequence to this reference sequence. In some embodiments relating to fragments, percent sequence identity for variants of nucleic acid or protein fragments can be calculated over the entire length of the fragment.

The nucleic acids can be in isolated form, or part of a vector or other construct, chromosome or host cell. It has been found that is many cases the full length gene (and protein) is not needed; for example, deletion of some or all of the N-terminal hydrophobic domain (typically an 18 amino acid domain starting with LPDW (SEQ ID NO: 115)) yields a still-functional gene. In addition, fusions of the specificity determining regions of the genes in Table 1 with catalytic domains of other acyl-ACP thioesterases can yield functional genes. Thus, in certain embodiments, the invention encompasses functional fragments (e.g., specificity determining regions) of the disclosed nucleic acid or amino acids fused to heterologous acyl-ACP thioesterase nucleic acid or amino acid sequences, respectively.

TABLE 1

FatB genes according to embodiments of the present invention

| Species | Gene Name | Sequence Variant (relative to dominant transcript idenitified) | Amino Acid Sequence of CDS (no additional tags) | Native CDS nucloetide sequence (not codon-optimized, no additional cloning sites) | *Prototheca moriformis* codon-optimized nucleotide sequence of CDS |
|---|---|---|---|---|---|
| *Cinnamomum camphora* | CcFATB1b | M25L, M322R, ΔT367-D368 | SEQ ID NO: 1 | SEQ ID NO: 2 | SEQ ID NO: 3 |
| *Cinnamomum camphora* | CcFATB4 | "wild-type" | SEQ ID NO: 4 | SEQ ID NO: 5 | SEQ ID NO: 6 |
| *Cinnamomum camphora* | CcFATB3 | "wild-type" | SEQ ID NO: 7 | SEQ ID NO: 8 | SEQ ID NO: 9 |
| *Cuphea hyssopifolia* | ChsFATB1 | "wild-type" | SEQ ID NO: 10 | SEQ ID NO: 11 | SEQ ID NO: 12 |
| *Cuphea hyssopifolia* | ChsFATB2 | "wild-type" | SEQ ID NO: 13 | SEQ ID NO: 14 | SEQ ID NO: 15 |
| *Cuphea hyssopifolia* | ChsFATB2b | +a.a.248-259 | SEQ ID NO: 16 | SEQ ID NO: 17 | SEQ ID NO: 18 |
| *Cuphea hyssopifolia* | ChsFATB3 | "wild-type" | SEQ ID NO: 19 | SEQ ID NO: 20 | SEQ ID NO: 21 |
| *Cuphea hyssopifolia* | ChsFATB3b | V204I, C239F, E243D, M251V | SEQ ID NO: 22 | SEQ ID NO: 23 | SEQ ID NO: 24 |
| *Cuphea* PSR23 | CuPSR23FATB3 | "wild-type" | SEQ ID NO: 25 | SEQ ID NO: 26 | SEQ ID NO: 27 |
| *Cuphea wrightii* | CwFATB3 | "wild-type" | SEQ ID NO: 28 | SEQ ID NO: 29 | SEQ ID NO: 30 |
| *Cuphea wrightii* | CwFATB4a | "wild-type" | SEQ ID NO: 31 | SEQ ID NO: 32 | SEQ ID NO: 33 |
| *Cuphea wrightii* | CwFATB4b | "wild-type" | SEQ ID NO: 34 | SEQ ID NO: 35 | SEQ ID NO: 36 |
| *Cuphea wrightii* | CwFATB5 | "wild-type" | SEQ ID NO: 37 | SEQ ID NO: 38 | SEQ ID NO: 39 |
| *Cuphea heterophylla* | ChtFATB1a | "wild-type" | SEQ ID NO: 40 | SEQ ID NO: 41 | SEQ ID NO: 42 |
| *Cuphea heterophylla* | ChtFATB1b | P16S, T20P, G94S, G105W, S293F, L305F | SEQ ID NO: 43 | SEQ ID NO: 44 | SEQ ID NO: 45 |
| *Cuphea heterophylla* | ChtFATB2b | "wild-type" | SEQ ID NO: 46 | SEQ ID NO: 47 | SEQ ID NO: 48 |
| *Cuphea heterophylla* | ChtFATB2a | S17P, P21S, T28N, L30P, S33L, G76D, S78P, G137W | SEQ IDO NO: 49 | SEQ ID NO: 50 | SEQ ID NO: 51 |
| *Cuphea heterophylla* | ChtFATB2c | G76D, S78P | SEQ ID NO: 52 | SEQ ID NO: 53 | SEQ ID NO: 54 |

TABLE 1-continued

| FatB genes according to embodiments of the present invention | | | | | |
|---|---|---|---|---|---|
| Species | Gene Name | Sequence Variant (relative to dominant transcript idenitified) | Amino Acid Sequence of CDS (no additional tags) | Native CDS nucleotide sequence (not codon-optimized, no additional cloning sites) | *Prototheca moriformis* codon-optimized nucleotide sequence of CDS |
| *Cuphea heterophylla* | ChtFATB2d | S21P, T28N, L30P, S33L, G76D, R97L, H124L, W127L, I132S, K258N, C303R, E309G, K334T, T386A | SEQ ID NO: 55 | SEQ ID NO: 56 | SEQ ID NO: 57 |
| *Cuphea heterophylla* | ChtFATB2e | G76D, R97L, H124L, I132S, G152S, H165L, T211N, K258N, C303R, E309G, K334T, T386A | SEQ ID NO: 58 | SEQ ID NO: 59 | SEQ ID NO: 60 |
| *Cuphea heterophylla* | ChtFATB2f | R97L, H124L, I132S, G152S, H165L, T211N | SEQ ID NO: 61 | SEQ ID NO: 62 | SEQ ID NO: 63 |
| *Cuphea heterophylla* | ChtFATB2g | A6T, A16V, S17P, G76D, R97L, H124L, I132S, S143I, G152S, A157T, H165L, T211N, G414A | SEQ ID NO: 64 | SEQ ID NO: 65 | SEQ ID NO: 66 |
| *Cuphea heterophylla* | ChtFATB3a | "wild-type" | SEQ ID NO: 67 | SEQ ID NO: 68 | SEQ ID NO: 69 |
| *Cuphea heterophylla* | ChtFATB3b | C67G, H72Q, L128F, N179I | SEQ ID NO: 70 | SEQ ID NO: 71 | SEQ ID NO: 72 |
| *Cuphea viscosissima* | CvisFATB1 | published | SEQ ID NO: 73 | N/A | SEQ ID NO: 74 |
| *Cuphea viscosissima* | CvisFATB2 | published | SEQ ID NO: 75 | N/A | SEQ ID NO: 76 |
| *Cuphea viscosissima* | CvisFATB3 | published | SEQ ID NO: 77 | N/A | SEQ ID NO: 78 |

TABLE 2

| Preferred codon usage in *Prototheca* strains | | | | | | | |
|---|---|---|---|---|---|---|---|
| Ala | GCG | 345 | (0.36) | Asn | AAT | 8 | (0.04) |
| | GCA | 66 | (0.07) | | AAC | 201 | (0.96) |
| | GCT | 101 | (0.11) | Pro | CCG | 161 | (0.29) |
| | GCC | 442 | (0.46) | | CCA | 49 | (0.09) |
| Cys | TGT | 12 | (0.10) | | CCT | 71 | (0.13) |
| | TGC | 105 | (0.90) | | CCC | 267 | (0.49) |
| Asp | GAT | 43 | (0.12) | Gln | CAG | 226 | (0.82) |
| | GAC | 316 | (0.88) | | CAA | 48 | (0.18) |
| Glu | GAG | 377 | (0.96) | Arg | AGG | 33 | (0.06) |
| | GAA | 14 | (0.04) | | AGA | 14 | (0.02) |
| Phe | TTT | 89 | (0.29) | | CGG | 102 | (0.18) |
| | TTC | 216 | (0.71) | | CGA | 49 | (0.08) |
| Gly | GGG | 92 | (0.12) | | CGT | 51 | (0.09) |
| | GGA | 56 | (0.07) | | CGC | 331 | (0.57) |
| | GGT | 76 | (0.10) | Ser | AGT | 16 | (0.03) |
| | GGC | 559 | (0.71) | | AGC | 123 | (0.22) |
| His | CAT | 42 | (0.21) | | TCG | 152 | (0.28) |
| | CAC | 154 | (0.79) | | TCA | 31 | (0.06) |
| Ile | ATA | 4 | (0.01) | | TCT | 55 | (0.10) |
| | ATT | 30 | (0.08) | | TCC | 173 | (0.31) |
| | ATC | 338 | (0.91) | Thr | ACG | 184 | (0.38) |
| Lys | AAG | 284 | (0.98) | | ACA | 24 | (0.05) |
| | AAA | 7 | (0.02) | | ACT | 21 | (0.05) |
| Leu | TTG | 26 | (0.04) | | ACC | 249 | (0.52) |
| | TTA | 3 | (0.00) | Val | GTG | 308 | (0.50) |
| | CTG | 447 | (0.61) | | GTA | 9 | (0.01) |
| | CTA | 20 | (0.03) | | GTT | 35 | (0.06) |
| | CTT | 45 | (0.06) | | GTC | 262 | (0.43) |
| | CTC | 190 | (0.26) | Trp | TGG | 107 | (1.00) |

TABLE 2-continued

| Preferred codon usage in *Prototheca* strains | | | | | | | |
|---|---|---|---|---|---|---|---|
| Met | ATG | 191 | (1.00) | Tyr | TAT | 10 | (0.05) |
| | | | | | TAC | 180 | (0.95) |
| | | | | Stop | TGA/TAG/TAA | | |

TABLE 3

| Preferred codon usage in *Chlorella protothecoides* | | | |
|---|---|---|---|
| TTC (Phe) | TAC (Tyr) | TGC (Cys) | TGA (Stop) |
| TGG (Trp) | CCC (Pro) | CAC (His) | CGC (Arg) |
| CTG (Leu) | CAG (Gln) | ATC (Ile) | ACC (Thr) |
| GAC (Asp) | TCC (Ser) | ATG (Met) | AAG (Lys) |
| GCC (Ala) | AAC (Asn) | GGC (Gly) | GTG (Val) |
| GAG (Glu) | | | |

Host Cells

The host cell can be a single cell or part of a multicellular organism such as a plant. Methods for expressing Fatb genes in a plant are given in U.S. Pat. Nos. 5,850,022; 5,723,761; 5,639,790; 5,807,893; 5,455,167; 5,654,495; 5,512,482; 5,298,421; 5,667,997; and 5,344,771; 5,304,481, or can be accomplished using other techniques generally known in plant biotechnology. Engineering of oleaginous microbes including Chlorophyta is disclosed in WO2010/063032, WO2011,150411, and WO2012/106560 and in the examples below.

Examples of oleaginous host cells include plant cells and microbial cells having a type II fatty acid biosynthetic pathway, including plastidic oleaginous cells such as those of oleaginous algae. Specific examples of microalgal cells include heterotrophic or obligate heterotrophic microalgae of the phylum Chlorophtya, the class Trebouxiophytae, the order Chlorellales, or the family Chlorellacae. Examples of oleaginous microalgae are provided in Published PCT Patent Applications WO2008/151149, WO2010/06032, WO2011/150410, and WO2011/150411, including species of *Chlorella* and *Prototheca*, a genus comprising obligate heterotrophs. The oleaginous cells can be, for example, capable of producing 25, 30, 40, 50, 60, 70, 80, 85, or about 90% oil by cell weight, ±5%. Optionally, the oils produced can be low in DHA or EPA fatty acids. For example, the oils can comprise less than 5%, 2%, or 1% DHA and/or EPA. The above-mentioned publications also disclose methods for cultivating such cells and extracting oil, especially from microalgal cells; such methods are applicable to the cells disclosed herein and incorporated by reference for these teachings. When microalgal cells are used they can be cultivated autotrophically (unless an obligate heterotroph) or in the dark using a sugar (e.g., glucose, fructose and/or sucrose). In any of the embodiments described herein, the cells can be heterotrophic cells comprising an exogenous invertase gene so as to allow the cells to produce oil from a sucrose feedstock. Alternately, or in addition, the cells can metabolize xylose from cellulosic feedstocks. For example, the cells can be genetically engineered to express one or more xylose metabolism genes such as those encoding an active xylose transporter, a xylulose-5-phosphate transporter, a xylose isomerase, a xylulokinase, a xylitol dehydrogenase and a xylose reductase. See WO2012/154626, "GENETICALLY ENGINEERED MICROORGANISMS THAT METABOLIZE XYLOSE", published Nov. 15, 2012.

Oils and Related Products

The oleaginous cells express one or more exogenous genes encoding fatty acid biosynthesis enzymes. As a result, some embodiments feature natural oils that were not obtainable from a non-plant or non-seed oil, or not obtainable at all.

The oleaginous cells produce a storage oil, which is primarily triacylglyceride and may be stored in storage bodies of the cell. A raw oil may be obtained from the cells by disrupting the cells and isolating the oil. WO2008/151149, WO2010/06032, WO2011/150410, and WO2011/1504 disclose heterotrophic cultivation and oil isolation techniques. For example, oil may be obtained by cultivating, drying and pressing the cells. The oils produced may be refined, bleached and deodorized (RBD) as known in the art or as described in WO2010/120939. The raw or RBD oils may be used in a variety of food, chemical, and industrial products or processes. After recovery of the oil, a valuable residual biomass remains. Uses for the residual biomass include the production of paper, plastics, absorbents, adsorbents, as animal feed, for human nutrition, or for fertilizer.

Where a fatty acid profile of a triglyceride (also referred to as a "triacylglyceride" or "TAG") cell oil is given here, it will be understood that this refers to a nonfractionated sample of the storage oil extracted from the cell analyzed under conditions in which phospholipids have been removed or with an analysis method that is substantially insensitive to the fatty acids of the phospholipids (e.g. using chromatography and mass spectrometry). The oil may be subjected to an RBD process to remove phospholipids, free fatty acids and odors yet have only minor or negligible changes to the fatty acid profile of the triglycerides in the oil. Because the cells are oleaginous, in some cases the storage oil will constitute the bulk of all the TAGs in the cell.

The stable carbon isotope value δ13C is an expression of the ratio of 13C/12C relative to a standard (e.g. PDB, carbonite of fossil skeleton of *Belemnite americana* from Peedee formation of South Carolina). The stable carbon isotope value δ13C (0/00) of the oils can be related to the δ13C value of the feedstock used. In some embodiments, the oils are derived from oleaginous organisms heterotrophically grown on sugar derived from a C4 plant such as corn or sugarcane. In some embodiments the δ13C (0/00) of the oil is from −10 to −17 0/00 or from −13 to −16 0/00.

The oils produced according to the above methods in some cases are made using a microalgal host cell. As described above, the microalga can be, without limitation, fall in the classification of Chlorophyta, Trebouxiophyceae, Chlorellales, Chlorellaceae, or Chlorophyceae. It has been found that microalgae of Trebouxiophyceae can be distinguished from vegetable oils based on their sterol profiles. Oil produced by *Chlorella protothecoides* was found to produce sterols that appeared to be brassicasterol, ergosterol, campesterol, stigmasterol, and β-sitosterol, when detected by GC-MS. However, it is believed that all sterols produced by *Chlorella* have C24β stereochemistry. Thus, it is believed that the molecules detected as campesterol, stigmasterol, and β-sitosterol, are actually 22,23-dihydrobrassicasterol, proferasterol and clionasterol, respectively. Thus, the oils produced by the microalgae described above can be distinguished from plant oils by the presence of sterols with C24β stereochemistry and the absence of C24α stereochemistry in the sterols present. For example, the oils produced may contain 22,23-dihydrobrassicasterol while lacking campesterol; contain clionasterol, while lacking in β-sitosterol, and/or contain poriferasterol while lacking stigmasterol. Alternately, or in addition, the oils may contain significant amounts of $\Delta^7$-poriferasterol.

In embodiments of the present invention, oleaginous cells expressing one or more of the genes of Table 1 can produce an oil with at least 20% of C8, C10, C12, C14 or C16 fatty acids. In a specific embodiment, the level of myristate (C14:0) in the oil is greater than 30%.

Thus, in embodiments of the invention, there is a process for producing an oil, triglyceride, fatty acid, or derivative of any of these, comprising transforming a cell with any of the nucleic acids discussed herein. In another embodiment, the transformed cell is cultivated to produce an oil and, optionally, the oil is extracted. Oil extracted in this way can be used to produce food, oleochemicals or other products.

The oils discussed above alone or in combination are useful in the production of foods, fuels and chemicals (including plastics, foams, films, etc). The oils, triglycerides, fatty acids from the oils may be subjected to C—H activation, hydroamino methylation, methoxy-carbonation, ozonolysis, enzymatic transformations, epoxidation, methylation, dimerization, thiolation, metathesis, hydro-alkylation, lactonization, or other chemical processes.

After extracting the oil, a residual biomass may be left, which may have use as a fuel, as an animal feed, or as an ingredient in paper, plastic, or other product. For example, residual biomass from heterotrophic algae can be used in such products.

The described embodiments of the invention are intended to be merely exemplary and numerous variations and modifications will be apparent to those skilled in the art. All such variations and modifications are intended to be within the scope of the present invention. For example, the various triglyceride oils can be tailored in for a mixture of midchain and long chain fatty acids in order to adjust parameters such as polarity, solvency, and foam-height of the oils or chemicals made from the oils.

EXAMPLE 1

Sequences of novel plant acyl-ACP thioesterases involved in seed-specific midchain (C8-C16) fatty acid biosynthesis in higher plants were isolated. Seed-specific lipid production genes were isolated through direct interrogation of RNA pools accumulating in oilseeds. Based on phylogenetic analysis, novel enzymes can be classified as members of FatB family of acyl-ACP thioesterases.

Seeds of oleaginous plants were obtained from local grocery stores or requested through USDA ARS National Plant Germplasm System (NPGS) from North Central Regional Plant Introduction Station (NCRIS) or USDA ARS North Central Soil Conservation Research Laboratory (Morris, Mich.). Dry seeds were homogenized in liquid nitrogen to powder, resuspended in cold extraction buffer containing 6-8M Urea and 3M LiCl and left on ice for a few hours to overnight at 4° C. The seed homogenate was passed through NucleoSpin Filters (Macherey-Nagel) by centrifugation at 20,000 g for 20 minutes in the refrigerated microcentrifuge (4° C.). The resulting RNA pellets were resuspended in the buffer containing 20 mM Tris HCl, pH7.5, 0.5% SDS, 100 mM NaCl, 25 mM EDTA, 2% PVPP) and RNA was subsequently extracted once with Phenol-Chloroform-Isoamyl Alcohol (25:24:1, v/v) and once with chloroform. RNA was finally precipitated with isopropyl alcohol (0.7 Vol.) in the presence of 150 mM of Na Acetate, pH5.2, washed with 80% ethanol by centrifugation, and dried. RNA samples were treated with Turbo DNAse (Lifetech) and purified further using RNeasy kits (Qiagen) following manufacturers' protocols. The resulting purified RNA samples were converted to pair-end cDNA libraries and subjected to next-generation sequencing (2×100 bp) using Illumina Hiseq 2000 platform. RNA sequence reads were assembled into corresponding seed transcriptomes using Trinity or Oases packages. Putative thioesterase-containg cDNA contigs were identified by mining transcriptomes for sequences with homology to known thioesterases. These in silico identified putative thioesterase cDNAs have been further verified by direct reverse transcription PCR analysis using seed RNA and primer pairs targeting full-length thioesterase cDNAs. The resulting amplified products were cloned and sequenced de novo to confirm authenticity of identified thioesterase genes.

To interrogate evolutionary and functional relationship between novel acyl-ACP thioesterases and the members of two existing thioesterase classes (FatA and FatB), we performed a phylogenetic analysis using published full-length (Mayer and Shanklin, 2007) and truncated (THYME database) amino acid thioesterase sequences. Novel proteins appear to group with known acyl-ACP FatB thioesterases involved in biosynthesis of C8-C16 fatty acids. Moreover, novel thioesterases appear to cluster into 3 predominant outgroups suggesting distinct functional similarity and evolutionary relatedness among members of each cluster.

The amino acid sequences of the FatB genes follow are shown in Table 4.

TABLE 4

| Amino acid sequences of FatB genes |
|---|
| CuPSR23 FATB3 (SEQ ID NO: 25):<br>MVVAAATSAFFPVPAPGTSPKPGKSGNWPSSLSPTFKPKSIPNAGFQVKANASAH<br>PKANGSAVNLKSGSLNTQEDTSSSPPPRAFLNQLPDWSMLLTAITTVFVAAEKQWTMLD<br>RKSKRPDMLVDSVGLKCIVRDGLVSRQSFLIRSYEIGADRTASIETLMNHLQETSINHCK<br>SLGLLNDGFGRTPGMCKNDLIWVLTKMQIMVNRYPTWGDTVEINTWFSQSGKIGMASD<br>WLISDCNTGEILIRATSVWAMMNQKTRRFSRLPYEVRQELTPHFVDSPHVIEDNDQKLH<br>KFDVKTGDSIRKGLTPRWNDLDVNQHVSNVKYIGWILESMPIEVLETQELCSLTVEYRR<br>ECGMDSVLESVTAVDPSENGGRSQYKHLLRLEDGTDIVKSRTEWRPKNAGTNGAISTST<br>AKTSNGNSVS |
| CuPSR23 FATB3b (SEQ ID NO: 79):<br>MVVAAATSAFFPVPAPGTSPKPGKSGNWPSSLSPTFKPKSIPNAGFQVKANASAH<br>PKANGSAVNLKSGSLNTQEDTSSSPPPRAFLNQLPDWSMLLTAITTVFVAAEKQWTMLD<br>RKSKRPDMLVDSVGLKSIVRDGLVSRQSFLIRSYEIGADRTASIETLMNHLQETSINHCKS<br>LGLLNDGFGRTPGMCKNDLIWVLTKMQIMVNRYPTWGDTVEINTWFSQSGKIGMASD<br>WLISDCNTGEILIRATSVWAMMNQKTRRFSRLPYEVRQELTPHFVDSPHVIEDNDQKLH<br>KFDVKTGDSIRKGLTPRWNDLDVNQHVSNVKYIGWILESMPIEVLETQELCSLTVEYRR<br>ECGMDSVLESVTAVDPSENGGRSQYKHLLRLEDGTDIVKSRTEWRPKNAGTNGAISTST<br>AKTSNGNSAS |
| CwFATB3 (SEQ ID NO: 28):<br>MVVAAAASSAFFPVPAPRTTPKPGKFGNWPSSLSPPFKPKSNPNGRFQVKANVSP<br>HPKANGSAVSLKSGSLNTLEDPPSSPPPRTFLNQLPDWSRLRTAITTVFVAAEKQFTRLD |

TABLE 4-continued

| Amino acid sequences of FatB genes |
|---|
| RKSKRPDMLVDWFGSETIVQDGLVFRERFSIRSYEIGADRTASIETLMNHLQDTSLNHCK |
| SVGLLNDGFGRTSEMCTRDLIWVLTKMQIVVNRYPTWGDTVEINSWFSQSGKIGMGRD |
| WLISDCNTGEILVRATSAWAMMNQKTRRFSKLPCEVRQEIAPHFVDAPPVIEDNDRKLH |
| KFDVKTGDSICKGLTPGWNDLDVNQHVSNVKYIGWILESMPTEVLETQELCSLTLEYRR |
| ECGRESVVESVTSMNPSKVGDRSQYQHLLRLEDGADIMKGRTEWRPKNAGTNRAIST |
| CwFATB3a (SEQ ID NO: 28): |
| MVVAAAASSAFFPVPAPRTTPKPGKFGNWPSSLSPPFKPKSNPNGRFQVKANVSP |
| HPKANGSAVSLKSGSLNTLEDPPSSPPPRTFLNQLPDWSRLRTAITTVFVAAEKQFTRLD |
| RKSKRPDMLVDWFGSETIVQDGLVFRERFSIRSYEIGADRTASIETLMNHLQDTSLNHCK |
| SVGLLNDGFGRTSEMCTRDLIWVLTKMQIVVNRYPTWGDTVEINSWFSQSGKIGMGRD |
| WLISDCNTGEILVRATSAWAMMNQKTRRFSKLPCEVRQEIAPHFVDAPPVIEDNDRKLH |
| KFDVKTGDSICKGLTPGWNDLDVNQHVSNVKYIGWILESMPTEVLETQELCSLTLEYRR |
| ECGRESVVESVTSMNPSKVGDRSQYQHLLRLEDGADIMKGRTEWRPKNAGTNRAIST |
| CwFATB3b (SEQ ID NO: 80): |
| MVVAAAASSAFFPVPAPRTTPKPGKFGNWPSSLSPPFKPKSNPNGRFQVKANVSP |
| HPKANGSAVSLKSGSLNTLEDLPSSPPPRTFLNQLPDWSRLRTAITTVFVAAEKQFTRLD |
| RKSKRPDMLVDWFGSETIVQDGLVFRERFSIRSYEIGADRTASIETLMNHLQDTSLNHCK |
| SVGLLNDGFGRTSEMCTRDLIWVLTKMQIVVNRYPTWGDTVEINSWFSQSGKIGMGRD |
| WLISDCNTGEILVRATSAWAMMNQKTRRFSKLPCEVRQEIAPHFVDAPPVIEDNDRKLH |
| KFDVKTGDSICKGLTPGWNDLDVNQHVSNVKYIGWILEKFWRPRSYALSPLNIGGNVE |
| GKVW |
| CwFATB3c (SEQ ID NO: 81): |
| MVVAAAASSAFFPVPAPRTTPKPGKFGNWPSSLSPPFKPKSNPNGRFQVKANVSP |
| HPKANGSAVSLKSGSLNTLEDLPSSPPPRTFLNQLPDWSRLRTAITTVFVATEKQFTRLD |
| RKSKRPDMLVDWFGSETIVQDGLVFRERFSIRSYEIGADRTASIETLMNHLQDTSLNHCK |
| SVGLLNDGFGRTSEMCTRDLIWVLTKMQIVVNRYPTWGDTVEINSWFSQSGKIGMGRD |
| WLISDCNTGEILVRATSAWAMMNQKTRRFSKLPCEVRQEIAPHFVDAPPVIEDNDRKLH |
| KFDVKTGDSICKGLTPGWNDLDVNQHVSNVKYIGWILEKFWRPRSYALSPLNIGGNVE |
| GKVW |
| CwFATB4a (SEQ ID NO: 31): |
| MVATAASSAFFPVPSADTSSSRPGKLGSGPSSLSPLKPKSIPNGGLQVKANASAPP |
| KINGSSVGLKSGGFKTQEDSPSAPPPRTFINQLPDWSMLLAAITTVFLAAEKQWMMLDW |
| KPKRPDMLVDPFGLGSIVQDGLVFRQNFSIRSYEIGADRTASIETVMNHLQETALNHVKI |
| AGLSNDGFGRTPEMYKRDLIWVVAKMQVMVNRYPTWGDTVEVNTWVAKSGKNGMR |
| RDWLISDCNTGEILTRASSVWVMMNQKTRRLSKIPDEVRNEIEPHFVDSAPVVEDDDRK |
| LPKLDENTADSIRKGLTPRWNDLDVNQHVNNVKYIGWILESTPPEVLETQELCSLTLEYR |
| RECGRESVLESLTAVDPSAEGYASRFQHLLRLEDGGEIVKARTEWRPKNAGINGVVPSE |
| ESSPGDFF |
| CwFATB4a.1 (SEQ ID NO: 82): |
| MVATAASSAFFPVPSADTSSSRPGKLGSGPSSLSPLKPKSIPNGGLQVKANASAPP |
| KINGSSVGLKSGGFKTQEDSPSAPPPRTFINQLPDWSMLLAAITTVFLAAEKQWMMLDW |

TABLE 4-continued

| Amino acid sequences of FatB genes |
|---|
| KPKRPDMLVDPFGLGSIVQDGLVFRQNFSIRSYEIGADRTASIETVMNHLQETALNHVKI |
| AGLSNDGFGRTPEMYKRDLIWVVAKMQVMVNRYPTWGDTVEVNTWVAKSGKNGMR |
| RDWLISDCNTGEILTRASSVWVMMNQKTRRLSKIPDEVRNEIEPHFVDSAPVVEDDDRK |
| LPKLDENTADSIRKGLTPRWNDLDVNQHVNNVKYIGWILESTPPEVLETQELCSLTLEYR |
| RECGRESVLESLTAVDPSAEGYASRFQHLLRLEDGGEIVKARTEWRPKNAGINWVVPSE |
| ESSPGDFF |
| CwFATB4a.2 (SEQ ID NO: 83):<br>MVATAASSAFFPVPSADTSSSRPGKLGNGPSSLSPLKPKSIPNGGLQVKANASAPP |
| KINGSSVGLKSGSFKTQEDAPSAPPPRTFINQLPDWSMLLAAITTVFLAAEKQWMMLDW |
| KPKRPDMLVDPFGLGSIVQDGLVFRQNFSIRSYEIGADRTASIETVMNHLQETALNHVKI |
| AGLSNDGFGRTPEMYKRDLIWVVAKMQVMVNRYPTWGDTVEVNTWVAKSGKNGMR |
| RDWLISDCNTGEILTRASSVWVMMNQKTRRLSKIPDEVRNEIEPHFVDSAPVVEDDDRK |
| LPKLDENTADSIRKGLTPRWNDLDVNQHVNNVKYIGWILESTPPEVLETQELCSLTLEYR |
| RECGRESVLESLTAVDPSAEGYASRFQHLLRLEDGGEIVKARTEWRPKNAGINGVVPSE |
| ESSPGDFF |
| CwFATB4a.3 (SEQ ID NO: 84):<br>MVATAASSAFFPVPSADTSSSRPGKLGSGPSSLSPLKPKSIPNGGLQVKANASAPP |
| KINGSSVGLKSGGFKTQEDSPSAPPPRTFINQLPDWSMLLAAITTVFLAAEKQWMMLDW |
| KPKRPDMLVDPFGLGSIVQDGLVFRQNFSIRSYEIGADRTASIETVMNHLQETALNHVKI |
| AGLSNDGFGRTPEMYKRDLIWVVAKMQVMVNRYPTWGDTVEVNTWVAKSGKNGMR |
| RDWLISDCNTGEILTRASSVWVMMNQKTRRLSKIPDEVRNEIEPHFVDSAPVVEDDDRK |
| LPKLDENTADSIRKGLTPRWNDLDVNQHVNNVKYIGWILESTPPEVLETQELCSLTLEYR |
| RECGRESVLESLTAVDPSAEGYVSRFQHLLRLEDGGEIVKARTEWRPKNAGINGVVPSE |
| ESSPGDFF |
| CwFATB4b (SEQ ID NO: 34):<br>MVATAASSAFFPVPSADTSSSRPGKLGNGPSSLSPLKPKSIPNGGLQVKANASAPP |
| KINGSSVGLKSGSFKTQEDAPSAPPPRTFINQLPDWSMLLAAITTVFLAAEKQWMMLDW |
| KPKRPDMLVDPFGLGSIVQDGLVFRQNFSIRSYEIGADRTASIETVMNHLQETALNHVKI |
| AGLSSDGFGRTPAMSKRDLIWVVAKMQVMVNRYPAWGDTVEVNTWVAKSGKNGMR |
| RDWLISDCNTGEILTRASSVWVMMNQKTRRLSKIPDEVRNEIEPHFVDSAPVVEDDDRK |
| LPKLDENTADSIRKGLTPRWNDLDVNQHVNNVKYIGWILESTPAEVLETQELCSLTLEY |
| RRECGRESVLESLTAVDPSGEGDGSKFQHLLRLEDGGEIVKARTEWRPKNAGINGVVPS |
| EESSPGGDFF |
| CwFATB4b.1 (SEQ ID NO: 85):<br>MVATAASSAFFPVPSADTSSSRPGKLGSGPSSLSPLKPKSIPNGGLQVKANASAPP |
| KINGSSVGLKSGSFKTQEDAPSAPPPRTFINQLPDWSMLLAAITTVFLAAEKQWMMLDW |
| KPKRPDMLVDPFGLGSIVQDGLVFRQNFSIRSYEIGADRTASIETVMNHLQETALNHVKI |
| AGLSSDGFGRTPAMSKRDLIWVVAKMQVMVNRYPAWGDTVEVNTWVAKSGKNGMR |
| RDWLISDCNTGEILTRASSVWVMMNQKTRRLSKIPDEVRNEIEPHFVDSAPVVEDDDRK |
| LPKLDENTADSIRKGLTPRWNDLDVNQHVNNVKYIGWILESTPAEVLETQELCSLTLEY |

TABLE 4-continued

| Amino acid sequences of FatB genes |
|---|

RRECGRESVLESLTAVDPSGEGDGSKFQHLLRLEDGGEIVKARTEWRPKNAGINGVVPS

EESSPGGDFF

CwFATB5 (SEQ ID NO: 37):
MVAAAASSAFFSVPTPGTPPKPGKFGNWPSSLSVPFKPDNGGFHVKANASAHPK

ANGSAVNLKSGSLETPPRSFINQLPDLSVLLSKITTVFGAAEKQWKRPGMLVEPFGVDRI

FQDGVFFRQSFSIRSYEIGVDRTASIETLMNIFQETSLNHCKSIGLLNDGFGRTPEMCKRD

LIWVVTKIQVEVNRYPTWGDTIEVNTWVSESGKNGMGRDWLISDCRTGEILIRATSVWA

MMNQNTRRLSKFPYEVRQEIAPHFVDSAPVIEDDQKLQKLDVKTGDSIRDGLTPRWND

LDVNQHVNNVKYIGWILKSVPIEVFETQELCGVTLEYRRECGRDSVLESVTAMDPAKEG

DRCVYQHLLRLEDGADITIGRTEWRPKNAGANGAMSSGKTSNGNCLIEGRGWQPFRVV

RLIF

CwFATB5a (SEQ ID NO: 86):
MVAAAASSAFFSVPTPGTPPKPGKFGNWPSSLSVPFKPDNGGFHVKANASAHPK

ANGSAVNLKSGSLETPPRSFINQLPDLSVLLSKITTVFGAAEKQWKRPGMLVEPFGVDRI

FQDGFFFRQSFSIRSYEIGVDRTASIETLMNIFQETSLNHCKSIGLLNDGFGRTPEMCKRD

LIWVVTKIQVEVNRYPTWGDTIEVNTWVSESGKNGMGRDWLISDCRTGEILIRATSVWA

MMNQNTRRLSKFPYEVRQEIAPHFVDSAPVIEDDQKLQKLDVKTGDSIRDGLTPRWND

LDVNQHVNNVKYIGWILKSVPIEVFETQELCGVTLEYRRECGRDSVLESVTAMDPAKEG

DRCVYQHLLRLEDGADITIGRTEWRPKNAGANGAMSSGKTSNGNCLIEGRGWQPFRVV

RLIF

CwFATB5b (SEQ ID NO: 87):
MVAAAASSAFFSVPTPGTPPKPGKFGNWPSSLSVPFKPDNGGFHVKANASAHPK

ANGSAVNLKSGSLETPPRSFINQLPDLSVLLSKITTVFGAAEKQWKRPGMLVEPFGVDRI

FQDGVFFRQSFSIRSYEIGVDRTASIETLMNIFQETSLNHCKSIGLLNDGFGRTPEMCKRD

LIWVVTKIQVEVNRYPTWGDTIEVNTWVSESGKNGMGRDWLISDCRTGEILIRATSVWA

MMNQNTRRLSKFPYEVRQEIAPHFVDSAPVIEDDQKLQKLDVKTGDSIRDGLTPRWND

LDVNQHVNNVKYIGWILKSVPIEVFETQELCGVTLEYRRECGRDSVLESVTAMDPAKEG

DRCVYQHLLWLEDGADITIGRTEWRPKNAGANGAMSSGKTSNGNCLIEGRGWQPFRV

VRLIF

CwFATB5c (SEQ ID NO: 88):
MVAAAASSAFFSVPTPGTPPKPGKFGNWPSSLSVPFKPDNGGFHVKANASAHPK

ANGSAVNLKSGSLETPPRSFINQLPDLSVLLSKITTVFGAAEKQWKRPGMLVEPFGVDRI

FQDGVFFRQSFSIRSYEIGVDRTASIETLMNIFQETSLNHCKSIGLLNDGFGRTPEMCKRD

LIWVVTKIQVEVNRYPIWGDTIEVNTWVSESGKNGMGRDWLISDCRTGEILIRATSVWA

MMNQNTRRLSKFPYEVRQEIAPHFVDSAPVIEDDQKLQKLDVKTGDSIRDGLTPRWND

LDVNQHVNNVKYIGWILKSVPIEVFETQELCGVTLEYRRECGRDSVLESVTAMDPAKEG

DRCVYQHLLRLEDGADITIGRTEWRPKNAGANGAMSSGKTSNGNCLIEGMGWQPFRVV

RLIF

CwFATB5.1 (SEQ ID NO: 89):
MVAAAASSAFFSVPTPGTSPKPGKFRNWPSSLSVPFKPETNHNGGFHIKANASAH

PKANGSALNLKSGSLETQEDTSLSSPPRTFIKQLPDWSMLLSKITTVFGAAEKQLKRPGM

TABLE 4-continued

| Amino acid sequences of FatB genes |
|---|
| LVEPFGVDRIFQDGVFFRQSFSIRSYEIGADRTASIETLMNIFQETSLNHCKSIGLLNDGFG |
| RTPEMCKRDLIWVVTKIQVEVNRYPTWGDTIEVNTWVSESGKNGMGRDWLISDCRTGE |
| ILIRATSVWAMMNQNTRRLSKFPYEVRQEIAPHFVDSAPVIEDDRKLYKLNVKTGDSIR |
| DGLTPRWNDLDVNQHVNNVKFIGWILKSVPTKVFETQELCGVTLEYRRECGKDSVLES |
| VTAMDPAKEGDRSVYQHLLRLEDGADITIGRTEWRPKNAGANEAISSGKTSNGNSAS |
| CwFATB5.1a (SEQ ID NO: 90):<br>MVAAAASSAFFSVPTPGTSPKPGKFRNWPLSLSVPFKPETNHNGGFHIKANASAH |
| PKANGSALNLKSGSLETQEDTSLSSPPRTFIKQLPDWSMLLSKITTVFGAAEKQLKRPGM |
| LVEPFGVDRIFQDGVFFRQSFSIRSYEIGADRTASIETLMNIFQETSLNHCKSIGLLNDGFG |
| RTPEMCKRDLIWVVTKIQVEVNRYPTWGDTIEVNTWVSESGKNGMGRDWLISDCRTGE |
| ILIRATSVWAMMNQNTRRLSKFPYEVRQEIAPHFVDSAPVIEDDRKLYKLNVKTGDSIR |
| DGLTPRWNDLDVNQHVNNVKFIGWILKSVPTKVFETQELCGVTLEYRRECGKDSVLES |
| VTAMDPAKEGDRSVYQHLLRLEDGADITIGRTEWRPKNAGANEAISSGKTSNGNSAS |
| CcFATB2b (SEQ ID NO: 91):<br>MVTTSLASAYFSMKAVMLAPDGRGIKPRSSGLQVRAGNERNSCKVINGTKVKD |
| TEGLKGCSTLQGQSMLDDHFGLHGLVFRRTFAIRCYEVGPDRSTSIMAVMNHLQEAAR |
| NHAESLGLLGDGFGETLEMSKRDLIWVVRRTHVAVERYPAWGDTVEVEAWVGASGNT |
| GMRRDFLVRDCKTGHILTRCTSVSVMMNMRTRRLSKIPQEVRAEIDPLFIEKVAVKEGEI |
| KKLQKLNDSTADYIQGGWTPRWNDLDVNQHVNNIIYVGWIFKSVPDSISENHHLSSITLE |
| YRRECIRGNKLQSLTTVCGGSSEAGIICEHLLQLEDGSEVLRARTEWRPKHTDSFQGISER |
| FPQQEPHK |
| CcFATB3 (SEQ ID NO: 7):<br>MVATAAASAFFPVGAPATSSATSAKASMMPDNLDARGIKPKPASSSGLQVKAN |
| AHASPKINGSKVSTDTLKGEDTLTSSPAPRTFINQLPDWSMFLAAITTIFLAAEKQWTNL |
| DWKPRRPDMLADPFGIGRFMQDGLIFRQHFAIRSYEIGADRTASIETLMNHLQETALNH |
| VRSAGLLGDGFGATPEMSRRDLIWVVTRMQVLVDRYPAWGDIVEVETWVGASGKNG |
| MRRDWLVRDSQTGEILTRATSVWVMMNKRTRRLSKLPEEVRGEIGPYFIEDVAIIEEDN |
| RKLQKLNENTADNVRRGLTPRWSDLDVNQHVNNVKYIGWILESAPGSILESHELSCMTL |
| EYRRECGKDSVLQSMTAVSGGGSAAGGSPESSVECDHLLQLESGPEVVRGRTEWRPKS |
| ANNSRSILEMPAESL |
| CcFATB3b (SEQ ID NO: 92):<br>MVATAAASAFFPVGAPATSSATSAKASMMPDNLDARGIKPKLASSSGLQVKAN |
| AHASPKINGSKVSTDTLKGEDTLTSSPAPRTFINQLPDWSMFLAAITTIFLAAEKQWTNL |
| DWKPRRPDMLADPFGIGRFMQDGLIFRQHFAIRSYEIGADRTASIETLMNHLQETALNH |
| VRSAGLLGDGFGATPEMSRRDLIWVVTRMQVLVDRYPAWGDIVEVETWVGASGKNG |
| MRRDWLVRDSQTGEILTRATSVWVMMNKRTRRLSKLPEEVRGEIGPYFIEDVAIIEEDN |
| RKLQKLNENTADNVRRGLTPRWSDLDVNQHVNNVKYIGWILESAPGSILESHELSCMTL |
| EYRRECGKDSVLQSMTAVSGGGSAAGGSPESSVECDHLLQLESGPEVVRGRTEWRPKS |
| ANNSRSILEMPAESL |
| CcFATB3c (SEQ ID NO: 93):<br>MVATAAASAFFPVGAPATSSATSAKASMMPDNLDARGIKPKPASSSGLQVKAN |
| AHASPKINGSKVSTDTLKGEDTLTSSPAPRTFINQLPDWSMFLAAITTIFLAAEKQWTNL |

TABLE 4-continued

| Amino acid sequences of FatB genes |
|---|
| DWKPRRPDMLADPFGIGRFMQDGLIFRQHFAIRSYEIGADRTASIETLMNHLQETALNH |
| VRSAGLLGDGFGATPEMSRRDLIWVVTRMQVLVDRYPAWGDIVEVETWVGASGKNG |
| MRRDWLVRDSQTGEILTRATSVWVMMNKRTRRLSKLPEEVRGEIGPYFIEDVAIIEEDN |
| RKLQKLNENTADNVRRGLTPRWSDLDVNQHVNNAKYIGWILESAPGSILESHELSCMTL |
| EYRRECGKDSVLQSMTAVSGGGSAAGGSPESSVECDHLLQLESGPEVVRGRTEWRPKS |
| ANNSRSILEMPAESL |
| ChtFATB1a (SEQ ID NO: 40):<br>MVAAAASSAFFSVPTPGTSTKPGNFGNWPSSLSVPFKPESNHNGGFRVKANASA |
| HPKANGSAVNLKSGSLETQEDTSSSSPPPRTFIKQLPDWGMLLSKITTVFGAAERQWKRP |
| GMLVEPFGVDRIFQDGVFFRQSFSIRSYEIGADRTASIETLMNIFQETSLNHCKSIGLLND |
| GFGRTPEMCKRDLIWVVTKIQVEVNRYPTWGDTIEVNTWVSESGKNGMGRDWLISDCR |
| TGEILIRATSVWAMMNRKTRRLSKFPYEVRQEIAPHFVDSAPVIEDDKKLHKLDVKTGD |
| SIRKGLTPRWNDLDVNQHVNNVKYIGWILKSVPAEVFETQELCGVTLEYRRECGRDSVL |
| ESVTAMDTAKEGDRSLYQHLLRLEDGADITIGRTEWRPKNAGANGAISTGKTSNENSVS |
| ChtFATB1a.1 (SEQ ID NO: 94):<br>MVAAAASSAFFSVPTPGTSPKPGNFGNWPSSLSVPFKPESNHNGGFRVKANASA |
| HPKANGSAVNLKSGSLETQEDTSSSSPPPRTFIKQLPDWGMLLSKITTVFGAAERQWKRP |
| GMLVEPFGVDRIFQDGVFFRHSFSIRSYEIGADRTASIETLMNIFQETSLNHCKSIGLLND |
| GFGRTPEMCKRDLIWVVTKIQVEVNRYPTWGDTIEVNTWVSESGKNGMGRDWLIGDC |
| RTGEILIRATSVWAMMNRKTRRLSKFPYEVRQEIAPHFVDSAPVIEDDKKLHKLDVKTG |
| DSIRKGLTPRWNDLDVNQHVNNVKYIGWILKSVPAEVFETQELCGVTLEYRRECGRDS |
| VLESVTAMDTAKEGDRSLYQHLLRLEDGADITIGRTEWRPKNAGANGALSTGKTSNGN |
| SVS |
| ChtFATB1a.2 (SEQ ID NO: 95):<br>MVAAAASSAFFSVPTPGTSPKPGNFGNWPSNLSVPFKPESNHNGGFRVKANASA |
| HPKANGSAVNLKSGSLETQEDTSSSSPPPRTFIKQLPDWGMLLSKITTVFGAAERQWKRP |
| GMLVEPFGVDRIFQDGVFFRQSFSIRSYEIGADRTASIETLMNIFQETSLNHCKSIGLLND |
| GFGRTPEMCKRDLIWVVTKIQVEVNRYPTWGDTIEVNTWVSESGKNGMGRDWLISDCR |
| TGEILIRATSVWAMMNRKTRRLSKFPYEVRQEIAPHFVDSAPVIEDDKKLHKLDVKTGD |
| SIRKGLTPRWNDFDVNQHVNNVKYIGWILKSVPAEVFETQELCGVTLEYRRECGRDSVL |
| ESVTAMDTAKEGDRSLYQHLLRLEDGADITIGRTEWRPKNAGANGAISTGKTSNENSVS |
| ChtFATB1a.3 (SEQ ID NO: 96):<br>MVAAAASSAFFSVPTPGTSPKPGNFGNWPSSLSVPFKPESNHNGGFRVKANASA |
| HPKANGSAVNLKSGSLETQEDTSSSSPPPRTFIKQLPDWGMLLSKITTVFGAAERQWKRP |
| GMLVEPFGVDRIFQDGVFFRQSFSIRSYEIGADRTASIETLMNIFQETSLNHCKSIGLLND |
| GFGRTPEMCKRDLIWVVTKIQVEVNRYPTWGDTIEVNTWVSESGKNGMGRDWLISDCR |
| TGEILIRATSVWAMMNRKTRRLSKFPYEVRQEIAPHFVDSAPVIEDDKKLHKLDVKTGD |
| SIRKGLTPRWNDFDVNQHVNNVKYIGWILKSVPAEVFETQELCGVTLEYRRECGRDSVL |
| ESVTAMDTAKEGDRSLYQHLLRLEDGADITIGRTEWRPKNAGVNGAISTGKTSNENSVS |
| ChtFATB1a.4 (SEQ ID NO: 97):<br>MVAAAASSAFFSVPTPGTSPKPGNFGNWPSSLSVPFKPESNHNGGFRVKANASA |

TABLE 4-continued

| Amino acid sequences of FatB genes |
|---|
| HPKANGSAVNLKSGSLETQEDTSSSSPPPRTFIKQLPDWSMLLSKITTVFGAAERQWKRP |
| GMLVEPFGVDRIFQDGVFFRQSFSIRSYEIGADRTASIETLMNIFQETSLNHCKSIGLLND |
| GFGRTPEMCKRDLIWVVTKIQVEVNRYPTWGDTIEVNTWVSESGKNGMGRDWLISDCR |
| TGEILIRATSVWAMMNRKTRRLSKFPYEVRQEIAPHFVDSAPVIEDDKKLHKLDVKTGD |
| SIRKGLTPRWNDFDVNQHVNNVKYIGWILKSVPAEVFETQELCGVTLEYRRECGRDSVL |
| ESVTAMDTAKEGDRSLYQHLLRLEDGADITIGRTEWRPKNAGANGAISTGKTSNENSVS |
| ChtFATB1b (SEQ ID NO: 43):<br>MVAAAASSAFFSVPTSGTSPKPGNFGNWPSSLSVPFKPESSHNGGFQVKANASA |
| HPKANGSAVNLKSGSLETQEDTSSSSPPPRTFIKQLPDWSMLLSKITTVFWAAERQWKRP |
| GMLVEPFGVDRIFQDGVFFRQSFSIRSYEIGADRTASIETLMNIFQETSLNHCKSIGLLND |
| GFGRTPEMCKRDLIWVVTKIQVEVNRYPTWGDTIEVNTWVSESGKNGMGRDWLISDCR |
| TGEILIRATSVWAMMNRKTRRLSKFPYEVRQEIAPHFVDSAPVIEDDKKLHKLDVKTGD |
| FIRKGLTPRWNDFDVNQHVNNVKYIGWILKSVPAEVFETQELCGVTLEYRRECGRDSVL |
| ESVTAMDTAKEGDRSLYQHLLRLEDGADITIGRTEWRPKNAGANGAISTGKTSNENSVS |
| ChtFATB2b (SEQ ID NO: 46):<br>MVVAAAASSAFFPVPASGTSPKPGKFGTWLSSSSPSYKPKSNPSGGFQVKANASA |
| HPKANGSAVSLKSGSLNTQEGTSSSPPPRTFLNQLPDWSRLRTAITTVFVAAEKQLTMLD |
| RKSKKPDMHVDWFGLEIIVQDGLVFRESFSIRSYEIGADRTASIETLMNHLQDTSLNHCK |
| SVGLLNDGFGRTPEMCKRDLIWVLTKMQIMVNRYPTWGDTVEINSWFSQSGKIGMGRN |
| WLISDCNTGEILIRATSIWAMMNQKTRRFSKLPNEVRQEIAPHFVDAPPVIEDNDRKLHK |
| FDVKTGDSICKGLTPEWNDLDVNQHVSNVKYIGWILESMPKEVLDTQELCSLTLEYRRE |
| CGRDSVLESVTAMDPSKVGDRSQYQHLLRLEDGTDIMKGRTEWRPKNAGTNGAISTGK |
| TSNGNSVS |
| ChtFATB2a (SEQ ID NO: 49):<br>MVVAAAASSAFFPVPAPGTTSKPGKFGNWPSSLSPSFKPKSNPNGGFQVKANAS |
| AHPKANGSAVSLKSGSLNTKEDTPSSPPPRTFLNQLPDWSRLRTAITTVFVAAEKQLTML |
| DRKSKKPDMHVDWFGLEIIVQDWLVFRESFSIRSYEIGADRTASIETLMNHLQDTSLNHC |
| KSVGLLNDGFGRTPEMCKRDLIWVLTKMQIMVNRYPTWGDTVEINSWFSQSGKIGMGR |
| NWLISDCNTGEILIRATSIWAMMNQKTRRFSKLPNEVRQEIAPHFVDAPPLIEDNDRKLH |
| KFDVKTGDSICKGLTPEWNDLDVNQHVSNVKYIGWILESMPKEVLDTQELCSLTLEYRR |
| ECGRDSVLESVTAMDPSKVGDRSQYQHLLRLEDGTDIMKGRTEWRPKNAGTNGAISTG |
| KTSNGNSVS |
| ChtFATB2c (SEQ ID NO: 52):<br>MVVAAAASSAFFPVPASGTSPKPGKFGTWLSSSSPSYKPKSNPSGGFQVKANASA |
| HPKANGSAVSLKSGSLNTKEDTPSSPPPRTFLNQLPDWNRLRTAITTVFVAAEKQLTML |
| DRKSKKPDMHVDWFGLEIIVQDGLVFRESFSIRSYEIGADRTASIETLMNHLQDTSLNHC |
| KSVGLLNDGFGRTPEMCKRDLIWVLTKMQIMVNRYPTWGDTVEINSWFSQSGKIGMGR |
| NWLISDCNTGEILIRATSIWAMMNQKTRRFSKLPNEVRQEIAPHFVDAPPVIEDNDRKLH |
| KFDVKTGDSICKGLTPEWNDLDVNQHVSNVKYIGWILESMPKEVLDTQELCSLTLEYRR |
| ECGRDSVLESVTAMDPSKVGDRSQYQHLLRLEDGTDIMKGRTEWRPKNAGTNGAISTG |
| KTSNGNSVS |

TABLE 4-continued

| Amino acid sequences of FatB genes |
|---|
| ChtFATB2d (SEQ ID NO: 55):<br>MVVAAAASSAFFPVPAPGTTSKPGKFGNWPSSLSPSFKPKSNPNGGFQVKANAS<br>AHPKANGSAVSLKSGSLNTQEDTSSSPPPRTFLNQLPDWSRLLTAISTVFVAAEKQLTML<br>DRKSKRPDMLVDLFGLESIVQDGLVFRESYSIRSYEIGADRTASIETLMNHLQDTSLNHC<br>KSVGLLNDGFGRTPEMCKRDLIWVLTKMQIMVNRYPTWGDTVEINSWFSQSGKIGMGR<br>NWLISDCNTGEILIRATSIWAMMNQNTRRFSKLPNEVRQEIAPHFVDAPPVIEDNDRKLH<br>KFDVKTGDSIRKGLTPGWNDLDVNQHVSNVKYIGWILESMPTEVLETQELCSLTLEYRR<br>ECGRESVLESVTAMNPSKVGDRSQYQHLLRLEDGADIMKGRTEWRPKNAGTNGAISTG<br>KTSNGNSVS |
| ChtFATB2e (SEQ ID NO: 58):<br>MVVAAAASSAFFPVPASGTSPKPGKFGTWLSSSSPSYKPKSNPSGGFQVKANASA<br>HPKANGSAVSLKSGSLNTQEDTSSSPPPQTFLNQLPDWSRLLTAISTVFVAAEKQLTMLD<br>RKSKRPDMLVDWFGLESIVQDGLVFRESYSIRSYEISADRTASIETVMNLLQETSLNHCK<br>SMGILNDGFGRTPEMCKRDLIWVLTKMQILVNRYPNWGDTVEINSWFSQSGKIGMGRN<br>WLISDCNTGEILIRATSIWAMMNQNTRRFSKLPNEVRQEIAPHFVDAPPVIEDNDRKLHK<br>FDVKTGDSIRKGLTPGWNDLDVNQHVSNVKYIGWILESMPTEVLETQELCSLTLEYRRE<br>CGRDSVLESVTAMNPSKVGDRSQYQHLLRLEDGADIMKGRTEWRPKNAGTNGAISTGK<br>TSNGNSVS |
| ChtFATB2f (SEQ ID NO: 61):<br>MVVAAAASSAFFPVPASGTSPKPGKFGTWLSSSSPSYKPKSNPSGGFQVKANASA<br>HPKANGSAVSLKSGSLNTQEGTSSSPPPRTFLNQLPDWSRLLTAISTVFVAAEKQLTMLD<br>RKSKRPDMLVDWFGLESIVQDGLVFRESYSIRSYEISADRTASIETVMNLLQETSLNHCK<br>SMGILNDGFGRTPEMCKRDLIWVLTKMQILVNRYPNWGDTVEINSWFSQSGKIGMGRN<br>WLISDCNTGEILIRATSIWAMMNQKTRRFSKLPNEVRQEIAPHFVDAPPVIEDNDRKLHK<br>FDVKTGDSICKGLTPEWNDLDVNQHVSNVKYIGWILESMPKEVLDTQELCSLTLEYRRE<br>CGRDSVLESVTAMDPSKVGDRSQYQHLLRLEDGTDIMKGRTEWRPKNAGTNGAISTGK<br>TSNGNSVS |
| ChtFATB2g (SEQ ID NO: 64):<br>MVVAATASSAFFPVPVPGTSPKPGKFGTWLSSSSPSYKPKSNPSGGFQVKANASA<br>HPKANGSAVSLKSGSLNTQEDTSSSPPPRTFLNQLPDWSRLLTAISTVFVAAEKQLTMLD<br>RKSKRPDMLVDWFGLESIVQDGLVFREIYSIRSYEISADRTTSIETVMNLLQETSLNHCKS<br>MGILNDGFGRTPEMCKRDLIWVLTKMQILVNRYPNWGDTVEINSWFSQSGKIGMGRN<br>WLISDCNTGEILIRATSIWAMMNQKTRRFSKLPNEVRQEIAPHFVDAPPVIEDNDRKLHK<br>FDVKTGDSICKGLTPEWNDLDVNQHVSNVKYIGWILESMPKEVLDTQELCSLTLEYRRE<br>CGRDSVLESVTAMDPSKVGDRSQYQHLLRLEDGTDIMKGRTEWRPKNAGTNGAISTGK<br>TSNANSVS |
| ChtFATB2h (SEQ ID NO: 98):<br>MVVAAAASSAFFPVPASGTSPKPGKFGTWLSSSSPSYKPKSNPSGGFQVKANASA<br>HPKANGSAVSLKSGSLNTQEGTSSSPPPRTFLNQLPDWSRLLTAISTVFVAAEKQLTMLD<br>RKSKRPDMLVDWFGLESIVQDGLVFRESYSIRSYEISADRTASIETVMNLLQETSLNHCK<br>SMGILNDGFGRTPEMCKRDLIWVLTKMQILVNRYPNWGDTVEINSWFSQSGKIGMGRN<br>WLISDCNTGEILIRATSIWAMMNQNTRRFSKLPNEVRQEIAPHFVDAPPVIEDNDRKLHK |

TABLE 4-continued

| Amino acid sequences of FatB genes |
|---|
| FDVKTGDSIRKGLTPGWNDLDVNQHVSNVKYIGWILESIPTEVLETQELCSLTLEYRREC |
| GRESVLESVTAMNPSKVGDRSQYQHLLRLEDGADIMKGRTEWRPKNAGTNGAISTGKT |
| SNGNSVS |
| ChtFATB3a (SEQ ID NO: 67):<br>MVATAASSAFFPVPSPDTSSRPGKLGNGSSSLRPLKPKFVANAGLQVKANASAPP |
| KINGSSVSLKSCSLKTHEDTPSAPPPRTFINQLPDWSMLLAAITTVFLAAEKQWMMLDW |
| KPKRPDMLVDPFGLGRIVQDGLVFRQNFSIRSYEIGADRTASIETVMNHLQETALNHVKS |
| AGLLNEGFGRTPEMYKRDLIWVVAKMQVMVNRYPTWGDTVEVNTWVAKSGKNGMR |
| RDWLISDCNTGEILTRASSVWVMMNQKTRKLSKIPDEVRHEIEPHFVDSAPVIEDDDWK |
| LPKLDEKTADSIRKGLTPKWNDLDVNQHVNNVKYIGWILESTPPEVLETQELCSLTLEY |
| RRECGRESVLESLTAVDPSGKGFGPQFQHLLRLEDGGEIVKGRTEWRPKTAGINGTIASG |
| ETSPGNS |
| ChtFATB3b (SEQ ID NO: 70):<br>MVATAASSAFFPVPSPDTSSRPGKLGNGSSSLRPLKPKFVANAGLQVKANASAPP |
| KINGSSVSLKSGSLKTQEDTPSAPPPRTFINQLPDWSMLLAAITTVFLAAEKQWMMLDW |
| KPKRPDMLVDPFGFGRIVQDGLVFRQNFSIRSYEIGADRTASIETVMNHLQETALNHVKS |
| AGLLIEGFGRTPEMYKRDLIWVVAKMQVMVNRYPTWGDTVEVNTWVAKSGKNGMRR |
| DWLISDCNTGEILTRASSVWVMMNQKTRKLSKIPDEVRHEIEPHFVDSAPVIEDDDWKL |
| PKLDEKTADSIRKGLTPKWNDLDVNQHVNNVKYIGWILESTPPEVLETQELCSLTLEYR |
| RECGRESVLESLTAVDPSGKGFGPQFQHLLRLEDGGEIVKGRTEWRPKTAGINGTIASGE |
| TSPGNS |
| ChtFATB3c (SEQ ID NO: 99):<br>MVATAASSAFFPVPSPDTSSRPGKLGNGSSSLRPLKPKFVANAGLQVKANASAPP |
| KINGSSVSLKSCSLKTHEDTPSAPPPRTFINQLPDWSMLLAAITTVFLAAEKQWMMLDW |
| KPKRPDMLVDPFGLGRIVQDGLVFRQNFSIRSYEIGADRTASIETVMNHLQETALNHVKS |
| AGLLNEGFGRTPEMYKRDLIWVVAKMQVMVNRYPTWGDTVEVNTWVAKSGKNGMR |
| RDWLISDCNTGEILTRASSVWVMMNQKTRKLSKIPDEVRHEIEPHFVDSAPVIEDDDRK |
| LPKLDEKTADSIRKGLTPKWNDLDVNQHVNNVKYIGWILESTPPEVLETQELCSLTLEY |
| RRECGRESVLESLTAVDPSEKGFGPQFQHLLRLEDGGEIVKGRTEWRPKTAGINGAIAFG |
| ETSPGDS |
| ChtFATB3d (SEQ ID NO: 100):<br>MVATAASSAFFPVPSPDTSSRPGKLGNGSSSLRPLKPKFVANAGLQVKANASAPP |
| KINGSSVSLKSCSLKTHEDTPSAPPPRTFINQLPDWSMLLAAITTVFLAAEKQWMMLDW |
| KPKRPDMLVDPFGLGRIVQDGLVFRQNFSIRSYEIGADRTASIKTVMNHLQETALNHVK |
| SAGLLNEGFGRTPEMYKRDLIWVVAKMQVMVNRYPTWGDTVEVNTWVAKSGKNGM |
| RRDWLISDCNTGEILTRASSVWVMMNQKTRKLSKIPDEVRHEIEPHFVDSAPVIEDDDW |
| KLPKLDEKTADSIRKGLTPKWNDLDVNQHVNNVKYIGWILESTPPEVLETQELCSLTLE |
| YRRECGRESVLESLTAVDPSGKGFGPQFQHLLRLEDGGEIVKGRTEWRPKTAGINGTIAS |
| GETSPGNS |
| ChtFATB3e (SEQ ID NO: 101):<br>MVATAASSAFFPVPSPDTSSRPGKLGNGSSSLRPLKPKFVANAGLQVKANASAPP |

TABLE 4-continued

| Amino acid sequences of FatB genes |
| --- |
| KINGSSVSLKSGSLKTHEDTPSAPPPRTFINQLPDWSMLLAAITTVFLAAEKQWMMLDW |
| KPKRPDMLVDPFGLGRIVQDGLVFRQNFSIRSYEIGADRTASIETVMNHLQETALNHVKS |
| AGLLNEGFGRTPEMYKRDLIWVVAKMQVMVNRYPTWGDTVEVNTWVAKSGKNGMR |
| RDWLISDCNTGEILTRASSVWVMMNQKTRKLSKIPDEVRHEIEPHFVDSAPVIEDDDWK |
| LPKLDEKTADSIRKGLTPKWNDLDVNQHVNNVKYIGWILESTPPEVLETQELCSLTLEY |
| RRECGRESVLESLTAVDPSGKGFGPQFQHLLRLEDGGEIVKGRTEWRPKTAGINGTIASG |
| ETSPGNS |
| ChtFATB3f (SEQ ID NO: 102):<br>MVATAASSAFFPVPSPDTSSRLGKLGNGSSSLRPLKPKFVANAGLQVKANASAPP |
| KINGSSVSLKSGSLKTQEDTPSAPPPRTFINQLPDWSMLLAAITTVFLAAEKQWMMLDW |
| KPKRPDMPVDPFGLGRIVQDGLVFRQNFSIRSYEIGADRTASIETVMNHLQETALNHVKS |
| AGLLNEGFGRTPEMYKRDLIWVVAKMQVMVNRYPTWGDTVEVNTWVAKSGKNGMR |
| RDWLISDCNTGEILTRASSVWVMMNQKTRKLSKIPDEVRHEIEPHFVDSAPVIEDDDWK |
| LPKLDEKTADSIRKGLTPKWNDLDVNQHVNNVKYIGWILESTPPEVLETQELCSLTLEY |
| RRECGRESVLESLTAVDPSEKGFGPQFQHLLRLEDGGEIVKGRTEWRPKTAGINGTIASG |
| ETSPGNS |
| ChtFATB3g (SEQ ID NO: 103):<br>MVATAASSAFFPVPSPDTSSRAGKLGNGSSSLRPLKPKFVANAGLQVKANASAPP |
| KINGSSVSLKSGSLKTQEDTPSAPPPRTFINQLPDWSMLLAAITTVFLAAEKQWMMLDW |
| KPKRPDMLVDPFGLGRIVQDGLVFRQNFSIRSYEIGADRTASIETVMNHLQETALNHVKS |
| AGLLNEGFGRTPEMYKRDLIWVVAKMQVMVNRYPTWGDTVEVNTWVAKSGKNGMR |
| RDWLISDCNTGEILTRASSVWVMMNQKTRKLSKIPDEVRHEIEPHFVDSAPVIEDDDWK |
| LPKLDEKTADSIRKGLTPKWNDLDVNQHVNNVKYIGWILESTPPEVLETQELCSLTLEY |
| RRECGRESVLESLTAVDPSGKGFGPQFQHLLRLEDGGEIVKGRTEWRPKTAGINGTIASG |
| ETSPGNS |
| ChsFATB1 (SEQ ID NO: 10):<br>MVATNAAAFSAYTFFLTSPTHGYSSKRLADTQNGYPGTSLKSKSTPPPAAAAAR |
| NGALPLLASICKCPKKADGSMQLDSSLVFGFQFYIRSYEVGADQTVSIQTVLNYLQEAAI |
| NHVQSAGYFGDSFGATPEMTKRNLIWVITKMQVLVDRYPAWGDVVQVDTWTCSSGKN |
| SMQRDWFVRDLKTGDIITRASSVWVLMNRLTRKLSKIPEAVLEEAKLFVMNTAPTVDD |
| NRKLPKLDGSSADYVLSGLTPRWSDLDMNQHVNNVKYIAWILESVPQSIPETHKLSAIT |
| VEYRRECGKNSVLQSLTNVSGDGITCGNSIIECHHLLQLETGPEILLARTEWISKEPGFRG |
| APIQAEKVYNNK |
| ChsFATB2 (SEQ ID NO: 13):<br>MVATAASSAFFPVPSPDASSRPGKLGNGSSSLSPLKPKLMANGGLQVKANASAP |
| PKINGSSVGLKSGSLKTQEDTPSAPPPRTFINQLPDWSMLLAAITTVFLAAEKQWMMLD |
| WKPKRPDMLVDPFGLGRIVQDGLVFRQNFSIRSYEIGADRTASIETVMNHLQETALNHV |
| KSAGLLNDGFGRTLEMYKRDLIWVVAKMQVMVNRYPTWGDTVEVNTWVAKSGKNG |
| MRRDWLISDCNTGEILTRASSVWVMMNQKTRRLSKIPDEVRHEIEPHFVDSAPVIEDDD |
| RKLPKLDEKTADSIRKGLTPKWNDLDVNQHVNNVKYIGWILESTPPEVLETQELCSLTL |
| EYRRECGRESVLESLTAVDPSGKGSGSQFQHLLRLEDGGEIVKGRTEWRPKTAGINGPIA |

TABLE 4-continued

| Amino acid sequences of FatB genes |
|---|
| SGETSPGDSS |
| ChsFatB2b (SEQ ID NO: 16):<br>MVATAASSAFFPVPSPDASSRPGKLGNGSSSLSPLKPKLMANGGLQVKANASAP<br>PKINGSSVGLKSGSLKTQEDTPSAPPPRTFINQLPDWSMLLAAITTVFLAAEKQWMMLD<br>WKPKRPDMLVDPFGLGRIVQDGLVFRQNFSIRSYEIGADRTASIETVMNHLQETALNHV<br>KSAGLLNDGFGRTLEMYKRDLIWVVAKMQVMVNRYPTWGDTVEVNTWVAKSGKNG<br>MRRDWLISDCNTGEILTRASSKSQIMLPLHYCSVWVMMNQKTRRLSKIPDEVRHEIEPH<br>FVDSAPVIEDDDRKLPKLDEKTADSIRKGLTPKWNDLDVNQHVNNVKYIGWILESTPPE<br>VLETQELCSLTLEYRRECGRESVLESLTAVDPSGKGSGSQFQHLLRLEDGGEIVKGRTEW<br>RPKTAGINGPIASGETSPGDSS |
| ChsFatB2c (SEQ ID NO: 104):<br>MVATAASSAFFPVPSPDASSRPGKLGNGSSSLSPLKPKLMANGGLQVKANASAP<br>PKINGSSVGLKSGSLKTQEDTPSAPPPRTFINQLPDWSMLLAAITTVFLAAEKQWMMLD<br>WKPKRPDMLVDPFGLGRIVQDGLVFRQNFSIRSYEIGADRTASIETVMNHLQETALNHV<br>KSAGLLNDGFGRTLEMYKRDLIWVVAKMQVMVNRYPTWGDTVEVNTWVAKSGKNG<br>MRRDWLISDCNTGEILTRASSVWVMMNQKTRRLSKIPDEVRHEIEPHFVDSAPVIEDDD<br>RKLPKLDEKTADSIRKGLTPKWNDLDVNQHVNNVKYIGWILESTPPEVLETQELCSLTL<br>EYRRECGRESVLESLTAVDPSGKGSGSQFQHLMRLEDGGEIVKGRTEWRPKTAGINGPI<br>ASGETSPGDSS |
| ChsFatB2d (SEQ ID NO: 105):<br>MVATAASSAFFPVPSPDASSRPGKLGNGSSSLSPLKPKLMANGGLQVKANASAP<br>PKINGSSVGLKSGSLKTQEDTPSAPPPRTFINQLPDWSMLLAAITTVFLAAEKQWMMLD<br>WKPKRPDMLVDPFGLGRIVQDGLVFRQNFSIRSYEIGADRTASIETVMNHLQETALNHV<br>KSAGLLNDGFGRTPEMYKRDLIWVVAKMQVMVNRYPTWGDTVEVNTWVAKSGKNG<br>MRRDWLISDCNTGEILTRASSVWVMMNQKTRRLSKIPDEVRHEIEPHFVDSAPVIEDDD<br>RKLPKLDEKTADSIRKGLTPKWNDLDVNQHVNNVKYIGWILESTPPEVLETQELCSLTL<br>EYRRECGRESVLESLTAVDPSGKGSGSQFQHLLRLEDGGEIVKGRTEWRPKTAGINGPIA<br>SGETSPGDSS |
| Chs FATB3 (SEQ ID NO: 19):<br>MVAAEASSALFSVRTPGTSPKPGKFGNWPTSLSVPFKSKSNHNGGFQVKANASA<br>RPKANGSAVSLKSGSLDTQEDTSSSSSPPRTFINQLPDWSMLLSAITTVFVAAEKQWTML<br>DRKSKRPDMLMDPFGVDRVVQDGAVFRQSFSIRSYEIGADRTASIETLMNIFQETSLNHC<br>KSIGLLNDGFGRTPEMCKRDLIWVVTKMHVEVNRYPTWGDTIEVNTWVSESGKTGMG<br>RDWLISDCHTGEILIRATSMCAMMNQKTRRFSKFPYEVRQELAPHFVDSAPVIEDYQKL<br>HKLDVKTGDSICNGLTPRWNDLDVNQHVNNVKYIGWILESVPTEVFETQELCGLTLEYR<br>RECGRDSVLESVTAMDPSKEGDRSLYQHLLRLEDGADIAKGRTKWRPKNAGTNGAIST<br>GKTSNGNSIS |
| ChsFatb3b (SEQ ID NO: 22):<br>MVAAEASSALFSVRTPGTSPKPGKFGNWPTSLSVPFKSKSNHNGGFQVKANASA<br>RPKANGSAVSLKSGSLDTQEDTSSSSSPPRTFINQLPDWSMLLSAITTVFVAAEKQWTML<br>DRKSKRPDMLMDPFGVDRVVQDGAVFRQSFSIRSYEIGADRTASIETLMNIFQETSLNHC<br>KSIGLLNDGFGRTPEMCKRDLIWVVTKMHIEVNRYPTWGDTIEVNTWVSESGKTGMGR |

TABLE 4-continued

| Amino acid sequences of FatB genes |
| --- |

DWLISDFHTGDILIRATSVCAMMNQKTRRFSKFPYEVRQELAPHFVDSAPVIEDYQKLH

KLDVKTGDSICNGLTPRWNDLDVNQHVNNVKYIGWILESVPTEVFETQELCGLTLEYRR

ECGRDSVLESVTAMDPSKEGDRSLYQHLLRLEDGADIAKGRTKWRPKNAGTNGAISTG

KTSNGNSIS

ChsFatB3c (SEQ ID NO: 106):
MVAAEASSALFSVRTPGTSPKPGKFGNWPTSLSVPFKSKSNHNGGFQVKANASA

RPKANGSAVSLKSGSLDTQEDTSSSSSPPRTFINQLPDWSMLLSAITTVFVAAEKQWTML

DRKSKRPDMLMDPFGVDRVVQDGAVFRQSFSIRSYEIGADRTASIETLMNIFQETSLNHC

KSIGLLNDGFGRTPEMCKRDLIWVVTKMHVEVNRYPTWGDTIEVNTWVSESGKTGMG

RDWLISDCHTGEILIRATSMCAMMNQKTRRFSKFPYEVRQELAPHFVDSAPVIEDYQKL

HKLDVKTGDSICNGLTPRWNDLDVNQHVNNVKYIGWILESVPTEVFETQELCGLTLEYR

QECGRDSVLESVTAMDPSKEGDRSLYQHLLRLEDGTDIAKGRTKWRPKNAGKTSNGNS

IS
ChsFATB3d (SEQ ID NO: 107):
MVAAEASSALFSVRTPGTSPKPGKFGNWPSSLSVPFKSKSNHNGGFQVKANASA

RPKANGSAVSLKSGSLDTQEDASSSSSPPRTFINQLPDWSMLLSAITTVFVAAEKQWTML

DRKSKRSDMLMDPFGVDRVVQDGAVFRQSFSIRSYEIGADRTASIETLMNIFQETSLNHC

KSIGLLNDGFGRTPEMCKRDLIWVVTKMHVEVNRYPTWGDTIEVNTWVSESGKTGMG

RDWLISDCHTGEILIRATSMCAMMNQKTRRFSKFPYEVRQELAPHFVDSAPVIEDYQKL

HKLDVKTGDSICNGLTPRWNDLDVNQHVNNVKYIGWILESVPTEVFETQELCGLTLEYR

RECGRDSVLESVTAMDPSKEGDRSLYQHLLRLEDGADIAKGRTKWRPKNAGTNGAIST

GKTSNGNSIS

ChsFATB3e (SEQ ID NO: 108):
MVAAEASSALFSVRTPGTSPKPGKFGNWPSSLSVPFKSKSNHNGGFQVKANASA

RPKANGSAVSLKSGSLDTQEDASSSSSPPRTFINQLPDWSMLLSAITTVFVAAEKQWTML

DRKSKRSDMLMDPFGVDRVVQDGVVFRQSFSIRSYEIGADRTASIETLMNIFQETSLNHC

KSIGLLNDGFGRTPEMCKRDLIWVVTKMHVEVNRYPTWGDTIEVNTWVSESGKTGMG

RDWLISDCHTGEILIRATSMCAMMNQKTRRFSKFPYEVRQELAPHFVDSAPVIEDYQKL

HKLDVKTGDSICNGLTPRWNDLDVNQHVNNVKYIGWILESVPTEVFETQELCGLTLEYR

RECGRDSVLESVTAMDPSKEGDRSLYQHLLRLEDGADIAKGRTKWRPKNAGTNGAIST

GKTSNGNSIS

ChsFATB3f (SEQ ID NO: 109):
MVAAEASSALFSVRTPGTSPKPGKFGNWPSSLSVPFKSKSNHNGGFQVKANASA

RPKANGSAVSLKSGSLDTQEDTSSSSSPPRTFINQLPDWSMLLSAITTVFVAAEKQWTML

DRKSKRPDMLMDPFGVDRVVQDGAVFRQSFSIRSYEIGADRTASIETLMNIFQETSLNHC

KSIGLLNDGFGRTPEMCKRDLIWVVTKMHVEVNRYPTWGDTIEVNTWVSESGKTGMG

RDWLISDCHTGEILIRATSMCAMMNQKTRRFSKFPYEVRQELAPHFVDSAPVIEDYQKL

HKLDVKTGDSICNGLTPRWNDLDVNQHVNNVKYIGWILESVPTEVFETQELCGLTLEYR

RECGRDSVLESVTAMDPSKEGDRSLYQHLLRLEDGADIAKGRTKWRPKNAGTNGAIST

GKTSNGNSIS

ChsFATB3g (SEQ ID NO: 110):
MVAAEASSALFSVRTPGTSPKPGKFGNWPTSLSVPFKSKSNHNGGFQVKANASA

TABLE 4-continued

| Amino acid sequences of FatB genes |
|---|
| RPKANGSAVSLKSGSLDTQEDTSSSSSPPRTFINQLPDWSMLLSAITTVFVAAEKQWTML |
| DRKSKRPDMLMDPFGVDRVVQDGAVFRQSFSIRSYEIGADRTASIETLMNIFQETSLNHC |
| KSIGLLNDGFGRTPEMCKRDLIWVVTKMHIEVNRYPTWGDTIEVNTWVSESGKTGMGR |
| DWLISDFHTGDILIRATSVCAMMNQKTRRFSKFPYEVRQELAPHFVDSAPVIEDYQKLH |
| KLDVKTGDSICNGLTPRWNDLDVNQHVNNVKYIGWILESVPTEVFETQELCGLTLEYRQ |
| ECGRDSVLESVTAMDPSKEGDRSLYQHLLRLEDGTDIAKGRTKWRPKNAGKTSNGNSIS |
| ChsFATB3h (SEQ ID NO: 111):<br>MVAAEASSALFSVRTPGTSPKPGKFGNWPSSLSVPFKSKSNHNGGFQVKANASA |
| RPKANGSAVSLKSGSLDTQEDASSSSSPPRTFINQLPDWSMLLSAITTVFVAAEKQWTML |
| DRKSKRSDMLMDPFGVDRVVQDGVVFRQSFSIRSYEIGADRTASIETLMNIFQETSLNHC |
| KSIGLLNDGFGRTPEMCKRDLIWVVTKMHIEVNRYPTWGDTIEVNTWVSESGKTGMGR |
| DWLISDFHTGDILIRATSVCAMMNQKTRRFSKFPYEVRQELAPHFVDSAPVIEDYQKLH |
| KLDVKTGDSICNGLTPRWNDLDVNQHVNNVKYIGWILESVPTEVFETQELCGLTLEYRQ |
| ECGRDSVLESVTAMDPSKEGDRSLYQHLLRLEDGTDIAKGRTKWRPKNAGKTSNGNSIS |
| ChsFATB3i (SEQ ID NO: 112):<br>MVAAEASSALFSVRTPGTSPKPGKFGNWPTSLSVPFKSKSNHNGGFQVKANASA |
| RPKANGSAVSLKSGSLDTQEDTSSSSSPPRTFINQLPDWSMLLSAITTVFVAAEKQWTML |
| DRKSKRPDMLMDPFGVDRVVQDGAVFRQSFSIRSYEIGADRTASIETLMNIFQETSLNHC |
| KSIGLLNDGFGRTPEMCKRDLIWVVTKMHVEVNRYPTWGDTIEVNTWVSESGKTGMG |
| RDWLISDCHTGEILIRATSMCAMMNQKTRRFSKFPYEVRQELAPHFVDSAPVIEDYQKL |
| HKLDVKTGDSICNGLTPRWNDLDVNQHVNNVKYIGWILESVPTEVFETQELCGLTLEYR |
| RECGGDSVLESVTAMDPSKEGDRSLYQHLLRLEDGADIAKGRTKWRPKNAGTNGAIST |
| GKTSNGNSIS |
| ChsFATB3j (SEQ ID NO: 113):<br>MVAAEASSALFSVRTPGTSPKPGKFGNWPTSLSVPFKSKSNHNGGFQVKANASA |
| RPKANGSAVSLKSGSLDTQEDTSSSSSPPRTFINQLPDWSMLLSAITTVFVAAEKQWTML |
| DRKSKRPDMLMDPFGVDRVVQDGAVFRQSFSIRSYEIGADRTASIETLMNIFQETSLNHC |
| KSIGLLNDGFGRTPEMCKRDLIWVVTKMHIEVNRYPTWGDTIEVNTWVSESGKTGMGR |
| DWLISDFHTGDILIRATSVCAMMNQKTRRFSKFPYEVRQELAPHFVDSAPVIEDYQKLH |
| KLDVKTGDSICNGLTPRWNDLDVNQHVNNVKYIGWILESVPTEVFETQELCGLTLEYRQ |
| ECGRDSVLESVTAMDPSKEGDRSLYQHLLRLEDGTDIAKGRTKWRPKNAGKTSNGNSIS |

EXAMPLE 2

In the example below, we detail the effect of expressing plant oilseed transcriptome-derived, heterologous thioesterases in the UTEX1435 (web.biosci.utexas.edu/utex/) strain, Strain A.

As in Example 1, RNA was extracted from dried plant seeds and submitted for paired-end sequencing using the Illumina Hiseq 2000 platform. RNA sequence reads were assembled into corresponding seed transcriptomes using Trinity or Oases packages and putative thioesterase-containing cDNA contigs were identified by mining transcriptomes for sequences with homology to known thioesterases. These in silico identified putative thioesterase cDNAs were verified by direct reverse transcription PCR analysis using seed RNA and primer pairs targeting full-length thioesterase cDNAs. The resulting amplified products were cloned and sequenced de novo to confirm authenticity of identified thioesterase genes and to identify sequence variants arising from expression of different gene alleles or diversity of sequences within a population of seeds. The resulting amino acid sequences were subjected to phylogenetic analysis using published full-length (Mayer and Shanklin, 2007) and truncated (THYME database) FatB sequences. The thioesterases that clustered with acyl-ACP FatB thioesterases, which are involved in biosynthesis of C8-C16 fatty acids, were pursued.

Construction of Transforming Vectors Expressing Acyl-ACP FatB Thioesterases 27 putative acyl-ACP FatB thioesterases from the species *Cinnamomum camphora, Cuphea hyssopifolia, Cuphea* PSR23, *Cuphea wrightii, Cuphea heterophylla*, and *Cuphea viscosissima* were synthesized in a codon-optimized form to reflect *Prototheca moriformis* (UTEX 1435) codon usage. Of the 27 genes synthesized, 24 were identified by our transcriptome sequencing efforts and the 3 genes from *Cuphea viscosissima*, were from published sequences in GenBank.

Transgenic strains were generated via transformation of the base strain Strain A (*Prototheca moriformis*, derived from UTEX 1435 by classical mutation and screening for high oil production) with a construct encoding 1 of the 27 FatB thioesterases. The construct pSZ2760 encoding *Cinnamomum camphora* (Cc) FATB1b is shown as an example, but identical methods were used to generate each of the remaining 26 constructs encoding the different respective thioesterases. Construct pSZ2760 can be written as 6S::CrTUB2: ScSUC2: CvNR::PmAMT3: CcFATB1b:CvNR::6S. The sequence of the transforming DNA is provided in Table 5 (pSZ2760). The relevant restriction sites in the construct from 5'-3', BspQ1, KpnI, AscI, MfeI, EcoRI, SpeI, XhoI, SacI, BspQ1, respectively, are indicated in lowercase, bold, and underlined. BspQ1 sites delimit the 5' and 3' ends of the transforming DNA. Bold, lowercase sequences at the 5' and 3' end of the construct represent genomic DNA from UTEX 1435 that target integration to the 6S locus via homologous recombination. Proceeding in the 5' to 3' direction, the selection cassette has the *C. reinhardtii* f3-tubulin promoter driving expression of the *S. cerevisiae* gene SUC2 (conferring the ability to grow on sucrose) and the *Chlorella vulgaris* Nitrate Reductase (NR) gene 3' UTR. The promoter is indicated by lowercase, boxed text. The initiator ATG and terminator TGA for ScSUC2 are indicated by bold, uppercase italics, while the coding region is indicated with lowercase italics. The 3' UTR is indicated by lowercase underlined text. The spacer region between the two cassettes is indicated by upper case text. The second cassette containing the codon optimized CcFATB1b gene (Table 5; pSZ2760) from *Cinnamomum camphora* is driven by the *Prototheca moriformis* endogenous AMT3 promoter, and has the *Chlorella vulgaris* Nitrate Reductase (NR) gene 3' UTR. In this cassette, the AMT3 promoter is indicated by lowercase, boxed text. The initiator ATG and terminator TGA for the CcFATB1b gene are indicated in bold, uppercase italics, while the coding region is indicated by lowercase italics and the spacer region is indicated by upper case text. The 3' UTR is indicated by lowercase underlined text. The final construct was sequenced to ensure correct reading frame and targeting sequences.

TABLE 5

| pSZ2760 Transforming construct (SEQ ID NO: 114) |
|---|
| **gctcttcgccgccgccactcctgctcgagcgcgcccgcgcgtgcgccgccagcgccttggccttttcgccgcgctcgtgcgcgtcgct** |
| **gatgtccatcaccaggtccatgaggtctgccttgcgccggctgagccactgcttcgtccgggcggccaagaggagcatgagggag** |
| **gactcctggtccagggtcctgacgtggtcgcggctctgggagcgggccagcatcatctggctctgccgcaccgaggccgcctccaa** |
| **ctggtcctccagcagccgcagtcgccgccgaccctggcagaggaagacaggtgaggggggtatgaattgtacagaacaaccacg** |
| **agccttgtctaggcagaatccctaccagtcatggctttacctggatgacggcctgcgaacagctgtccagcgaccctcgctgccgcc** |
| **gcttctcccgcacgcttctttccagcaccgtgatggcgcgagccagcgccgcacgctggcgctgcgcttcgccgatctgaggacagt** |
| **cggggaactctgatcagtctaaacccccttgcgcgttagtgttgccatcctttgcagaccggtgagagccgacttgttgtgcgccacc** |
| **ccccacaccacctcctcccagaccaattctgtcacctttttggcgaaggcatcggcctcggcctgcagagaggacagcagtgccca** |
| **gccgctgggggttggcggatgcacgctcaggtacc**ctttcttgcgctatgacacttccagcaaaaggtagggcgggctgcgagacggct |
| tcccggcgctgcatgcaacaccgatgatgcttcgaccccccgaagctccttcggggctgcatgggcgctccgatgccgctccagggcga |
| gcgctgtttaaatagccaggcccccgattgcaaagacattatagcgagctaccaaagccatattcaaacacctagatcactaccacttctaca |
| caggccactcgagcttgtgatcgcactccgctaagggggcgcctcttcctcttcgtttcagtcacaacccgcaaac**ggcgcgcc*ATG***ctg |
| *ctgcaggccttcctgttcctgctggccggcttcgccgccaagatcagcgcctccatgacgaacgagacgtccgaccgcccccctggtgca* |
| *cttcacccccaacaagggctggatgaacgaccccaacggcctgtggtacgacgagaaggacgccaagtggcacctgtacttccagt* |
| *acaacccgaacgacaccgtctgggggacgcccttgttctggggccacgccacgtccgacgacctgaccaactgggaggaccagccc* |
| *atcgccatcgccccgaagcgcaacgactccggcgccttctccggctccatggtggtggactacaacaacacctccggcttcttcaacga* |
| *caccatcgacccgcgccagcgctgcgtggccatctggacctacaacaccccggagtccgaggagcagtacatctcctacagcctgga* |
| *cggcggctacaccttcaccgagtaccagaagaaccccgtgctggccgccaactccacccagttccgcgacccgaaggtcttctggtac* |
| *gagccctcccagaagtggatcatgaccgcggccaagtcccaggactacaagatcgagatctactcctccgacgacctgaagtcctgg* |
| *aagctggagtccgcgttcgccaacgagggcttcctcggctaccagtacgagtgccccggcctgatcgaggtccccaccgagcaggac* |
| *cccagcaagtcctactgggtgatgttcatctccatcaaccccggcgccccggccggcggctccttcaaccagtacttcgtcggcagcttc* |

TABLE 5-continued

| pSZ2760 Transforming construct (SEQ ID NO: 114) |
|---|
| *aacggcacccacttcgaggccttcgacaaccagtcccgcgtggtggacttcggcaaggactactacgccctgcagaccttcttcaaca* |
| *ccgacccgacctacgggagcgccctgggcatcgcgtgggcctccaactgggagtactccgccttcgtgcccaccaacccctggcgctc* |
| *ctccatgtccctcgtgcgcaagttctccctcaacaccgagtaccaggccaacccggagacggagctgatcaacctgaaggccgagcc* |
| *gatcctgaacatcagcaacgccggcccctggagccggttcgccaccaacaccacgttgacgaaggccaacagctacaacgtcgacc* |
| *tgtccaacagcaccggcaccctggagttcgagctggtgtacgccgtcaacaccacccagacgatctccaagtccgtgttcgcggacct* |
| *ctccctctggttcaagggcctggaggaccccgaggagtacctccgcatgggcttcgaggtgtccgcgtcctcctcttcctggaccgcgg* |
| *gaacagcaaggtgaagttcgtgaaggagaacccctacttcaccaaccgcatgagcgtgaacaaccagcccttcaagagcgagaac* |
| *gacctgtcctactacaaggtgtacggcttgctggaccagaacatcctggagctgtacttcaacgacggcgacgtcgtgtccaccaacac* |
| *ctacttcatgaccaccgggaacgccctgggctccgtgaacatgacgacgggggtggacaacctgttctacatcgacaagttccaggtg* |
| cgcgaggtcaag***TGA*****caattg**gcagcagcagctcggatagtatcgacacactctggacgctggtcgtgtgatggactgttgccgccac |
| acttgctgccttgacctgtgaatatccctgccgcttttatcaaacagcctcagtgtgtttgatcttgtgtgtacgcgcttttgcgagttgctagctgc |
| ttgtgctatttgcgaataccacccccagcatccccttccctcgtttcatatcgcttgcatcccaaccgcaacttatctacgctgtcctgctatccct |
| cagcgctgctcctgctcctgctcactgcccctcgcacagccttggtttgggctccgcctgtattctcctggtactgcaacctgtaaaccagcac |
| tgcaatgctgatgcacgggaagtagtgggatgggaacacaaatggaAAGCTGTATAGGGATAA**gaattc**ggccgacag |
| gacgcgcgtcaaaggtgctggtcgtgtatgccctggccggcaggtcgttgctgctgctggttagtgattccgcaaccctgattttggcgtctt |
| attttggcgtggcaaacgctggcgcccgcgagccgggccggcggcgatgcggtgccccacggctgccggaatccaagggaggcaag |
| agcgcccgggtcagttgaagggctttacgcgcaaggtacagccgctcctgcaaggctgcgtggtggaattggacgtgcaggtcctgctga |
| agttcctccaccgcctcaccagcggacaaagcaccggtgtatcaggtccgtgtcatccactctaaagaactcgactacgacctactgatggc |
| cctagattcttcatcaaaaacgcctgagacacttgcccaggattgaaactccctgaagggaccaccaggggccctgagttgttccttccccc |
| cgtggcgagctgccagccaggctgtacctgtgatcgaggctggcgggaaaataggcttcgtgtgctcaggtcatgggaggtgcaggaca |
| gctcatgaaacgccaacaatcgcacaattcatgtcaagctaatcagctatttcctcttcacgagctgtaattgtcccaaaattctggtctaccgg |
| gggtgatccttcgtgtacgggcccttccctcaaccctaggtatgcgcgcatgcggtcgccgcgcaactcgcgcgagggccgagggtttgg |
| gacgggccgtcccgaaatgcagttgcacccggatgcgtggcacctttttttgcgataatttatgcaatggactgctctgcaaaattctggctctg |
| tcgccaaccctaggatcagcggcgtaggatttcgtaatcattcgtcctgatggggagctaccgactaccctaatatcagcccgactgcctga |
| cgccagcgtccacttttgtgcacacattccattcgtgcccaagacatttcattgtggtgcgaagcgtccccagttacgctcacctgtttcccgac |
| ctccttactgttctgtcgacagagcgggcccacaggccggtcgcagcc**actagtATG***gccaccacctccctggcctccgccttctgctc* |
| *catgaaggccgtgatgctggcccgcgacggccgcggcctgaagccccgctcctccgacctgcagctgcgcgccggcaacgcccaga* |
| *cctccctgaagatgatcaacggcaccaagttctcctacaccgagtccctgaagaagctgcccgactggtccatgctgttcgccgtgatc* |
| *accaccatcttctccgccgccgagaagcagtggaccaacctggagtggaagcccaagcccaacccccccagctgctggacgacca* |
| *cttcggcccccacggcctggtgttccgccgcaccttcgccatccgctcctacgaggtgggccccgaccgctccacctccatcgtggccgt* |
| *gatgaaccacctgcaggaggccgccctgaaccacgccaagtccgtgggcatcctgggcgacggcttcggcaccaccctggagatgt* |
| *ccaagcgcgacctgatctgggtggtgaagcgcacccacgtggccgtggagcgctaccccgcctggggcgacaccgtggaggtgga* |
| *gtgctgggtgggcgcctccggcaacaacggccgccgccacgacttcctggtgcgcgactgcaagaccggcgagatcctgacccgct* |
| *gcacctccctgtccgtgatgatgaacacccgcacccgccgcctgtccaagatccccgaggaggtgcgcggcgagatcggccccgcct* |

TABLE 5-continued

| pSZ2760 Transforming construct (SEQ ID NO: 114) |
|---|
| *tcatcgacaacgtggccgtgaaggacgaggagatcaagaagccccagaagctgaacgactccaccgccgactacatccagggcg* |
| *gcctgaccccccgctggaacgacctggacatcaaccagcacgtgaacaacatcaagtacgtggactggatcctggagaccgtgccc* |
| *gactccatcttcgagtcccaccacatctcctccttcaccatcgagtaccgccgcgagtgcacccgcgactccgtgctgcagtccctgacc* |
| *accgtgtccggcggctcctccgaggccggcctggtgtgcgagcacctgctgcagctggagggcggctccgaggtgctgcgcgccaag* |
| *accgagtggcgccccaagctgtccttccgcggcatctccgtgatccccgccgagtcctccgtgatggactacaaggaccacgacggcg* |
| *actacaaggaccacgacatcgactacaaggacgacgacgacaag***TGActcgag**gcagcagcagctcggatagtatcgacacact |
| ctggacgctggtcgtgtgatggactgttgccgccacacttgctgccttgacctgtgaatatccctgccgcttttatcaaacagcctcagtgtgttt |
| gatcttgtgtgtacgcgcttttgcgagttgctagctgcttgtgctatttgcgaataccacccccagcatccccttccctcgtttcatatcgcttgcat |
| cccaaccgcaacttatctacgctgtcctgctatccctcagcgctgctcctgctcctgctcactgcccctcgcacagccttggtttgggctccgc |
| ctgtattctcctggtactgcaacctgtaaaccagcactgcaatgctgatgcacgggaagtagtgggatgggaacacaaatggaAAGCT |
| GTATAGGGATAACAGGGTAAT**gagctcttgttttccagaaggagttgctccttgagcctttcattctcagcctcgata** |
| **acctccaaagccgctctaattgtggagggggttcgaatttaaaagcttggaatgttggttcgtgcgtctggaacaagcccagacttgt** |
| **tgctcactgggaaaaggaccatcagctccaaaaaacttgccgctcaaaccgcgtacctctgctttcgcgcaatctgccctgttgaaa** |
| **tcgccaccacattcatattgtgacgcttgagcagtctgtaattgcctcagaatgtggaatcatctgcccccctgtgcgagcccatgcca** |
| **ggcatgtcgcgggcgaggacacccgccactcgtacagcagaccattatgctacctcacaatagttcataacagtgaccatatttctc** |
| **gaagctccccaacgagcacctccatgctctgagtggccaccccccggccctggtgcttgcggagggcaggtcaaccggcatgggg** |
| **ctaccgaaatccccgaccggatcccaccacccccgcgatgggaagaatctctccccgggatgtgggcccaccaccagcacaacct** |
| **gctggcccaggcgagcgtcaaaccataccacacaaatatccttggcatcggccctgaattccttctgccgctctgctacccggtgctt** |
| **ctgtccgaagcaggggttgctagggatcgctccgagtccgcaaacccttgtcgcgtggcggggcttgttcgagcttgaagagc** |

Constructs encoding the identified heterologous FatB genes, such as CcFATB1b from pSZ2760 in Table 6, were transformed into Strain A, and selected for the ability to grow on sucrose. Transformations, cell culture, lipid production and fatty acid analysis were all carried out as previously described. After cultivating on sucrose under low nitrogen conditions to accumulate oil, fatty acid profiles were determined by FAME-GC. The top performer from each transformation, as judged by the ability to produce the highest level of midchain fatty acids, is shown in Table 4.

TABLE 6

Alteration of Fatty Acid Profiles in S3150 upon Expression of Heterologous FatB Thioesterases

| Species | Gene Name | SZ Plasmid | FA profile of top performer from each transformation (%; primary lipid in Strain A background) Strain | C8:0 | C10:0 | C12:0 | C14:0 | C16:0 | C18:0 | C18:1 | C18:2 | C18:3α |
|---|---|---|---|---|---|---|---|---|---|---|---|---|
| *Cinnamomum camphora* | CcFATB1b | pSZ2760 | A; T526; D1670-13 | 0 | 0 | 1 | 15 | 26 | 2 | 46 | 9 | 1 |
| *Cinnamomum camphora* | CcFATB4 | pSZ2756 | A; T525; D1666-31 | 0 | 1 | 33 | 4 | 7 | 2 | 41 | 10 | 1 |
| *Cinnamomum camphora* | CcFATB3 | pSZ2755 | A; T525; D1665-4 | 0 | 0 | 0 | 3 | 44 | 3 | 41 | 8 | 0 |
| *Cuphea hyssopifolia* | ChsFATB1 | pSZ2778 | A; T535; D1689-30 | 0 | 0 | 0 | 2 | 22 | 4 | 63 | 8 | 1 |
| *Cuphea hyssopifolia* | ChsFATB2 | pSZ2796 | A; T537; D1700-46 | 0 | 0 | 0 | 6 | 53 | 3 | 32 | 6 | 0 |
| *Cuphea hyssopifolia* | ChsFATB2b | pSZ2792 | A; T537; D1696-9 | 0 | 0 | 0 | 5 | 26 | 2 | 56 | 9 | 1 |
| *Cuphea hyssopifolia* | ChsFATB3 | pSZ2797 | A; T537; D1701-48 | 0 | 0 | 8 | 34 | 27 | 2 | 24 | 5 | 1 |
| *Cuphea hyssopifolia* | ChsFATB3b | pSZ2795 | A; T537; D1699-1 | 0 | 0 | 7 | 29 | 27 | 1 | 28 | 6 | 1 |
| *Cuphea* PSR23 | CuPSR23FATB3 | pSZ2793 | A; T537; D1697-13 | 0 | 1 | 0 | 2 | 24 | 3 | 61 | 8 | 1 |
| *Cuphea wrightii* | CwFATB3 | pSZ2751 | A; T525; D1661-22 | 0 | 2 | 17 | 9 | 19 | 2 | 41 | 8 | 1 |

TABLE 6-continued

Alteration of Fatty Acid Profiles in S3150 upon Expression of Heterologous FatB Thioesterases

| Species | Gene Name | SZ Plasmid | FA profile of top performer from each transformation (%; primary lipid in Strain A background) Strain | C8:0 | C10:0 | C12:0 | C14:0 | C16:0 | C18:0 | C18:1 | C18:2 | C18:3α |
|---|---|---|---|---|---|---|---|---|---|---|---|---|
| *Cuphea wrightii* | CwFATB4a | pSZ2752 | A; T525; D1662-30 | 0 | 0 | 0 | 4 | 48 | 3 | 36 | 7 | 1 |
| *Cuphea wrightii* | CwFATB4b | pSZ2753 | A; T525; D1663-29 | 0 | 0 | 0 | 5 | 52 | 3 | 32 | 6 | 1 |
| *Cuphea wrightii* | CwFATB5 | pSZ2754 | A; T525; D1664-39 | 0 | 0 | 0 | 3 | 27 | 3 | 57 | 7 | 1 |
| *Cuphea heterophylla* | ChtFATB1a | pSZ2757 | A; T525; D1667-19 | 0 | 0 | 5 | 18 | 27 | 2 | 39 | 7 | 1 |
| *Cuphea heterophylla* | ChtFATB1b | pSZ2773 | A; T535; D1685-29 | 0 | 0 | 2 | 7 | 27 | 3 | 53 | 8 | 1 |
| *Cuphea heterophylla* | ChtFATB2b | pSZ2780 | A; T535; D1691-8 | 0 | 0 | 0 | 2 | 25 | 3 | 61 | 8 | 1 |
| *Cuphea heterophylla* | ChtFATB2a | pSZ2774 | A; T537; D1702-24 | 0 | 0 | 0 | 2 | 27 | 3 | 59 | 6 | 0 |
| *Cuphea heterophylla* | ChtFATB2c | pSZ2758 | A; T525; D1668-22 | 0 | 0 | 3 | 2 | 23 | 3 | 58 | 7 | 1 |
| *Cuphea heterophylla* | ChtFATB2d | pSZ2759 | A; T526; D1669-19 | 0 | 0 | 4 | 4 | 23 | 3 | 54 | 9 | 1 |
| *Cuphea heterophylla* | ChtFATB2e | pSZ2775 | A; T535; D1686-23 | 0 | 1 | 2 | 3 | 24 | 3 | 57 | 8 | 1 |
| *Cuphea heterophylla* | ChtFATB2f | pSZ2777 | A; T535; D1688-33 | 0 | 0 | 0 | 2 | 28 | 3 | 57 | 8 | 1 |
| *Cuphea heterophylla* | ChtFATB2g | pSZ2794 | A; T537; D1698-19 | 0 | 0 | 0 | 2 | 22 | 3 | 62 | 9 | 1 |
| *Cuphea heterophylla* | ChtFATB3a | pSZ2776 | A; T535; D1687-23 | 0 | 0 | 0 | 5 | 47 | 4 | 37 | 7 | 1 |
| *Cuphea heterophylla* | ChtFATB3b | pSZ2779 | A; T535; D1690-31 | 0 | 0 | 0 | 6 | 49 | 5 | 32 | 7 | 0 |
| *Cuphea viscosissima* | CvisFATB1 | pSZ2810 | A; T540; D1711-30 | 0 | 1 | 0 | 2 | 24 | 3 | 60 | 8 | 0 |
| *Cuphea viscosissima* | CvisFATB2 | pSZ2817 | A; T547; D1718-1 | 0 | 0 | 0 | 4 | 51 | 2 | 36 | 6 | 0 |
| *Cuphea viscosissima* | CvisFATB3 | pSZ2791 | A; T537; D1695-1 | 0 | 0 | 0 | 8 | 28 | 2 | 52 | 8 | 1 |
| | | | A (parent strain): | 0 | 0 | 0 | 2 | 28 | 3 | 58 | 7 | 0 |

Many of the acyl-ACP FatB thioesterases were found to exhibit midchain activity when expressed in *Prototheca moriformis*. For example, expression of CcFATB1b causes an increase in myristate levels from 2% of total fatty acids in the parent, Strain A, to ~15% in the D1670-13 primary transformant. Other examples include CcFATB4, which exhibits an increase in laurate levels from 0% in Strain A to ~33%, and ChsFATB3, which exhibits an increase in myristate levels to ~34%. Although some of the acyl-ACP thioesterases did not exhibit dramatic effects on midchain levels in the current incarnation, efforts will likely develop to optimize some of these constructs.

Sequences of the Heterologous Acyl-ACP Thioesterases Identified and Transformed into *P. moriformis* (UTEX 1435)

A complete listing of relevant sequences for the transforming constructs, such as the deduced amino acid sequence of the encoded acyl-ACP thioesterase, the native CDS coding sequence, the *Prototheca moriformis* codon-optimized coding sequence, and the nature of the sequence variants examined, is provided as SEQ ID NOS: 1-78.

What is claimed is:

1. A recombinant nucleic acid having at least 97% sequence identity to any of SEQ ID NOS: 5 or 6, or any equivalent sequences by virtue of the degeneracy of the genetic code, wherein the recombinant nucleic acid encodes a protein having acyl-ACP thioesterase activity.

2. A recombinant nucleic acid encoding a protein having at least 90% sequence identity to SEQ ID NO: 4 and acyl-ACP thioesterase activity, wherein the recombinant nucleic acid also comprises a heterologous nucleic acid.

3. A method of producing a recombinant cell, the method comprising transforming the cell with a nucleic acid according to any of claim 1 or 2.

4. A host cell comprising a recombinant nucleic acid encoding a protein having at least 90% sequence identity to SEQ ID NO:4 and acyl-ACP thioesterase activity, wherein the recombinant nucleic acid comprises an exogenous nucleic acid, and wherein the host cell has an altered fatty acid profile.

5. The host cell of claim 4, wherein the host cell is selected from a plant cell, a microbial cell, and a microalgal cell.

6. A method for producing an oil or oil-derived product, the method comprising cultivating a host cell of claim 4 and extracting oil produced thereby, optionally wherein the cultivation is heterotrophic growth on sugar.

7. The method of claim 6, further comprising producing a fatty acid, fuel, chemical, or other oil-derived product from the oil.

8. A vector comprising the recombinant nucleic acid of claim 1 or 2.

* * * * *

SEQUENCE LISTING

```
<160> NUMBER OF SEQ ID NOS: 115

<210> SEQ ID NO 1
<211> LENGTH: 380
<212> TYPE: PRT
<213> ORGANISM: Cinnamomum camphora

<400> SEQUENCE: 1

Met Ala Thr Thr Ser Leu Ala Ser Ala Phe Cys Ser Met Lys Ala Val
1               5                   10                  15

Met Leu Ala Arg Asp Gly Arg Gly Leu Lys Pro Arg Ser Ser Asp Leu
            20                  25                  30
```

```
Gln Leu Arg Ala Gly Asn Ala Gln Thr Ser Leu Lys Met Ile Asn Gly
        35                  40                  45

Thr Lys Phe Ser Tyr Thr Glu Ser Leu Lys Lys Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Asn Pro Pro Gln Leu Leu
                85                  90                  95

Asp Asp His Phe Gly Pro His Gly Leu Val Phe Arg Arg Thr Phe Ala
            100                 105                 110

Ile Arg Ser Tyr Glu Val Gly Pro Asp Arg Ser Thr Ser Ile Val Ala
        115                 120                 125

Val Met Asn His Leu Gln Glu Ala Ala Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Ile Trp Val Val Lys Arg Thr His Val Ala Val Glu Arg Tyr
                165                 170                 175

Pro Ala Trp Gly Asp Thr Val Glu Val Glu Cys Trp Val Gly Ala Ser
            180                 185                 190

Gly Asn Asn Gly Arg Arg His Asp Phe Leu Val Arg Asp Cys Lys Thr
        195                 200                 205

Gly Glu Ile Leu Thr Arg Cys Thr Ser Leu Ser Val Met Met Asn Thr
    210                 215                 220

Arg Thr Arg Arg Leu Ser Lys Ile Pro Glu Glu Val Arg Gly Glu Ile
225                 230                 235                 240

Gly Pro Ala Phe Ile Asp Asn Val Ala Val Lys Asp Glu Glu Ile Lys
                245                 250                 255

Lys Pro Gln Lys Leu Asn Asp Ser Thr Ala Asp Tyr Ile Gln Gly Gly
            260                 265                 270

Leu Thr Pro Arg Trp Asn Asp Leu Asp Ile Asn Gln His Val Asn Asn
        275                 280                 285

Ile Lys Tyr Val Asp Trp Ile Leu Glu Thr Val Pro Asp Ser Ile Phe
    290                 295                 300

Glu Ser His His Ile Ser Ser Phe Thr Ile Glu Tyr Arg Arg Glu Cys
305                 310                 315                 320

Thr Arg Asp Ser Val Leu Gln Ser Leu Thr Thr Val Ser Gly Gly Ser
                325                 330                 335

Ser Glu Ala Gly Leu Val Cys Glu His Leu Leu Gln Leu Glu Gly Gly
            340                 345                 350

Ser Glu Val Leu Arg Ala Lys Thr Glu Trp Arg Pro Lys Leu Ser Phe
        355                 360                 365

Arg Gly Ile Ser Val Ile Pro Ala Glu Ser Ser Val
    370                 375                 380
```

<210> SEQ ID NO 2
<211> LENGTH: 1128
<212> TYPE: DNA
<213> ORGANISM: Cinnamomum camphora

<400> SEQUENCE: 2

```
ttagcttctg ctttctgctc gatgaaagct gtaatgttgg ctcgtgatgg caggggcttg      60

aaacccagga gcagtgattt gcagctgagg gcgggaaatg cacaaacctc tttgaagatg     120
```

-continued

```
atcaatggga ccaagttcag ttacacagag agcttgaaaa agttgcctga ctggagcatg    180

ctctttgcag tgatcacgac catcttttcg gctgctgaga agcagtggac caatctagag    240

tggaagccga agccgaatcc accccagttg cttgatgacc attttgggcc gcatgggtta    300

gttttcaggc gcacctttgc catcagatcg tatgaggtgg gacctgaccg ctccacatct    360

atagtggctg ttatgaatca cttgcaggag gctgcactta atcatgcgaa gagtgtggga    420

attctaggag atggattcgg tacgacgcta gagatgagta agagagatct gatatgggtt    480

gtgaaacgca cgcatgttgc tgtggaacgg taccctgctt ggggtgatac tgttgaagta    540

gagtgctggg ttggtgcatc gggaaataat ggcaggcgcc atgatttcct tgtccgggac    600

tgcaaaacag gcgaaattct tacaagatgt accagtcttt cggtgatgat gaatacaagg    660

acaaggaggt tgtccaaaat ccctgaagaa gttagagggg agatagggcc tgcattcatt    720

gataatgtgg ctgtcaagga cgaggaaatt aagaaaccac agaagctcaa tgacagcact    780

gcagattaca tccaaggagg attgactcct cgatggaatg atttggatat caatcagcac    840

gttaacaaca tcaaatacgt tgactggatt cttgagactg tcccagactc aatctttgag    900

agtcatcata tttccagctt cactattgaa tacaggagag agtgcacgag ggatagcgtg    960

ctgcagtccc tgaccactgt ctccggtggc tcgtcggaag ctgggttagt gtgcgagcac   1020

ttgctccagc ttgaaggtgg gtctgaggta ttgagggcaa aaacagagtg gaggcctaag   1080

cttagtttca gagggattag tgtgataccc gcagaatcga gtgtctaa                1128
```

<210> SEQ ID NO 3
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
ttagcttctg ctttctgctc gatgaaagct gtaatgttgg ctcgtgatgg caggggcttg     60

aaacccagga gcagtgattt gcagctgagg gcgggaaatg cacaaacctc tttgaagatg    120

atcaatggga ccaagttcag ttacacagag agcttgaaaa agttgcctga ctggagcatg    180

ctctttgcag tgatcacgac catcttttcg gctgctgaga agcagtggac caatctagag    240

tggaagccga agccgaatcc accccagttg cttgatgacc attttgggcc gcatgggtta    300

gttttcaggc gcacctttgc catcagatcg tatgaggtgg gacctgaccg ctccacatct    360

atagtggctg ttatgaatca cttgcaggag gctgcactta atcatgcgaa gagtgtggga    420

attctaggag atggattcgg tacgacgcta gagatgagta agagagatct gatatgggtt    480

gtgaaacgca cgcatgttgc tgtggaacgg taccctgctt ggggtgatac tgttgaagta    540

gagtgctggg ttggtgcatc gggaaataat ggcaggcgcc atgatttcct tgtccgggac    600

tgcaaaacag gcgaaattct tacaagatgt accagtcttt cggtgatgat gaatacaagg    660

acaaggaggt tgtccaaaat ccctgaagaa gttagagggg agatagggcc tgcattcatt    720

gataatgtgg ctgtcaagga cgaggaaatt aagaaaccac agaagctcaa tgacagcact    780

gcagattaca tccaaggagg attgactcct cgatggaatg atttggatat caatcagcac    840

gttaacaaca tcaaatacgt tgactggatt cttgagactg tcccagactc aatctttgag    900

agtcatcata tttccagctt cactattgaa tacaggagag agtgcacgag ggatagcgtg    960

ctgcagtccc tgaccactgt ctccggtggc tcgtcggaag ctgggttagt gtgcgagcac   1020
```

-continued

```
ttgctccagc ttgaaggtgg gtctgaggta ttgagggcaa aaacagagtg gaggcctaag   1080

cttagtttca gagggattag tgtgataccc gcagaatcga gtgtctaa                1128


<210> SEQ ID NO 4
<211> LENGTH: 357
<212> TYPE: PRT
<213> ORGANISM: Cinnamomum camphora

<400> SEQUENCE: 4

Met Val Thr Thr Ser Leu Ala Ser Ala Tyr Phe Ser Met Lys Ala Val
1               5                   10                  15

Met Leu Ala Pro Asp Gly Arg Gly Ile Lys Pro Arg Ser Ser Gly Leu
            20                  25                  30

Gln Val Arg Ala Gly Asn Glu Arg Asn Ser Cys Lys Val Ile Asn Gly
        35                  40                  45

Thr Lys Val Lys Asp Thr Glu Gly Leu Lys Gly Cys Ser Thr Leu Gln
    50                  55                  60

Gly Gln Ser Met Leu Asp Asp His Phe Gly Leu His Gly Leu Val Phe
65                  70                  75                  80

Arg Arg Thr Phe Ala Ile Arg Cys Tyr Glu Val Gly Pro Asp Arg Ser
                85                  90                  95

Thr Ser Ile Met Ala Val Met Asn His Leu Gln Glu Ala Ala Arg Asn
            100                 105                 110

His Ala Glu Ser Leu Gly Leu Leu Gly Asp Gly Phe Gly Glu Thr Leu
        115                 120                 125

Glu Met Ser Lys Arg Asp Leu Ile Trp Val Val Arg Arg Thr His Val
    130                 135                 140

Ala Val Glu Arg Tyr Pro Ala Trp Gly Asp Thr Val Glu Val Glu Ala
145                 150                 155                 160

Trp Val Gly Ala Ser Gly Asn Thr Gly Met Arg Arg Asp Phe Leu Val
                165                 170                 175

Arg Asp Cys Lys Thr Gly His Ile Leu Thr Arg Cys Thr Ser Val Ser
            180                 185                 190

Val Met Met Asn Met Arg Thr Arg Arg Leu Ser Lys Ile Pro Gln Glu
        195                 200                 205

Val Arg Ala Glu Ile Asp Pro Leu Phe Ile Glu Lys Val Ala Val Lys
    210                 215                 220

Glu Gly Glu Ile Lys Lys Leu Gln Lys Leu Asn Asp Ser Thr Ala Asp
225                 230                 235                 240

Tyr Ile Gln Gly Gly Trp Thr Pro Arg Trp Asn Asp Leu Asp Val Asn
                245                 250                 255

Gln His Val Asn Asn Ile Ile Tyr Val Gly Trp Ile Phe Lys Ser Val
            260                 265                 270

Pro Asp Ser Ile Ser Glu Asn His His Leu Ser Ser Ile Thr Leu Glu
        275                 280                 285

Tyr Arg Arg Glu Cys Thr Arg Gly Asn Lys Leu Gln Ser Leu Thr Thr
    290                 295                 300

Val Cys Gly Gly Ser Ser Glu Ala Gly Ile Ile Cys Glu His Leu Leu
305                 310                 315                 320

Gln Leu Glu Asp Gly Ser Glu Val Leu Arg Ala Arg Thr Glu Trp Arg
                325                 330                 335

Pro Lys His Thr Asp Ser Phe Gln Gly Ile Ser Glu Arg Phe Pro Gln
            340                 345                 350

Gln Glu Pro His Lys
```

-continued

355

<210> SEQ ID NO 5
<211> LENGTH: 1074
<212> TYPE: DNA
<213> ORGANISM: Cinnamomum camphora

<400> SEQUENCE: 5

```
atggtcacca cctctttagc ttccgcttac ttctcgatga aagctgtaat gttggctcct     60
gacggcaggg gcataaagcc caggagcagt ggtttgcagg tgagggcggg aaatgaacga    120
aactcttgca aggtgatcaa tgggaccaag gtcaaagaca cggagggctt gaaagggtgc    180
agcacgttgc aaggccagag catgcttgat gaccattttg gtctgcatgg gctagttttc    240
aggcgcacct ttgcaatcag atgctatgag gttggacctg accgctccac atccataatg    300
gctgttatga atcacttgca ggaagctgca cgtaatcatg cggagagtct gggacttcta    360
ggagatggat tcggtgagac actggagatg agtaagagag atctgatatg ggttgtgaga    420
cgcacgcatg ttgctgtgga acggtaccct gcttggggcg atactgttga agtcgaggcc    480
tgggtgggtg catcaggtaa cactggcatg cgccgcgatt tccttgtccg cgactgcaaa    540
actggccaca ttcttacaag atgtaccagt gtttcagtga tgatgaatat gaggacaagg    600
agattgtcca aaattcccca agaagttaga gcggagattg accctctttt cattgaaaag    660
gttgctgtca aggaagggga aattaaaaaa ttacagaagt tgaatgatag cactgcagat    720
tacattcaag gggttggac tcctcgatgg aatgatttgg atgtcaatca gcacgtgaac    780
aatatcatat acgttggctg gattttttaag agcgtcccag actctatctc tgagaatcat    840
catctttcta gcatcactct cgaatacagg agagagtgca caaggggcaa caagctgcag    900
tccctgacca ctgtttgtgg tggctcgtcg gaagctggga tcatatgtga gcacctactc    960
cagcttgagg atgggtctga ggttttgagg gcaagaacag agtggaggcc caagcacacc   1020
gatagtttcc aaggcattag tgagagattc ccgcagcaag aaccgcataa gtaa         1074
```

<210> SEQ ID NO 6
<211> LENGTH: 1074
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
atggtgacca cctccctggc ctccgcctac ttctccatga aggccgtgat gctggccccc     60
gacggccgcg gcatcaagcc ccgctcctcc ggcctgcagg tgcgcgccgg caacgagcgc    120
aactcctgca aggtgatcaa cggcaccaag gtgaaggaca ccgagggcct gaagggctgc    180
tccaccctgc agggccagtc catgctggac gaccacttcg gcctgcacgg cctggtgttc    240
cgccgcacct tcgccatccg ctgctacgag gtgggccccg accgctccac ctccatcatg    300
gccgtgatga accacctgca ggaggccgcc cgcaaccacg ccgagtccct gggcctgctg    360
ggcgacggct tcggcgagac cctggagatg tccaagcgcg acctgatctg ggtggtgcgc    420
cgcacccacg tggccgtgga gcgctacccc gcctggggcg acaccgtgga ggtggaggcc    480
tgggtgggcg cctccggcaa caccggcatg cgccgcgact tcctggtgcg cgactgcaag    540
accggccaca tcctgacccg ctgcacctcc gtgtccgtga tgatgaacat gcgcacccgc    600
cgcctgtcca agatccccca ggaggtgcgc gccgagatcg acccccctgtt catcgagaag    660
```

-continued gtggccgtga aggagggcga gatcaagaag ctgcagaagc tgaacgactc caccgccgac 720
tacatccagg gcggctggac cccccgctgg aacgacctgg acgtgaacca gcacgtgaac 780
aacatcatct acgtgggctg gatcttcaag tccgtgcccg actccatctc cgagaaccac 840
cacctgtcct ccatcaccct ggagtaccgc cgcgagtgca cccgcggcaa caagctgcag 900
tccctgacca ccgtgtgcgg cggctcctcc gaggccggca tcatctgcga gcacctgctg 960
cagctggagg acggctccga ggtgctgcgc gcccgcaccg agtggcgccc caagcacacc 1020
gactccttcc agggcatctc cgagcgcttc ccccagcagg agccccacaa gtga 1074

<210> SEQ ID NO 7
<211> LENGTH: 419
<212> TYPE: PRT
<213> ORGANISM: Cinnamomum camphora

<400> SEQUENCE: 7

Met Val Ala Thr Ala Ala Ala Ser Ala Phe Phe Pro Val Gly Ala Pro
1 5 10 15

Ala Thr Ser Ser Ala Thr Ser Ala Lys Ala Ser Met Met Pro Asp Asn
20 25 30

Leu Asp Ala Arg Gly Ile Lys Pro Lys Pro Ala Ser Ser Ser Gly Leu
35 40 45

Gln Val Lys Ala Asn Ala His Ala Ser Pro Lys Ile Asn Gly Ser Lys
50 55 60

Val Ser Thr Asp Thr Leu Lys Gly Glu Asp Thr Leu Thr Ser Ser Pro
65 70 75 80

Ala Pro Arg Thr Phe Ile Asn Gln Leu Pro Asp Trp Ser Met Phe Leu
85 90 95

Ala Ala Ile Thr Thr Ile Phe Leu Ala Ala Glu Lys Gln Trp Thr Asn
100 105 110

Leu Asp Trp Lys Pro Arg Arg Pro Asp Met Leu Ala Asp Pro Phe Gly
115 120 125

Ile Gly Arg Phe Met Gln Asp Gly Leu Ile Phe Arg Gln His Phe Ala
130 135 140

Ile Arg Ser Tyr Glu Ile Gly Ala Asp Arg Thr Ala Ser Ile Glu Thr
145 150 155 160

Leu Met Asn His Leu Gln Glu Thr Ala Leu Asn His Val Arg Ser Ala
165 170 175

Gly Leu Leu Gly Asp Gly Phe Gly Ala Thr Pro Glu Met Ser Arg Arg
180 185 190

Asp Leu Ile Trp Val Val Thr Arg Met Gln Val Leu Val Asp Arg Tyr
195 200 205

Pro Ala Trp Gly Asp Ile Val Glu Val Glu Thr Trp Val Gly Ala Ser
210 215 220

Gly Lys Asn Gly Met Arg Arg Asp Trp Leu Val Arg Asp Ser Gln Thr
225 230 235 240

Gly Glu Ile Leu Thr Arg Ala Thr Ser Val Trp Val Met Met Asn Lys
245 250 255

Arg Thr Arg Arg Leu Ser Lys Leu Pro Glu Glu Val Arg Gly Glu Ile
260 265 270

Gly Pro Tyr Phe Ile Glu Asp Val Ala Ile Ile Glu Glu Asp Asn Arg
275 280 285

Lys Leu Gln Lys Leu Asn Glu Asn Thr Ala Asp Asn Val Arg Arg Gly
290 295 300

```
Leu Thr Pro Arg Trp Ser Asp Leu Asp Val Asn Gln His Val Asn Asn
305                 310                 315                 320

Val Lys Tyr Ile Gly Trp Ile Leu Glu Ser Ala Pro Gly Ser Ile Leu
                325                 330                 335

Glu Ser His Glu Leu Ser Cys Met Thr Leu Glu Tyr Arg Arg Glu Cys
            340                 345                 350

Gly Lys Asp Ser Val Leu Gln Ser Met Thr Ala Val Ser Gly Gly Gly
        355                 360                 365

Ser Ala Ala Gly Gly Ser Pro Glu Ser Ser Val Glu Cys Asp His Leu
    370                 375                 380

Leu Gln Leu Glu Ser Gly Pro Glu Val Val Arg Gly Arg Thr Glu Trp
385                 390                 395                 400

Arg Pro Lys Ser Ala Asn Asn Ser Arg Ser Ile Leu Glu Met Pro Ala
                405                 410                 415

Glu Ser Leu


<210> SEQ ID NO 8
<211> LENGTH: 1254
<212> TYPE: DNA
<213> ORGANISM: Cinnamomum camphora

<400> SEQUENCE: 8

atggttgcca ccgctgctgc ttctgctttc ttcccggtcg gtgctccggc tacgtcatct      60

gcaacttcag ccaaagcgtc gatgatgcct gataatttgg atgccagagg catcaaaccg     120

aagccggctt cgtccagcgg cttgcaggtt aaggcaaatg cccatgcctc tcccaagatt     180

aatggttcca aggtgagcac ggataccttg aagggggaag acaccttaac ttcctcgccc     240

gccccacgga cctttatcaa ccaattgcct gactggagca tgttccttgc tgccatcaca     300

actattttct tggctgccga gaagcagtgg acgaatctcg actggaagcc cagaagaccc     360

gacatgcttg ctgacccgtt tggcatcggg aggtttatgc aggatgggct gattttcagg     420

cagcactttg caatcagatc ttatgagatt ggggctgata gaacggcgtc tatagagact     480

ttaatgaatc acttgcagga gactgcactt aatcatgtga ggagtgctgg actcctaggt     540

gatggatttg gtgcgacacc tgagatgagt agaagagatc tgatatgggt tgtaacacgt     600

atgcaggttc ttgtggaccg ctaccctgct tggggtgata ttgttgaagt agagacctgg     660

gttggtgcat ctggaaaaaa tggtatgcgc cgtgattggc ttgttcggga cagccaaact     720

ggtgaaattc tcacacgagc taccagtgtt tgggtgatga tgaataaacg gacaaggcga     780

ttgtccaaac ttcctgaaga agttagaggg gaaatagggc cttattttat agaagatgtt     840

gctatcatag aggaggacaa caggaaacta cagaagctca atgaaaacac tgctgataat     900

gttcgaaggg gtttgactcc tcgctggagt gatctggatg ttaatcagca tgtgaacaat     960

gtcaaataca ttggttggat tcttgagagt gcaccaggat ccatcttgga gagtcatgag    1020

ctttcctgca tgacccttga atacaggaga gaatgtggga aggacagtgt gctgcagtca    1080

atgactgctg tctctggtgg aggcagtgca gcaggtggct caccagaatc tagcgttgag    1140

tgtgaccact tgctccagct agagagtggg cctgaagttg tgaggggaag aaccgagtgg    1200

aggcccaaga gtgctaataa ctcgaggagc atcctggaga tgccggccga gagc          1254


<210> SEQ ID NO 9
<211> LENGTH: 1260
<212> TYPE: DNA
<213> ORGANISM: Artificial Sequence
<220> FEATURE:
```

-continued

<223> OTHER INFORMATION: Description of Artificial Sequence: Synthetic
      polynucleotide

<400> SEQUENCE: 9

```
atggtggcca ccgccgccgc ctccgccttc ttccccgtgg gcgcccccgc cacctcctcc      60

gccacctccg ccaaggcctc catgatgccc gacaacctgg acgcccgcgg catcaagccc     120

aagcccgcct cctcctccgg cctgcaggtg aaggccaacg cccacgcctc ccccaagatc     180

aacggctcca aggtgtccac cgacaccctg aagggcgagg acaccctgac ctcctccccc     240

gcccccccgca ccttcatcaa ccagctgccc gactggtcca tgttcctggc cgccatcacc     300

accatcttcc tggccgccga gaagcagtgg accaacctgg actggaagcc ccgccgcccc     360

gacatgctgg ccgacccctt cggcatcggc cgcttcatgc aggacggcct gatcttccgc     420

cagcacttcg ccatccgctc ctacgagatc ggcgccgacc gcaccgcctc catcgagacc     480

ctgatgaacc acctgcagga gaccgccctg aaccacgtgc gctccgccgg cctgctgggc     540

gacggcttcg gcgccacccc cgagatgtcc cgccgcgacc tgatctgggt ggtgacccgc     600

atgcaggtgc tggtggaccg ctaccccgcc tggggcgaca tcgtggaggt ggagacctgg     660

gtgggcgcct ccggcaagaa cggcatgcgc cgcgactggc tggtgcgcga ctcccagacc     720

ggcgagatcc tgacccgcgc cacctccgtg tgggtgatga tgaacaagcg cacccgccgc     780

ctgtccaagc tgcccgagga ggtgcgcggc gagatcggcc cctacttcat cgaggacgtg     840

gccatcatcg aggaggacaa ccgcaagctg cagaagctga acgagaacac cgccgacaac     900

gtgcgccgcg gcctgacccc ccgctggtcc gacctggacg tgaaccagca cgtgaacaac     960

gtgaagtaca tcggctggat cctggagtcc gcccccggct ccatcctgga gtcccacgag    1020

ctgtcctgca tgaccctgga gtaccgccgc gagtgcggca aggactccgt gctgcagtcc    1080

atgaccgccg tgtccggcgg cggctccgcc gccggcggct cccccgagtc ctccgtggag    1140

tgcgaccacc tgctgcagct ggagtccggc cccgaggtgg tgcgcggccg caccgagtgg    1200

cgccccaagt ccgccaacaa ctcccgctcc atcctggaga tgcccgccga gtccctgtga    1260
```

<210> SEQ ID NO 10
<211> LENGTH: 361
<212> TYPE: PRT
<213> ORGANISM: Cuphea hyssopifolia

<400> SEQUENCE: 10

```
Met Val Ala Thr Asn Ala Ala Ala Phe Ser Ala Tyr Thr Phe Phe Leu
1               5                   10                  15

Thr Ser Pro Thr His Gly Tyr Ser Ser Lys Arg Leu Ala Asp Thr Gln
            20                  25                  30

Asn Gly Tyr Pro Gly Thr Ser Leu Lys Ser Lys Ser Thr Pro Pro Pro
        35                  40                  45

Ala Ala Ala Ala Ala Arg Asn Gly Ala Leu Pro Leu Leu Ala Ser Ile
    50                  55                  60

Cys Lys Cys Pro Lys Lys Ala Asp Gly Ser Met Gln Leu Asp Ser Ser
65                  70                  75                  80

Leu Val Phe Gly Phe Gln Phe Tyr Ile Arg Ser Tyr Glu Val Gly Ala
                85                  90                  95

Asp Gln Thr Val Ser Ile Gln Thr Val Leu Asn Tyr Leu Gln Glu Ala
            100                 105                 110

Ala Ile Asn His Val Gln Ser Ala Gly Tyr Phe Gly Asp Ser Phe Gly
        115                 120                 125
```

-continued

```
Ala Thr Pro Glu Met Thr Lys Arg Asn Leu Ile Trp Val Ile Thr Lys
    130                 135                 140

Met Gln Val Leu Val Asp Arg Tyr Pro Ala Trp Gly Asp Val Val Gln
145                 150                 155                 160

Val Asp Thr Trp Thr Cys Ser Ser Gly Lys Asn Ser Met Gln Arg Asp
                165                 170                 175

Trp Phe Val Arg Asp Leu Lys Thr Gly Asp Ile Ile Thr Arg Ala Ser
            180                 185                 190

Ser Val Trp Val Leu Met Asn Arg Leu Thr Arg Lys Leu Ser Lys Ile
        195                 200                 205

Pro Glu Ala Val Leu Glu Glu Ala Lys Leu Phe Val Met Asn Thr Ala
    210                 215                 220

Pro Thr Val Asp Asp Asn Arg Lys Leu Pro Lys Leu Asp Gly Ser Ser
225                 230                 235                 240

Ala Asp Tyr Val Leu Ser Gly Leu Thr Pro Arg Trp Ser Asp Leu Asp
                245                 250                 255

Met Asn Gln His Val Asn Asn Val Lys Tyr Ile Ala Trp Ile Leu Glu
            260                 265                 270

Ser Val Pro Gln Ser Ile Pro Glu Thr His Lys Leu Ser Ala Ile Thr
        275                 280                 285

Val Glu Tyr Arg Arg Glu Cys Gly Lys Asn Ser Val Leu Gln Ser Leu
    290                 295                 300

Thr Asn Val Ser Gly Asp Gly Ile Thr Cys Gly Asn Ser Ile Ile Glu
305                 310                 315                 320

Cys His His Leu Leu Gln Leu Glu Thr Gly Pro Glu Ile Leu Leu Ala
                325                 330                 335

Arg Thr Glu Trp Ile Ser Lys Glu Pro Gly Phe Arg Gly Ala Pro Ile
            340                 345                 350

Gln Ala Glu Lys Val Tyr Asn Asn Lys
        355                 360


<210> SEQ ID NO 11
<211> LENGTH: 1086
<212> TYPE: DNA
<213> ORGANISM: Cuphea hyssopifolia

<400> SEQUENCE: 11

atggttgcca ctaatgctgc tgccttttct gcttatactt tcttccttac ttcaccaact     60

catggttact cttccaaacg tctcgccgat actcaaaatg gttatccggg tacctccttg    120

aaatcgaaat ccactcctcc accagctgct gctgctgctc gtaacggtgc attgccactg    180

ctggcctcca tctgcaaatg ccccaaaaag gctgatggga gtatgcaact agacagctcc    240

ttggtcttcg ggtttcaatt ttacattaga tcatatgaag tgggtgcgga tcaaaccgtg    300

tcaatacaga cagtactcaa ttacttacag gaggcagcca tcaatcatgt tcagagtgct    360

ggctattttg gtgatagttt tggcgccacc ccggaaatga ccaagaggaa cctcatctgg    420

gttatcacta agatgcaggt tttggtggat cgctatcccg cttggggcga tgttgttcaa    480

gttgatacat ggacctgtag ttctggtaaa aacagcatgc agcgtgattg gttcgtacgg    540

gatctcaaaa ctggagatat tataacaaga gcctcgagcg tgtgggtgct gatgaataga    600

ctcaccagaa aattatcaaa aattcctgaa gcagttctgg aagaagcaaa actttttgtg    660

atgaacactg cccccaccgt agatgacaac aggaagctac caaagctgga tggcagcagt    720

gctgattatg tcctctctgg cttaactcct agatggagcg acttagatat gaaccagcat    780
```

gtcaacaatg tgaagtacat agcctggatc cttgagagtg tccctcagag cataccggag 840
acacacaagc tgtcagcgat aaccgtggag tacaggagag aatgtggcaa gaacagcgtc 900
ctccagtctc tgaccaacgt ctccggggat ggaatcacat gtggaaacag tattatcgag 960
tgccaccatt tgcttcaact tgagactggc ccagagattc tactagcgcg gacggagtgg 1020
atatccaagg aacctgggtt caggggagct ccaatccagg cagagaaagt ctacaacaac 1080
aaataa 1086

<210> SEQ ID NO 12
<211> LENGTH: 1086
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12
atggtggcca ccaacgccgc cgccttctcc gcctacacct tcttcctgac ctcccccacc 60
cacggctact cctccaagcg cctggccgac acccagaacg gctaccccgg cacctccctg 120
aagtccaagt ccaccccccc ccccgccgcc gccgccgccc gcaacggcgc cctgcccctg 180
ctggcctcca tctgcaagtg ccccaagaag gccgacggct ccatgcagct ggactcctcc 240
ctggtgttcg gcttccagtt ctacatccgc tcctacgagg tgggcgccga ccagaccgtg 300
tccatccaga ccgtgctgaa ctacctgcag gaggccgcca tcaaccacgt gcagtccgcc 360
ggctacttcg gcgactcctt cggcgccacc cccgagatga ccaagcgcaa cctgatctgg 420
gtgatcacca agatgcaggt gctggtggac cgctaccccg cctggggcga cgtggtgcag 480
gtggacacct ggacctgctc ctccggcaag aactccatgc agcgcgactg gttcgtgcgc 540
gacctgaaga ccggcgacat catcacccgc gcctcctccg tgtgggtgct gatgaaccgc 600
ctgacccgca agctgtccaa gatccccgag gccgtgctgg aggaggccaa gctgttcgtg 660
atgaacaccg cccccaccgt ggacgacaac cgcaagctgc ccaagctgga cggctcctcc 720
gccgactacg tgctgtccgg cctgaccccc cgctggtccg acctggacat gaaccagcac 780
gtgaacaacg tgaagtacat cgcctggatc ctggagtccg tgccccagtc catccccgag 840
acccacaagc tgtccgccat caccgtggag taccgccgcg agtgcggcaa gaactccgtg 900
ctgcagtccc tgaccaacgt gtccggcgac ggcatcacct gcggcaactc catcatcgag 960
tgccaccacc tgctgcagct ggagaccggc cccgagatcc tgctggcccg caccgagtgg 1020
atctccaagg agcccggctt ccgcggcgcc cccatccagg ccgagaaggt gtacaacaac 1080
aagtga 1086

<210> SEQ ID NO 13
<211> LENGTH: 415
<212> TYPE: PRT
<213> ORGANISM: Cuphea hyssopifolia

<400> SEQUENCE: 13

Met Val Ala Thr Ala Ala Ser Ser Ala Phe Phe Pro Val Pro Ser Pro
1 5 10 15

Asp Ala Ser Ser Arg Pro Gly Lys Leu Gly Asn Gly Ser Ser Ser Leu
20 25 30

Ser Pro Leu Lys Pro Lys Leu Met Ala Asn Gly Gly Leu Gln Val Lys
35 40 45

Ala Asn Ala Ser Ala Pro Pro Lys Ile Asn Gly Ser Ser Val Gly Leu

-continued

```
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Leu Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg His Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Ser Gly Ser Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Pro Ile Ala Ser Gly Glu Thr Ser Pro Gly Asp Ser Ser
                405                 410                 415


<210> SEQ ID NO 14
<211> LENGTH: 1248
<212> TYPE: DNA
<213> ORGANISM: Cuphea hyssopifolia

<400> SEQUENCE: 14

atggtggcta ccgctgcaag ttcagcattc ttccctgtgc cgtcccccga cgcctcctct      60

agacctggaa agctcggcaa tggtcatcg agcttgagcc ccctcaagcc caaattgatg    120
```

gccaatggcg ggttgcaggt taaggcaaac gccagtgccc ctcctaagat caatggttct 180
tcggtcggtc taaagtccgg cagtctcaag actcaggaag acactccttc ggcgcctcct 240
ccccggactt ttattaacca gctgcctgat tggagtatgc ttcttgctgc aatcactact 300
gtcttcttgg cagcagagaa gcagtggatg atgcttgatt ggaaacccaa gaggcctgac 360
atgcttgtgg acccgttcgg attgggaagg attgttcaag atgggcttgt gttcaggcag 420
aatttttcga ttaggtccta tgaaataggc gctgatcgca ctgcgtctat agagacggtg 480
atgaaccact tgcaggaaac agctctcaat catgttaaga gtgctgggct tcttaatgac 540
ggctttggtc gtactcttga gatgtataaa agggacctta tttgggttgt tgcaaaaatg 600
caggtcatgg ttaaccgcta tcctacttgg ggcgacacgg ttgaagtgaa tacttgggtt 660
gccaagtcag ggaaaaatgg tatgcgtcgt gattggctca taagtgattg caatacagga 720
gaaattctta ctagagcatc aagtgtgtgg gtcatgatga atcaaaagac aagaagattg 780
tcaaaaattc cagatgaggt tcgacatgag atagagcctc atttcgtgga ctctgctccc 840
gtcattgaag atgatgaccg gaaacttccc aagctggatg agaagactgc tgactccatc 900
cgcaagggtc taactccgaa gtggaatgac ttggatgtca atcagcacgt caacaacgtg 960
aagtacattg ggtggattct tgagagtact ccaccagaag ttctggagac ccaggagtta 1020
tgttccctta ccctggaata taggcgggaa tgcggaaggg agagcgtgct ggagtccctc 1080
actgctgtgg acccctctgg aaagggctct gggtctcagt tccagcacct tctgcggctt 1140
gaggatggag gtgagattgt gaaggggaga actgagtggc gacccaagac tgcaggaatc 1200
aatgggccaa tagcatccgg ggagacctca cctggagact cttcttag 1248

<210> SEQ ID NO 15
<211> LENGTH: 1248
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15
atggtggcca ccgccgcctc ctccgccttc ttccccgtgc cctcccccga cgcctcctcc 60
cgccccggca agctgggcaa cggctcctcc tccctgtccc ccctgaagcc caagctgatg 120
gccaacggcg gcctgcaggt gaaggccaac gcctccgccc cccccaagat caacggctcc 180
tccgtgggcc tgaagtccgg ctccctgaag acccaggagg acaccccctc cgcccccccc 240
ccccgcacct tcatcaacca gctgcccgac tggtccatgc tgctggccgc catcaccacc 300
gtgttcctgg ccgccgagaa gcagtggatg atgctggact ggaagcccaa gcgccccgac 360
atgctggtgg accccttcgg cctgggccgc atcgtgcagg acggcctggt gttccgccag 420
aacttctcca tccgctccta cgagatcggc gccgaccgca ccgcctccat cgagaccgtg 480
atgaaccacc tgcaggagac cgccctgaac cacgtgaagt ccgccggcct gctgaacgac 540
ggcttcggcc gcaccctgga gatgtacaag cgcgacctga tctgggtggt ggccaagatg 600
caggtgatgg tgaaccgcta ccccacctgg ggcgacaccg tggaggtgaa cacctgggtg 660
gccaagtccg gcaagaacgg catgcgccgc gactggctga tctccgactg caacaccggc 720
gagatcctga cccgcgcctc ctccgtgtgg gtgatgatga accagaagac ccgccgcctg 780
tccaagatcc ccgacgaggt gcgccacgag atcgagcccc acttcgtgga ctccgccccc 840
gtgatcgagg acgacgaccg caagctgccc aagctggacg agaagaccgc cgactccatc 900

```
cgcaagggcc tgacccccaa gtggaacgac ctggacgtga accagcacgt gaacaacgtg    960

aagtacatcg gctggatcct ggagtccacc ccccccgagg tgctggagac ccaggagctg   1020

tgctccctga ccctggagta ccgccgcgag tgcggccgcg agtccgtgct ggagtccctg   1080

accgccgtgg accccctccgg caagggctcc ggctcccagt tccagcacct gctgcgcctg   1140

gaggacggcg gcgagatcgt gaagggccgc accgagtggc gccccaagac cgccggcatc   1200

aacggcccca tcgcctccgg cgagacctcc cccggcgact cctcctga                 1248


<210> SEQ ID NO 16
<211> LENGTH: 427
<212> TYPE: PRT
<213> ORGANISM: Cuphea hyssopifolia

<400> SEQUENCE: 16

Met Val Ala Thr Ala Ala Ser Ser Ala Phe Phe Pro Val Pro Ser Pro
1               5                   10                  15

Asp Ala Ser Ser Arg Pro Gly Lys Leu Gly Asn Gly Ser Ser Ser Leu
            20                  25                  30

Ser Pro Leu Lys Pro Lys Leu Met Ala Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Leu Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Lys Ser Gln Ile Met Leu Pro Leu
                245                 250                 255

His Tyr Cys Ser Val Trp Val Met Met Asn Gln Lys Thr Arg Arg Leu
            260                 265                 270

Ser Lys Ile Pro Asp Glu Val Arg His Glu Ile Glu Pro His Phe Val
        275                 280                 285

Asp Ser Ala Pro Val Ile Glu Asp Asp Asp Arg Lys Leu Pro Lys Leu
    290                 295                 300

Asp Glu Lys Thr Ala Asp Ser Ile Arg Lys Gly Leu Thr Pro Lys Trp
```

```
305                 310                 315                 320

Asn Asp Leu Asp Val Asn Gln His Val Asn Asn Val Lys Tyr Ile Gly
                325                 330                 335

Trp Ile Leu Glu Ser Thr Pro Pro Glu Val Leu Glu Thr Gln Glu Leu
            340                 345                 350

Cys Ser Leu Thr Leu Glu Tyr Arg Arg Glu Cys Gly Arg Glu Ser Val
        355                 360                 365

Leu Glu Ser Leu Thr Ala Val Asp Pro Ser Gly Lys Gly Ser Gly Ser
    370                 375                 380

Gln Phe Gln His Leu Leu Arg Leu Glu Asp Gly Gly Glu Ile Val Lys
385                 390                 395                 400

Gly Arg Thr Glu Trp Arg Pro Lys Thr Ala Gly Ile Asn Gly Pro Ile
                405                 410                 415

Ala Ser Gly Glu Thr Ser Pro Gly Asp Ser Ser
            420                 425
```

<210> SEQ ID NO 17
<211> LENGTH: 1284
<212> TYPE: DNA
<213> ORGANISM: Cuphea hyssopifolia

<400> SEQUENCE: 17

```
atggtggcta ccgctgcaag ttcagcattc ttccctgtgc cgtcccccga cgcctcctct      60

agacctggaa agctcggcaa tgggtcatcg agcttgagcc ccctcaagcc caaattgatg     120

gccaatggcg ggttgcaggt taaggcaaac gccagtgccc ctcctaagat caatggttct     180

tcggtcggtc taaagtccgg cagtctcaag actcaggaag acactccttc ggcgcctcct     240

ccccggactt ttattaacca gctgcctgat tggagtatgc ttcttgctgc aatcactact     300

gtcttcttgg cagcagagaa gcagtggatg atgcttgatt ggaaacccaa gaggcctgac     360

atgcttgtgg acccgttcgg attgggaagg attgttcaag atgggcttgt gttcaggcag     420

aatttttcga ttaggtccta tgaaataggc gctgatcgca ctgcgtctat agagacggtg     480

atgaaccact tgcaggaaac agctctcaat catgttaaga gtgctgggct tcttaatgac     540

ggctttggtc gtactcttga gatgtataaa agggacctta tttgggttgt tgcaaaaatg     600

caggtcatgg ttaaccgcta tcctacttgg ggcgacacgg ttgaagtgaa tacttgggtt     660

gccaagtcag ggaaaaatgg tatgcgtcgt gattggctca taagtgattg caatacagga     720

gaaattctta ctagagcatc aagtaaaagc caaattatgt taccccttaca ttattgcagt     780

gtgtgggtca tgatgaatca aaagacaaga agattgtcaa aaattccaga tgaggttcga     840

catgagatag agcctcattt cgtggactct gctcccgtca ttgaagatga tgaccggaaa     900

cttcccaagc tggatgagaa gactgctgac tccatccgca agggtctaac tccgaagtgg     960

aatgacttgg atgtcaatca gcacgtcaac aacgtgaagt acattgggtg gattcttgag    1020

agtactccac cagaagttct ggagacccag gagttatgtt cccttaccct ggaatatagg    1080

cgggaatgcg gaagggagag cgtgctggag tccctcactg ctgtggaccc ctctggaaag    1140

ggctctgggt ctcagttcca gcaccttctg cggcttgagg atggaggtga gattgtgaag    1200

ggagaactg agtggcgacc caagactgca ggaatcaatg ggccaatagc atccggggag    1260

acctcacctg gagactcttc ttag                                           1284
```

<210> SEQ ID NO 18
<211> LENGTH: 1284
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 18
atggtggcca ccgccgcctc ctccgccttc ttccccgtgc cctcccccga cgcctcctcc 60
cgccccggca agctgggcaa cggctcctcc tccctgtccc ccctgaagcc caagctgatg 120
gccaacggcg gcctgcaggt gaaggccaac gcctccgccc cccccaagat caacggctcc 180
tccgtgggcc tgaagtccgg ctccctgaag acccaggagg acaccccctc cgcccccccc 240
ccccgcacct tcatcaacca gctgcccgac tggtccatgc tgctggccgc catcaccacc 300
gtgttcctgg ccgccgagaa gcagtggatg atgctggact ggaagcccaa gcgccccgac 360
atgctggtgg acccccttcgg cctgggccgc atcgtgcagg acggcctggt gttccgccag 420
aacttctcca tccgctccta cgagatcggc gccgaccgca ccgcctccat cgagaccgtg 480
atgaaccacc tgcaggagac cgccctgaac cacgtgaagt ccgccggcct gctgaacgac 540
ggcttcggcc gcaccctgga gatgtacaag cgcgacctga tctgggtggt ggccaagatg 600
caggtgatgg tgaaccgcta ccccacctgg ggcgacaccg tggaggtgaa cacctgggtg 660
gccaagtccg gcaagaacgg catgcgccgc gactggctga tctccgactg caacaccggc 720
gagatcctga cccgcgcctc ctccaagtcc cagatcatgc tgcccctgca ctactgctcc 780
gtgtgggtga tgatgaacca gaagacccgc cgcctgtcca agatccccga cgaggtgcgc 840
cacgagatcg agccccactt cgtggactcc gcccccgtga tcgaggacga cgaccgcaag 900
ctgcccaagc tggacgagaa gaccgccgac tccatccgca agggcctgac ccccaagtgg 960
aacgacctgg acgtgaacca gcacgtgaac aacgtgaagt acatcggctg gatcctggag 1020
tccacccccc ccgaggtgct ggagacccag gagctgtgct ccctgaccct ggagtaccgc 1080
cgcgagtgcg gccgcgagtc cgtgctggag tccctgaccg ccgtggaccc ctccggcaag 1140
ggctccggct cccagttcca gcacctgctg cgcctggagg acggcggcga gatcgtgaag 1200
ggccgcaccg agtggcgccc caagaccgcc ggcatcaacg gccccatcgc ctccggcgag 1260
acctcccccg gcgactcctc ctga 1284

<210> SEQ ID NO 19
<211> LENGTH: 417
<212> TYPE: PRT
<213> ORGANISM: Cuphea hyssopifolia

<400> SEQUENCE: 19

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Pro Asp Met Leu Met Asp Pro Phe
115 120 125

Gly Val Asp Arg Val Val Gln Asp Gly Ala Val Phe Arg Gln Ser Phe
130 135 140

Ser Ile Arg Ser Tyr Glu Ile Gly Ala Asp Arg Thr Ala Ser Ile Glu
145 150 155 160

Thr Leu Met Asn Ile Phe Gln Glu Thr Ser Leu Asn His Cys Lys Ser
165 170 175

Ile Gly Leu Leu Asn Asp Gly Phe Gly Arg Thr Pro Glu Met Cys Lys
180 185 190

Arg Asp Leu Ile Trp Val Val Thr Lys Met His Val Glu Val Asn Arg
195 200 205

Tyr Pro Thr Trp Gly Asp Thr Ile Glu Val Asn Thr Trp Val Ser Glu
210 215 220

Ser Gly Lys Thr Gly Met Gly Arg Asp Trp Leu Ile Ser Asp Cys His
225 230 235 240

Thr Gly Glu Ile Leu Ile Arg Ala Thr Ser Met Cys Ala Met Met Asn
245 250 255

Gln Lys Thr Arg Arg Phe Ser Lys Phe Pro Tyr Glu Val Arg Gln Glu
260 265 270

Leu Ala Pro His Phe Val Asp Ser Ala Pro Val Ile Glu Asp Tyr Gln
275 280 285

Lys Leu His Lys Leu Asp Val Lys Thr Gly Asp Ser Ile Cys Asn Gly
290 295 300

Leu Thr Pro Arg Trp Asn Asp Leu Asp Val Asn Gln His Val Asn Asn
305 310 315 320

Val Lys Tyr Ile Gly Trp Ile Leu Glu Ser Val Pro Thr Glu Val Phe
325 330 335

Glu Thr Gln Glu Leu Cys Gly Leu Thr Leu Glu Tyr Arg Arg Glu Cys
340 345 350

Gly Arg Asp Ser Val Leu Glu Ser Val Thr Ala Met Asp Pro Ser Lys
355 360 365

Glu Gly Asp Arg Ser Leu Tyr Gln His Leu Leu Arg Leu Glu Asp Gly
370 375 380

Ala Asp Ile Ala Lys Gly Arg Thr Lys Trp Arg Pro Lys Asn Ala Gly
385 390 395 400

Thr Asn Gly Ala Ile Ser Thr Gly Lys Thr Ser Asn Gly Asn Ser Ile
405 410 415

Ser

<210> SEQ ID NO 20
<211> LENGTH: 1254
<212> TYPE: DNA
<213> ORGANISM: Cuphea hyssopifolia

<400> SEQUENCE: 20
atggtggctg ccgaagcaag ttctgcactc ttctccgttc gaaccccggg aacctcccct 60
aaacccggga agttcgggaa ttggccaacg agcttgagcg tccccttcaa gtccaaatca 120
aaccacaatg gcggctttca ggttaaggca aacgccagtg cccgtcctaa ggctaacggt 180
tctgcagtaa gtctaaagtc tggcagcctc gacactcagg aggacacttc atcgtcgtcc 240
tctcctcctc ggactttcat taaccagttg cccgactgga gtatgctgct gtccgcgatc 300
acgaccgtct tcgtggcggc tgagaagcag tggacgatgc ttgatcggaa atctaagagg 360

-continued cccgacatgc tcatggaccc gtttggggtt gacagggttg ttcaggatgg ggctgtgttc 420
agacagagtt tttcgattag gtcttacgaa ataggcgctg atcgaacagc ctctatagag 480
acgctgatga acatcttcca ggaaacatct ctcaatcatt gtaagagtat cggtcttctc 540
aatgacggct ttggtcgtac tcctgagatg tgtaagaggg acctcatttg ggtggttaca 600
aaaatgcacg tcgaggttaa tcgctatcct acttggggtg atactatcga ggtcaatact 660
tgggtctccg agtcggggaa aaccggtatg ggtcgtgatt ggctgataag tgattgtcat 720
acaggagaaa ttctaataag agcaacgagc atgtgtgcta tgatgaatca aaagacgaga 780
agattctcaa aatttccata tgaggttcga caggagttgg cgcctcattt tgtggactct 840
gctcctgtca ttgaagacta tcaaaaattg cacaagcttg atgtgaagac gggtgattcc 900
atttgcaatg gcctaactcc aaggtggaat gacttggatg tcaatcagca cgttaacaat 960
gtgaagtaca ttgggtggat tctcgagagt gttccaacgg aagttttcga gacccaggag 1020
ctatgtggcc tcacccttga gtataggcgg gaatgcggaa gggacagtgt gctggagtcc 1080
gtgaccgcta tggatccatc aaaagaggga gacagatctc tgtaccagca ccttcttcgg 1140
cttgaggatg gggctgatat cgcgaagggc agaaccaagt ggcggccgaa gaatgcagga 1200
accaatgggg caatatcaac aggaaagact tcaaatggaa actcgatctc ttag 1254

<210> SEQ ID NO 21
<211> LENGTH: 1254
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 21
atggtggccg ccgaggcctc ctccgccctg ttctccgtgc gcacccccgg cacctccccc 60
aagcccggca agttcggcaa ctggcccacc tccctgtccg tgcccttcaa gtccaagtcc 120
aaccacaacg gcggcttcca ggtgaaggcc aacgcctccg cccgccccaa ggccaacggc 180
tccgccgtgt ccctgaagtc cggctccctg gacacccagg aggacacctc ctcctcctcc 240 tcccccccc gcaccttcat caaccagctg cccgactggt ccatgctgct gtccgccatc 300
accaccgtgt tcgtggccgc cgagaagcag tggaccatgc tggaccgcaa gtccaagcgc 360
cccgacatgc tgatggaccc cttcggcgtg gaccgcgtgg tgcaggacgg cgccgtgttc 420
cgccagtcct tctccatccg ctcctacgag atcggcgccg accgcaccgc ctccatcgag 480
accctgatga acatcttcca ggagacctcc ctgaaccact gcaagtccat cggcctgctg 540
aacgacggct tcggccgcac ccccgagatg tgcaagcgcg acctgatctg ggtggtgacc 600
aagatgcacg tggaggtgaa ccgctacccc acctggggcg acaccatcga ggtgaacacc 660
tgggtgtccg agtccggcaa gaccggcatg ggccgcgact ggctgatctc cgactgccac 720
accggcgaga tcctgatccg cgccacctcc atgtgcgcca tgatgaacca gaagacccgc 780
cgcttctcca agttccccta cgaggtgcgc caggagctgg ccccccactt cgtggactcc 840 gccccgtga tcgaggacta ccagaagctg cacaagctgg acgtgaagac cggcgactcc 900
atctgcaacg gcctgacccc ccgctggaac gacctggacg tgaaccagca cgtgaacaac 960
gtgaagtaca tcggctggat cctggagtcc gtgcccaccg aggtgttcga gacccaggag 1020
ctgtgcggcc tgaccctgga gtaccgccgc gagtgcggcc gcgactccgt gctggagtcc 1080
gtgaccgcca tggacccctc caaggagggc gaccgctccc tgtaccagca cctgctgcgc 1140
ctggaggacg gcgccgacat cgccaagggc cgcaccaagt ggcgccccaa gaacgccggc 1200
accaacggcg ccatctccac cggcaagacc tccaacggca actccatctc ctga 1254

<210> SEQ ID NO 22
<211> LENGTH: 417
<212> TYPE: PRT
<213> ORGANISM: Cuphea hyssopifolia

<400> SEQUENCE: 22

Met Val Ala Ala Glu Ala Ser Ser Ala Leu Phe Ser Val Arg Thr Pro
1 5 10 15

Gly Thr Ser Pro Lys Pro Gly Lys Phe Gly Asn Trp Pro Thr Ser Leu
20 25 30

Ser Val Pro Phe Lys Ser Lys Ser Asn His Asn Gly Gly Phe Gln Val
35 40 45

Lys Ala Asn Ala Ser Ala Arg Pro Lys Ala Asn Gly Ser Ala Val Ser
50 55 60

Leu Lys Ser Gly Ser Leu Asp Thr Gln Glu Asp Thr Ser Ser Ser Ser
65 70 75 80

Ser Pro Pro Arg Thr Phe Ile Asn Gln Leu Pro Asp Trp Ser Met Leu
85 90 95

Leu Ser Ala Ile Thr Thr Val Phe Val Ala Ala Glu Lys Gln Trp Thr
100 105 110

Met Leu Asp Arg Lys Ser Lys Arg Pro Asp Met Leu Met Asp Pro Phe
115 120 125

Gly Val Asp Arg Val Val Gln Asp Gly Ala Val Phe Arg Gln Ser Phe
130 135 140

Ser Ile Arg Ser Tyr Glu Ile Gly Ala Asp Arg Thr Ala Ser Ile Glu
145 150 155 160

Thr Leu Met Asn Ile Phe Gln Glu Thr Ser Leu Asn His Cys Lys Ser
165 170 175

Ile Gly Leu Leu Asn Asp Gly Phe Gly Arg Thr Pro Glu Met Cys Lys
180 185 190

Arg Asp Leu Ile Trp Val Val Thr Lys Met His Ile Glu Val Asn Arg
195 200 205

Tyr Pro Thr Trp Gly Asp Thr Ile Glu Val Asn Thr Trp Val Ser Glu
210 215 220

Ser Gly Lys Thr Gly Met Gly Arg Asp Trp Leu Ile Ser Asp Phe His
225 230 235 240

Thr Gly Asp Ile Leu Ile Arg Ala Thr Ser Val Cys Ala Met Met Asn
245 250 255

Gln Lys Thr Arg Arg Phe Ser Lys Phe Pro Tyr Glu Val Arg Gln Glu
260 265 270

Leu Ala Pro His Phe Val Asp Ser Ala Pro Val Ile Glu Asp Tyr Gln
275 280 285

Lys Leu His Lys Leu Asp Val Lys Thr Gly Asp Ser Ile Cys Asn Gly
290 295 300

Leu Thr Pro Arg Trp Asn Asp Leu Asp Val Asn Gln His Val Asn Asn
305 310 315 320

Val Lys Tyr Ile Gly Trp Ile Leu Glu Ser Val Pro Thr Glu Val Phe
325 330 335

Glu Thr Gln Glu Leu Cys Gly Leu Thr Leu Glu Tyr Arg Arg Glu Cys
340 345 350

-continued

```
Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Ala Asp Ile Ala Lys Gly Arg Thr Lys Trp Arg Pro Lys Asn Ala Gly
385                 390                 395                 400

Thr Asn Gly Ala Ile Ser Thr Gly Lys Thr Ser Asn Gly Asn Ser Ile
                405                 410                 415

Ser


<210> SEQ ID NO 23
<211> LENGTH: 1254
<212> TYPE: DNA
<213> ORGANISM: Cuphea hyssopifolia

<400> SEQUENCE: 23

atggtggctg ccgaagcaag ttctgcactc ttctccgttc gaaccccggg aacctcccct      60

aaacccggga agttcgggaa ttggccaacg agcttgagcg tccccttcaa gtccaaatca     120

aaccacaatg gcggctttca ggttaaggca aacgccagtg cccgtcctaa ggctaacggt     180

tctgcagtaa gtctaaagtc tggcagcctc gacactcagg aggacacttc atcgtcgtcc     240

tctcctcctc ggactttcat taaccagttg cccgactgga gtatgctgct gtccgcgatc     300

acgaccgtct tcgtggcggc tgagaagcag tggacgatgc ttgatcggaa atctaagagg     360

cccgacatgc tcatggaccc gtttggggtt gacagggttg ttcaggatgg ggctgtgttc     420

agacagagtt tttcgattag gtcttacgaa ataggcgctg atcgaacagc ctctatagag     480

acgctgatga acatcttcca ggaaacatct ctcaatcatt gtaagagtat cggtcttctc     540

aatgacggct ttggtcgtac tcctgagatg tgtaagaggg acctcatttg ggtggttaca     600

aaaatgcaca tcgaggttaa tcgctatcct acttggggtg atactatcga ggtcaatact     660

tgggtctccg agtcggggaa aaccggtatg ggtcgtgatt ggctgataag tgattttcat     720

acaggagaca ttctaataag agcaacgagc gtgtgtgcta tgatgaatca aaagacgaga     780

agattctcaa aatttccata tgaggttcga caggagttag cgcctcattt tgtggactct     840

gctccagtca ttgaagacta tcaaaaattg cacaagcttg atgtgaagac gggtgattcc     900

atttgcaatg gcctaactcc aaggtggaat gacttggatg tcaatcagca cgttaacaat     960

gtgaagtaca ttgggtggat tctcgagagt gttccaacgg aagttttcga gacccaggag    1020

ctatgtggcc tcacccttga gtataggcgg gaatgcggaa gggacagtgt gctggagtcc    1080

gtgaccgcta tggatccctc aaaagaggga gacagatctc tgtaccagca ccttcttcgg    1140

cttgaggatg gggctgatat cgcgaagggc agaaccaagt ggcggccgaa gaatgcagga    1200

accaatgggg caatatcaac aggaaagact tcaaatggaa actcgatctc ttag          1254


<210> SEQ ID NO 24
<211> LENGTH: 1254
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

atggtggccg ccgaggcctc ctccgccctg ttctccgtgc gcacccccgg cacctccccc      60

aagcccggca agttcggcaa ctggcccacc tccctgtccg tgcccttcaa gtccaagtcc     120
```

-continued

```
aaccacaacg gcggcttcca ggtgaaggcc aacgcctccg cccgccccaa ggccaacggc    180

tccgccgtgt ccctgaagtc cggctccctg gacacccagg aggacacctc ctcctcctcc    240

tcccccccc gcaccttcat caaccagctg cccgactggt ccatgctgct gtccgccatc    300

accaccgtgt tcgtggccgc cgagaagcag tggaccatgc tggaccgcaa gtccaagcgc    360

cccgacatgc tgatggaccc cttcggcgtg gaccgcgtgg tgcaggacgg cgccgtgttc    420

cgccagtcct tctccatccg ctcctacgag atcggcgccg accgcaccgc ctccatcgag    480

accctgatga acatcttcca ggagacctcc ctgaaccact gcaagtccat cggcctgctg    540

aacgacggct tcggccgcac ccccgagatg tgcaagcgcg acctgatctg ggtggtgacc    600

aagatgcaca tcgaggtgaa ccgctacccc acctggggcg acaccatcga ggtgaacacc    660

tgggtgtccg agtccggcaa gaccggcatg ggccgcgact ggctgatctc cgacttccac    720

accggcgaca tcctgatccg cgccacctcc gtgtgcgcca tgatgaacca gaagacccgc    780

cgcttctcca agttccccta cgaggtgcgc caggagctgg ccccccactt cgtggactcc    840

gcccccgtga tcgaggacta ccagaagctg cacaagctgg acgtgaagac cggcgactcc    900

atctgcaacg gcctgacccc ccgctggaac gacctggacg tgaaccagca cgtgaacaac    960

gtgaagtaca tcggctggat cctggagtcc gtgcccaccg aggtgttcga gacccaggag   1020

ctgtgcggcc tgaccctgga gtaccgccgc gagtgcggcc gcgactccgt gctggagtcc   1080

gtgaccgcca tggacccctc caaggagggc gaccgctccc tgtaccagca cctgctgcgc   1140

ctggaggacg gcgccgacat cgccaagggc cgcaccaagt ggcgccccaa gaacgccggc   1200

accaacggcg ccatctccac cggcaagacc tccaacggca actccatctc ctga         1254
```

```
<210> SEQ ID NO 25
<211> LENGTH: 419
<212> TYPE: PRT
<213> ORGANISM: Cuphea sp.

<400> SEQUENCE: 25

Met Val Val Ala Ala Ala Thr Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Thr Phe Lys Pro Lys Ser Ile Pro Asn Ala Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Cys Ile Val Arg Asp Gly Leu Val Ser Arg Gln Ser Phe Leu
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175
```

```
Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser Gln Ser
    210                 215                 220

Gly Lys Ile Gly Met Ala Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Gln
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Val Asp Pro Ser Glu
        355                 360                 365

Asn Gly Gly Arg Ser Gln Tyr Lys His Leu Leu Arg Leu Glu Asp Gly
    370                 375                 380

Thr Asp Ile Val Lys Ser Arg Thr Glu Trp Arg Pro Lys Asn Ala Gly
385                 390                 395                 400

Thr Asn Gly Ala Ile Ser Thr Ser Thr Ala Lys Thr Ser Asn Gly Asn
                405                 410                 415

Ser Val Ser


<210> SEQ ID NO 26
<211> LENGTH: 1260
<212> TYPE: DNA
<213> ORGANISM: Cuphea sp.

<400> SEQUENCE: 26

atggtggtgg ctgcagcaac ttctgcattc ttccccgttc cagccccggg aacctcccct      60

aaacccggga agtccggcaa ctggccatcg agcttgagcc ctaccttcaa gcccaagtca     120

atccccaatg ccggatttca ggttaaggca aatgccagtg cccatcctaa ggctaacggt     180

tctgcagtaa atctaaagtc tggcagcctc aacactcagg aggacacttc gtcgtcccct     240

cctccccggg ctttccttaa ccagttgcct gattggagta tgcttctgac tgcaatcacg     300

accgtcttcg tggcggcaga gaagcagtgg actatgcttg ataggaaatc taagaggcct     360

gacatgctcg tggactcggt tgggttgaag tgtattgttc gggatgggct cgtgtccaga     420

cagagttttt tgattagatc ttatgaaata ggcgctgatc gaacagcctc tatagagacg     480

ctgatgaacc acttgcagga aacatctatc aatcattgta agagtttggg tcttctcaat     540

gacggctttg gtcgtactcc tgggatgtgt aaaaacgacc tcatttgggt gcttacaaaa     600

atgcagatca tggtgaatcg ctacccaact tggggcgata ctgttgagat caatacctgg     660

ttctctcagt cggggaaaat cggtatggct agcgattggc taataagtga ttgcaacaca     720
```

ggagaaattc ttataagagc aacgagcgtg tgggctatga tgaatcaaaa gacgagaaga 780
ttctcaagac ttccatacga ggttcgccag gagttaacgc ctcattttgt ggactctcct 840
catgtcattg aagacaatga tcagaaattg cataagtttg atgtgaagac tggtgattcc 900
attcgcaagg gtctaactcc gaggtggaac gacttggatg tgaatcagca cgtaagcaac 960
gtgaagtaca ttgggtggat tctcgagagt atgccaatag aagttttgga gacacaggag 1020
ctatgctctc tcaccgtaga atataggcgg gaatgcggaa tggacagtgt gctggagtcc 1080
gtgactgctg tggatccctc agaaaatgga ggccggtctc agtacaagca ccttctgcgg 1140
cttgaggatg ggactgatat cgtgaagagc agaactgagt ggcgaccgaa gaatgcagga 1200
actaacgggg cgatatcaac atcaacagca aagacttcaa atggaaactc ggtctcttag 1260

<210> SEQ ID NO 27
<211> LENGTH: 1260
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27
atggtggtgg ccgccgccac ctccgccttc ttccccgtgc ccgcccccgg cacctccccc 60
aagcccggca agtccggcaa ctggccctcc tccctgtccc ccaccttcaa gcccaagtcc 120
atccccaacg ccggcttcca ggtgaaggcc aacgcctccg cccaccccaa ggccaacggc 180
tccgccgtga acctgaagtc cggctccctg aacacccagg aggacacctc ctcctccccc 240 ccccccgcg ccttcctgaa ccagctgccc gactggtcca tgctgctgac cgccatcacc 300
accgtgttcg tggccgccga gaagcagtgg accatgctgg accgcaagtc caagcgcccc 360
gacatgctgg tggactccgt gggcctgaag tgcatcgtgc gcgacggcct ggtgtcccgc 420
cagtccttcc tgatccgctc ctacgagatc ggcgccgacc gcaccgcctc catcgagacc 480
ctgatgaacc acctgcagga gacctccatc aaccactgca agtccctggg cctgctgaac 540
gacggcttcg gccgcacccc cggcatgtgc aagaacgacc tgatctgggt gctgaccaag 600
atgcagatca tggtgaaccg ctaccccacc tggggcgaca ccgtggagat caacacctgg 660
ttctcccagt ccggcaagat cggcatggcc tccgactggc tgatctccga ctgcaacacc 720
ggcgagatcc tgatccgcgc cacctccgtg tgggccatga tgaaccagaa gacccgccgc 780
ttctcccgcc tgccctacga ggtgcgccag gagctgaccc cccacttcgt ggactccccc 840
cacgtgatcg aggacaacga ccagaagctg cacaagttcg acgtgaagac cggcgactcc 900
atccgcaagg gcctgacccc ccgctggaac gacctggacg tgaaccagca cgtgtccaac 960
gtgaagtaca tcggctggat cctggagtcc atgcccatcg aggtgctgga gacccaggag 1020
ctgtgctccc tgaccgtgga gtaccgccgc gagtgcggca tggactccgt gctggagtcc 1080
gtgaccgccg tggacccctc cgagaacggc ggccgctccc agtacaagca cctgctgcgc 1140
ctggaggacg gcaccgacat cgtgaagtcc cgcaccgagt ggcgccccaa gaacgccggc 1200
accaacggcg ccatctccac ctccaccgcc aagacctcca acggcaactc cgtgtcctga 1260

<210> SEQ ID NO 28
<211> LENGTH: 408
<212> TYPE: PRT
<213> ORGANISM: Cuphea wrightii

<400> SEQUENCE: 28

-continued

```
Met Val Val Ala Ala Ala Ala Ser Ser Ala Phe Phe Pro Val Pro Ala
1               5                   10                  15

Pro Arg Thr Thr Pro Lys Pro Gly Lys Phe Gly Asn Trp Pro Ser Ser
            20                  25                  30

Leu Ser Pro Pro Phe Lys Pro Lys Ser Asn Pro Asn Gly Arg Phe Gln
        35                  40                  45

Val Lys Ala Asn Val Ser Pro His Pro Lys Ala Asn Gly Ser Ala Val
    50                  55                  60

Ser Leu Lys Ser Gly Ser Leu Asn Thr Leu Glu Asp Pro Pro Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Ala Glu Lys Gln Phe Thr
            100                 105                 110

Arg Leu Asp Arg Lys Ser Lys Arg Pro Asp Met Leu Val Asp Trp Phe
        115                 120                 125

Gly Ser Glu Thr Ile Val Gln Asp Gly Leu Val Phe Arg Glu Arg Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Ser Glu Met Cys Thr
            180                 185                 190

Arg Asp Leu Ile Trp Val Leu Thr Lys Met Gln Ile Val Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asp Trp Leu Ile Ser Asp Cys Asn
225                 230                 235                 240

Thr Gly Glu Ile Leu Val Arg Ala Thr Ser Ala Trp Ala Met Met Asn
                245                 250                 255

Gln Lys Thr Arg Arg Phe Ser Lys Leu Pro Cys Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Glu Ser Val Val Glu Ser Val Thr Ser Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Arg Ala Ile Ser Thr
                405
```

<210> SEQ ID NO 29
<211> LENGTH: 1227
<212> TYPE: DNA
<213> ORGANISM: Cuphea wrightii

<400> SEQUENCE: 29
atggtggtgg ctgctgcagc aagttctgca ttcttccctg ttccagcacc tagaaccacg 60
cctaaacccg ggaagttcgg caattggcca tcgagcttga gcccgccctt caagcccaag 120
tcaaacccca atggtagatt tcaggttaag gcaaatgtca gtcctcatcc taaggctaac 180
ggttctgcag taagtctaaa gtctggcagc ctcaacactc tggaggaccc tccgtcgtcc 240
cctcctcctc ggactttcct taaccagttg cctgattgga gtaggcttcg gactgcaatc 300
acgaccgtct tcgtggcggc agagaagcag ttcactaggc tcgatcgaaa atctaagagg 360
cctgacatgc tagtggactg gtttgggtca gagactattg ttcaggatgg gctcgtgttc 420
agagagagat tttcgatcag gtcttacgaa ataggcgctg atcgaacagc ctctatagag 480
acgctgatga accacttgca ggacacatct ctgaatcatt gtaagagtgt gggtcttctc 540
aatgacggct ttggtcgtac ctcggagatg tgtacaagag acctcatttg ggtgcttaca 600
aaaatgcaga tcgtggtgaa tcgctatcca acttggggcg atactgtcga gatcaatagc 660
tggttctccc agtcggggaa aatcggtatg ggtcgcgatt ggctaataag tgattgcaac 720
acaggagaaa ttcttgtaag agcaacgagc gcttgggcca tgatgaatca aaagacgaga 780
agattctcaa aacttccatg cgaggttcgc caggagatag cgcctcattt tgtggacgct 840
cctcctgtca ttgaagacaa tgatcggaaa ttgcataagt ttgatgtgaa gactggtgat 900
tccatttgca agggtctaac tccggggtgg aatgacttgg atgtcaatca gcacgtaagc 960
aacgtgaagt acattgggtg gattctcgag agtatgccta cagaagtttt ggagacccag 1020
gagctatgct ctctcaccct tgaatatagg cgggaatgtg gaagggaaag tgtggtagag 1080
tccgtgacct ctatgaatcc ctcaaaagtt ggagaccggt ctcagtacca acaccttctg 1140
cggcttgagg atggggctga tatcatgaag ggcagaactg agtggagacc aaagaatgca 1200
ggaaccaacc gggcgatatc aacatga 1227

<210> SEQ ID NO 30
<211> LENGTH: 1227
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 30
atggtggtgg ccgccgccgc ctcctccgcc ttcttccccg tgcccgcccc ccgcaccacc 60
cccaagcccg gcaagttcgg caactggccc tcctccctgt cccccccctt caagcccaag 120
tccaacccca acggccgctt ccaggtgaag gccaacgtgt ccccccaccc caaggccaac 180
ggctccgccg tgtccctgaa gtccggctcc ctgaacaccc tggaggaccc cccctcctcc 240
cccccccccc gcaccttcct gaaccagctg cccgactggt cccgcctgcg caccgccatc 300
accaccgtgt tcgtggccgc cgagaagcag ttcacccgcc tggaccgcaa gtccaagcgc 360
cccgacatgc tggtggactg gttcggctcc gagaccatcg tgcaggacgg cctggtgttc 420
cgcgagcgct tctccatccg ctcctacgag atcggcgccg accgcaccgc ctccatcgag 480
accctgatga accacctgca ggacacctcc ctgaaccact gcaagtccgt gggcctgctg 540
aacgacggct tcggccgcac ctccgagatg tgcacccgcg acctgatctg ggtgctgacc 600

```
aagatgcaga tcgtggtgaa ccgctacccc acctggggcg acaccgtgga gatcaactcc    660

tggttctccc agtccggcaa gatcggcatg ggccgcgact ggctgatctc cgactgcaac    720

accggcgaga tcctggtgcg cgccacctcc gcctgggcca tgatgaacca gaagacccgc    780

cgcttctcca agctgccctg cgaggtgcgc caggagatcg ccccccactt cgtggacgcc    840

ccccccgtga tcgaggacaa cgaccgcaag ctgcacaagt tcgacgtgaa gaccggcgac    900

tccatctgca agggcctgac ccccggctgg aacgacctgg acgtgaacca gcacgtgtcc    960

aacgtgaagt acatcggctg gatcctggag tccatgccca ccgaggtgct ggagacccag   1020

gagctgtgct ccctgaccct ggagtaccgc cgcgagtgcg gccgcgagtc cgtggtggag   1080

tccgtgacct ccatgaaccc ctccaaggtg ggcgaccgct cccagtacca gcacctgctg   1140

cgcctggagg acggcgccga catcatgaag ggccgcaccg agtggcgccc caagaacgcc   1200

ggcaccaacc gcgccatctc cacctga                                       1227
```

<210> SEQ ID NO 31
<211> LENGTH: 416
<212> TYPE: PRT
<213> ORGANISM: Cuphea wrightii

<400> SEQUENCE: 31

```
Met Val Ala Thr Ala Ala Ser Ser Ala Phe Phe Pro Val Pro Ser Ala
1               5                   10                  15

Asp Thr Ser Ser Ser Arg Pro Gly Lys Leu Gly Ser Gly Pro Ser Ser
            20                  25                  30

Leu Ser Pro Leu Lys Pro Lys Ser Ile Pro Asn Gly Gly Leu Gln Val
        35                  40                  45

Lys Ala Asn Ala Ser Ala Pro Pro Lys Ile Asn Gly Ser Ser Val Gly
    50                  55                  60

Leu Lys Ser Gly Gly Phe Lys Thr Gln Glu Asp Ser Pro Ser Ala Pro
65                  70                  75                  80

Pro Pro Arg Thr Phe Ile Asn Gln Leu Pro Asp Trp Ser Met Leu Leu
                85                  90                  95

Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125

Leu Gly Ser Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
                165                 170                 175

Gly Leu Ser Asn Asp Gly Phe Gly Arg Thr Pro Glu Met Tyr Lys Arg
            180                 185                 190

Asp Leu Ile Trp Val Val Ala Lys Met Gln Val Met Val Asn Arg Tyr
        195                 200                 205

Pro Thr Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240

Gly Glu Ile Leu Thr Arg Ala Ser Ser Val Trp Val Met Met Asn Gln
                245                 250                 255
```

-continued

```
Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Pro Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Ala
        355                 360                 365

Glu Gly Tyr Ala Ser Arg Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Gly Val Val Pro Ser Glu Glu Ser Ser Pro Gly Asp Phe Phe
                405                 410                 415


<210> SEQ ID NO 32
<211> LENGTH: 1251
<212> TYPE: DNA
<213> ORGANISM: Cuphea wrightii

<400> SEQUENCE: 32

ttggtggcta ccgctgcaag ttctgcattt ttccccgtgc catccgccga cacctcctcc      60

tcgagacccg gaaagctcgg cagtggacca tcgagcttga gccccctcaa gcccaaatcg     120

atccccaatg gcggcttgca ggttaaggca aacgccagtg cccctcctaa gatcaatggt     180

tcctcggtcg gtctaaagtc gggcggtttc aagactcagg aagactctcc ttcggcccct     240

cctccgcgga cttttatcaa ccagttgcct gattggagta tgcttcttgc tgcaatcact     300

actgtcttct tggctgcaga gaagcagtgg atgatgcttg attggaaacc taagaggcct     360

gacatgctcg tggacccgtt cggattggga agtattgttc aggatgggct tgtgttcagg     420

cagaattttt caattaggtc ctacgaaata ggcgccgatc gaactgcgtc tatagagacg     480

gtgatgaacc atttgcagga aacagctctc aatcatgtca agattgctgg gctttctaat     540

gacggctttg gtcgtactcc tgagatgtat aaaagagacc ttatttgggt tgttgcaaaa     600

atgcaggtca tggttaaccg ctatcctact tggggtgaca cggttgaagt gaatacttgg     660

gttgccaagt cagggaaaaa tggtatgcgt cgtgactggc tcataagtga ttgcaatact     720

ggagagattc ttacaagagc atcaagcgtg tgggtcatga tgaatcaaaa gacaagaaga     780

ttgtcaaaaa ttccagatga ggttcgaaat gagatagagc ctcattttgt ggactctgct     840

cccgtcgttg aagatgatga tcggaaactt cccaagctgg atgagaacac tgctgactcc     900

atccgcaagg gtctaactcc gaggtggaat gacttggatg tcaatcagca cgtcaacaac     960

gtgaagtaca tcggatggat tcttgagagt actccaccag aagttctgga gacccaggag    1020

ttatgctccc tgaccctgga atacaggcgg gaatgtggaa gggagagcgt gctggagtcc    1080

ctcactgctg tcgacccgtc tgcagagggc tatgcgtccc ggtttcagca ccttctgcgg    1140

cttgaggatg gaggtgagat cgtgaaggcg agaactgagt ggcgacccaa gaatgctgga    1200

atcaatgggg tggtaccatc cgaggagtcc tcacctggag acttctttta g             1251
```

<210> SEQ ID NO 33
<211> LENGTH: 1251
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 33
atggtggcca ccgccgcctc ctccgccttc ttccccgtgc cctccgccga cacctcctcc 60
tcccgccccg gcaagctggg ctccggcccc tcctccctgt ccccccctgaa gcccaagtcc 120 atccccaacg gcggcctgca ggtgaaggcc aacgcctccg cccccccccaa gatcaacggc 180 tcctccgtgg gcctgaagtc cggcggcttc aagacccagg aggactcccc ctccgccccc 240
cccccccgca ccttcatcaa ccagctgccc gactggtcca tgctgctggc cgccatcacc 300
accgtgttcc tggccgccga gaagcagtgg atgatgctgg actggaagcc caagcgcccc 360
gacatgctgg tggacccctt cggcctgggc tccatcgtgc aggacggcct ggtgttccgc 420
cagaacttct ccatccgctc ctacgagatc ggcgccgacc gcaccgcctc catcgagacc 480
gtgatgaacc acctgcagga gaccgccctg aaccacgtga agatcgccgg cctgtccaac 540
gacggcttcg gccgcacccc cgagatgtac aagcgcgacc tgatctgggt ggtggccaag 600
atgcaggtga tggtgaaccg ctaccccacc tggggcgaca ccgtggaggt gaacacctgg 660
gtggccaagt ccggcaagaa cggcatgcgc cgcgactggc tgatctccga ctgcaacacc 720
ggcgagatcc tgacccgcgc ctcctccgtg tgggtgatga tgaaccagaa gacccgccgc 780
ctgtccaaga tccccgacga ggtgcgcaac gagatcgagc cccacttcgt ggactccgcc 840
cccgtggtgg aggacgacga ccgcaagctg cccaagctgg acgagaacac cgccgactcc 900
atccgcaagg gcctgacccc ccgctggaac gacctggacg tgaaccagca cgtgaacaac 960
gtgaagtaca tcggctggat cctggagtcc accccccccg aggtgctgga gacccaggag 1020
ctgtgctccc tgaccctgga gtaccgccgc gagtgcggcc gcgagtccgt gctggagtcc 1080
ctgaccgccg tggacccctc cgccgagggc tacgcctccc gcttccagca cctgctgcgc 1140
ctggaggacg gcggcgagat cgtgaaggcc cgcaccgagt ggcgccccaa gaacgccggc 1200
atcaacggcg tggtgccctc cgaggagtcc tcccccggcg acttcttctg a 1251

<210> SEQ ID NO 34
<211> LENGTH: 417
<212> TYPE: PRT
<213> ORGANISM: Cuphea wrightii

<400> SEQUENCE: 34

Met Val Ala Thr Ala Ala Ser Ser Ala Phe Phe Pro Val Pro Ser Ala
1 5 10 15

Asp Thr Ser Ser Ser Arg Pro Gly Lys Leu Gly Asn Gly Pro Ser Ser
20 25 30

Leu Ser Pro Leu Lys Pro Lys Ser Ile Pro Asn Gly Gly Leu Gln Val
35 40 45

Lys Ala Asn Ala Ser Ala Pro Pro Lys Ile Asn Gly Ser Ser Val Gly
50 55 60

Leu Lys Ser Gly Ser Phe Lys Thr Gln Glu Asp Ala Pro Ser Ala Pro
65 70 75 80

Pro Pro Arg Thr Phe Ile Asn Gln Leu Pro Asp Trp Ser Met Leu Leu
85 90 95

```
Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125

Leu Gly Ser Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
                165                 170                 175

Gly Leu Ser Ser Asp Gly Phe Gly Arg Thr Pro Ala Met Ser Lys Arg
            180                 185                 190

Asp Leu Ile Trp Val Val Ala Lys Met Gln Val Met Val Asn Arg Tyr
        195                 200                 205

Pro Ala Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240

Gly Glu Ile Leu Thr Arg Ala Ser Ser Val Trp Val Met Met Asn Gln
                245                 250                 255

Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Ala Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Gly
        355                 360                 365

Glu Gly Asp Gly Ser Lys Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Gly Val Val Pro Ser Glu Glu Ser Ser Pro Gly Gly Asp Phe
                405                 410                 415

Phe
```

<210> SEQ ID NO 35
<211> LENGTH: 1254
<212> TYPE: DNA
<213> ORGANISM: Cuphea wrightii

<400> SEQUENCE: 35

```
ttggtggcta ccgctgcaag ttctgcattt ttccccgtac catccgccga cacctcctca      60

tcgagacccg gaaagctcgg caatgggcca tcgagcttga gccccctcaa gccgaaatcg     120

atccccaatg gcgggttgca ggttaaggca aacgccagtg cccctcctaa gatcaatggt     180

tcctcggtcg gtctgaagtc gggcagtttc aagactcagg aagacgctcc ttcggcccct     240
```

cctcctcgga cttttatcaa ccagttgcct gattggagta tgcttcttgc tgcaatcact 300
actgtcttct tggctgcaga gaagcagtgg atgatgcttg attggaaacc taagaggcct 360
gacatgcttg tcgacccgtt cggattggga agtattgttc aggatgggct tgttttcagg 420
cagaatttct cgattaggtc ctacgaaata ggcgctgatc gcactgcgtc tatagagacg 480
gtgatgaacc atttgcagga aacagctctc aatcatgtta agattgctgg gctttctagt 540
gatggctttg gtcgtactcc tgcgatgtct aaacgggacc tcatttgggt tgttgcgaaa 600
atgcaggtca tggttaaccg ctaccctgct tggggtgaca cggttgaagt gaatacttgg 660
gttgccaagt cagggaaaaa tggtatgcgt cgtgactggc tcataagtga ttgcaacact 720
ggagagattc ttacaagagc atcaagcgtg tgggtcatga tgaatcaaaa gacaagaaga 780
ttgtcaaaaa ttccagatga ggttcgaaat gagatagagc ctcattttgt ggactctgcg 840
cccgtcgttg aagacgatga ccggaaactt cccaagctgg atgagaacac tgctgactcc 900
atccgcaagg gtctaactcc gaggtggaat gacttggatg tcaatcagca cgtcaacaac 960
gtgaagtaca ttgggtggat tcttgagagt actccagcag aagttctgga gacccaggaa 1020
ttatgttccc tgaccctgga atacaggcgg gaatgtggaa gggagagcgt gctggagtcc 1080
ctcactgctg tagatccgtc tggagagggc gatgggtcca agttccagca ccttctgcgg 1140
cttgaggatg gaggtgagat cgtgaaggcg agaactgagt ggcgaccaaa gaatgctgga 1200
atcaatgggg tggtaccatc cgaggagtcc tcacctggtg gagacttctt ttaa 1254

<210> SEQ ID NO 36
<211> LENGTH: 1254
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36
atggtggcca ccgccgcctc ctccgccttc ttccccgtgc cctccgccga cacctcctcc 60
tcccgccccg gcaagctggg caacggcccc tcctccctgt ccccccctgaa gcccaagtcc 120 atccccaacg gcggcctgca ggtgaaggcc aacgcctccg ccccccccaa gatcaacggc 180
tcctccgtgg gcctgaagtc cggctccttc aagacccagg aggacgcccc ctccgccccc 240
cccccccgca ccttcatcaa ccagctgccc gactggtcca tgctgctggc cgccatcacc 300
accgtgttcc tggccgccga gaagcagtgg atgatgctgg actggaagcc caagcgcccc 360
gacatgctgg tggacccctt cggcctgggc tccatcgtgc aggacggcct ggtgttccgc 420
cagaacttct ccatccgctc ctacgagatc ggcgccgacc gcaccgcctc catcgagacc 480
gtgatgaacc acctgcagga gaccgccctg aaccacgtga agatcgccgg cctgtcctcc 540
gacggcttcg gccgcacccc cgccatgtcc aagcgcgacc tgatctgggt ggtggccaag 600
atgcaggtga tggtgaaccg ctaccccgcc tggggcgaca ccgtggaggt gaacacctgg 660
gtggccaagt ccggcaagaa cggcatgcgc cgcgactggc tgatctccga ctgcaacacc 720
ggcgagatcc tgacccgcgc ctcctccgtg tgggtgatga tgaaccagaa gacccgccgc 780
ctgtccaaga tccccgacga ggtgcgcaac gagatcgagc cccacttcgt ggactccgcc 840
cccgtggtgg aggacgacga ccgcaagctg cccaagctgg acgagaacac cgccgactcc 900
atccgcaagg gcctgacccc ccgctggaac gacctggacg tgaaccagca cgtgaacaac 960
gtgaagtaca tcggctggat cctggagtcc acccccgccg aggtgctgga gacccaggag 1020

```
ctgtgctccc tgaccctgga gtaccgccgc gagtgcggcc gcgagtccgt gctggagtcc   1080

ctgaccgccg tggacccctc cggcgagggc gacggctcca agttccagca cctgctgcgc   1140

ctggaggacg gcggcgagat cgtgaaggcc cgcaccgagt ggcgccccaa gaacgccggc   1200

atcaacggcg tggtgccctc cgaggagtcc tcccccggcg gcgacttctt ctga         1254


<210> SEQ ID NO 37
<211> LENGTH: 413
<212> TYPE: PRT
<213> ORGANISM: Cuphea wrightii

<400> SEQUENCE: 37

Met Val Ala Ala Ala Ala Ser Ser Ala Phe Phe Ser Val Pro Thr Pro
1               5                   10                  15

Gly Thr Pro Pro Lys Pro Gly Lys Phe Gly Asn Trp Pro Ser Ser Leu
            20                  25                  30

Ser Val Pro Phe Lys Pro Asp Asn Gly Gly Phe His Val Lys Ala Asn
        35                  40                  45

Ala Ser Ala His Pro Lys Ala Asn Gly Ser Ala Val Asn Leu Lys Ser
    50                  55                  60

Gly Ser Leu Glu Thr Pro Pro Arg Ser Phe Ile Asn Gln Leu Pro Asp
65                  70                  75                  80

Leu Ser Val Leu Leu Ser Lys Ile Thr Thr Val Phe Gly Ala Ala Glu
                85                  90                  95

Lys Gln Trp Lys Arg Pro Gly Met Leu Val Glu Pro Phe Gly Val Asp
            100                 105                 110

Arg Ile Phe Gln Asp Gly Val Phe Phe Arg Gln Ser Phe Ser Ile Arg
        115                 120                 125

Ser Tyr Glu Ile Gly Val Asp Arg Thr Ala Ser Ile Glu Thr Leu Met
    130                 135                 140

Asn Ile Phe Gln Glu Thr Ser Leu Asn His Cys Lys Ser Ile Gly Leu
145                 150                 155                 160

Leu Asn Asp Gly Phe Gly Arg Thr Pro Glu Met Cys Lys Arg Asp Leu
                165                 170                 175

Ile Trp Val Val Thr Lys Ile Gln Val Glu Val Asn Arg Tyr Pro Thr
            180                 185                 190

Trp Gly Asp Thr Ile Glu Val Asn Thr Trp Val Ser Glu Ser Gly Lys
        195                 200                 205

Asn Gly Met Gly Arg Asp Trp Leu Ile Ser Asp Cys Arg Thr Gly Glu
    210                 215                 220

Ile Leu Ile Arg Ala Thr Ser Val Trp Ala Met Met Asn Gln Asn Thr
225                 230                 235                 240

Arg Arg Leu Ser Lys Phe Pro Tyr Glu Val Arg Gln Glu Ile Ala Pro
                245                 250                 255

His Phe Val Asp Ser Ala Pro Val Ile Glu Asp Asp Gln Lys Leu Gln
            260                 265                 270

Lys Leu Asp Val Lys Thr Gly Asp Ser Ile Arg Asp Gly Leu Thr Pro
        275                 280                 285

Arg Trp Asn Asp Leu Asp Val Asn Gln His Val Asn Asn Val Lys Tyr
    290                 295                 300

Ile Gly Trp Ile Leu Lys Ser Val Pro Ile Glu Val Phe Glu Thr Gln
305                 310                 315                 320

Glu Leu Cys Gly Val Thr Leu Glu Tyr Arg Arg Glu Cys Gly Arg Asp
                325                 330                 335
```

```
Ser Val Leu Glu Ser Val Thr Ala Met Asp Pro Ala Lys Glu Gly Asp
            340                 345                 350

Arg Cys Val Tyr Gln His Leu Leu Arg Leu Glu Asp Gly Ala Asp Ile
        355                 360                 365

Thr Ile Gly Arg Thr Glu Trp Arg Pro Lys Asn Ala Gly Ala Asn Gly
    370                 375                 380

Ala Met Ser Ser Gly Lys Thr Ser Asn Gly Asn Cys Leu Ile Glu Gly
385                 390                 395                 400

Arg Gly Trp Gln Pro Phe Arg Val Val Arg Leu Ile Phe
                405                 410


<210> SEQ ID NO 38
<211> LENGTH: 1242
<212> TYPE: DNA
<213> ORGANISM: Cuphea wrightii

<400> SEQUENCE: 38

atggtggctg ccgcagcaag ttctgcattc ttctctgttc caaccccggg aacgccccct     60

aaacccggga agttcggtaa ctggccatcg agcttgagcg tccccttcaa gcccgacaat    120

ggtggctttc atgtcaaggc aaacgccagt gcccatccta aggctaatgg ttctgcggta    180

aatctaaagt ctggcagcct cgagactcct cctcggagtt tcattaacca gctgccggac    240

ttgagtgtgc ttctgtccaa aatcacgact gtcttcgggg cggctgagaa gcagtggaag    300

aggcccggca tgctcgtgga accgtttggg gttgacagga tttttcagga tggtgttttt    360

ttcagacaga gtttttctat caggtcttac gaaataggcg ttgatcgaac agcctcgata    420

gagacactga tgaacatctt ccaggaaaca tctttgaatc attgcaagag tatcggtctt    480

ctcaacgatg gctttggtcg tactcctgag atgtgtaaga gggacctcat ttgggtggtt    540

acgaaaattc aggtcgaggt gaatcgctat cctacttggg gtgacactat cgaagtcaat    600

acttgggtct cggagtcggg gaaaaacggt atgggtcggg attggctgat aagtgattgc    660

cgtactggag agattcttat aagagcaacg agcgtgtggg cgatgatgaa tcaaaacacg    720

agaagattgt caaaatttcc atatgaggtt cgacaggaga tagcgcctca ttttgtggac    780

tctgctcctg tcattgaaga cgatcaaaag ttgcagaagc ttgatgtgaa gacaggtgat    840

tccattcgcg atggtctaac tccgagatgg aatgacttgg atgtcaatca acacgttaac    900

aatgtgaagt acattggatg gattctcaag agtgttccaa tagaagtttt cgagacacag    960

gagctatgcg gcgtcacact tgaatatagg cgggaatgcg gaagggacag tgtgctggag   1020

tcagtgaccg ctatggatcc agcaaaagag ggagaccggt gtgtgtacca gcaccttctt   1080

cggcttgagg atggagctga tatcactata ggcagaaccg agtggcggcc gaagaatgca   1140

ggagccaatg gtgcaatgtc atcaggaaag acttcaaatg gaaactgtct catagaagga   1200

aggggttggc aacctttccg agttgtgcgt ttaattttct ga                      1242


<210> SEQ ID NO 39
<211> LENGTH: 1242
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

atggtggccg ccgccgcctc ctccgccttc ttctccgtgc ccacccccgg cacccccccc     60

aagcccggca agttcggcaa ctggccctcc tccctgtccg tgcccttcaa gcccgacaac    120
```

```
ggcggcttcc acgtgaaggc caacgcctcc gcccacccca aggccaacgg ctccgccgtg    180

aacctgaagt ccggctccct ggagaccccc ccccgctcct tcatcaacca gctgcccgac    240

ctgtccgtgc tgctgtccaa gatcaccacc gtgttcggcg ccgccgagaa gcagtggaag    300

cgccccggca tgctggtgga gcccttcggc gtggaccgca tcttccagga cggcgtgttc    360

ttccgccagt ccttctccat ccgctcctac gagatcggcg tggaccgcac cgcctccatc    420

gagaccctga tgaacatctt ccaggagacc tccctgaacc actgcaagtc catcggcctg    480

ctgaacgacg gcttcggccg cacccccgag atgtgcaagc gcgacctgat ctgggtggtg    540

accaagatcc aggtggaggt gaaccgctac cccacctggg gcgacaccat cgaggtgaac    600

acctgggtgt ccgagtccgg caagaacggc atgggccgcg actggctgat ctccgactgc    660

cgcaccggcg agatcctgat ccgcgccacc tccgtgtggg ccatgatgaa ccagaacacc    720

cgccgcctgt ccaagttccc ctacgaggtg cgccaggaga tcgcccccca cttcgtggac    780

tccgcccccg tgatcgagga cgaccagaag ctgcagaagc tggacgtgaa gaccggcgac    840

tccatccgcg acggcctgac cccccgctgg aacgacctgg acgtgaacca gcacgtgaac    900

aacgtgaagt acatcggctg gatcctgaag tccgtgccca tcgaggtgtt cgagacccag    960

gagctgtgcg gcgtgaccct ggagtaccgc cgcgagtgcg gccgcgactc cgtgctggag   1020

tccgtgaccg ccatggaccc cgccaaggag ggcgaccgct gcgtgtacca gcacctgctg   1080

cgcctggagg acggcgccga catcaccatc ggccgcaccg agtggcgccc caagaacgcc   1140

ggcgccaacg gcgccatgtc ctccggcaag acctccaacg gcaactgcct gatcgagggc   1200

cgcggctggc agcccttccg cgtggtgcgc ctgatcttct ga                      1242
```

<210> SEQ ID NO 40
<211> LENGTH: 410
<212> TYPE: PRT
<213> ORGANISM: Cuphea heterophylla

<400> SEQUENCE: 40

```
Met Val Ala Ala Ala Ala Ser Ser Ala Phe Phe Ser Val Pro Thr Pro
1               5                   10                  15

Gly Thr Ser Thr Lys Pro Gly Asn Phe Gly Asn Trp Pro Ser Ser Leu
            20                  25                  30

Ser Val Pro Phe Lys Pro Glu Ser Asn His Asn Gly Gly Phe Arg Val
        35                  40                  45

Lys Ala Asn Ala Ser Ala His Pro Lys Ala Asn Gly Ser Ala Val Asn
    50                  55                  60

Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Gly Met Leu
                85                  90                  95

Leu Ser Lys Ile Thr Thr Val Phe Gly Ala Ala Glu Arg Gln Trp Lys
            100                 105                 110

Arg Pro Gly Met Leu Val Glu Pro Phe Gly Val Asp Arg Ile Phe Gln
        115                 120                 125

Asp Gly Val Phe Phe Arg Gln Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160

Glu Thr Ser Leu Asn His Cys Lys Ser Ile Gly Leu Leu Asn Asp Gly
                165                 170                 175
```

```
Phe Gly Arg Thr Pro Glu Met Cys Lys Arg Asp Leu Ile Trp Val Val
            180                 185                 190

Thr Lys Ile Gln Val Glu Val Asn Arg Tyr Pro Thr Trp Gly Asp Thr
        195                 200                 205

Ile Glu Val Asn Thr Trp Val Ser Glu Ser Gly Lys Asn Gly Met Gly
    210                 215                 220

Arg Asp Trp Leu Ile Ser Asp Cys Arg Thr Gly Glu Ile Leu Ile Arg
225                 230                 235                 240

Ala Thr Ser Val Trp Ala Met Met Asn Arg Lys Thr Arg Arg Leu Ser
                245                 250                 255

Lys Phe Pro Tyr Glu Val Arg Gln Glu Ile Ala Pro His Phe Val Asp
            260                 265                 270

Ser Ala Pro Val Ile Glu Asp Asp Lys Lys Leu His Lys Leu Asp Val
        275                 280                 285

Lys Thr Gly Asp Ser Ile Arg Lys Gly Leu Thr Pro Arg Trp Asn Asp
    290                 295                 300

Leu Asp Val Asn Gln His Val Asn Asn Val Lys Tyr Ile Gly Trp Ile
305                 310                 315                 320

Leu Lys Ser Val Pro Ala Glu Val Phe Glu Thr Gln Glu Leu Cys Gly
                325                 330                 335

Val Thr Leu Glu Tyr Arg Arg Glu Cys Gly Arg Asp Ser Val Leu Glu
            340                 345                 350

Ser Val Thr Ala Met Asp Thr Ala Lys Glu Gly Asp Arg Ser Leu Tyr
        355                 360                 365

Gln His Leu Leu Arg Leu Glu Asp Gly Ala Asp Ile Thr Ile Gly Arg
    370                 375                 380

Thr Glu Trp Arg Pro Lys Asn Ala Gly Ala Asn Gly Ala Ile Ser Thr
385                 390                 395                 400

Gly Lys Thr Ser Asn Glu Asn Ser Val Ser
                405                 410


<210> SEQ ID NO 41
<211> LENGTH: 1233
<212> TYPE: DNA
<213> ORGANISM: Cuphea heterophylla

<400> SEQUENCE: 41

atggtggctg ccgcagcaag ttctgcattc ttctccgttc caaccccggg aacctccact      60

aaacccggga acttcggcaa ttggccatcg agcttgagcg tccccttcaa gcccgaatca     120

aaccacaatg gtggctttcg ggtcaaggca aacgccagtg ctcatcctaa ggctaacggt     180

tctgcagtaa atctaaagtc tggcagcctc gagactcagg aggacacttc atcgtcgtcc     240

cctcctcctc ggacttttat taagcagttg cccgactggg gtatgcttct gtccaaaatc     300

acgactgtct tcggggcggc tgagaggcag tggaagaggc ccggcatgct tgtggaaccg     360

tttggggttg acaggatttt tcaggatggg gttttttca gacagagttt ttcgatcagg     420

tcttacgaaa taggcgctga tcgaacagcc tcaatagaga cgctgatgaa catcttccag     480

gaaacatctc tgaatcattg taagagtatc ggtcttctca atgacggctt tggtcgtact     540

cctgagatgt gtaagaggga cctcatttgg gtggttacga aaattcaggt cgaggtgaat     600

cgctatccta cttggggtga tactattgag gtcaatactt gggtctcaga gtcggggaaa     660

aacggtatgg gtcgtgattg gctgataagc gattgccgta ccggagaaat tcttataaga     720

gcaacgagcg tgtgggctat gatgaatcga aagacgagaa gattgtcaaa atttccatat     780
```

gaggttcgac aggagatagc gcctcatttt gtggactctg ctcctgtcat tgaagacgat 840
aaaaaattgc acaagcttga tgttaagacg ggtgattcca ttcgcaaggg tctaactcca 900
aggtggaatg acttggatgt caatcagcac gttaacaatg tgaagtacat tgggtggatt 960
ctcaagagtg ttccagcaga agttttcgag acccaggagc tatgcggagt cacccttgag 1020
tacaggcggg aatgtggaag ggacagtgtg ctggagtccg tgaccgctat ggataccgca 1080
aaagagggag accggtctct gtaccagcac cttcttcggc ttgaggatgg ggctgatatc 1140
accataggca gaaccgagtg gcggccgaag aatgcaggag ccaatggggc aatatcaaca 1200
ggaaagactt caaatgaaaa ctctgtctct tag 1233

<210> SEQ ID NO 42
<211> LENGTH: 1233
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42
atggtggccg ccgccgcctc ctccgccttc ttctccgtgc ccacccccgg cacctccacc 60
aagcccggca acttcggcaa ctggccctcc tccctgtccg tgcccttcaa gcccgagtcc 120
aaccacaacg gcggcttccg cgtgaaggcc aacgcctccg cccaccccaa ggccaacggc 180
tccgccgtga acctgaagtc cggctccctg gagacccagg aggacacctc ctcctcctcc 240
cccccccccc gcaccttcat caagcagctg cccgactggg gcatgctgct gtccaagatc 300
accaccgtgt tcggcgccgc cgagcgccag tggaagcgcc ccggcatgct ggtggagccc 360
ttcggcgtgg accgcatctt ccaggacggc gtgttcttcc gccagtcctt ctccatccgc 420
tcctacgaga tcggcgccga ccgcaccgcc tccatcgaga ccctgatgaa catcttccag 480
gagacctccc tgaaccactg caagtccatc ggcctgctga acgacggctt cggccgcacc 540
cccgagatgt gcaagcgcga cctgatctgg gtggtgacca agatccaggt ggaggtgaac 600
cgctacccca cctggggcga caccatcgag gtgaacacct gggtgtccga gtccggcaag 660
aacggcatgg gccgcgactg gctgatctcc gactgccgca ccggcgagat cctgatccgc 720
gccacctccg tgtgggccat gatgaaccgc aagacccgcc gcctgtccaa gttcccctac 780
gaggtgcgcc aggagatcgc cccccacttc gtggactccg cccccgtgat cgaggacgac 840
aagaagctgc acaagctgga cgtgaagacc ggcgactcca tccgcaaggg cctgaccccc 900
cgctggaacg acctggacgt gaaccagcac gtgaacaacg tgaagtacat cggctggatc 960
ctgaagtccg tgcccgccga ggtgttcgag acccaggagc tgtgcggcgt gaccctggag 1020
taccgccgcg agtgcggccg cgactccgtg ctggagtccg tgaccgccat ggacaccgcc 1080
aaggagggcg accgctccct gtaccagcac ctgctgcgcc tggaggacgg cgccgacatc 1140
accatcggcc gcaccgagtg gcgccccaag aacgccggcg ccaacggcgc catctccacc 1200
ggcaagacct ccaacgagaa ctccgtgtcc tga 1233

<210> SEQ ID NO 43
<211> LENGTH: 410
<212> TYPE: PRT
<213> ORGANISM: Cuphea heterophylla

<400> SEQUENCE: 43

Met Val Ala Ala Ala Ala Ser Ser Ala Phe Phe Ser Val Pro Thr Ser

```
1               5                   10                  15

Gly Thr Ser Pro Lys Pro Gly Asn Phe Gly Asn Trp Pro Ser Ser Leu
            20                  25                  30

Ser Val Pro Phe Lys Pro Glu Ser Ser His Asn Gly Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Ser Met Leu
                85                  90                  95

Leu Ser Lys Ile Thr Thr Val Phe Trp Ala Ala Glu Arg Gln Trp Lys
            100                 105                 110

Arg Pro Gly Met Leu Val Glu Pro Phe Gly Val Asp Arg Ile Phe Gln
        115                 120                 125

Asp Gly Val Phe Phe Arg Gln Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160

Glu Thr Ser Leu Asn His Cys Lys Ser Ile Gly Leu Leu Asn Asp Gly
                165                 170                 175

Phe Gly Arg Thr Pro Glu Met Cys Lys Arg Asp Leu Ile Trp Val Val
            180                 185                 190

Thr Lys Ile Gln Val Glu Val Asn Arg Tyr Pro Thr Trp Gly Asp Thr
        195                 200                 205

Ile Glu Val Asn Thr Trp Val Ser Glu Ser Gly Lys Asn Gly Met Gly
    210                 215                 220

Arg Asp Trp Leu Ile Ser Asp Cys Arg Thr Gly Glu Ile Leu Ile Arg
225                 230                 235                 240

Ala Thr Ser Val Trp Ala Met Met Asn Arg Lys Thr Arg Arg Leu Ser
                245                 250                 255

Lys Phe Pro Tyr Glu Val Arg Gln Glu Ile Ala Pro His Phe Val Asp
            260                 265                 270

Ser Ala Pro Val Ile Glu Asp Asp Lys Lys Leu His Lys Leu Asp Val
        275                 280                 285

Lys Thr Gly Asp Phe Ile Arg Lys Gly Leu Thr Pro Arg Trp Asn Asp
    290                 295                 300

Phe Asp Val Asn Gln His Val Asn Asn Val Lys Tyr Ile Gly Trp Ile
305                 310                 315                 320

Leu Lys Ser Val Pro Ala Glu Val Phe Glu Thr Gln Glu Leu Cys Gly
                325                 330                 335

Val Thr Leu Glu Tyr Arg Arg Glu Cys Gly Arg Asp Ser Val Leu Glu
            340                 345                 350

Ser Val Thr Ala Met Asp Thr Ala Lys Glu Gly Asp Arg Ser Leu Tyr
        355                 360                 365

Gln His Leu Leu Arg Leu Glu Asp Gly Ala Asp Ile Thr Ile Gly Arg
    370                 375                 380

Thr Glu Trp Arg Pro Lys Asn Ala Gly Ala Asn Gly Ala Ile Ser Thr
385                 390                 395                 400

Gly Lys Thr Ser Asn Glu Asn Ser Val Ser
                405                 410
```

<210> SEQ ID NO 44

<211> LENGTH: 1233
<212> TYPE: DNA
<213> ORGANISM: Cuphea heterophylla

<400> SEQUENCE: 44
atggtggctg ccgcagcaag ttctgcattc ttctccgttc caacctcggg aacctcccct 60
aaacccggga acttcggcaa ttggccatcg agcttgagcg tccccttcaa gcccgaatca 120
agccacaatg gtggctttca ggtcaaggca aacgccagtg cccatcctaa ggctaacggt 180
tctgcagtaa atctaaagtc tggcagcctc gagactcagg aggacacttc atcgtcgtcc 240
cctcctcctc ggacttttat taagcagttg cccgactgga gtatgcttct gtccaaaatc 300
acgactgtct tctgggcggc tgagaggcag tggaagaggc ccggcatgct tgtggaaccg 360
tttggggttg acaggatttt tcaggatggg gttttttca gacagagttt ttcgatcagg 420
tcttacgaaa taggcgctga tcgaacagcc tcaatagaga cgctgatgaa catcttccag 480
gaaacatctc tgaatcattg taagagtatc ggtcttctca atgacggctt tggtcgtact 540
cctgagatgt gtaagaggga cctcatttgg gtggttacga aaattcaggt cgaggtgaat 600
cgctatccta cttggggtga tactattgag gtcaatactt gggtctcaga gtcggggaaa 660
aacggtatgg gtcgtgattg gctgataagc gattgccgta ccggagaaat tcttataaga 720
gcaacgagcg tgtgggctat gatgaatcga aagacgagaa gattgtcaaa atttccatat 780
gaggttcgac aggagatagc gcctcatttt gtggactctg ctcctgtcat tgaagacgat 840
aaaaaattgc acaagcttga tgttaagacg ggtgatttca ttcgcaaggg tctaactcca 900
aggtggaatg actttgatgt caatcagcac gttaacaatg tgaagtacat tgggtggatt 960
ctcaagagtg ttccagcaga agttttcgag acccaggagc tatgcggagt cacccttgag 1020
tataggcggg aatgtggaag ggacagtgtg ctggagtccg tgaccgctat ggataccgca 1080
aaagagggag accggtctct gtaccagcac cttcttcggc ttgaggatgg ggctgatatc 1140
accataggca gaaccgagtg gcggccgaag aatgcaggag ccaatggggc aatatcaaca 1200
ggaaagactt caaatgaaaa ctctgtctct tag 1233

<210> SEQ ID NO 45
<211> LENGTH: 1233
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 45
atggtggccg ccgccgcctc ctccgccttc ttctccgtgc ccacctccgg cacctccccc 60
aagcccggca acttcggcaa ctggccctcc tccctgtccg tgcccttcaa gcccgagtcc 120
tcccacaacg gcggcttcca ggtgaaggcc aacgcctccg cccaccccaa ggccaacggc 180
tccgccgtga acctgaagtc cggctccctg gagacccagg aggacacctc ctcctcctcc 240
cccccccccc gcaccttcat caagcagctg cccgactggt ccatgctgct gtccaagatc 300
accaccgtgt tctgggccgc cgagcgccag tggaagcgcc ccggcatgct ggtggagccc 360
ttcggcgtgg accgcatctt ccaggacggc gtgttcttcc gccagtcctt ctccatccgc 420
tcctacgaga tcggcgccga ccgcaccgcc tccatcgaga ccctgatgaa catcttccag 480
gagacctccc tgaaccactg caagtccatc ggcctgctga acgacggctt cggccgcacc 540
cccgagatgt gcaagcgcga cctgatctgg gtggtgacca agatccaggt ggaggtgaac 600

```
cgctacccca cctggggcga caccatcgag gtgaacacct gggtgtccga gtccggcaag    660

aacggcatgg gccgcgactg gctgatctcc gactgccgca ccggcgagat cctgatccgc    720

gccacctccg tgtgggccat gatgaaccgc aagacccgcc gcctgtccaa gttcccctac    780

gaggtgcgcc aggagatcgc cccccacttc gtggactccg cccccgtgat cgaggacgac    840

aagaagctgc acaagctgga cgtgaagacc ggcgacttca tccgcaaggg cctgaccccc    900

cgctggaacg acttcgacgt gaaccagcac gtgaacaacg tgaagtacat cggctggatc    960

ctgaagtccg tgcccgccga ggtgttcgag acccaggagc tgtgcggcgt gaccctggag   1020

taccgccgcg agtgcggccg cgactccgtg ctggagtccg tgaccgccat ggacaccgcc   1080

aaggagggcg accgctccct gtaccagcac ctgctgcgcc tggaggacgg cgccgacatc   1140

accatcggcc gcaccgagtg gcgccccaag aacgccggcg ccaacggcgc catctccacc   1200

ggcaagacct ccaacgagaa ctccgtgtcc tga                                1233


<210> SEQ ID NO 46
<211> LENGTH: 418
<212> TYPE: PRT
<213> ORGANISM: Cuphea heterophylla

<400> SEQUENCE: 46

Met Val Val Ala Ala Ala Ala Ser Ser Ala Phe Phe Pro Val Pro Ala
1               5                   10                  15

Ser Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Gln Glu Gly Thr Ser Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Ala Glu Lys Gln Leu Thr
            100                 105                 110

Met Leu Asp Arg Lys Ser Lys Lys Pro Asp Met His Val Asp Trp Phe
        115                 120                 125

Gly Leu Glu Ile Ile Val Gln Asp Gly Leu Val Phe Arg Glu Ser Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Pro Glu Met Cys Lys
            180                 185                 190

Arg Asp Leu Ile Trp Val Leu Thr Lys Met Gln Ile Met Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
```

-continued

```
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser


<210> SEQ ID NO 47
<211> LENGTH: 1257
<212> TYPE: DNA
<213> ORGANISM: Cuphea heterophylla

<400> SEQUENCE: 47

atggtggtgg ctgctgcagc aagctctgca ttcttccctg ttccggcatc tggaacctcc      60

cctaaacccg ggaagttcgg gacttggcta tcgagctcga gcccttccta caagcccaag     120

tcaaacccca gtggtggatt tcaggttaag gcaaatgcca gtgctcatcc taaggctaac     180

ggttccgcag taagtctaaa gtctggcagc ctcaacactc aggagggcac ttcgtcgtcc     240

cctcctcctc ggactttcct taaccagttg cctgattgga gtaggcttcg gactgcaatc     300

acgaccgtct tcgtggcggc agagaagcag ttgactatgc tcgatcgaaa gtctaagaag     360

cctgacatgc acgtggactg gtttgggttg gagattattg ttcaggatgg gctcgtgttc     420

agagagagtt tttcgatcag gtcttacgaa ataggcgctg atcgaacagc ctctatagaa     480

acgttgatga accatttgca ggacacatct ttgaaccatt gtaagagtgt gggtcttctc     540

aatgacggct ttggtcgtac ccggagatg tgtaaaaggg acctcatttg ggtgcttaca      600

aaaatgcaga tcatggtgaa tcgctatcca acttggggcg atactgtcga gatcaatagc     660

tggttctccc agtccgggaa aatcggtatg ggtcgcaatt ggctaataag tgattgcaac     720

acaggagaaa ttcttataag agcaacgagc atttgggcca tgatgaatca aaagacgaga     780

agattctcaa aacttccaaa cgaggttcgc caggagatag cgcctcattt tgtggacgcc     840

cctcctgtca ttgaagacaa tgatcgaaaa ttgcataagt ttgatgtgaa gactggtgat     900

tccatttgca agggtctaac accggagtgg aatgacttgg atgtcaatca gcacgtaagc     960

aacgtgaagt acattgggtg gattctcgag agtatgccaa aagaagtttt ggacacccag    1020

gagctatgct ctctcaccct tgaatatagg cgggaatgcg gaagggatag tgtgctggag    1080

tctgtgaccg ctatggatcc ctcaaaagtt ggagaccgat ctcagtacca gcaccttctg    1140

cggcttgaag atgggactga tatcatgaag ggcagaactg agtggcgacc aaagaatgca    1200
```

ggaaccaacg gggctatatc aacaggaaag acttcaaatg gaaactcggt ctcttag 1257

<210> SEQ ID NO 48
<211> LENGTH: 1257
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 48
atggtggtgg ccgccgccgc ctcctccgcc ttcttccccg tgcccgcctc cggcacctcc 60
cccaagcccg gcaagttcgg cacctggctg tcctcctcct ccccctccta caagcccaag 120
tccaacccct ccggcggctt ccaggtgaag gccaacgcct ccgcccaccc caaggccaac 180
ggctccgccg tgtccctgaa gtccggctcc ctgaacaccc aggagggcac ctcctcctcc 240
cccccccccc gcaccttcct gaaccagctg cccgactggt cccgcctgcg caccgccatc 300
accaccgtgt tcgtggccgc cgagaagcag ctgaccatgc tggaccgcaa gtccaagaag 360
cccgacatgc acgtggactg gttcggcctg gagatcatcg tgcaggacgg cctggtgttc 420
cgcgagtcct tctccatccg ctcctacgag atcggcgccg accgcaccgc ctccatcgag 480
accctgatga accacctgca ggacacctcc ctgaaccact gcaagtccgt gggcctgctg 540
aacgacggct tcggccgcac ccccgagatg tgcaagcgcg acctgatctg ggtgctgacc 600
aagatgcaga tcatggtgaa ccgctacccc acctggggcg acaccgtgga gatcaactcc 660
tggttctccc agtccggcaa gatcggcatg ggccgcaact ggctgatctc cgactgcaac 720
accggcgaga tcctgatccg cgccacctcc atctgggcca tgatgaacca gaagacccgc 780
cgcttctcca agctgcccaa cgaggtgcgc caggagatcg ccccccactt cgtggacgcc 840
ccccccgtga tcgaggacaa cgaccgcaag ctgcacaagt tcgacgtgaa gaccggcgac 900
tccatctgca agggcctgac ccccgagtgg aacgacctgg acgtgaacca gcacgtgtcc 960
aacgtgaagt acatcggctg gatcctggag tccatgccca aggaggtgct ggacacccag 1020
gagctgtgct ccctgaccct ggagtaccgc cgcgagtgcg gccgcgactc cgtgctggag 1080
tccgtgaccg ccatggaccc ctccaaggtg ggcgaccgct cccagtacca gcacctgctg 1140
cgcctggagg acggcaccga catcatgaag ggccgcaccg agtggcgccc caagaacgcc 1200
ggcaccaacg gcgccatctc caccggcaag acctccaacg gcaactccgt gtcctga 1257

<210> SEQ ID NO 49
<211> LENGTH: 418
<212> TYPE: PRT
<213> ORGANISM: Cuphea heterophylla

<400> SEQUENCE: 49

Met Val Val Ala Ala Ala Ala Ser Ser Ala Phe Phe Pro Val Pro Ala
1 5 10 15

Pro Gly Thr Thr Ser Lys Pro Gly Lys Phe Gly Asn Trp Pro Ser Ser
20 25 30

Leu Ser Pro Ser Phe Lys Pro Lys Ser Asn Pro Asn Gly Gly Phe Gln
35 40 45

Val Lys Ala Asn Ala Ser Ala His Pro Lys Ala Asn Gly Ser Ala Val
50 55 60

Ser Leu Lys Ser Gly Ser Leu Asn Thr Lys Glu Asp Thr Pro Ser Ser
65 70 75 80

Pro Pro Pro Arg Thr Phe Leu Asn Gln Leu Pro Asp Trp Ser Arg Leu

-continued

```
                85                  90                  95

Arg Thr Ala Ile Thr Thr Val Phe Val Ala Ala Glu Lys Gln Leu Thr
            100                 105                 110

Met Leu Asp Arg Lys Ser Lys Lys Pro Asp Met His Val Asp Trp Phe
        115                 120                 125

Gly Leu Glu Ile Ile Val Gln Asp Trp Leu Val Phe Arg Glu Ser Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Pro Glu Met Cys Lys
            180                 185                 190

Arg Asp Leu Ile Trp Val Leu Thr Lys Met Gln Ile Met Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Leu Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser


<210> SEQ ID NO 50
<211> LENGTH: 1257
<212> TYPE: DNA
<213> ORGANISM: Cuphea heterophylla

<400> SEQUENCE: 50

atggtggtgg ctgctgcagc aagttctgca ttcttccctg ttccagcacc tggaaccacg      60

tctaaacccg ggaagttcgg caattggcca tcgagcttga gcccttcctt caagcccaag     120

tcaaacccca atggtggatt tcaggttaag gcaaatgcca gcgctcatcc taaggctaac     180

gggtctgcag taagtctaaa gtctggcagc ctcaacacta aggaggacac tccgtcgtcc     240
```

cctcctcctc ggactttcct taaccagttg cctgattgga gtaggcttcg gactgcaatc 300
acgaccgtct tcgtggcggc agagaagcag ttgactatgc tcgatcgaaa gtctaagaag 360
cctgacatgc acgtggactg gtttgggttg gagattattg ttcaggattg gctcgtgttc 420
agagagagtt tttcgatcag gtcttacgaa ataggcgctg atcgaacagc ctctatagaa 480
acgttgatga accatttgca ggacacatct ttgaaccatt gtaagagtgt gggtcttctc 540
aatgacggct ttggtcgtac cccggagatg tgtaaaaggg acctcatttg ggtgcttaca 600
aaaatgcaga tcatggtgaa tcgctatcca acttggggcg atactgtcga gatcaatagc 660
tggttctccc agtccgggaa aatcggtatg ggtcgcaatt ggctaataag tgattgcaac 720
acaggagaaa ttcttataag agcaacgagc atttgggcca tgatgaatca aaagacgaga 780
agattctcaa aacttccaaa cgaggttcgc caggagatag ctcctcattt tgtggacgcc 840
cctcctctca ttgaagacaa tgatcgaaaa ttgcataagt ttgatgtgaa gactggtgat 900
tccatttgca agggtctaac accggagtgg aatgacttgg atgtcaatca gcacgtaagc 960
aacgtgaagt acattgggtg gattctcgag agtatgccaa aagaagtttt ggacacccag 1020
gagctatgct ctctcaccct tgaatatagg cgggaatgcg gaagggacag tgtgctggag 1080
tctgtgaccg ctatggatcc ctcaaaagtt ggagaccgat ctcagtacca gcaccttctg 1140
cggcttgaag atgggactga tatcatgaag ggcagaactg agtggcgacc aaagaatgca 1200
ggaaccaacg ggcgatatc aacaggaaag acttcaaatg gaaactcggt ctcttag 1257

<210> SEQ ID NO 51
<211> LENGTH: 1257
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51
atggtggtgg ccgccgccgc ctcctccgcc ttcttccccg tgcccgcccc cggcaccacc 60
tccaagcccg gcaagttcgg caactggccc tcctccctgt ccccctcctt caagcccaag 120
tccaacccca acggcggctt ccaggtgaag gccaacgcct ccgcccaccc caaggccaac 180
ggctccgccg tgtccctgaa gtccggctcc ctgaacacca aggaggacac cccctcctcc 240
cccccccccc gcaccttcct gaaccagctg cccgactggt cccgcctgcg caccgccatc 300
accaccgtgt tcgtggccgc cgagaagcag ctgaccatgc tggaccgcaa gtccaagaag 360
cccgacatgc acgtggactg gttcggcctg gagatcatcg tgcaggactg gctggtgttc 420
cgcgagtcct tctccatccg ctcctacgag atcggcgccg accgcaccgc ctccatcgag 480
accctgatga accacctgca ggacacctcc ctgaaccact gcaagtccgt gggcctgctg 540
aacgacggct tcggccgcac ccccgagatg tgcaagcgcg acctgatctg ggtgctgacc 600
aagatgcaga tcatggtgaa ccgctacccc acctggggcg acaccgtgga gatcaactcc 660
tggttctccc agtccggcaa gatcggcatg ggccgcaact ggctgatctc cgactgcaac 720
accggcgaga tcctgatccg cgccacctcc atctgggcca tgatgaacca gaagacccgc 780
cgcttctcca agctgcccaa cgaggtgcgc caggagatcg ccccccactt cgtggacgcc 840
ccccccctga tcgaggacaa cgaccgcaag ctgcacaagt tcgacgtgaa gaccggcgac 900
tccatctgca agggcctgac ccccgagtgg aacgacctgg acgtgaacca gcacgtgtcc 960
aacgtgaagt acatcggctg gatcctggag tccatgccca aggaggtgct ggacacccag 1020
gagctgtgct ccctgaccct ggagtaccgc cgcgagtgcg gccgcgactc cgtgctggag 1080
tccgtgaccg ccatggaccc ctccaaggtg ggcgaccgct cccagtacca gcacctgctg 1140
cgcctggagg acggcaccga catcatgaag ggccgcaccg agtggcgccc caagaacgcc 1200
ggcaccaacg gcgccatctc caccggcaag acctccaacg gcaactccgt gtcctga 1257

<210> SEQ ID NO 52
<211> LENGTH: 418
<212> TYPE: PRT
<213> ORGANISM: Cuphea heterophylla

<400> SEQUENCE: 52

Met Val Val Ala Ala Ala Ala Ser Ser Ala Phe Phe Pro Val Pro Ala
1 5 10 15

Ser Gly Thr Ser Pro Lys Pro Gly Lys Phe Gly Thr Trp Leu Ser Ser
20 25 30

Ser Ser Pro Ser Tyr Lys Pro Lys Ser Asn Pro Ser Gly Gly Phe Gln
35 40 45

Val Lys Ala Asn Ala Ser Ala His Pro Lys Ala Asn Gly Ser Ala Val
50 55 60

Ser Leu Lys Ser Gly Ser Leu Asn Thr Lys Glu Asp Thr Pro Ser Ser
65 70 75 80

Pro Pro Pro Arg Thr Phe Leu Asn Gln Leu Pro Asp Trp Asn Arg Leu
85 90 95

Arg Thr Ala Ile Thr Thr Val Phe Val Ala Ala Glu Lys Gln Leu Thr
100 105 110

Met Leu Asp Arg Lys Ser Lys Lys Pro Asp Met His Val Asp Trp Phe
115 120 125

Gly Leu Glu Ile Ile Val Gln Asp Gly Leu Val Phe Arg Glu Ser Phe
130 135 140

Ser Ile Arg Ser Tyr Glu Ile Gly Ala Asp Arg Thr Ala Ser Ile Glu
145 150 155 160

Thr Leu Met Asn His Leu Gln Asp Thr Ser Leu Asn His Cys Lys Ser
165 170 175

Val Gly Leu Leu Asn Asp Gly Phe Gly Arg Thr Pro Glu Met Cys Lys
180 185 190

Arg Asp Leu Ile Trp Val Leu Thr Lys Met Gln Ile Met Val Asn Arg
195 200 205

Tyr Pro Thr Trp Gly Asp Thr Val Glu Ile Asn Ser Trp Phe Ser Gln
210 215 220

Ser Gly Lys Ile Gly Met Gly Arg Asn Trp Leu Ile Ser Asp Cys Asn
225 230 235 240

Thr Gly Glu Ile Leu Ile Arg Ala Thr Ser Ile Trp Ala Met Met Asn
245 250 255

Gln Lys Thr Arg Arg Phe Ser Lys Leu Pro Asn Glu Val Arg Gln Glu
260 265 270

Ile Ala Pro His Phe Val Asp Ala Pro Pro Val Ile Glu Asp Asn Asp
275 280 285

Arg Lys Leu His Lys Phe Asp Val Lys Thr Gly Asp Ser Ile Cys Lys
290 295 300

Gly Leu Thr Pro Glu Trp Asn Asp Leu Asp Val Asn Gln His Val Ser
305 310 315 320

Asn Val Lys Tyr Ile Gly Trp Ile Leu Glu Ser Met Pro Lys Glu Val
325 330 335

```
Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser


<210> SEQ ID NO 53
<211> LENGTH: 1257
<212> TYPE: DNA
<213> ORGANISM: Cuphea heterophylla

<400> SEQUENCE: 53

atggtggtgg ctgctgcagc aagctctgca ttcttccctg ttccggcatc tggaacctcc     60

cctaaacccg ggaagttcgg gacttggcta tcgagctcga gcccttccta caagcccaag    120

tcaaacccca gtggtggatt tcaggttaag gcaaatgcca gtgctcatcc taaggctaac    180

ggttccgcag taagtctaaa gtctggcagc ctcaacacta aggaggacac tccgtcgtcc    240

cctcctcctc ggactttcct taaccagttg cctgattgga ataggcttcg gactgcaatc    300

acgaccgtct tcgtggcggc agagaagcag ttgactatgc tcgatcgaaa gtctaagaag    360

cctgacatgc acgtggactg gtttgggttg gagattattg ttcaggatgg gctcgtgttc    420

agagagagtt tttcgatcag gtcttacgaa ataggcgctg atcgaacagc ctctatagaa    480

acgttgatga accatttgca ggacacatct ttgaaccatt gtaagagtgt gggtcttctc    540

aatgacggct ttggtcgtac ccccggagatg tgtaaaaggg acctcatttg ggtgcttaca    600

aaaatgcaga tcatggtgaa tcgctatcca acttggggcg atactgtcga gatcaatagc    660

tggttctccc agtccgggaa aatcggtatg ggtcgcaatt ggctaataag tgattgcaac    720

acaggagaaa ttcttataag agcaacgagc atttgggcca tgatgaatca aaagacgaga    780

agattctcaa aacttccaaa cgaggttcgc caggagatag cgcctcattt tgtggacgcc    840

cctcctgtca ttgaagacaa tgatcgaaaa ttgcataagt ttgatgtgaa gactggtgat    900

tccatttgca agggtctaac accggagtgg aatgacttgg atgtcaatca gcacgtaagc    960

aacgtgaagt acattgggtg gattctcgag agtatgccaa aagaagtttt ggacacccag   1020

gagctatgct ctctcaccct tgaatatagg cgggaatgcg gaagggacag tgtgctggag   1080

tctgtgaccg ctatggatcc ctcaaaagtt ggggaccgat ctcagtacca gcaccttctg   1140

cggcttgaag atgggactga tatcatgaag ggcagaactg agtggcgacc aaagaatgca   1200

ggaaccaacg gggctatatc aacaggaaag acttcaaatg gaaactcggt ctcttag      1257


<210> SEQ ID NO 54
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
```

-continued

```
atggtggtgg ccgccgccgc ctcctccgcc ttcttccccg tgcccgcctc cggcacctcc      60

cccaagcccg gcaagttcgg cacctggctg tcctcctcct ccccctccta caagcccaag     120

tccaacccct ccggcggctt ccaggtgaag gccaacgcct ccgcccaccc caaggccaac     180

ggctccgccg tgtccctgaa gtccggctcc ctgaacacca aggaggacac cccctcctcc     240

cccccccccc gcaccttcct gaaccagctg cccgactgga accgcctgcg caccgccatc     300

accaccgtgt tcgtggccgc cgagaagcag ctgaccatgc tggaccgcaa gtccaagaag     360

cccgacatgc acgtggactg gttcggcctg gagatcatcg tgcaggacgg cctggtgttc     420

cgcgagtcct tctccatccg ctcctacgag atcggcgccg accgcaccgc ctccatcgag     480

accctgatga accacctgca ggacacctcc ctgaaccact gcaagtccgt gggcctgctg     540

aacgacggct tcggccgcac ccccgagatg tgcaagcgcg acctgatctg ggtgctgacc     600

aagatgcaga tcatggtgaa ccgctacccc acctggggcg acaccgtgga gatcaactcc     660

tggttctccc agtccggcaa gatcggcatg ggccgcaact ggctgatctc cgactgcaac     720

accggcgaga tcctgatccg cgccacctcc atctgggcca tgatgaacca gaagacccgc     780

cgcttctcca agctgcccaa cgaggtgcgc caggagatcg ccccccactt cgtggacgcc     840

ccccccgtga tcgaggacaa cgaccgcaag ctgcacaagt tcgacgtgaa gaccggcgac     900

tccatctgca agggcctgac ccccgagtgg aacgacctgg acgtgaacca gcacgtgtcc     960

aacgtgaagt acatcggctg gatcctggag tccatgccca aggaggtgct ggacacccag    1020

gagctgtgct ccctgaccct ggagtaccgc cgcgagtgcg gccgcgactc cgtgctggag    1080

tccgtgaccg ccatggaccc ctccaaggtg ggcgaccgct cccagtacca gcacctgctg    1140

cgcctggagg acggcaccga catcatgaag ggccgcaccg agtggcgccc caagaacgcc    1200

ggcaccaacg gcgccatctc caccggcaag acctccaacg gcaactccgt gtcctga       1257
```

<210> SEQ ID NO 55
<211> LENGTH: 418
<212> TYPE: PRT
<213> ORGANISM: Cuphea heterophylla

<400> SEQUENCE: 55

```
Met Val Val Ala Ala Ala Ala Ser Ser Ala Phe Phe Pro Val Pro Ala
1               5                   10                  15

Pro Gly Thr Thr Ser Lys Pro Gly Lys Phe Gly Asn Trp Pro Ser Ser
            20                  25                  30

Leu Ser Pro Ser Phe Lys Pro Lys Ser Asn Pro Asn Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Gln Glu Asp Thr Ser Ser Ser
65                  70                  75                  80

Pro Pro Pro Arg Thr Phe Leu Asn Gln Leu Pro Asp Trp Ser Arg Leu
                85                  90                  95

Leu Thr Ala Ile Ser Thr Val Phe Val Ala Ala Glu Lys Gln Leu Thr
            100                 105                 110

Met Leu Asp Arg Lys Ser Lys Arg Pro Asp Met Leu Val Asp Leu Phe
        115                 120                 125

Gly Leu Glu Ser Ile Val Gln Asp Gly Leu Val Phe Arg Glu Ser Tyr
    130                 135                 140

Ser Ile Arg Ser Tyr Glu Ile Gly Ala Asp Arg Thr Ala Ser Ile Glu
145                 150                 155                 160
```

```
Thr Leu Met Asn His Leu Gln Asp Thr Ser Leu Asn His Cys Lys Ser
                165                 170                 175

Val Gly Leu Leu Asn Asp Gly Phe Gly Arg Thr Pro Glu Met Cys Lys
            180                 185                 190

Arg Asp Leu Ile Trp Val Leu Thr Lys Met Gln Ile Met Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Asn Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Arg Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Glu Ser Val Leu Glu Ser Val Thr Ala Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser
```

<210> SEQ ID NO 56
<211> LENGTH: 1257
<212> TYPE: DNA
<213> ORGANISM: Cuphea heterophylla

<400> SEQUENCE: 56

```
atggtggtgg ctgctgcagc aagttctgca ttcttccctg ttccagcacc tggaaccacg      60

tctaaacccg ggaagttcgg caattggcca tcgagcttga gcccttcctt caagcccaag     120

tcaaacccca atggtggatt tcaggttaag gcaaatgcca gtgctcatcc taaggctaac     180

ggttctgcgg taagtctaaa gtctggcagc ctcaacactc aggaggacac ttcgtcgtcc     240

cctcctcctc ggacattcct taaccagttg cctgattgga gtaggcttct gactgcaatc     300

tcgaccgtct tcgtggcggc agagaagcag ttgactatgc tcgatcgaaa atctaagagg     360

cctgacatgc tcgtggactt gtttgggttg gagagtattg ttcaggatgg gctcgtgttc     420

agagagagtt attcgatcag gtcttacgaa ataggcgctg atcgaacagc ctctatagaa     480

acgttgatga accatttgca ggacacatct ttgaaccatt gtaagagtgt gggtcttctc     540

aatgacggct ttggtcgtac ccccggagatg tgtaaaaggg acctcatttg ggtgcttaca     600
```

-continued

```
aaaatgcaga tcatggtgaa tcgctatcca acttggggcg atactgtcga gatcaatagc    660

tggttctccc agtccgggaa aatcggtatg ggtcgcaatt ggctaataag tgattgcaac    720

acaggagaaa ttcttataag agcaacgagc atttgggcca tgatgaatca aaatacgaga    780

agattctcaa aacttccaaa cgaggttcgc caggagatag cgcctcattt tgttgacgct    840

cctcctgtca ttgaagacaa tgatcgaaaa ttgcataagt ttgatgtgaa gactggtgat    900

tccattcgca agggtctaac tccggggtgg aatgacttgg atgtcaatca gcacgtaagc    960

aacgtgaagt acattgggtg gattctcgag agtatgccaa cagaagtttt ggagacccag   1020

gagctatgct ctctcaccct tgaatatagg cgggaatgcg gaagggaaag tgtgctggag   1080

tccgtgaccg ctatgaatcc ctcaaaagtt ggagaccggt ctcagtacca gcaccttcta   1140

cggcttgagg atggggctga tatcatgaag ggcagaactg agtggcgacc aaagaatgca   1200

ggaaccaacg ggcgatatc aacaggaaag acttcaaatg gaaactcggt ctcttag        1257
```

```
<210> SEQ ID NO 57
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

atggtggtgg ccgccgccgc ctcctccgcc ttcttccccg tgcccgcccc cggcaccacc     60

tccaagcccg gcaagttcgg caactggccc tcctccctgt ccccctcctt caagcccaag    120

tccaacccca acggcggctt ccaggtgaag gccaacgcct ccgcccaccc caaggccaac    180

ggctccgccg tgtccctgaa gtccggctcc ctgaacaccc aggaggacac ctcctcctcc    240

cccccccccc gcaccttcct gaaccagctg cccgactggt cccgcctgct gaccgccatc    300

tccaccgtgt tcgtggccgc cgagaagcag ctgaccatgc tggaccgcaa gtccaagcgc    360

cccgacatgc tggtggacct gttcggcctg gagtccatcg tgcaggacgg cctggtgttc    420

cgcgagtcct actccatccg ctcctacgag atcggcgccg accgcaccgc ctccatcgag    480

accctgatga accacctgca ggacacctcc ctgaaccact gcaagtccgt gggcctgctg    540

aacgacggct tcggccgcac ccccgagatg tgcaagcgcg acctgatctg ggtgctgacc    600

aagatgcaga tcatggtgaa ccgctacccc acctggggcg acaccgtgga gatcaactcc    660

tggttctccc agtccggcaa gatcggcatg ggccgcaact ggctgatctc cgactgcaac    720

accggcgaga tcctgatccg cgccacctcc atctgggcca tgatgaacca gaacacccgc    780

cgcttctcca agctgcccaa cgaggtgcgc caggagatcg ccccccactt cgtggacgcc    840

ccccccgtga tcgaggacaa cgaccgcaag ctgcacaagt tcgacgtgaa gaccggcgac    900

tccatccgca agggcctgac ccccggctgg aacgacctgg acgtgaacca gcacgtgtcc    960

aacgtgaagt acatcggctg gatcctggag tccatgccca ccgaggtgct ggagacccag   1020

gagctgtgct ccctgaccct ggagtaccgc cgcgagtgcg gccgcgagtc cgtgctggag   1080

tccgtgaccg ccatgaaccc ctccaaggtg ggcgaccgct cccagtacca gcacctgctg   1140

cgcctggagg acggcgccga catcatgaag ggccgcaccg agtggcgccc caagaacgcc   1200

ggcaccaacg gcgccatctc caccggcaag acctccaacg gcaactccgt gtcctga       1257
```

```
<210> SEQ ID NO 58
<211> LENGTH: 418
<212> TYPE: PRT
```

-continued

<213> ORGANISM: Cuphea heterophylla

<400> SEQUENCE: 58

```
Met Val Val Ala Ala Ala Ala Ser Ser Ala Phe Phe Pro Val Pro Ala
1               5                   10                  15

Ser Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Gln Glu Asp Thr Ser Ser Ser
65                  70                  75                  80

Pro Pro Pro Gln Thr Phe Leu Asn Gln Leu Pro Asp Trp Ser Arg Leu
                85                  90                  95

Leu Thr Ala Ile Ser Thr Val Phe Val Ala Ala Glu Lys Gln Leu Thr
            100                 105                 110

Met Leu Asp Arg Lys Ser Lys Arg Pro Asp Met Leu Val Asp Trp Phe
        115                 120                 125

Gly Leu Glu Ser Ile Val Gln Asp Gly Leu Val Phe Arg Glu Ser Tyr
    130                 135                 140

Ser Ile Arg Ser Tyr Glu Ile Ser Ala Asp Arg Thr Ala Ser Ile Glu
145                 150                 155                 160

Thr Val Met Asn Leu Leu Gln Glu Thr Ser Leu Asn His Cys Lys Ser
                165                 170                 175

Met Gly Ile Leu Asn Asp Gly Phe Gly Arg Thr Pro Glu Met Cys Lys
            180                 185                 190

Arg Asp Leu Ile Trp Val Leu Thr Lys Met Gln Ile Leu Val Asn Arg
        195                 200                 205

Tyr Pro Asn Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Asn Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Arg Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400
```

Gly Thr Asn Gly Ala Ile Ser Thr Gly Lys Thr Ser Asn Gly Asn Ser
            405                 410                 415

Val Ser

<210> SEQ ID NO 59
<211> LENGTH: 1257
<212> TYPE: DNA
<213> ORGANISM: Cuphea heterophylla

<400> SEQUENCE: 59

| | | | | | | |
|---|---|---|---|---|---|---|
| atggtggtgg | ctgctgcagc | aagctctgca | ttcttccctg | ttccggcatc | tggaacctcc | 60 |
| cctaaacccg | ggaagttcgg | gacttggcta | tcgagctcga | gcccttccta | caagcccaag | 120 |
| tcaaacccca | gtggtggatt | tcaggttaag | gcaaatgcca | gtgctcatcc | taaggctaac | 180 |
| ggttctgcag | taagtctaaa | gtctggcagc | ctcaacactc | aggaggacac | ttcgtcgtcc | 240 |
| cctcctcctc | agacattcct | taaccagttg | cctgattgga | gtaggcttct | gacagcaatc | 300 |
| tcgaccgtct | tcgtggcggc | agagaagcag | ttgactatgc | tcgatcgaaa | atctaaaagg | 360 |
| cctgacatgc | tcgtggactg | gtttgggttg | agagtattg | ttcaggatgg | gctcgtgttc | 420 |
| agagagagtt | attcgatcag | gtcttacgaa | ataagcgctg | atcgaacagc | ctctatagag | 480 |
| acggtgatga | acctcttgca | ggaaacatct | ctcaatcatt | gtaagagtat | gggtattctc | 540 |
| aatgacggct | ttggtcgtac | cccggagatg | tgcaaaaggg | acctcatttg | ggtgcttaca | 600 |
| aaaatgcaga | tcttggtgaa | tcgctatcca | aattggggtg | atactgtcga | gatcaatagc | 660 |
| tggttctccc | agtccgggaa | aatcggtatg | ggtcgcaatt | ggctaataag | tgattgcaac | 720 |
| acaggagaaa | ttcttataag | agcaacgagc | atttgggcca | tgatgaatca | aaatacgaga | 780 |
| agattctcaa | aacttccaaa | cgaggttcgc | caggagatag | cgcctcattt | tgttgacgct | 840 |
| cctcctgtca | ttgaagacaa | tgatcgaaaa | ttgcataagt | ttgatgtgaa | gactggtgat | 900 |
| tccattcgca | agggtctaac | tccggggtgg | aatgacttgg | atgtcaatca | gcacgtaagc | 960 |
| aacgtgaagt | acattgggtg | gattctcgag | agtatgccaa | cagaagtttt | ggagacccag | 1020 |
| gagctatgct | ctctcaccct | tgaatatagg | cgggaatgcg | gaagggacag | tgtgctggag | 1080 |
| tccgtgaccg | ctatgaatcc | ctcaaaagtt | ggagaccggt | ctcagtacca | gcaccttcta | 1140 |
| cggcttgagg | atggggctga | tatcatgaag | ggcagaactg | agtggcgacc | aaagaatgca | 1200 |
| ggaaccaacg | gggcgatatc | aacaggaaag | acttcaaatg | gaaactcggt | ctcttag | 1257 |

<210> SEQ ID NO 60
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

| | | | | | | |
|---|---|---|---|---|---|---|
| atggtggtgg | ccgccgccgc | ctcctccgcc | ttcttccccg | tgcccgcctc | cggcacctcc | 60 |
| cccaagcccg | gcaagttcgg | cacctggctg | tcctcctcct | ccccctccta | caagcccaag | 120 |
| tccaacccct | ccgcgggctt | ccaggtgaag | gccaacgcct | ccgcccaccc | caaggccaac | 180 |
| ggctccgccg | tgtccctgaa | gtccggctcc | ctgaacaccc | aggaggacac | ctcctcctcc | 240 |
| cccccccccc | agaccttcct | gaaccagctg | cccgactggt | cccgcctgct | gaccgccatc | 300 |
| tccaccgtgt | tcgtggccgc | cgagaagcag | ctgaccatgc | tggaccgcaa | gtccaagcgc | 360 |
| cccgacatgc | tggtggactg | gttcggcctg | gagtccatcg | tgcaggacgg | cctggtgttc | 420 |

```
cgcgagtcct actccatccg ctcctacgag atctccgccg accgcaccgc ctccatcgag    480

accgtgatga acctgctgca ggagacctcc ctgaaccact gcaagtccat gggcatcctg    540

aacgacggct tcggccgcac ccccgagatg tgcaagcgcg acctgatctg ggtgctgacc    600

aagatgcaga tcctggtgaa ccgctacccc aactggggcg acaccgtgga gatcaactcc    660

tggttctccc agtccggcaa gatcggcatg ggccgcaact ggctgatctc cgactgcaac    720

accggcgaga tcctgatccg cgccacctcc atctgggcca tgatgaacca gaacacccgc    780

cgcttctcca agctgcccaa cgaggtgcgc caggagatcg ccccccactt cgtggacgcc    840

ccccccgtga tcgaggacaa cgaccgcaag ctgcacaagt tcgacgtgaa gaccggcgac    900

tccatccgca agggcctgac ccccggctgg aacgacctgg acgtgaacca gcacgtgtcc    960

aacgtgaagt acatcggctg gatcctggag tccatgccca ccgaggtgct ggagacccag   1020

gagctgtgct ccctgaccct ggagtaccgc cgcgagtgcg gccgcgactc cgtgctggag   1080

tccgtgaccg ccatgaaccc ctccaaggtg ggcgaccgct cccagtacca gcacctgctg   1140

cgcctggagg acggcgccga catcatgaag ggccgcaccg agtggcgccc caagaacgcc   1200

ggcaccaacg gcgccatctc caccggcaag acctccaacg gcaactccgt gtcctga      1257


<210> SEQ ID NO 61
<211> LENGTH: 418
<212> TYPE: PRT
<213> ORGANISM: Cuphea heterophylla

<400> SEQUENCE: 61

Met Val Val Ala Ala Ala Ala Ser Ser Ala Phe Phe Pro Val Pro Ala
1               5                   10                  15

Ser Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Gln Glu Gly Thr Ser Ser Ser
65                  70                  75                  80

Pro Pro Pro Arg Thr Phe Leu Asn Gln Leu Pro Asp Trp Ser Arg Leu
                85                  90                  95

Leu Thr Ala Ile Ser Thr Val Phe Val Ala Ala Glu Lys Gln Leu Thr
            100                 105                 110

Met Leu Asp Arg Lys Ser Lys Arg Pro Asp Met Leu Val Asp Trp Phe
        115                 120                 125

Gly Leu Glu Ser Ile Val Gln Asp Gly Leu Val Phe Arg Glu Ser Tyr
    130                 135                 140

Ser Ile Arg Ser Tyr Glu Ile Ser Ala Asp Arg Thr Ala Ser Ile Glu
145                 150                 155                 160

Thr Val Met Asn Leu Leu Gln Glu Thr Ser Leu Asn His Cys Lys Ser
                165                 170                 175

Met Gly Ile Leu Asn Asp Gly Phe Gly Arg Thr Pro Glu Met Cys Lys
            180                 185                 190

Arg Asp Leu Ile Trp Val Leu Thr Lys Met Gln Ile Leu Val Asn Arg
        195                 200                 205

Tyr Pro Asn Trp Gly Asp Thr Val Glu Ile Asn Ser Trp Phe Ser Gln
    210                 215                 220
```

```
Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser
```

<210> SEQ ID NO 62
<211> LENGTH: 1257
<212> TYPE: DNA
<213> ORGANISM: Cuphea heterophylla

<400> SEQUENCE: 62

```
atggtggtgg ctgctgcagc aagctctgca ttcttccctg ttccggcatc tggaacctcc      60

cctaaacccg ggaagttcgg gacttggcta tcgagctcga gcccttccta caagcccaag     120

tcaaacccca gtggtggatt tcaggttaaa gcaaatgcca gtgctcatcc taaggctaac     180

ggttccgcag taagtctaaa gtctggcagc ctcaacactc aggagggcac ttcgtcgtcc     240

cctcctcctc ggacattcct taaccagttg cctgattgga gtaggcttct gactgcaatc     300

tcgaccgtct tcgtggcggc agagaagcag ttgactatgc tcgatcgaaa atctaagagg     360

cctgacatgc tcgtggactg gtttgggttg gagagtattg ttcaggatgg gctcgtgttc     420

agagagagtt attcgatcag gtcttacgaa ataagcgctg atcgaacagc ctctatagag     480

acggtgatga acctcttgca ggaaacatct ctcaatcatt gtaagagtat gggtattctc     540

aatgacggct ttggtcgtac cccggagatg tgcaaaaggg acctcatttg ggtgcttaca     600

aaaatgcaga tcttggtgaa tcgctatcca aattggggtg atactgtcga gatcaatagc     660

tggttctccc agtccgggaa aatcggtatg ggtcgcaatt ggctaataag tgattgcaac     720

acaggagaaa ttcttataag agcaacgagc atttgggcca tgatgaatca aaagacgaga     780

agattctcaa aacttccaaa tgaggttcgc caggagatag cgcctcattt tgtggacgcc     840

cctcctgtca ttgaagacaa tgatcgaaaa ttgcataagt ttgatgtgaa gactggtgat     900

tccatttgca agggtctaac accggagtgg aacgacttgg atgtcaatca gcacgtaagc     960

aacgtgaagt acattgggtg gattctcgag agtatgccaa aagaagtttt ggacacccag    1020
```

```
gagctatgct ctctcaccct tgaatatagg cgggaatgcg gaagggacag tgtgctggag   1080

tctgtgaccg ctatggatcc ctcaaaagtt ggagaccgat ctcagtacca gcaccttctg   1140

cggcttgaag atgggactga tatcatgaag ggcagaactg agtggcgacc aaagaatgca   1200

ggaaccaacg ggcgatatc aacaggaaag acttcaaatg gaaactcggt ctcttag      1257
```

<210> SEQ ID NO 63
<211> LENGTH: 1257
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63

```
atggtggtgg ccgccgccgc ctcctccgcc ttcttccccg tgcccgcctc cggcacctcc     60

cccaagcccg gcaagttcgg cacctggctg tcctcctcct ccccctccta caagcccaag    120

tccaacccct ccggcggctt ccaggtgaag gccaacgcct ccgcccaccc caaggccaac    180

ggctccgccg tgtccctgaa gtccggctcc ctgaacaccc aggagggcac ctcctcctcc    240

cccccccccc gcaccttcct gaaccagctg cccgactggt cccgcctgct gaccgccatc    300

tccaccgtgt tcgtggccgc cgagaagcag ctgaccatgc tggaccgcaa gtccaagcgc    360

cccgacatgc tggtggactg gttcggcctg gagtccatcg tgcaggacgg cctggtgttc    420

cgcgagtcct actccatccg ctcctacgag atctccgccg accgcaccgc ctccatcgag    480

accgtgatga acctgctgca ggagacctcc ctgaaccact gcaagtccat gggcatcctg    540

aacgacggct tcggccgcac ccccgagatg tgcaagcgcg acctgatctg ggtgctgacc    600

aagatgcaga tcctggtgaa ccgctacccc aactggggcg acaccgtgga gatcaactcc    660

tggttctccc agtccggcaa gatcggcatg ggccgcaact ggctgatctc cgactgcaac    720

accggcgaga tcctgatccg cgccacctcc atctgggcca tgatgaacca gaagacccgc    780

cgcttctcca agctgcccaa cgaggtgcgc caggagatcg ccccccactt cgtggacgcc    840

ccccccgtga tcgaggacaa cgaccgcaag ctgcacaagt tcgacgtgaa gaccggcgac    900

tccatctgca agggcctgac ccccgagtgg aacgacctgg acgtgaacca gcacgtgtcc    960

aacgtgaagt acatcggctg gatcctggag tccatgccca aggaggtgct ggacacccag   1020

gagctgtgct ccctgaccct ggagtaccgc cgcgagtgcg gccgcgactc cgtgctggag   1080

tccgtgaccg ccatggaccc ctccaaggtg ggcgaccgct cccagtacca gcacctgctg   1140

cgcctggagg acggcaccga catcatgaag ggccgcaccg agtggcgccc caagaacgcc   1200

ggcaccaacg gcgccatctc caccggcaag acctccaacg gcaactccgt gtcctga      1257
```

<210> SEQ ID NO 64
<211> LENGTH: 418
<212> TYPE: PRT
<213> ORGANISM: Cuphea heterophylla

<400> SEQUENCE: 64

```
Met Val Val Ala Ala Thr Ala Ser Ser Ala Phe Phe Pro Val Pro Val
1               5                   10                  15

Pro Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45
```

-continued

```
Val Lys Ala Asn Ala Ser Ala His Pro Lys Ala Asn Gly Ser Ala Val
    50                  55                  60

Ser Leu Lys Ser Gly Ser Leu Asn Thr Gln Glu Asp Thr Ser Ser Ser
65                  70                  75                  80

Pro Pro Pro Arg Thr Phe Leu Asn Gln Leu Pro Asp Trp Ser Arg Leu
                85                  90                  95

Leu Thr Ala Ile Ser Thr Val Phe Val Ala Ala Glu Lys Gln Leu Thr
            100                 105                 110

Met Leu Asp Arg Lys Ser Lys Arg Pro Asp Met Leu Val Asp Trp Phe
        115                 120                 125

Gly Leu Glu Ser Ile Val Gln Asp Gly Leu Val Phe Arg Glu Ile Tyr
    130                 135                 140

Ser Ile Arg Ser Tyr Glu Ile Ser Ala Asp Arg Thr Thr Ser Ile Glu
145                 150                 155                 160

Thr Val Met Asn Leu Leu Gln Glu Thr Ser Leu Asn His Cys Lys Ser
                165                 170                 175

Met Gly Ile Leu Asn Asp Gly Phe Gly Arg Thr Pro Glu Met Cys Lys
            180                 185                 190

Arg Asp Leu Ile Trp Val Leu Thr Lys Met Gln Ile Leu Val Asn Arg
        195                 200                 205

Tyr Pro Asn Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Ala Asn Ser
                405                 410                 415

Val Ser
```

<210> SEQ ID NO 65
<211> LENGTH: 1257
<212> TYPE: DNA
<213> ORGANISM: Cuphea heterophylla

<400> SEQUENCE: 65

-continued

```
atggtggtgg ctgctacagc aagttctgca ttcttccctg ttcctgtacc tggaacctcc     60

cctaaacccg gaaagttcgg gacttggcta tcgagctcga gcccttccta caagcccaag    120

tcaaacccca gtggtggatt tcaggttaag gcaaatgcca gtgctcatcc taaggctaac    180

ggttctgcag taagtctaaa gtctggcagc ctcaacactc aggaggacac ttcgtcgtcc    240

cctcctcctc ggacattcct taaccagttg cctgattgga gtaggcttct gactgcaatc    300

tcgaccgtct tcgtggcggc agagaagcag ttgactatgc tcgatcgaaa atctaagagg    360

cctgacatgc tcgtggactg gtttgggttg gagagtattg ttcaggatgg gctcgtgttc    420

agagagattt attcgatcag gtcttacgaa ataagcgctg atcgaacaac ctctatagag    480

acggtgatga acctcttgca ggaaacatct ctcaatcatt gtaagagtat gggtattctc    540

aatgacggct ttggtcgtac cccggagatg tgcaaaaggg acctcatttg ggtgcttaca    600

aaaatgcaga tcttggtgaa tcgctatcca aattggggtg atactgtcga gatcaatagc    660

tggttctccc agtccgggaa aatcggtatg ggtcgcaatt ggctaataag tgattgcaac    720

acaggagaaa ttcttataag agcaacgagc atttgggcca tgatgaatca aaagacgaga    780

agattctcaa aacttccaaa cgaggttcgc caggagatag cgcctcattt tgtggacgcc    840

cctcctgtca ttgaagacaa tgatcgaaaa ttgcataagt ttgatgtgaa gactggtgat    900

tccatttgca agggtctaac accggagtgg aatgacttgg atgtcaatca gcacgtaagc    960

aacgtgaagt acattgggtg gattctcgag agtatgccaa aagaagtttt ggacacccag   1020

gagctatgct ctctcaccct tgaatatagg cgggaatgcg gaagggacag tgtgctggag   1080

tctgtgaccg ctatggatcc ctcaaaagtt ggagaccgat ctcagtacca gcaccttctg   1140

cggcttgaag atgggactga tatcatgaag ggcagaactg agtggcgacc aaagaatgca   1200

ggaaccaacg ggcgatatc aacaggaaag acttcaaatg caaactcggt ctcttag       1257
```

<210> SEQ ID NO 66
<211> LENGTH: 1257
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66

```
atggtggtgg ccgccaccgc ctcctccgcc ttcttccccg tgcccgtgcc cggcacctcc     60

cccaagcccg gcaagttcgg cacctggctg tcctcctcct ccccctccta caagcccaag    120

tccaacccct ccggcggctt ccaggtgaag gccaacgcct ccgcccaccc caaggccaac    180

ggctccgccg tgtccctgaa gtccggctcc ctgaacaccc aggaggacac ctcctcctcc    240

cccccccccc gcaccttcct gaaccagctg cccgactggt cccgcctgct gaccgccatc    300

tccaccgtgt tcgtggccgc cgagaagcag ctgaccatgc tggaccgcaa gtccaagcgc    360

cccgacatgc tggtggactg gttcggcctg gagtccatcg tgcaggacgg cctggtgttc    420

cgcgagatct actccatccg ctcctacgag atctccgccg accgcaccac ctccatcgag    480

accgtgatga acctgctgca ggagacctcc ctgaaccact gcaagtccat gggcatcctg    540

aacgacggct tcggccgcac ccccgagatg tgcaagcgcg acctgatctg ggtgctgacc    600

aagatgcaga tcctggtgaa ccgctacccc aactggggcg acaccgtgga gatcaactcc    660

tggttctccc agtccggcaa gatcggcatg ggccgcaact ggctgatctc cgactgcaac    720

accggcgaga tcctgatccg cgccacctcc atctgggcca tgatgaacca gaagacccgc    780
```

-continued

```
cgcttctcca agctgcccaa cgaggtgcgc caggagatcg ccccccactt cgtggacgcc    840

ccccccgtga tcgaggacaa cgaccgcaag ctgcacaagt tcgacgtgaa gaccggcgac    900

tccatctgca agggcctgac ccccgagtgg aacgacctgg acgtgaacca gcacgtgtcc    960

aacgtgaagt acatcggctg gatcctggag tccatgccca aggaggtgct ggacacccag   1020

gagctgtgct ccctgaccct ggagtaccgc cgcgagtgcg gccgcgactc cgtgctggag   1080

tccgtgaccg ccatggaccc ctccaaggtg ggcgaccgct cccagtacca gcacctgctg   1140

cgcctggagg acggcaccga catcatgaag ggccgcaccg agtggcgccc caagaacgcc   1200

ggcaccaacg gcgccatctc caccggcaag acctccaacg ccaactccgt gtcctga      1257


<210> SEQ ID NO 67
<211> LENGTH: 414
<212> TYPE: PRT
<213> ORGANISM: Cuphea heterophylla

<400> SEQUENCE: 67

Met Val Ala Thr Ala Ala Ser Ser Ala Phe Phe Pro Val Pro Ser Pro
1               5                   10                  15

Asp Thr Ser Ser Arg Pro Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Cys Ser Leu Lys Thr His Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
```

-continued

```
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410
```

<210> SEQ ID NO 68
<211> LENGTH: 1245
<212> TYPE: DNA
<213> ORGANISM: Cuphea heterophylla

<400> SEQUENCE: 68

```
atggtggcca ccgctgcaag ttctgcattc ttcccggtgc cgtccccgga cacctcctct     60

agaccgggaa agctcggaaa tgggtcatca agcttgaggc ccctcaagcc caaatttgtt    120

gccaatgctg ggctgcaggt taaggcaaac gccagtgccc ctcctaagat caatggttcc    180

tcggtcagtc taaagtcttg cagtctcaag actcatgaag acactccttc agctcctcct    240

ccgcggactt ttatcaacca gttgcctgat tggagcatgc ttcttgctgc aatcactact    300

gtcttcttgg cagcagagaa gcagtggatg atgcttgatt ggaaaccaaa gaggcctgac    360

atgcttgtgg acccgttcgg attgggaagg attgttcagg atgggcttgt gttcaggcag    420

aatttttcga ttaggtccta tgaaataggc gctgatcgca ctgcatccat agagacggtg    480

atgaaccact tgcaggaaac ggctctcaat catgttaaga gtgcggggct tcttaatgaa    540

ggctttggtc gtactcctga gatgtataaa agggacctta tttgggttgt cgcgaaaatg    600

caggtcatgg ttaaccgcta tcctacttgg ggtgacacgg ttgaagtgaa tacttgggtt    660

gccaagtcag ggaaaaatgg tatgcgtcgt gattggctca taagtgattg caatacagga    720

gaaattctta caagggcatc aagtgtgtgg gtcatgatga atcaaaagac aagaaaattg    780

tcaaagattc cagatgaggt tcggcatgag atagagcctc attttgtgga ctctgctccc    840

gtcattgaag acgatgactg gaaacttccc aagctggatg agaaaactgc tgactccatc    900

cgcaagggtc taactccgaa gtggaatgac ttggatgtca atcagcacgt caacaacgtg    960

aagtacattg ggtggattct tgagagtact ccaccagaag ttctggagac ccaggagtta   1020

tgttccctta ccctggaata caggcgggaa tgcggaaggg agagtgtgct ggagtccctc   1080

actgctgtgg acccctctgg aaagggcttt gggccccagt ttcagcacct tctgaggctt   1140

gaggatggag gtgagatcgt aaaggggaga actgagtggc gacccaagac tgcaggtatc   1200

aatgggacga ttgcatctgg ggagacctca cctggaaact cttag                   1245
```

<210> SEQ ID NO 69
<211> LENGTH: 1245
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 69

```
atggtggcca ccgccgcctc ctccgccttc ttccccgtgc cctcccccga cacctcctcc     60
cgccccggca agctgggcaa cggctcctcc tccctgcgcc ccctgaagcc caagttcgtg    120
gccaacgccg gcctgcaggt gaaggccaac gcctccgccc cccccaagat caacggctcc    180
tccgtgtccc tgaagtcctg ctccctgaag acccacgagg acacccccctc cgccccccccc    240
ccccgcacct tcatcaacca gctgcccgac tggtccatgc tgctggccgc catcaccacc    300
gtgttcctgg ccgccgagaa gcagtggatg atgctggact ggaagcccaa gcgccccgac    360
atgctggtgg accccttcgg cctgggccgc atcgtgcagg acggcctggt gttccgccag    420
aacttctcca tccgctccta cgagatcggc gccgaccgca ccgcctccat cgagaccgtg    480
atgaaccacc tgcaggagac cgccctgaac cacgtgaagt ccgccggcct gctgaacgag    540
ggcttcggcc gcacccccga gatgtacaag cgcgacctga tctgggtggt ggccaagatg    600
caggtgatgg tgaaccgcta ccccacctgg ggcgacaccg tggaggtgaa cacctgggtg    660
gccaagtccg gcaagaacgg catgcgccgc gactggctga tctccgactg caacaccggc    720
gagatcctga cccgcgcctc ctccgtgtgg gtgatgatga accagaagac ccgcaagctg    780
tccaagatcc ccgacgaggt gcgccacgag atcgagcccc acttcgtgga ctccgccccc    840
gtgatcgagg acgacgactg gaagctgccc aagctggacg agaagaccgc cgactccatc    900
cgcaagggcc tgacccccaa gtggaacgac ctggacgtga accagcacgt gaacaacgtg    960
aagtacatcg gctggatcct ggagtccacc ccccccgagg tgctggagac ccaggagctg   1020
tgctccctga ccctggagta ccgccgcgag tgcggccgcg agtccgtgct ggagtccctg   1080
accgccgtgg acccctccgg caagggcttc ggcccccagt tccagcacct gctgcgcctg   1140
gaggacggcg gcgagatcgt gaagggccgc accgagtggc gccccaagac cgccggcatc   1200
aacggcacca tcgcctccgg cgagacctcc cccggcaact cctga                  1245
```

<210> SEQ ID NO 70
<211> LENGTH: 414
<212> TYPE: PRT
<213> ORGANISM: Cuphea heterophylla

<400> SEQUENCE: 70

```
Met Val Ala Thr Ala Ala Ser Ser Ala Phe Phe Pro Val Pro Ser Pro
1               5                   10                  15

Asp Thr Ser Ser Arg Pro Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Phe
        115                 120                 125
```

```
Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Ile Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410
```

<210> SEQ ID NO 71
<211> LENGTH: 1245
<212> TYPE: DNA
<213> ORGANISM: Cuphea heterophylla

<400> SEQUENCE: 71

```
atggtggcca ccgctgcaag ttctgcattc ttcccggtgc catccccgga cacctcctct      60

agaccgggaa agctcggaaa tgggtcatca agcttgaggc ccctcaagcc caaatttgtt     120

gccaatgctg ggctgcaggt taaggcaaac gccagtgccc ctcctaagat caatggttcc     180

tcggtcagtc taaagtctgg cagtctcaag actcaggaag acactccttc ggctcctcct     240

ccgcggactt ttatcaacca gttgcctgat tggagcatgc ttcttgctgc aatcactact     300

gtcttcttgg cagcagagaa gcagtggatg atgcttgatt ggaaaccaaa gaggcctgac     360

atgcttgtgg acccgttcgg atttggaagg attgttcagg atgggcttgt gttcaggcag     420

aatttttcga ttaggtccta tgaaataggc gctgatcgca ctgcatctat agagacggtg     480

atgaaccact tgcaggaaac ggctctcaat catgttaaga gtgcggggct tcttattgaa     540
```

ggctttggtc gtactcctga gatgtataaa agggacctta tttgggttgt cgcgaaaatg 600
caggtcatgg ttaaccgcta tcctacttgg ggtgacacgg ttgaagtgaa tacttgggtt 660
gccaagtcag ggaaaaatgg tatgcgtcgt gattggctca taagtgattg caatacagga 720
gaaattctta ctagagcatc aagtgtgtgg gtcatgatga atcaaaagac aagaaaattg 780
tcaaagattc cagatgaggt tcggcatgag atagagcctc attttgtgga ctctgctccc 840
gtcattgaag acgatgactg gaaacttccc aagctggatg agaaaactgc tgactccatc 900
cgcaagggtc taactccgaa gtggaatgac ttggatgtca atcagcacgt caacaacgtg 960
aagtacattg ggtggattct tgagagtact ccaccagaag ttctggagac ccaggagtta 1020
tgttccctta ccctggaata caggcgggaa tgcggaaggg agagtgtgct ggagtccctc 1080
actgctgtgg acccctctgg aaagggcttt gggccccagt ttcagcacct tctgaggctt 1140
gaggatggag gtgagatcgt aaaggggaga actgagtggc gacccaagac tgcaggtatc 1200
aatgggacga ttgcatctgg ggagacctca cctggaaact cttag 1245

<210> SEQ ID NO 72
<211> LENGTH: 1245
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72
atggtggcca ccgccgcctc ctccgccttc ttccccgtgc cctcccccga cacctcctcc 60
cgccccggca agctgggcaa cggctcctcc tccctgcgcc ccctgaagcc caagttcgtg 120
gccaacgccg gcctgcaggt gaaggccaac gcctccgccc cccccaagat caacggctcc 180
tccgtgtccc tgaagtccgg ctccctgaag acccaggagg acacccccctc cgcccccccc 240 ccccgcacct tcatcaacca gctgcccgac tggtccatgc tgctggccgc catcaccacc 300
gtgttcctgg ccgccgagaa gcagtggatg atgctggact ggaagcccaa gcgccccgac 360
atgctggtgg accccttcgg cttcggccgc atcgtgcagg acggcctggt gttccgccag 420
aacttctcca tccgctccta cgagatcggc gccgaccgca ccgcctccat cgagaccgtg 480
atgaaccacc tgcaggagac cgccctgaac cacgtgaagt ccgccggcct gctgatcgag 540
ggcttcggcc gcacccccga gatgtacaag cgcgacctga tctgggtggt ggccaagatg 600
caggtgatgg tgaaccgcta ccccacctgg ggcgacaccg tggaggtgaa cacctgggtg 660
gccaagtccg gcaagaacgg catgcgccgc gactggctga tctccgactg caacaccggc 720
gagatcctga cccgcgcctc ctccgtgtgg gtgatgatga accagaagac ccgcaagctg 780
tccaagatcc ccgacgaggt gcgccacgag atcgagcccc acttcgtgga ctccgccccc 840
gtgatcgagg acgacgactg gaagctgccc aagctggacg agaagaccgc cgactccatc 900
cgcaagggcc tgacccccaa gtggaacgac ctggacgtga accagcacgt gaacaacgtg 960
aagtacatcg gctggatcct ggagtccacc ccccccgagg tgctggagac ccaggagctg 1020
tgctccctga ccctggagta ccgccgcgag tgcggccgcg agtccgtgct ggagtccctg 1080
accgccgtgg acccctccgg caagggcttc ggcccccagt tccagcacct gctgcgcctg 1140
gaggacggcg gcgagatcgt gaagggccgc accgagtggc gccccaagac cgccggcatc 1200
aacggcacca tcgcctccgg cgagacctcc cccggcaact cctga 1245

-continued

```
<210> SEQ ID NO 73
<211> LENGTH: 419
<212> TYPE: PRT
<213> ORGANISM: Cuphea viscosissima

<400> SEQUENCE: 73

Met Val Ala Ala Ala Ala Thr Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Thr Phe Lys Pro Lys Ser Ile Pro Asn Gly Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Ser Ile Val Arg Asp Gly Leu Val Ser Arg His Ser Phe Ser
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Thr Ile Asn His Cys Lys Ser Leu
                165                 170                 175

Gly Leu His Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser Gln Ser
    210                 215                 220

Gly Lys Ile Gly Met Ala Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Gln
        275                 280                 285

Lys Leu Arg Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Val Asp Pro Ser Glu
        355                 360                 365

Asn Gly Gly Arg Ser Gln Tyr Lys His Leu Leu Arg Leu Glu Asp Gly
    370                 375                 380
```

```
Thr Asp Ile Val Lys Ser Arg Thr Glu Trp Arg Pro Lys Asn Ala Gly
385                 390                 395                 400

Thr Asn Gly Ala Ile Ser Thr Ser Thr Ala Lys Thr Ser Asn Gly Asn
                405                 410                 415

Ser Val Ser


<210> SEQ ID NO 74
<211> LENGTH: 1260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

atggtggccg ccgccgccac ctccgccttc ttccccgtgc ccgcccccgg cacctccccc     60

aagcccggca agtccggcaa ctggccctcc tccctgtccc ccaccttcaa gcccaagtcc    120

atccccaacg gcggcttcca ggtgaaggcc aacgcctccg cccaccccaa ggccaacggc    180

tccgccgtga acctgaagtc cggctccctg aacacccagg aggacacctc ctcctccccc    240

ccccccgcg ccttcctgaa ccagctgccc gactggtcca tgctgctgac cgccatcacc    300

accgtgttcg tggccgccga gaagcagtgg accatgctgg accgcaagtc caagcgcccc    360

gacatgctgg tggactccgt gggcctgaag tccatcgtgc gcgacggcct ggtgtcccgc    420

cactccttct ccatccgctc ctacgagatc ggcgccgacc gcaccgcctc catcgagacc    480

ctgatgaacc acctgcagga gaccaccatc aaccactgca agtccctggg cctgcacaac    540

gacggcttcg gccgcacccc cggcatgtgc aagaacgacc tgatctgggt gctgaccaag    600

atgcagatca tggtgaaccg ctaccccacc tggggcgaca ccgtggagat caacacctgg    660

ttctcccagt ccggcaagat cggcatggcc tccgactggc tgatctccga ctgcaacacc    720

ggcgagatcc tgatccgcgc cacctccgtg tgggccatga tgaaccagaa gacccgccgc    780

ttctcccgcc tgccctacga ggtgcgccag gagctgaccc cccacttcgt ggactccccc    840

cacgtgatcg aggacaacga ccagaagctg cgcaagttcg acgtgaagac cggcgactcc    900

atccgcaagg gcctgacccc ccgctggaac gacctggacg tgaaccagca cgtgtccaac    960

gtgaagtaca tcggctggat cctggagtcc atgcccatcg aggtgctgga gacccaggag   1020

ctgtgctccc tgaccgtgga gtaccgccgc gagtgcggca tggactccgt gctggagtcc   1080

gtgaccgccg tggacccctc cgagaacggc ggccgctccc agtacaagca cctgctgcgc   1140

ctggaggacg gcaccgacat cgtgaagtcc cgcaccgagt ggcgccccaa gaacgccggc   1200

accaacggcg ccatctccac ctccaccgcc aagacctcca acggcaactc cgtgtcctga   1260


<210> SEQ ID NO 75
<211> LENGTH: 415
<212> TYPE: PRT
<213> ORGANISM: Cuphea viscosissima

<400> SEQUENCE: 75

Met Val Ala Thr Ala Ala Ser Ser Ala Phe Phe Pro Val Pro Ser Ala
1               5                   10                  15

Asp Thr Ser Ser Arg Pro Gly Lys Leu Gly Asn Gly Pro Ser Ser Phe
            20                  25                  30

Ser Pro Leu Lys Pro Lys Ser Ile Pro Asn Gly Gly Leu Gln Val Lys
        35                  40                  45

Ala Ser Ala Ser Ala Pro Pro Lys Ile Asn Gly Ser Ser Val Gly Leu
```

-continued

```
    50                  55                  60

Lys Ser Gly Gly Leu Lys Thr His Asp Asp Ala Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Ala Phe Leu Ala Ala Glu Lys Gln Trp Met Met Leu
            100                 105                 110

Asp Arg Lys Pro Lys Arg Leu Asp Met Leu Glu Asp Pro Phe Gly Leu
        115                 120                 125

Gly Arg Val Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Thr Ala Gly
                165                 170                 175

Leu Ser Asn Asp Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg Arg Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Ser Ala Asp Ser Ile Arg Lys Gly Leu
    290                 295                 300

Thr Pro Arg Trp Asn Asp Leu Asp Val Asn Gln His Val Asn Asn Ala
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Glu
        355                 360                 365

Gly Tyr Gly Ser Gln Phe Gln His Leu Leu Arg Leu Glu Asp Gly Gly
    370                 375                 380

Glu Ile Val Lys Gly Arg Thr Glu Trp Arg Pro Lys Asn Ala Gly Ile
385                 390                 395                 400

Asn Gly Val Val Pro Ser Glu Glu Ser Ser Pro Gly Asp Tyr Ser
                405                 410                 415


<210> SEQ ID NO 76
<211> LENGTH: 1248
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
```

-continued

```
atggtggcca ccgccgcctc ctccgccttc ttccccgtgc cctccgccga cacctcctcc     60
cgccccggca agctgggcaa cggcccctcc tccttctccc ccctgaagcc caagtccatc    120
cccaacggcg gcctgcaggt gaaggcctcc gcctccgccc cccccaagat caacggctcc    180
tccgtgggcc tgaagtccgg cggcctgaag acccacgacg acgccccctc cgcccccccc    240
ccccgcacct tcatcaacca gctgcccgac tggtccatgc tgctggccgc catcaccacc    300
gccttcctgg ccgccgagaa gcagtggatg atgctggacc gcaagcccaa gcgcctggac    360
atgctggagg acccettcgg cctgggccgc gtggtgcagg acggcctggt gttccgccag    420
aacttctcca tccgctccta cgagatcggc gccgaccgca ccgcctccat cgagaccgtg    480
atgaaccacc tgcaggagac cgccctgaac cacgtgaaga ccgccggcct gtccaacgac    540
ggcttcggcc gcacccccga gatgtacaag cgcgacctga tctgggtggt ggccaagatg    600
caggtgatgg tgaaccgcta ccccacctgg ggcgacaccg tggaggtgaa cacctgggtg    660
gccaagtccg gcaagaacgg catgcgccgc gactggctga tctccgactg caacaccggc    720
gagatcctga cccgcgcctc ctccgtgtgg gtgatgatga accagaagac ccgcaagctg    780
tccaagatcc ccgacgaggt gcgccgcgag atcgagcccc acttcgtgga ctccgccccc    840
gtgatcgagg acgacgaccg caagctgccc aagctggacg agaagtccgc cgactccatc    900
cgcaagggcc tgaccccccg ctggaacgac ctggacgtga accagcacgt gaacaacgcc    960
aagtacatcg gctggatcct ggagtccacc ccccccgagg tgctggagac ccaggagctg   1020
tgctccctga ccctggagta ccgccgcgag tgcggccgcg agtccgtgct ggagtccctg   1080
accgccgtgg acccctccgg cgagggctac ggctcccagt tccagcacct gctgcgcctg   1140
gaggacggcg gcgagatcgt gaagggccgc accgagtggc gccccaagaa cgccggcatc   1200
aacggcgtgg tgccctccga ggagtcctcc cccggcgact actcctga                 1248
```

<210> SEQ ID NO 77
<211> LENGTH: 412
<212> TYPE: PRT
<213> ORGANISM: Cuphea viscosissima

<400> SEQUENCE: 77

```
Met Val Ala Ala Ala Ala Ser Ser Ala Phe Phe Ser Phe Pro Thr Pro
1               5                   10                  15

Gly Thr Ser Pro Lys Pro Gly Lys Phe Gly Asn Trp Pro Ser Ser Leu
            20                  25                  30

Ser Ile Pro Phe Asn Pro Lys Ser Asn His Asn Gly Gly Ile Gln Val
        35                  40                  45

Lys Ala Asn Ala Ser Ala His Pro Lys Ala Asn Gly Ser Ala Val Ser
    50                  55                  60

Leu Lys Ala Gly Ser Leu Glu Thr Gln Glu Asp Thr Ser Ser Pro Ser
65                  70                  75                  80

Pro Pro Pro Arg Thr Phe Ile Ser Gln Leu Pro Asp Trp Ser Met Leu
                85                  90                  95

Val Ser Ala Ile Thr Thr Val Phe Val Ala Ala Glu Lys Gln Trp Thr
            100                 105                 110

Met Leu Asp Arg Lys Ser Lys Arg Pro Asp Val Leu Val Glu Pro Phe
        115                 120                 125

Val Gln Asp Gly Val Ser Phe Arg Gln Ser Phe Ser Ile Arg Ser Tyr
    130                 135                 140

Glu Ile Gly Val Asp Arg Thr Ala Ser Ile Glu Thr Leu Met Asn Ile
145                 150                 155                 160
```

Phe Gln Glu Thr Ser Leu Asn His Cys Lys Ser Leu Gly Leu Leu Asn
165 170 175

Asp Gly Phe Gly Arg Thr Pro Glu Met Cys Lys Arg Asp Leu Ile Trp
180 185 190

Val Val Thr Lys Met Gln Ile Glu Val Asn Arg Tyr Pro Thr Trp Gly
195 200 205

Asp Thr Ile Glu Val Thr Thr Trp Val Ser Glu Ser Gly Lys Asn Gly
210 215 220

Met Ser Arg Asp Trp Leu Ile Ser Asp Cys His Ser Gly Glu Ile Leu
225 230 235 240

Ile Arg Ala Thr Ser Val Trp Ala Met Met Asn Gln Lys Thr Arg Arg
245 250 255

Leu Ser Lys Ile Pro Asp Glu Val Arg Gln Glu Ile Val Pro Tyr Phe
260 265 270

Val Asp Ser Ala Pro Val Ile Glu Asp Asp Arg Lys Leu His Lys Leu
275 280 285

Asp Val Lys Thr Gly Asp Ser Ile Arg Asn Gly Leu Thr Pro Arg Trp
290 295 300

Asn Asp Phe Asp Val Asn Gln His Val Asn Asn Val Lys Tyr Ile Ala
305 310 315 320

Trp Leu Leu Lys Ser Val Pro Thr Glu Val Phe Glu Thr Gln Glu Leu
325 330 335

Cys Gly Leu Thr Leu Glu Tyr Arg Arg Glu Cys Arg Arg Asp Ser Val
340 345 350

Leu Glu Ser Val Thr Ala Met Asp Pro Ser Lys Glu Gly Asp Arg Ser
355 360 365

Leu Tyr Gln His Leu Leu Arg Leu Glu Asn Gly Ala Asp Ile Ala Leu
370 375 380

Gly Arg Thr Glu Trp Arg Pro Lys Asn Ala Gly Ala Thr Gly Ala Val
385 390 395 400

Ser Thr Gly Lys Thr Ser Asn Gly Asn Ser Val Ser
405 410

<210> SEQ ID NO 78
<211> LENGTH: 1239
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 78
atggtggccg ccgccgcctc ctccgccttc ttctccttcc ccacccccgg cacctccccc 60
aagcccggca agttcggcaa ctggccctcc tccctgtcca tccccttcaa ccccaagtcc 120
aaccacaacg gcggcatcca ggtgaaggcc aacgcctccg cccaccccaa ggccaacggc 180
tccgccgtgt ccctgaaggc cggctccctg gagacccagg aggacacctc ctcccccctcc 240 cccccccccc gcaccttcat ctcccagctg cccgactggt ccatgctggt gtccgccatc 300
accaccgtgt tcgtggccgc cgagaagcag tggaccatgc tggaccgcaa gtccaagcgc 360
cccgacgtgc tggtggagcc cttcgtgcag gacggcgtgt ccttccgcca gtccttctcc 420
atccgctcct acgagatcgg cgtggaccgc accgcctcca tcgagaccct gatgaacatc 480
ttccaggaga cctccctgaa ccactgcaag tccctgggcc tgctgaacga cggcttcggc 540
cgcacccccg agatgtgcaa gcgcgacctg atctgggtgg tgaccaagat gcagatcgag 600

-continued

```
gtgaaccgct accccacctg gggcgacacc atcgaggtga ccacctgggt gtccgagtcc    660

ggcaagaacg gcatgtcccg cgactggctg atctccgact gccactccgg cgagatcctg    720

atccgcgcca cctccgtgtg ggccatgatg aaccagaaga cccgccgcct gtccaagatc    780

cccgacgagg tgcgccagga gatcgtgccc tacttcgtgg actccgcccc cgtgatcgag    840

gacgaccgca agctgcacaa gctggacgtg aagaccggcg actccatccg caacggcctg    900

accccccgct ggaacgactt cgacgtgaac cagcacgtga acaacgtgaa gtacatcgcc    960

tggctgctga agtccgtgcc caccgaggtg ttcgagaccc aggagctgtg cggcctgacc   1020

ctggagtacc gccgcgagtg ccgccgcgac tccgtgctgg agtccgtgac cgccatggac   1080

ccctccaagg agggcgaccg ctccctgtac cagcacctgc tgcgcctgga gaacggcgcc   1140

gacatcgccc tgggccgcac cgagtggcgc cccaagaacg ccggcgccac cggcgccgtg   1200

tccaccggca agacctccaa cggcaactcc gtgtcctga                          1239


<210> SEQ ID NO 79
<211> LENGTH: 419
<212> TYPE: PRT
<213> ORGANISM: Cuphea sp.

<400> SEQUENCE: 79

Met Val Val Ala Ala Ala Thr Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Thr Phe Lys Pro Lys Ser Ile Pro Asn Ala Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Ser Ile Val Arg Asp Gly Leu Val Ser Arg Gln Ser Phe Leu
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser Gln Ser
    210                 215                 220

Gly Lys Ile Gly Met Ala Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255
```

```
Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Gln
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Val Asp Pro Ser Glu
        355                 360                 365

Asn Gly Gly Arg Ser Gln Tyr Lys His Leu Leu Arg Leu Glu Asp Gly
    370                 375                 380

Thr Asp Ile Val Lys Ser Arg Thr Glu Trp Arg Pro Lys Asn Ala Gly
385                 390                 395                 400

Thr Asn Gly Ala Ile Ser Thr Ser Thr Ala Lys Thr Ser Asn Gly Asn
                405                 410                 415

Ser Ala Ser


<210> SEQ ID NO 80
<211> LENGTH: 354
<212> TYPE: PRT
<213> ORGANISM: Cuphea wrightii

<400> SEQUENCE: 80

Met Val Val Ala Ala Ala Ala Ser Ser Ala Phe Phe Pro Val Pro Ala
1               5                   10                  15

Pro Arg Thr Thr Pro Lys Pro Gly Lys Phe Gly Asn Trp Pro Ser Ser
            20                  25                  30

Leu Ser Pro Pro Phe Lys Pro Lys Ser Asn Pro Asn Gly Arg Phe Gln
        35                  40                  45

Val Lys Ala Asn Val Ser Pro His Pro Lys Ala Asn Gly Ser Ala Val
    50                  55                  60

Ser Leu Lys Ser Gly Ser Leu Asn Thr Leu Glu Asp Leu Pro Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Ala Glu Lys Gln Phe Thr
            100                 105                 110

Arg Leu Asp Arg Lys Ser Lys Arg Pro Asp Met Leu Val Asp Trp Phe
        115                 120                 125

Gly Ser Glu Thr Ile Val Gln Asp Gly Leu Val Phe Arg Glu Arg Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Ser Glu Met Cys Thr
            180                 185                 190

Arg Asp Leu Ile Trp Val Leu Thr Lys Met Gln Ile Val Val Asn Arg
        195                 200                 205
```

-continued

```
Tyr Pro Thr Trp Gly Asp Thr Val Glu Ile Asn Ser Trp Phe Ser Gln
    210                 215                 220

Ser Gly Lys Ile Gly Met Gly Arg Asp Trp Leu Ile Ser Asp Cys Asn
225                 230                 235                 240

Thr Gly Glu Ile Leu Val Arg Ala Thr Ser Ala Trp Ala Met Met Asn
                245                 250                 255

Gln Lys Thr Arg Arg Phe Ser Lys Leu Pro Cys Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Lys Phe Trp Arg Pro Arg
                325                 330                 335

Ser Tyr Ala Leu Ser Pro Leu Asn Ile Gly Gly Asn Val Glu Gly Lys
            340                 345                 350

Val Trp


<210> SEQ ID NO 81
<211> LENGTH: 354
<212> TYPE: PRT
<213> ORGANISM: Cuphea wrightii

<400> SEQUENCE: 81

Met Val Val Ala Ala Ala Ala Ser Ser Ala Phe Phe Pro Val Pro Ala
1               5                   10                  15

Pro Arg Thr Thr Pro Lys Pro Gly Lys Phe Gly Asn Trp Pro Ser Ser
            20                  25                  30

Leu Ser Pro Pro Phe Lys Pro Lys Ser Asn Pro Asn Gly Arg Phe Gln
        35                  40                  45

Val Lys Ala Asn Val Ser Pro His Pro Lys Ala Asn Gly Ser Ala Val
    50                  55                  60

Ser Leu Lys Ser Gly Ser Leu Asn Thr Leu Glu Asp Leu Pro Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Thr Glu Lys Gln Phe Thr
            100                 105                 110

Arg Leu Asp Arg Lys Ser Lys Arg Pro Asp Met Leu Val Asp Trp Phe
        115                 120                 125

Gly Ser Glu Thr Ile Val Gln Asp Gly Leu Val Phe Arg Glu Arg Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Ser Glu Met Cys Thr
            180                 185                 190

Arg Asp Leu Ile Trp Val Leu Thr Lys Met Gln Ile Val Val Asn Arg
        195                 200                 205

Tyr Pro Thr Trp Gly Asp Thr Val Glu Ile Asn Ser Trp Phe Ser Gln
    210                 215                 220
```

-continued

```
Ser Gly Lys Ile Gly Met Gly Arg Asp Trp Leu Ile Ser Asp Cys Asn
225                 230                 235                 240

Thr Gly Glu Ile Leu Val Arg Ala Thr Ser Ala Trp Ala Met Met Asn
                245                 250                 255

Gln Lys Thr Arg Arg Phe Ser Lys Leu Pro Cys Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Lys Phe Trp Arg Pro Arg
                325                 330                 335

Ser Tyr Ala Leu Ser Pro Leu Asn Ile Gly Gly Asn Val Glu Gly Lys
            340                 345                 350

Val Trp


<210> SEQ ID NO 82
<211> LENGTH: 416
<212> TYPE: PRT
<213> ORGANISM: Cuphea wrightii

<400> SEQUENCE: 82

Met Val Ala Thr Ala Ala Ser Ser Ala Phe Phe Pro Val Pro Ser Ala
1               5                   10                  15

Asp Thr Ser Ser Ser Arg Pro Gly Lys Leu Gly Ser Gly Pro Ser Ser
            20                  25                  30

Leu Ser Pro Leu Lys Pro Lys Ser Ile Pro Asn Gly Gly Leu Gln Val
        35                  40                  45

Lys Ala Asn Ala Ser Ala Pro Pro Lys Ile Asn Gly Ser Ser Val Gly
    50                  55                  60

Leu Lys Ser Gly Gly Phe Lys Thr Gln Glu Asp Ser Pro Ser Ala Pro
65                  70                  75                  80

Pro Pro Arg Thr Phe Ile Asn Gln Leu Pro Asp Trp Ser Met Leu Leu
                85                  90                  95

Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125

Leu Gly Ser Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
                165                 170                 175

Gly Leu Ser Asn Asp Gly Phe Gly Arg Thr Pro Glu Met Tyr Lys Arg
            180                 185                 190

Asp Leu Ile Trp Val Val Ala Lys Met Gln Val Met Val Asn Arg Tyr
        195                 200                 205

Pro Thr Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240
```

-continued

```
Gly Glu Ile Leu Thr Arg Ala Ser Ser Val Trp Val Met Met Asn Gln
                245                 250                 255

Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Pro Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Ala
        355                 360                 365

Glu Gly Tyr Ala Ser Arg Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Trp Val Val Pro Ser Glu Glu Ser Ser Pro Gly Asp Phe Phe
                405                 410                 415


<210> SEQ ID NO 83
<211> LENGTH: 416
<212> TYPE: PRT
<213> ORGANISM: Cuphea wrightii

<400> SEQUENCE: 83

Met Val Ala Thr Ala Ala Ser Ser Ala Phe Phe Pro Val Pro Ser Ala
1               5                   10                  15

Asp Thr Ser Ser Ser Arg Pro Gly Lys Leu Gly Asn Gly Pro Ser Ser
            20                  25                  30

Leu Ser Pro Leu Lys Pro Lys Ser Ile Pro Asn Gly Gly Leu Gln Val
        35                  40                  45

Lys Ala Asn Ala Ser Ala Pro Pro Lys Ile Asn Gly Ser Ser Val Gly
    50                  55                  60

Leu Lys Ser Gly Ser Phe Lys Thr Gln Glu Asp Ala Pro Ser Ala Pro
65                  70                  75                  80

Pro Pro Arg Thr Phe Ile Asn Gln Leu Pro Asp Trp Ser Met Leu Leu
                85                  90                  95

Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125

Leu Gly Ser Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
                165                 170                 175

Gly Leu Ser Asn Asp Gly Phe Gly Arg Thr Pro Glu Met Tyr Lys Arg
            180                 185                 190

Asp Leu Ile Trp Val Val Ala Lys Met Gln Val Met Val Asn Arg Tyr
        195                 200                 205
```

```
Pro Thr Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240

Gly Glu Ile Leu Thr Arg Ala Ser Ser Val Trp Val Met Met Asn Gln
                245                 250                 255

Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Pro Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Ala
        355                 360                 365

Glu Gly Tyr Ala Ser Arg Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Gly Val Val Pro Ser Glu Glu Ser Ser Pro Gly Asp Phe Phe
                405                 410                 415


<210> SEQ ID NO 84
<211> LENGTH: 416
<212> TYPE: PRT
<213> ORGANISM: Cuphea wrightii

<400> SEQUENCE: 84

Met Val Ala Thr Ala Ala Ser Ser Ala Phe Phe Pro Val Pro Ser Ala
1               5                   10                  15

Asp Thr Ser Ser Ser Arg Pro Gly Lys Leu Gly Ser Gly Pro Ser Ser
            20                  25                  30

Leu Ser Pro Leu Lys Pro Lys Ser Ile Pro Asn Gly Gly Leu Gln Val
        35                  40                  45

Lys Ala Asn Ala Ser Ala Pro Pro Lys Ile Asn Gly Ser Ser Val Gly
    50                  55                  60

Leu Lys Ser Gly Gly Phe Lys Thr Gln Glu Asp Ser Pro Ser Ala Pro
65                  70                  75                  80

Pro Pro Arg Thr Phe Ile Asn Gln Leu Pro Asp Trp Ser Met Leu Leu
                85                  90                  95

Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125

Leu Gly Ser Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
```

-continued

```
                165                 170                 175

Gly Leu Ser Asn Asp Gly Phe Gly Arg Thr Pro Glu Met Tyr Lys Arg
            180                 185                 190

Asp Leu Ile Trp Val Val Ala Lys Met Gln Val Met Val Asn Arg Tyr
        195                 200                 205

Pro Thr Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240

Gly Glu Ile Leu Thr Arg Ala Ser Ser Val Trp Val Met Met Asn Gln
                245                 250                 255

Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Pro Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Ala
        355                 360                 365

Glu Gly Tyr Val Ser Arg Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Gly Val Val Pro Ser Glu Glu Ser Ser Pro Gly Asp Phe Phe
                405                 410                 415


<210> SEQ ID NO 85
<211> LENGTH: 417
<212> TYPE: PRT
<213> ORGANISM: Cuphea wrightii

<400> SEQUENCE: 85

Met Val Ala Thr Ala Ala Ser Ser Ala Phe Phe Pro Val Pro Ser Ala
1               5                   10                  15

Asp Thr Ser Ser Ser Arg Pro Gly Lys Leu Gly Ser Gly Pro Ser Ser
            20                  25                  30

Leu Ser Pro Leu Lys Pro Lys Ser Ile Pro Asn Gly Gly Leu Gln Val
        35                  40                  45

Lys Ala Asn Ala Ser Ala Pro Pro Lys Ile Asn Gly Ser Ser Val Gly
    50                  55                  60

Leu Lys Ser Gly Ser Phe Lys Thr Gln Glu Asp Ala Pro Ser Ala Pro
65                  70                  75                  80

Pro Pro Arg Thr Phe Ile Asn Gln Leu Pro Asp Trp Ser Met Leu Leu
                85                  90                  95

Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125
```

-continued

```
Leu Gly Ser Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
                165                 170                 175

Gly Leu Ser Ser Asp Gly Phe Gly Arg Thr Pro Ala Met Ser Lys Arg
            180                 185                 190

Asp Leu Ile Trp Val Val Ala Lys Met Gln Val Met Val Asn Arg Tyr
        195                 200                 205

Pro Ala Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240

Gly Glu Ile Leu Thr Arg Ala Ser Ser Val Trp Val Met Met Asn Gln
                245                 250                 255

Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Ala Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Gly
        355                 360                 365

Glu Gly Asp Gly Ser Lys Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Gly Val Val Pro Ser Glu Glu Ser Ser Pro Gly Gly Asp Phe
                405                 410                 415

Phe


<210> SEQ ID NO 86
<211> LENGTH: 413
<212> TYPE: PRT
<213> ORGANISM: Cuphea wrightii

<400> SEQUENCE: 86

Met Val Ala Ala Ala Ala Ser Ser Ala Phe Phe Ser Val Pro Thr Pro
1               5                   10                  15

Gly Thr Pro Pro Lys Pro Gly Lys Phe Gly Asn Trp Pro Ser Ser Leu
            20                  25                  30

Ser Val Pro Phe Lys Pro Asp Asn Gly Gly Phe His Val Lys Ala Asn
        35                  40                  45

Ala Ser Ala His Pro Lys Ala Asn Gly Ser Ala Val Asn Leu Lys Ser
    50                  55                  60

Gly Ser Leu Glu Thr Pro Pro Arg Ser Phe Ile Asn Gln Leu Pro Asp
65                  70                  75                  80
```

-continued

```
Leu Ser Val Leu Leu Ser Lys Ile Thr Thr Val Phe Gly Ala Ala Glu
                85                  90                  95

Lys Gln Trp Lys Arg Pro Gly Met Leu Val Glu Pro Phe Gly Val Asp
            100                 105                 110

Arg Ile Phe Gln Asp Gly Phe Phe Phe Arg Gln Ser Phe Ser Ile Arg
        115                 120                 125

Ser Tyr Glu Ile Gly Val Asp Arg Thr Ala Ser Ile Glu Thr Leu Met
    130                 135                 140

Asn Ile Phe Gln Glu Thr Ser Leu Asn His Cys Lys Ser Ile Gly Leu
145                 150                 155                 160

Leu Asn Asp Gly Phe Gly Arg Thr Pro Glu Met Cys Lys Arg Asp Leu
                165                 170                 175

Ile Trp Val Val Thr Lys Ile Gln Val Glu Val Asn Arg Tyr Pro Thr
            180                 185                 190

Trp Gly Asp Thr Ile Glu Val Asn Thr Trp Val Ser Glu Ser Gly Lys
        195                 200                 205

Asn Gly Met Gly Arg Asp Trp Leu Ile Ser Asp Cys Arg Thr Gly Glu
    210                 215                 220

Ile Leu Ile Arg Ala Thr Ser Val Trp Ala Met Met Asn Gln Asn Thr
225                 230                 235                 240

Arg Arg Leu Ser Lys Phe Pro Tyr Glu Val Arg Gln Glu Ile Ala Pro
                245                 250                 255

His Phe Val Asp Ser Ala Pro Val Ile Glu Asp Asp Gln Lys Leu Gln
            260                 265                 270

Lys Leu Asp Val Lys Thr Gly Asp Ser Ile Arg Asp Gly Leu Thr Pro
        275                 280                 285

Arg Trp Asn Asp Leu Asp Val Asn Gln His Val Asn Asn Val Lys Tyr
    290                 295                 300

Ile Gly Trp Ile Leu Lys Ser Val Pro Ile Glu Val Phe Glu Thr Gln
305                 310                 315                 320

Glu Leu Cys Gly Val Thr Leu Glu Tyr Arg Arg Glu Cys Gly Arg Asp
                325                 330                 335

Ser Val Leu Glu Ser Val Thr Ala Met Asp Pro Ala Lys Glu Gly Asp
            340                 345                 350

Arg Cys Val Tyr Gln His Leu Leu Arg Leu Glu Asp Gly Ala Asp Ile
        355                 360                 365

Thr Ile Gly Arg Thr Glu Trp Arg Pro Lys Asn Ala Gly Ala Asn Gly
    370                 375                 380

Ala Met Ser Ser Gly Lys Thr Ser Asn Gly Asn Cys Leu Ile Glu Gly
385                 390                 395                 400

Arg Gly Trp Gln Pro Phe Arg Val Val Arg Leu Ile Phe
                405                 410


<210> SEQ ID NO 87
<211> LENGTH: 413
<212> TYPE: PRT
<213> ORGANISM: Cuphea wrightii

<400> SEQUENCE: 87

Met Val Ala Ala Ala Ala Ser Ser Ala Phe Phe Ser Val Pro Thr Pro
1               5                   10                  15

Gly Thr Pro Pro Lys Pro Gly Lys Phe Gly Asn Trp Pro Ser Ser Leu
            20                  25                  30

Ser Val Pro Phe Lys Pro Asp Asn Gly Gly Phe His Val Lys Ala Asn
        35                  40                  45
```

```
Ala Ser Ala His Pro Lys Ala Asn Gly Ser Ala Val Asn Leu Lys Ser
    50                  55                  60

Gly Ser Leu Glu Thr Pro Pro Arg Ser Phe Ile Asn Gln Leu Pro Asp
65                  70                  75                  80

Leu Ser Val Leu Leu Ser Lys Ile Thr Thr Val Phe Gly Ala Ala Glu
                85                  90                  95

Lys Gln Trp Lys Arg Pro Gly Met Leu Val Glu Pro Phe Gly Val Asp
            100                 105                 110

Arg Ile Phe Gln Asp Gly Val Phe Phe Arg Gln Ser Phe Ser Ile Arg
        115                 120                 125

Ser Tyr Glu Ile Gly Val Asp Arg Thr Ala Ser Ile Glu Thr Leu Met
    130                 135                 140

Asn Ile Phe Gln Glu Thr Ser Leu Asn His Cys Lys Ser Ile Gly Leu
145                 150                 155                 160

Leu Asn Asp Gly Phe Gly Arg Thr Pro Glu Met Cys Lys Arg Asp Leu
                165                 170                 175

Ile Trp Val Val Thr Lys Ile Gln Val Glu Val Asn Arg Tyr Pro Thr
            180                 185                 190

Trp Gly Asp Thr Ile Glu Val Asn Thr Trp Val Ser Glu Ser Gly Lys
        195                 200                 205

Asn Gly Met Gly Arg Asp Trp Leu Ile Ser Asp Cys Arg Thr Gly Glu
    210                 215                 220

Ile Leu Ile Arg Ala Thr Ser Val Trp Ala Met Met Asn Gln Asn Thr
225                 230                 235                 240

Arg Arg Leu Ser Lys Phe Pro Tyr Glu Val Arg Gln Glu Ile Ala Pro
                245                 250                 255

His Phe Val Asp Ser Ala Pro Val Ile Glu Asp Asp Gln Lys Leu Gln
            260                 265                 270

Lys Leu Asp Val Lys Thr Gly Asp Ser Ile Arg Asp Gly Leu Thr Pro
        275                 280                 285

Arg Trp Asn Asp Leu Asp Val Asn Gln His Val Asn Asn Val Lys Tyr
    290                 295                 300

Ile Gly Trp Ile Leu Lys Ser Val Pro Ile Glu Val Phe Glu Thr Gln
305                 310                 315                 320

Glu Leu Cys Gly Val Thr Leu Glu Tyr Arg Arg Glu Cys Gly Arg Asp
                325                 330                 335

Ser Val Leu Glu Ser Val Thr Ala Met Asp Pro Ala Lys Glu Gly Asp
            340                 345                 350

Arg Cys Val Tyr Gln His Leu Leu Trp Leu Glu Asp Gly Ala Asp Ile
        355                 360                 365

Thr Ile Gly Arg Thr Glu Trp Arg Pro Lys Asn Ala Gly Ala Asn Gly
    370                 375                 380

Ala Met Ser Ser Gly Lys Thr Ser Asn Gly Asn Cys Leu Ile Glu Gly
385                 390                 395                 400

Arg Gly Trp Gln Pro Phe Arg Val Val Arg Leu Ile Phe
                405                 410
```

<210> SEQ ID NO 88
<211> LENGTH: 413
<212> TYPE: PRT
<213> ORGANISM: Cuphea wrightii

<400> SEQUENCE: 88

```
Met Val Ala Ala Ala Ala Ser Ser Ala Phe Phe Ser Val Pro Thr Pro
```

-continued

```
1               5                   10                  15

Gly Thr Pro Pro Lys Pro Gly Lys Phe Gly Asn Trp Pro Ser Ser Leu
            20                  25                  30

Ser Val Pro Phe Lys Pro Asp Asn Gly Gly Phe His Val Lys Ala Asn
        35                  40                  45

Ala Ser Ala His Pro Lys Ala Asn Gly Ser Ala Val Asn Leu Lys Ser
    50                  55                  60

Gly Ser Leu Glu Thr Pro Pro Arg Ser Phe Ile Asn Gln Leu Pro Asp
65                  70                  75                  80

Leu Ser Val Leu Leu Ser Lys Ile Thr Thr Val Phe Gly Ala Ala Glu
                85                  90                  95

Lys Gln Trp Lys Arg Pro Gly Met Leu Val Glu Pro Phe Gly Val Asp
            100                 105                 110

Arg Ile Phe Gln Asp Gly Val Phe Phe Arg Gln Ser Phe Ser Ile Arg
        115                 120                 125

Ser Tyr Glu Ile Gly Val Asp Arg Thr Ala Ser Ile Glu Thr Leu Met
    130                 135                 140

Asn Ile Phe Gln Glu Thr Ser Leu Asn His Cys Lys Ser Ile Gly Leu
145                 150                 155                 160

Leu Asn Asp Gly Phe Gly Arg Thr Pro Glu Met Cys Lys Arg Asp Leu
                165                 170                 175

Ile Trp Val Val Thr Lys Ile Gln Val Glu Val Asn Arg Tyr Pro Ile
            180                 185                 190

Trp Gly Asp Thr Ile Glu Val Asn Thr Trp Val Ser Glu Ser Gly Lys
        195                 200                 205

Asn Gly Met Gly Arg Asp Trp Leu Ile Ser Asp Cys Arg Thr Gly Glu
    210                 215                 220

Ile Leu Ile Arg Ala Thr Ser Val Trp Ala Met Met Asn Gln Asn Thr
225                 230                 235                 240

Arg Arg Leu Ser Lys Phe Pro Tyr Glu Val Arg Gln Glu Ile Ala Pro
                245                 250                 255

His Phe Val Asp Ser Ala Pro Val Ile Glu Asp Asp Gln Lys Leu Gln
            260                 265                 270

Lys Leu Asp Val Lys Thr Gly Asp Ser Ile Arg Asp Gly Leu Thr Pro
        275                 280                 285

Arg Trp Asn Asp Leu Asp Val Asn Gln His Val Asn Asn Val Lys Tyr
    290                 295                 300

Ile Gly Trp Ile Leu Lys Ser Val Pro Ile Glu Val Phe Glu Thr Gln
305                 310                 315                 320

Glu Leu Cys Gly Val Thr Leu Glu Tyr Arg Arg Glu Cys Gly Arg Asp
                325                 330                 335

Ser Val Leu Glu Ser Val Thr Ala Met Asp Pro Ala Lys Glu Gly Asp
            340                 345                 350

Arg Cys Val Tyr Gln His Leu Leu Arg Leu Glu Asp Gly Ala Asp Ile
        355                 360                 365

Thr Ile Gly Arg Thr Glu Trp Arg Pro Lys Asn Ala Gly Ala Asn Gly
    370                 375                 380

Ala Met Ser Ser Gly Lys Thr Ser Asn Gly Asn Cys Leu Ile Glu Gly
385                 390                 395                 400

Met Gly Trp Gln Pro Phe Arg Val Val Arg Leu Ile Phe
                405                 410
```

<210> SEQ ID NO 89

-continued

<211> LENGTH: 409
<212> TYPE: PRT
<213> ORGANISM: Cuphea wrightii

<400> SEQUENCE: 89

```
Met Val Ala Ala Ala Ala Ser Ser Ala Phe Phe Ser Val Pro Thr Pro
1               5                   10                  15

Gly Thr Ser Pro Lys Pro Gly Lys Phe Arg Asn Trp Pro Ser Ser Leu
            20                  25                  30

Ser Val Pro Phe Lys Pro Glu Thr Asn His Asn Gly Gly Phe His Ile
        35                  40                  45

Lys Ala Asn Ala Ser Ala His Pro Lys Ala Asn Gly Ser Ala Leu Asn
    50                  55                  60

Leu Lys Ser Gly Ser Leu Glu Thr Gln Glu Asp Thr Ser Leu Ser Ser
65                  70                  75                  80

Pro Pro Arg Thr Phe Ile Lys Gln Leu Pro Asp Trp Ser Met Leu Leu
                85                  90                  95

Ser Lys Ile Thr Thr Val Phe Gly Ala Ala Glu Lys Gln Leu Lys Arg
            100                 105                 110

Pro Gly Met Leu Val Glu Pro Phe Gly Val Asp Arg Ile Phe Gln Asp
        115                 120                 125

Gly Val Phe Phe Arg Gln Ser Phe Ser Ile Arg Ser Tyr Glu Ile Gly
    130                 135                 140

Ala Asp Arg Thr Ala Ser Ile Glu Thr Leu Met Asn Ile Phe Gln Glu
145                 150                 155                 160

Thr Ser Leu Asn His Cys Lys Ser Ile Gly Leu Leu Asn Asp Gly Phe
                165                 170                 175

Gly Arg Thr Pro Glu Met Cys Lys Arg Asp Leu Ile Trp Val Val Thr
            180                 185                 190

Lys Ile Gln Val Glu Val Asn Arg Tyr Pro Thr Trp Gly Asp Thr Ile
        195                 200                 205

Glu Val Asn Thr Trp Val Ser Glu Ser Gly Lys Asn Gly Met Gly Arg
    210                 215                 220

Asp Trp Leu Ile Ser Asp Cys Arg Thr Gly Glu Ile Leu Ile Arg Ala
225                 230                 235                 240

Thr Ser Val Trp Ala Met Met Asn Gln Asn Thr Arg Arg Leu Ser Lys
                245                 250                 255

Phe Pro Tyr Glu Val Arg Gln Glu Ile Ala Pro His Phe Val Asp Ser
            260                 265                 270

Ala Pro Val Ile Glu Asp Asp Arg Lys Leu Tyr Lys Leu Asn Val Lys
        275                 280                 285

Thr Gly Asp Ser Ile Arg Asp Gly Leu Thr Pro Arg Trp Asn Asp Leu
    290                 295                 300

Asp Val Asn Gln His Val Asn Asn Val Lys Phe Ile Gly Trp Ile Leu
305                 310                 315                 320

Lys Ser Val Pro Thr Lys Val Phe Glu Thr Gln Glu Leu Cys Gly Val
                325                 330                 335

Thr Leu Glu Tyr Arg Arg Glu Cys Gly Lys Asp Ser Val Leu Glu Ser
            340                 345                 350

Val Thr Ala Met Asp Pro Ala Lys Glu Gly Asp Arg Ser Val Tyr Gln
        355                 360                 365

His Leu Leu Arg Leu Glu Asp Gly Ala Asp Ile Thr Ile Gly Arg Thr
    370                 375                 380

Glu Trp Arg Pro Lys Asn Ala Gly Ala Asn Glu Ala Ile Ser Ser Gly
```

```
385                 390                 395                 400

Lys Thr Ser Asn Gly Asn Ser Ala Ser
                405


<210> SEQ ID NO 90
<211> LENGTH: 409
<212> TYPE: PRT
<213> ORGANISM: Cuphea wrightii

<400> SEQUENCE: 90

Met Val Ala Ala Ala Ala Ser Ser Ala Phe Phe Ser Val Pro Thr Pro
1               5                   10                  15

Gly Thr Ser Pro Lys Pro Gly Lys Phe Arg Asn Trp Pro Leu Ser Leu
            20                  25                  30

Ser Val Pro Phe Lys Pro Glu Thr Asn His Asn Gly Gly Phe His Ile
        35                  40                  45

Lys Ala Asn Ala Ser Ala His Pro Lys Ala Asn Gly Ser Ala Leu Asn
    50                  55                  60

Leu Lys Ser Gly Ser Leu Glu Thr Gln Glu Asp Thr Ser Leu Ser Ser
65                  70                  75                  80

Pro Pro Arg Thr Phe Ile Lys Gln Leu Pro Asp Trp Ser Met Leu Leu
                85                  90                  95

Ser Lys Ile Thr Thr Val Phe Gly Ala Ala Glu Lys Gln Leu Lys Arg
            100                 105                 110

Pro Gly Met Leu Val Glu Pro Phe Gly Val Asp Arg Ile Phe Gln Asp
        115                 120                 125

Gly Val Phe Phe Arg Gln Ser Phe Ser Ile Arg Ser Tyr Glu Ile Gly
    130                 135                 140

Ala Asp Arg Thr Ala Ser Ile Glu Thr Leu Met Asn Ile Phe Gln Glu
145                 150                 155                 160

Thr Ser Leu Asn His Cys Lys Ser Ile Gly Leu Leu Asn Asp Gly Phe
                165                 170                 175

Gly Arg Thr Pro Glu Met Cys Lys Arg Asp Leu Ile Trp Val Val Thr
            180                 185                 190

Lys Ile Gln Val Glu Val Asn Arg Tyr Pro Thr Trp Gly Asp Thr Ile
        195                 200                 205

Glu Val Asn Thr Trp Val Ser Glu Ser Gly Lys Asn Gly Met Gly Arg
    210                 215                 220

Asp Trp Leu Ile Ser Asp Cys Arg Thr Gly Glu Ile Leu Ile Arg Ala
225                 230                 235                 240

Thr Ser Val Trp Ala Met Met Asn Gln Asn Thr Arg Arg Leu Ser Lys
                245                 250                 255

Phe Pro Tyr Glu Val Arg Gln Glu Ile Ala Pro His Phe Val Asp Ser
            260                 265                 270

Ala Pro Val Ile Glu Asp Asp Arg Lys Leu Tyr Lys Leu Asn Val Lys
        275                 280                 285

Thr Gly Asp Ser Ile Arg Asp Gly Leu Thr Pro Arg Trp Asn Asp Leu
    290                 295                 300

Asp Val Asn Gln His Val Asn Asn Val Lys Phe Ile Gly Trp Ile Leu
305                 310                 315                 320

Lys Ser Val Pro Thr Lys Val Phe Glu Thr Gln Glu Leu Cys Gly Val
                325                 330                 335

Thr Leu Glu Tyr Arg Arg Glu Cys Gly Lys Asp Ser Val Leu Glu Ser
            340                 345                 350
```

```
Val Thr Ala Met Asp Pro Ala Lys Glu Gly Asp Arg Ser Val Tyr Gln
        355                 360                 365

His Leu Leu Arg Leu Glu Asp Gly Ala Asp Ile Thr Ile Gly Arg Thr
    370                 375                 380

Glu Trp Arg Pro Lys Asn Ala Gly Ala Asn Glu Ala Ile Ser Ser Gly
385                 390                 395                 400

Lys Thr Ser Asn Gly Asn Ser Ala Ser
                405


<210> SEQ ID NO 91
<211> LENGTH: 357
<212> TYPE: PRT
<213> ORGANISM: Cinnamomum camphora

<400> SEQUENCE: 91

Met Val Thr Thr Ser Leu Ala Ser Ala Tyr Phe Ser Met Lys Ala Val
1               5                   10                  15

Met Leu Ala Pro Asp Gly Arg Gly Ile Lys Pro Arg Ser Ser Gly Leu
            20                  25                  30

Gln Val Arg Ala Gly Asn Glu Arg Asn Ser Cys Lys Val Ile Asn Gly
        35                  40                  45

Thr Lys Val Lys Asp Thr Glu Gly Leu Lys Gly Cys Ser Thr Leu Gln
    50                  55                  60

Gly Gln Ser Met Leu Asp Asp His Phe Gly Leu His Gly Leu Val Phe
65                  70                  75                  80

Arg Arg Thr Phe Ala Ile Arg Cys Tyr Glu Val Gly Pro Asp Arg Ser
                85                  90                  95

Thr Ser Ile Met Ala Val Met Asn His Leu Gln Glu Ala Ala Arg Asn
            100                 105                 110

His Ala Glu Ser Leu Gly Leu Leu Gly Asp Gly Phe Gly Glu Thr Leu
        115                 120                 125

Glu Met Ser Lys Arg Asp Leu Ile Trp Val Val Arg Arg Thr His Val
    130                 135                 140

Ala Val Glu Arg Tyr Pro Ala Trp Gly Asp Thr Val Glu Val Glu Ala
145                 150                 155                 160

Trp Val Gly Ala Ser Gly Asn Thr Gly Met Arg Arg Asp Phe Leu Val
                165                 170                 175

Arg Asp Cys Lys Thr Gly His Ile Leu Thr Arg Cys Thr Ser Val Ser
            180                 185                 190

Val Met Met Asn Met Arg Thr Arg Arg Leu Ser Lys Ile Pro Gln Glu
        195                 200                 205

Val Arg Ala Glu Ile Asp Pro Leu Phe Ile Glu Lys Val Ala Val Lys
    210                 215                 220

Glu Gly Glu Ile Lys Lys Leu Gln Lys Leu Asn Asp Ser Thr Ala Asp
225                 230                 235                 240

Tyr Ile Gln Gly Gly Trp Thr Pro Arg Trp Asn Asp Leu Asp Val Asn
                245                 250                 255

Gln His Val Asn Asn Ile Ile Tyr Val Gly Trp Ile Phe Lys Ser Val
            260                 265                 270

Pro Asp Ser Ile Ser Glu Asn His His Leu Ser Ser Ile Thr Leu Glu
        275                 280                 285

Tyr Arg Arg Glu Cys Ile Arg Gly Asn Lys Leu Gln Ser Leu Thr Thr
    290                 295                 300

Val Cys Gly Gly Ser Ser Glu Ala Gly Ile Ile Cys Glu His Leu Leu
305                 310                 315                 320
```

```
Gln Leu Glu Asp Gly Ser Glu Val Leu Arg Ala Arg Thr Glu Trp Arg
                325                 330                 335

Pro Lys His Thr Asp Ser Phe Gln Gly Ile Ser Glu Arg Phe Pro Gln
            340                 345                 350

Gln Glu Pro His Lys
        355


<210> SEQ ID NO 92
<211> LENGTH: 419
<212> TYPE: PRT
<213> ORGANISM: Cinnamomum camphora

<400> SEQUENCE: 92

Met Val Ala Thr Ala Ala Ala Ser Ala Phe Phe Pro Val Gly Ala Pro
1               5                   10                  15

Ala Thr Ser Ser Ala Thr Ser Ala Lys Ala Ser Met Met Pro Asp Asn
            20                  25                  30

Leu Asp Ala Arg Gly Ile Lys Pro Lys Leu Ala Ser Ser Ser Gly Leu
        35                  40                  45

Gln Val Lys Ala Asn Ala His Ala Ser Pro Lys Ile Asn Gly Ser Lys
    50                  55                  60

Val Ser Thr Asp Thr Leu Lys Gly Glu Asp Thr Leu Thr Ser Ser Pro
65                  70                  75                  80

Ala Pro Arg Thr Phe Ile Asn Gln Leu Pro Asp Trp Ser Met Phe Leu
                85                  90                  95

Ala Ala Ile Thr Thr Ile Phe Leu Ala Ala Glu Lys Gln Trp Thr Asn
            100                 105                 110

Leu Asp Trp Lys Pro Arg Arg Pro Asp Met Leu Ala Asp Pro Phe Gly
        115                 120                 125

Ile Gly Arg Phe Met Gln Asp Gly Leu Ile Phe Arg Gln His Phe Ala
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ala Leu Asn His Val Arg Ser Ala
                165                 170                 175

Gly Leu Leu Gly Asp Gly Phe Gly Ala Thr Pro Glu Met Ser Arg Arg
            180                 185                 190

Asp Leu Ile Trp Val Val Thr Arg Met Gln Val Leu Val Asp Arg Tyr
        195                 200                 205

Pro Ala Trp Gly Asp Ile Val Glu Val Glu Thr Trp Val Gly Ala Ser
    210                 215                 220

Gly Lys Asn Gly Met Arg Arg Asp Trp Leu Val Arg Asp Ser Gln Thr
225                 230                 235                 240

Gly Glu Ile Leu Thr Arg Ala Thr Ser Val Trp Val Met Met Asn Lys
                245                 250                 255

Arg Thr Arg Arg Leu Ser Lys Leu Pro Glu Glu Val Arg Gly Glu Ile
            260                 265                 270

Gly Pro Tyr Phe Ile Glu Asp Val Ala Ile Ile Glu Glu Asp Asn Arg
        275                 280                 285

Lys Leu Gln Lys Leu Asn Glu Asn Thr Ala Asp Asn Val Arg Arg Gly
    290                 295                 300

Leu Thr Pro Arg Trp Ser Asp Leu Asp Val Asn Gln His Val Asn Asn
305                 310                 315                 320

Val Lys Tyr Ile Gly Trp Ile Leu Glu Ser Ala Pro Gly Ser Ile Leu
```

```
                325                 330                 335

Glu Ser His Glu Leu Ser Cys Met Thr Leu Glu Tyr Arg Arg Glu Cys
            340                 345                 350

Gly Lys Asp Ser Val Leu Gln Ser Met Thr Ala Val Ser Gly Gly Gly
        355                 360                 365

Ser Ala Ala Gly Gly Ser Pro Glu Ser Ser Val Glu Cys Asp His Leu
    370                 375                 380

Leu Gln Leu Glu Ser Gly Pro Glu Val Val Arg Gly Arg Thr Glu Trp
385                 390                 395                 400

Arg Pro Lys Ser Ala Asn Asn Ser Arg Ser Ile Leu Glu Met Pro Ala
                405                 410                 415

Glu Ser Leu


<210> SEQ ID NO 93
<211> LENGTH: 419
<212> TYPE: PRT
<213> ORGANISM: Cinnamomum camphora

<400> SEQUENCE: 93

Met Val Ala Thr Ala Ala Ala Ser Ala Phe Phe Pro Val Gly Ala Pro
1               5                   10                  15

Ala Thr Ser Ser Ala Thr Ser Ala Lys Ala Ser Met Met Pro Asp Asn
            20                  25                  30

Leu Asp Ala Arg Gly Ile Lys Pro Lys Pro Ala Ser Ser Ser Gly Leu
        35                  40                  45

Gln Val Lys Ala Asn Ala His Ala Ser Pro Lys Ile Asn Gly Ser Lys
    50                  55                  60

Val Ser Thr Asp Thr Leu Lys Gly Glu Asp Thr Leu Thr Ser Ser Pro
65                  70                  75                  80

Ala Pro Arg Thr Phe Ile Asn Gln Leu Pro Asp Trp Ser Met Phe Leu
                85                  90                  95

Ala Ala Ile Thr Thr Ile Phe Leu Ala Ala Glu Lys Gln Trp Thr Asn
            100                 105                 110

Leu Asp Trp Lys Pro Arg Arg Pro Asp Met Leu Ala Asp Pro Phe Gly
        115                 120                 125

Ile Gly Arg Phe Met Gln Asp Gly Leu Ile Phe Arg Gln His Phe Ala
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ala Leu Asn His Val Arg Ser Ala
                165                 170                 175

Gly Leu Leu Gly Asp Gly Phe Gly Ala Thr Pro Glu Met Ser Arg Arg
            180                 185                 190

Asp Leu Ile Trp Val Val Thr Arg Met Gln Val Leu Val Asp Arg Tyr
        195                 200                 205

Pro Ala Trp Gly Asp Ile Val Glu Val Glu Thr Trp Val Gly Ala Ser
    210                 215                 220

Gly Lys Asn Gly Met Arg Arg Asp Trp Leu Val Arg Asp Ser Gln Thr
225                 230                 235                 240

Gly Glu Ile Leu Thr Arg Ala Thr Ser Val Trp Val Met Met Asn Lys
                245                 250                 255

Arg Thr Arg Arg Leu Ser Lys Leu Pro Glu Glu Val Arg Gly Glu Ile
            260                 265                 270

Gly Pro Tyr Phe Ile Glu Asp Val Ala Ile Ile Glu Glu Asp Asn Arg
```

```
        275                 280                 285

Lys Leu Gln Lys Leu Asn Glu Asn Thr Ala Asp Asn Val Arg Arg Gly
    290                 295                 300

Leu Thr Pro Arg Trp Ser Asp Leu Asp Val Asn Gln His Val Asn Asn
305                 310                 315                 320

Ala Lys Tyr Ile Gly Trp Ile Leu Glu Ser Ala Pro Gly Ser Ile Leu
                325                 330                 335

Glu Ser His Glu Leu Ser Cys Met Thr Leu Glu Tyr Arg Arg Glu Cys
            340                 345                 350

Gly Lys Asp Ser Val Leu Gln Ser Met Thr Ala Val Ser Gly Gly Gly
        355                 360                 365

Ser Ala Ala Gly Gly Ser Pro Glu Ser Ser Val Glu Cys Asp His Leu
    370                 375                 380

Leu Gln Leu Glu Ser Gly Pro Glu Val Val Arg Gly Arg Thr Glu Trp
385                 390                 395                 400

Arg Pro Lys Ser Ala Asn Asn Ser Arg Ser Ile Leu Glu Met Pro Ala
                405                 410                 415

Glu Ser Leu


<210> SEQ ID NO 94
<211> LENGTH: 410
<212> TYPE: PRT
<213> ORGANISM: Cuphea heterophylla

<400> SEQUENCE: 94

Met Val Ala Ala Ala Ala Ser Ser Ala Phe Phe Ser Val Pro Thr Pro
1               5                   10                  15

Gly Thr Ser Pro Lys Pro Gly Asn Phe Gly Asn Trp Pro Ser Ser Leu
            20                  25                  30

Ser Val Pro Phe Lys Pro Glu Ser Asn His Asn Gly Gly Phe Arg Val
        35                  40                  45

Lys Ala Asn Ala Ser Ala His Pro Lys Ala Asn Gly Ser Ala Val Asn
    50                  55                  60

Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Gly Met Leu
                85                  90                  95

Leu Ser Lys Ile Thr Thr Val Phe Gly Ala Ala Glu Arg Gln Trp Lys
            100                 105                 110

Arg Pro Gly Met Leu Val Glu Pro Phe Gly Val Asp Arg Ile Phe Gln
        115                 120                 125

Asp Gly Val Phe Phe Arg His Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160

Glu Thr Ser Leu Asn His Cys Lys Ser Ile Gly Leu Leu Asn Asp Gly
                165                 170                 175

Phe Gly Arg Thr Pro Glu Met Cys Lys Arg Asp Leu Ile Trp Val Val
            180                 185                 190

Thr Lys Ile Gln Val Glu Val Asn Arg Tyr Pro Thr Trp Gly Asp Thr
        195                 200                 205

Ile Glu Val Asn Thr Trp Val Ser Glu Ser Gly Lys Asn Gly Met Gly
    210                 215                 220

Arg Asp Trp Leu Ile Gly Asp Cys Arg Thr Gly Glu Ile Leu Ile Arg
```

```
225                 230                 235                 240

Ala Thr Ser Val Trp Ala Met Met Asn Arg Lys Thr Arg Arg Leu Ser
                245                 250                 255

Lys Phe Pro Tyr Glu Val Arg Gln Glu Ile Ala Pro His Phe Val Asp
            260                 265                 270

Ser Ala Pro Val Ile Glu Asp Asp Lys Lys Leu His Lys Leu Asp Val
        275                 280                 285

Lys Thr Gly Asp Ser Ile Arg Lys Gly Leu Thr Pro Arg Trp Asn Asp
    290                 295                 300

Leu Asp Val Asn Gln His Val Asn Asn Val Lys Tyr Ile Gly Trp Ile
305                 310                 315                 320

Leu Lys Ser Val Pro Ala Glu Val Phe Glu Thr Gln Glu Leu Cys Gly
                325                 330                 335

Val Thr Leu Glu Tyr Arg Arg Glu Cys Gly Arg Asp Ser Val Leu Glu
            340                 345                 350

Ser Val Thr Ala Met Asp Thr Ala Lys Glu Gly Asp Arg Ser Leu Tyr
        355                 360                 365

Gln His Leu Leu Arg Leu Glu Asp Gly Ala Asp Ile Thr Ile Gly Arg
    370                 375                 380

Thr Glu Trp Arg Pro Lys Asn Ala Gly Ala Asn Gly Ala Leu Ser Thr
385                 390                 395                 400

Gly Lys Thr Ser Asn Gly Asn Ser Val Ser
                405                 410


<210> SEQ ID NO 95
<211> LENGTH: 410
<212> TYPE: PRT
<213> ORGANISM: Cuphea heterophylla

<400> SEQUENCE: 95

Met Val Ala Ala Ala Ala Ser Ser Ala Phe Phe Ser Val Pro Thr Pro
1               5                   10                  15

Gly Thr Ser Pro Lys Pro Gly Asn Phe Gly Asn Trp Pro Ser Asn Leu
            20                  25                  30

Ser Val Pro Phe Lys Pro Glu Ser Asn His Asn Gly Gly Phe Arg Val
        35                  40                  45

Lys Ala Asn Ala Ser Ala His Pro Lys Ala Asn Gly Ser Ala Val Asn
    50                  55                  60

Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Gly Met Leu
                85                  90                  95

Leu Ser Lys Ile Thr Thr Val Phe Gly Ala Ala Glu Arg Gln Trp Lys
            100                 105                 110

Arg Pro Gly Met Leu Val Glu Pro Phe Gly Val Asp Arg Ile Phe Gln
        115                 120                 125

Asp Gly Val Phe Phe Arg Gln Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160

Glu Thr Ser Leu Asn His Cys Lys Ser Ile Gly Leu Leu Asn Asp Gly
                165                 170                 175

Phe Gly Arg Thr Pro Glu Met Cys Lys Arg Asp Leu Ile Trp Val Val
            180                 185                 190
```

Thr Lys Ile Gln Val Glu Val Asn Arg Tyr Pro Thr Trp Gly Asp Thr
195 200 205

Ile Glu Val Asn Thr Trp Val Ser Glu Ser Gly Lys Asn Gly Met Gly
210 215 220

Arg Asp Trp Leu Ile Ser Asp Cys Arg Thr Gly Glu Ile Leu Ile Arg
225 230 235 240

Ala Thr Ser Val Trp Ala Met Met Asn Arg Lys Thr Arg Arg Leu Ser
245 250 255

Lys Phe Pro Tyr Glu Val Arg Gln Glu Ile Ala Pro His Phe Val Asp
260 265 270

Ser Ala Pro Val Ile Glu Asp Asp Lys Lys Leu His Lys Leu Asp Val
275 280 285

Lys Thr Gly Asp Ser Ile Arg Lys Gly Leu Thr Pro Arg Trp Asn Asp
290 295 300

Phe Asp Val Asn Gln His Val Asn Asn Val Lys Tyr Ile Gly Trp Ile
305 310 315 320

Leu Lys Ser Val Pro Ala Glu Val Phe Glu Thr Gln Glu Leu Cys Gly
325 330 335

Val Thr Leu Glu Tyr Arg Arg Glu Cys Gly Arg Asp Ser Val Leu Glu
340 345 350

Ser Val Thr Ala Met Asp Thr Ala Lys Glu Gly Asp Arg Ser Leu Tyr
355 360 365

Gln His Leu Leu Arg Leu Glu Asp Gly Ala Asp Ile Thr Ile Gly Arg
370 375 380

Thr Glu Trp Arg Pro Lys Asn Ala Gly Ala Asn Gly Ala Ile Ser Thr
385 390 395 400

Gly Lys Thr Ser Asn Glu Asn Ser Val Ser
405 410

<210> SEQ ID NO 96
<211> LENGTH: 410
<212> TYPE: PRT
<213> ORGANISM: Cuphea heterophylla

<400> SEQUENCE: 96

Met Val Ala Ala Ala Ala Ser Ser Ala Phe Phe Ser Val Pro Thr Pro
1 5 10 15

Gly Thr Ser Pro Lys Pro Gly Asn Phe Gly Asn Trp Pro Ser Ser Leu
20 25 30

Ser Val Pro Phe Lys Pro Glu Ser Asn His Asn Gly Gly Phe Arg Val
35 40 45

Lys Ala Asn Ala Ser Ala His Pro Lys Ala Asn Gly Ser Ala Val Asn
50 55 60

Leu Lys Ser Gly Ser Leu Glu Thr Gln Glu Asp Thr Ser Ser Ser Ser
65 70 75 80

Pro Pro Pro Arg Thr Phe Ile Lys Gln Leu Pro Asp Trp Gly Met Leu
85 90 95

Leu Ser Lys Ile Thr Thr Val Phe Gly Ala Ala Glu Arg Gln Trp Lys
100 105 110

Arg Pro Gly Met Leu Val Glu Pro Phe Gly Val Asp Arg Ile Phe Gln
115 120 125

Asp Gly Val Phe Phe Arg Gln Ser Phe Ser Ile Arg Ser Tyr Glu Ile
130 135 140

Gly Ala Asp Arg Thr Ala Ser Ile Glu Thr Leu Met Asn Ile Phe Gln
145 150 155 160

Glu Thr Ser Leu Asn His Cys Lys Ser Ile Gly Leu Leu Asn Asp Gly
165 170 175

Phe Gly Arg Thr Pro Glu Met Cys Lys Arg Asp Leu Ile Trp Val Val
180 185 190

Thr Lys Ile Gln Val Glu Val Asn Arg Tyr Pro Thr Trp Gly Asp Thr
195 200 205

Ile Glu Val Asn Thr Trp Val Ser Glu Ser Gly Lys Asn Gly Met Gly
210 215 220

Arg Asp Trp Leu Ile Ser Asp Cys Arg Thr Gly Glu Ile Leu Ile Arg
225 230 235 240

Ala Thr Ser Val Trp Ala Met Met Asn Arg Lys Thr Arg Arg Leu Ser
245 250 255

Lys Phe Pro Tyr Glu Val Arg Gln Glu Ile Ala Pro His Phe Val Asp
260 265 270

Ser Ala Pro Val Ile Glu Asp Asp Lys Lys Leu His Lys Leu Asp Val
275 280 285

Lys Thr Gly Asp Ser Ile Arg Lys Gly Leu Thr Pro Arg Trp Asn Asp
290 295 300

Phe Asp Val Asn Gln His Val Asn Asn Val Lys Tyr Ile Gly Trp Ile
305 310 315 320

Leu Lys Ser Val Pro Ala Glu Val Phe Glu Thr Gln Glu Leu Cys Gly
325 330 335

Val Thr Leu Glu Tyr Arg Arg Glu Cys Gly Arg Asp Ser Val Leu Glu
340 345 350

Ser Val Thr Ala Met Asp Thr Ala Lys Glu Gly Asp Arg Ser Leu Tyr
355 360 365

Gln His Leu Leu Arg Leu Glu Asp Gly Ala Asp Ile Thr Ile Gly Arg
370 375 380

Thr Glu Trp Arg Pro Lys Asn Ala Gly Val Asn Gly Ala Ile Ser Thr
385 390 395 400

Gly Lys Thr Ser Asn Glu Asn Ser Val Ser
405 410

<210> SEQ ID NO 97
<211> LENGTH: 410
<212> TYPE: PRT
<213> ORGANISM: Cuphea heterophylla

<400> SEQUENCE: 97

Met Val Ala Ala Ala Ala Ser Ser Ala Phe Phe Ser Val Pro Thr Pro
1 5 10 15

Gly Thr Ser Pro Lys Pro Gly Asn Phe Gly Asn Trp Pro Ser Ser Leu
20 25 30

Ser Val Pro Phe Lys Pro Glu Ser Asn His Asn Gly Gly Phe Arg Val
35 40 45

Lys Ala Asn Ala Ser Ala His Pro Lys Ala Asn Gly Ser Ala Val Asn
50 55 60

Leu Lys Ser Gly Ser Leu Glu Thr Gln Glu Asp Thr Ser Ser Ser Ser
65 70 75 80

Pro Pro Pro Arg Thr Phe Ile Lys Gln Leu Pro Asp Trp Ser Met Leu
85 90 95

Leu Ser Lys Ile Thr Thr Val Phe Gly Ala Ala Glu Arg Gln Trp Lys
100 105 110

Arg Pro Gly Met Leu Val Glu Pro Phe Gly Val Asp Arg Ile Phe Gln

-continued

```
        115                 120                 125

Asp Gly Val Phe Phe Arg Gln Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160

Glu Thr Ser Leu Asn His Cys Lys Ser Ile Gly Leu Leu Asn Asp Gly
                165                 170                 175

Phe Gly Arg Thr Pro Glu Met Cys Lys Arg Asp Leu Ile Trp Val Val
            180                 185                 190

Thr Lys Ile Gln Val Glu Val Asn Arg Tyr Pro Thr Trp Gly Asp Thr
        195                 200                 205

Ile Glu Val Asn Thr Trp Val Ser Glu Ser Gly Lys Asn Gly Met Gly
    210                 215                 220

Arg Asp Trp Leu Ile Ser Asp Cys Arg Thr Gly Glu Ile Leu Ile Arg
225                 230                 235                 240

Ala Thr Ser Val Trp Ala Met Met Asn Arg Lys Thr Arg Arg Leu Ser
                245                 250                 255

Lys Phe Pro Tyr Glu Val Arg Gln Glu Ile Ala Pro His Phe Val Asp
            260                 265                 270

Ser Ala Pro Val Ile Glu Asp Asp Lys Lys Leu His Lys Leu Asp Val
        275                 280                 285

Lys Thr Gly Asp Ser Ile Arg Lys Gly Leu Thr Pro Arg Trp Asn Asp
    290                 295                 300

Phe Asp Val Asn Gln His Val Asn Asn Val Lys Tyr Ile Gly Trp Ile
305                 310                 315                 320

Leu Lys Ser Val Pro Ala Glu Val Phe Glu Thr Gln Glu Leu Cys Gly
                325                 330                 335

Val Thr Leu Glu Tyr Arg Arg Glu Cys Gly Arg Asp Ser Val Leu Glu
            340                 345                 350

Ser Val Thr Ala Met Asp Thr Ala Lys Glu Gly Asp Arg Ser Leu Tyr
        355                 360                 365

Gln His Leu Leu Arg Leu Glu Asp Gly Ala Asp Ile Thr Ile Gly Arg
    370                 375                 380

Thr Glu Trp Arg Pro Lys Asn Ala Gly Ala Asn Gly Ala Ile Ser Thr
385                 390                 395                 400

Gly Lys Thr Ser Asn Glu Asn Ser Val Ser
                405                 410


<210> SEQ ID NO 98
<211> LENGTH: 418
<212> TYPE: PRT
<213> ORGANISM: Cuphea heterophylla

<400> SEQUENCE: 98

Met Val Val Ala Ala Ala Ala Ser Ser Ala Phe Phe Pro Val Pro Ala
1               5                   10                  15

Ser Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Gln Glu Gly Thr Ser Ser Ser
65                  70                  75                  80
```

```
Pro Pro Pro Arg Thr Phe Leu Asn Gln Leu Pro Asp Trp Ser Arg Leu
                85                  90                  95

Leu Thr Ala Ile Ser Thr Val Phe Val Ala Ala Glu Lys Gln Leu Thr
            100                 105                 110

Met Leu Asp Arg Lys Ser Lys Arg Pro Asp Met Leu Val Asp Trp Phe
        115                 120                 125

Gly Leu Glu Ser Ile Val Gln Asp Gly Leu Val Phe Arg Glu Ser Tyr
    130                 135                 140

Ser Ile Arg Ser Tyr Glu Ile Ser Ala Asp Arg Thr Ala Ser Ile Glu
145                 150                 155                 160

Thr Val Met Asn Leu Leu Gln Glu Thr Ser Leu Asn His Cys Lys Ser
                165                 170                 175

Met Gly Ile Leu Asn Asp Gly Phe Gly Arg Thr Pro Glu Met Cys Lys
            180                 185                 190

Arg Asp Leu Ile Trp Val Leu Thr Lys Met Gln Ile Leu Val Asn Arg
        195                 200                 205

Tyr Pro Asn Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Asn Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Arg Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Ser Ile Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Glu Ser Val Leu Glu Ser Val Thr Ala Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser


<210> SEQ ID NO 99
<211> LENGTH: 414
<212> TYPE: PRT
<213> ORGANISM: Cuphea heterophylla

<400> SEQUENCE: 99

Met Val Ala Thr Ala Ala Ser Ser Ala Phe Phe Pro Val Pro Ser Pro
1               5                   10                  15

Asp Thr Ser Ser Arg Pro Gly Lys Leu Gly Asn Gly Ser Ser Ser Leu
            20                  25                  30
```

-continued

```
Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Cys Ser Leu Lys Thr His Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Glu Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Ala Ile Ala Phe Gly Glu Thr Ser Pro Gly Asp Ser
                405                 410


<210> SEQ ID NO 100
<211> LENGTH: 414
<212> TYPE: PRT
<213> ORGANISM: Cuphea heterophylla

<400> SEQUENCE: 100
```

```
Met Val Ala Thr Ala Ala Ser Ser Ala Phe Phe Pro Val Pro Ser Pro
1               5                   10                  15

Asp Thr Ser Ser Arg Pro Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Cys Ser Leu Lys Thr His Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Lys Thr Val
145                 150                 155                 160

Met Asn His Leu Gln Glu Thr Ala Leu Asn His Val Lys Ser Ala Gly
                165                 170                 175

Leu Leu Asn Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410
```

<210> SEQ ID NO 101
<211> LENGTH: 414
<212> TYPE: PRT
<213> ORGANISM: Cuphea heterophylla

<400> SEQUENCE: 101

```
Met Val Ala Thr Ala Ala Ser Ser Ala Phe Phe Pro Val Pro Ser Pro
1               5                   10                  15

Asp Thr Ser Ser Arg Pro Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Gly Ser Leu Lys Thr His Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Phe Gly Pro Gln Phe Gln His Leu Leu Arg Leu Glu Asp Gly Gly
    370                 375                 380
```

```
Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410


<210> SEQ ID NO 102
<211> LENGTH: 414
<212> TYPE: PRT
<213> ORGANISM: Cuphea heterophylla

<400> SEQUENCE: 102

Met Val Ala Thr Ala Ala Ser Ser Ala Phe Phe Pro Val Pro Ser Pro
1               5                   10                  15

Asp Thr Ser Ser Arg Leu Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Pro Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
```

```
            340                 345                 350

Arg Glu Ser Val Leu Glu Ser Leu Thr Ala Val Asp Pro Ser Glu Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410


<210> SEQ ID NO 103
<211> LENGTH: 414
<212> TYPE: PRT
<213> ORGANISM: Cuphea heterophylla

<400> SEQUENCE: 103

Met Val Ala Thr Ala Ala Ser Ser Ala Phe Phe Pro Val Pro Ser Pro
1               5                   10                  15

Asp Thr Ser Ser Arg Ala Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
    290                 295                 300
```

```
Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410


<210> SEQ ID NO 104
<211> LENGTH: 415
<212> TYPE: PRT
<213> ORGANISM: Cuphea hyssopifolia

<400> SEQUENCE: 104

Met Val Ala Thr Ala Ala Ser Ser Ala Phe Phe Pro Val Pro Ser Pro
1               5                   10                  15

Asp Ala Ser Ser Arg Pro Gly Lys Leu Gly Asn Gly Ser Ser Ser Leu
            20                  25                  30

Ser Pro Leu Lys Pro Lys Leu Met Ala Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Leu Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg His Glu Ile Glu
            260                 265                 270
```

```
Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Ser Gly Ser Gln Phe Gln His Leu Met Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Pro Ile Ala Ser Gly Glu Thr Ser Pro Gly Asp Ser Ser
                405                 410                 415


<210> SEQ ID NO 105
<211> LENGTH: 415
<212> TYPE: PRT
<213> ORGANISM: Cuphea hyssopifolia

<400> SEQUENCE: 105

Met Val Ala Thr Ala Ala Ser Ser Ala Phe Phe Pro Val Pro Ser Pro
1               5                   10                  15

Asp Ala Ser Ser Arg Pro Gly Lys Leu Gly Asn Gly Ser Ser Ser Leu
            20                  25                  30

Ser Pro Leu Lys Pro Lys Leu Met Ala Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
```

```
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg His Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Ser Gly Ser Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Pro Ile Ala Ser Gly Glu Thr Ser Pro Gly Asp Ser Ser
                405                 410                 415


<210> SEQ ID NO 106
<211> LENGTH: 409
<212> TYPE: PRT
<213> ORGANISM: Cuphea hyssopifolia

<400> SEQUENCE: 106

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Pro Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190
```

Arg Asp Leu Ile Trp Val Val Thr Lys Met His Val Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Cys His
225                 230                 235                 240

Thr Gly Glu Ile Leu Ile Arg Ala Thr Ser Met Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Gln Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Thr Asp Ile Ala Lys Gly Arg Thr Lys Trp Arg Pro Lys Asn Ala Gly
385                 390                 395                 400

Lys Thr Ser Asn Gly Asn Ser Ile Ser
                405

<210> SEQ ID NO 107
<211> LENGTH: 417
<212> TYPE: PRT
<213> ORGANISM: Cuphea hyssopifolia

<400> SEQUENCE: 107

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Ser Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Ala Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Ser Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
165 170 175

Ile Gly Leu Leu Asn Asp Gly Phe Gly Arg Thr Pro Glu Met Cys Lys
180 185 190

Arg Asp Leu Ile Trp Val Val Thr Lys Met His Val Glu Val Asn Arg
195 200 205

Tyr Pro Thr Trp Gly Asp Thr Ile Glu Val Asn Thr Trp Val Ser Glu
210 215 220

Ser Gly Lys Thr Gly Met Gly Arg Asp Trp Leu Ile Ser Asp Cys His
225 230 235 240

Thr Gly Glu Ile Leu Ile Arg Ala Thr Ser Met Cys Ala Met Met Asn
245 250 255

Gln Lys Thr Arg Arg Phe Ser Lys Phe Pro Tyr Glu Val Arg Gln Glu
260 265 270

Leu Ala Pro His Phe Val Asp Ser Ala Pro Val Ile Glu Asp Tyr Gln
275 280 285

Lys Leu His Lys Leu Asp Val Lys Thr Gly Asp Ser Ile Cys Asn Gly
290 295 300

Leu Thr Pro Arg Trp Asn Asp Leu Asp Val Asn Gln His Val Asn Asn
305 310 315 320

Val Lys Tyr Ile Gly Trp Ile Leu Glu Ser Val Pro Thr Glu Val Phe
325 330 335

Glu Thr Gln Glu Leu Cys Gly Leu Thr Leu Glu Tyr Arg Arg Glu Cys
340 345 350

Gly Arg Asp Ser Val Leu Glu Ser Val Thr Ala Met Asp Pro Ser Lys
355 360 365

Glu Gly Asp Arg Ser Leu Tyr Gln His Leu Leu Arg Leu Glu Asp Gly
370 375 380

Ala Asp Ile Ala Lys Gly Arg Thr Lys Trp Arg Pro Lys Asn Ala Gly
385 390 395 400

Thr Asn Gly Ala Ile Ser Thr Gly Lys Thr Ser Asn Gly Asn Ser Ile
405 410 415

Ser

<210> SEQ ID NO 108
<211> LENGTH: 417
<212> TYPE: PRT
<213> ORGANISM: Cuphea hyssopifolia

<400> SEQUENCE: 108

Met Val Ala Ala Glu Ala Ser Ser Ala Leu Phe Ser Val Arg Thr Pro
1 5 10 15

Gly Thr Ser Pro Lys Pro Gly Lys Phe Gly Asn Trp Pro Ser Ser Leu
20 25 30

Ser Val Pro Phe Lys Ser Lys Ser Asn His Asn Gly Gly Phe Gln Val
35 40 45

Lys Ala Asn Ala Ser Ala Arg Pro Lys Ala Asn Gly Ser Ala Val Ser
50 55 60

Leu Lys Ser Gly Ser Leu Asp Thr Gln Glu Asp Ala Ser Ser Ser Ser
65 70 75 80

Ser Pro Pro Arg Thr Phe Ile Asn Gln Leu Pro Asp Trp Ser Met Leu
85 90 95

Leu Ser Ala Ile Thr Thr Val Phe Val Ala Ala Glu Lys Gln Trp Thr
100 105 110

Met Leu Asp Arg Lys Ser Lys Arg Ser Asp Met Leu Met Asp Pro Phe
115 120 125

Gly Val Asp Arg Val Val Gln Asp Gly Val Val Phe Arg Gln Ser Phe
130 135 140

Ser Ile Arg Ser Tyr Glu Ile Gly Ala Asp Arg Thr Ala Ser Ile Glu
145 150 155 160

Thr Leu Met Asn Ile Phe Gln Glu Thr Ser Leu Asn His Cys Lys Ser
165 170 175

Ile Gly Leu Leu Asn Asp Gly Phe Gly Arg Thr Pro Glu Met Cys Lys
180 185 190

Arg Asp Leu Ile Trp Val Val Thr Lys Met His Val Glu Val Asn Arg
195 200 205

Tyr Pro Thr Trp Gly Asp Thr Ile Glu Val Asn Thr Trp Val Ser Glu
210 215 220

Ser Gly Lys Thr Gly Met Gly Arg Asp Trp Leu Ile Ser Asp Cys His
225 230 235 240

Thr Gly Glu Ile Leu Ile Arg Ala Thr Ser Met Cys Ala Met Met Asn
245 250 255

Gln Lys Thr Arg Arg Phe Ser Lys Phe Pro Tyr Glu Val Arg Gln Glu
260 265 270

Leu Ala Pro His Phe Val Asp Ser Ala Pro Val Ile Glu Asp Tyr Gln
275 280 285

Lys Leu His Lys Leu Asp Val Lys Thr Gly Asp Ser Ile Cys Asn Gly
290 295 300

Leu Thr Pro Arg Trp Asn Asp Leu Asp Val Asn Gln His Val Asn Asn
305 310 315 320

Val Lys Tyr Ile Gly Trp Ile Leu Glu Ser Val Pro Thr Glu Val Phe
325 330 335

Glu Thr Gln Glu Leu Cys Gly Leu Thr Leu Glu Tyr Arg Arg Glu Cys
340 345 350

Gly Arg Asp Ser Val Leu Glu Ser Val Thr Ala Met Asp Pro Ser Lys
355 360 365

Glu Gly Asp Arg Ser Leu Tyr Gln His Leu Leu Arg Leu Glu Asp Gly
370 375 380

Ala Asp Ile Ala Lys Gly Arg Thr Lys Trp Arg Pro Lys Asn Ala Gly
385 390 395 400

Thr Asn Gly Ala Ile Ser Thr Gly Lys Thr Ser Asn Gly Asn Ser Ile
405 410 415

Ser

<210> SEQ ID NO 109
<211> LENGTH: 417
<212> TYPE: PRT
<213> ORGANISM: Cuphea hyssopifolia

<400> SEQUENCE: 109

Met Val Ala Ala Glu Ala Ser Ser Ala Leu Phe Ser Val Arg Thr Pro
1 5 10 15

Gly Thr Ser Pro Lys Pro Gly Lys Phe Gly Asn Trp Pro Ser Ser Leu
20 25 30

Ser Val Pro Phe Lys Ser Lys Ser Asn His Asn Gly Gly Phe Gln Val
35 40 45

Lys Ala Asn Ala Ser Ala Arg Pro Lys Ala Asn Gly Ser Ala Val Ser
50 55 60

Leu Lys Ser Gly Ser Leu Asp Thr Gln Glu Asp Thr Ser Ser Ser Ser
65 70 75 80

Ser Pro Pro Arg Thr Phe Ile Asn Gln Leu Pro Asp Trp Ser Met Leu
85 90 95

Leu Ser Ala Ile Thr Thr Val Phe Val Ala Ala Glu Lys Gln Trp Thr
100 105 110

Met Leu Asp Arg Lys Ser Lys Arg Pro Asp Met Leu Met Asp Pro Phe
115 120 125

Gly Val Asp Arg Val Val Gln Asp Gly Ala Val Phe Arg Gln Ser Phe
130 135 140

Ser Ile Arg Ser Tyr Glu Ile Gly Ala Asp Arg Thr Ala Ser Ile Glu
145 150 155 160

Thr Leu Met Asn Ile Phe Gln Glu Thr Ser Leu Asn His Cys Lys Ser
165 170 175

Ile Gly Leu Leu Asn Asp Gly Phe Gly Arg Thr Pro Glu Met Cys Lys
180 185 190

Arg Asp Leu Ile Trp Val Val Thr Lys Met His Val Glu Val Asn Arg
195 200 205

Tyr Pro Thr Trp Gly Asp Thr Ile Glu Val Asn Thr Trp Val Ser Glu
210 215 220

Ser Gly Lys Thr Gly Met Gly Arg Asp Trp Leu Ile Ser Asp Cys His
225 230 235 240

Thr Gly Glu Ile Leu Ile Arg Ala Thr Ser Met Cys Ala Met Met Asn
245 250 255

Gln Lys Thr Arg Arg Phe Ser Lys Phe Pro Tyr Glu Val Arg Gln Glu
260 265 270

Leu Ala Pro His Phe Val Asp Ser Ala Pro Val Ile Glu Asp Tyr Gln
275 280 285

Lys Leu His Lys Leu Asp Val Lys Thr Gly Asp Ser Ile Cys Asn Gly
290 295 300

Leu Thr Pro Arg Trp Asn Asp Leu Asp Val Asn Gln His Val Asn Asn
305 310 315 320

Val Lys Tyr Ile Gly Trp Ile Leu Glu Ser Val Pro Thr Glu Val Phe
325 330 335

Glu Thr Gln Glu Leu Cys Gly Leu Thr Leu Glu Tyr Arg Arg Glu Cys
340 345 350

Gly Arg Asp Ser Val Leu Glu Ser Val Thr Ala Met Asp Pro Ser Lys
355 360 365

Glu Gly Asp Arg Ser Leu Tyr Gln His Leu Leu Arg Leu Glu Asp Gly
370 375 380

Ala Asp Ile Ala Lys Gly Arg Thr Lys Trp Arg Pro Lys Asn Ala Gly
385 390 395 400

Thr Asn Gly Ala Ile Ser Thr Gly Lys Thr Ser Asn Gly Asn Ser Ile
405 410 415

Ser

<210> SEQ ID NO 110
<211> LENGTH: 409
<212> TYPE: PRT
<213> ORGANISM: Cuphea hyssopifolia

<400> SEQUENCE: 110

Met Val Ala Ala Glu Ala Ser Ser Ala Leu Phe Ser Val Arg Thr Pro
1 5 10 15

-continued

```
Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Pro Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Ile Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Phe His
225                 230                 235                 240

Thr Gly Asp Ile Leu Ile Arg Ala Thr Ser Val Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Gln Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Thr Asp Ile Ala Lys Gly Arg Thr Lys Trp Arg Pro Lys Asn Ala Gly
385                 390                 395                 400

Lys Thr Ser Asn Gly Asn Ser Ile Ser
                405
```

<210> SEQ ID NO 111
<211> LENGTH: 409

<212> TYPE: PRT
<213> ORGANISM: Cuphea hyssopifolia

<400> SEQUENCE: 111

```
Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Ser Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Ala Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Ser Asp Met Leu Met Asp Pro Phe
        115                 120                 125

Gly Val Asp Arg Val Val Gln Asp Gly Val Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Ile Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Phe His
225                 230                 235                 240

Thr Gly Asp Ile Leu Ile Arg Ala Thr Ser Val Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Gln Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Thr Asp Ile Ala Lys Gly Arg Thr Lys Trp Arg Pro Lys Asn Ala Gly
385                 390                 395                 400
```

Lys Thr Ser Asn Gly Asn Ser Ile Ser
405

<210> SEQ ID NO 112
<211> LENGTH: 417
<212> TYPE: PRT
<213> ORGANISM: Cuphea hyssopifolia

<400> SEQUENCE: 112

Met Val Ala Ala Glu Ala Ser Ser Ala Leu Phe Ser Val Arg Thr Pro
1 5 10 15

Gly Thr Ser Pro Lys Pro Gly Lys Phe Gly Asn Trp Pro Thr Ser Leu
20 25 30

Ser Val Pro Phe Lys Ser Lys Ser Asn His Asn Gly Gly Phe Gln Val
35 40 45

Lys Ala Asn Ala Ser Ala Arg Pro Lys Ala Asn Gly Ser Ala Val Ser
50 55 60

Leu Lys Ser Gly Ser Leu Asp Thr Gln Glu Asp Thr Ser Ser Ser Ser
65 70 75 80

Ser Pro Pro Arg Thr Phe Ile Asn Gln Leu Pro Asp Trp Ser Met Leu
85 90 95

Leu Ser Ala Ile Thr Thr Val Phe Val Ala Ala Glu Lys Gln Trp Thr
100 105 110

Met Leu Asp Arg Lys Ser Lys Arg Pro Asp Met Leu Met Asp Pro Phe
115 120 125

Gly Val Asp Arg Val Val Gln Asp Gly Ala Val Phe Arg Gln Ser Phe
130 135 140

Ser Ile Arg Ser Tyr Glu Ile Gly Ala Asp Arg Thr Ala Ser Ile Glu
145 150 155 160

Thr Leu Met Asn Ile Phe Gln Glu Thr Ser Leu Asn His Cys Lys Ser
165 170 175

Ile Gly Leu Leu Asn Asp Gly Phe Gly Arg Thr Pro Glu Met Cys Lys
180 185 190

Arg Asp Leu Ile Trp Val Val Thr Lys Met His Val Glu Val Asn Arg
195 200 205

Tyr Pro Thr Trp Gly Asp Thr Ile Glu Val Asn Thr Trp Val Ser Glu
210 215 220

Ser Gly Lys Thr Gly Met Gly Arg Asp Trp Leu Ile Ser Asp Cys His
225 230 235 240

Thr Gly Glu Ile Leu Ile Arg Ala Thr Ser Met Cys Ala Met Met Asn
245 250 255

Gln Lys Thr Arg Arg Phe Ser Lys Phe Pro Tyr Glu Val Arg Gln Glu
260 265 270

Leu Ala Pro His Phe Val Asp Ser Ala Pro Val Ile Glu Asp Tyr Gln
275 280 285

Lys Leu His Lys Leu Asp Val Lys Thr Gly Asp Ser Ile Cys Asn Gly
290 295 300

Leu Thr Pro Arg Trp Asn Asp Leu Asp Val Asn Gln His Val Asn Asn
305 310 315 320

Val Lys Tyr Ile Gly Trp Ile Leu Glu Ser Val Pro Thr Glu Val Phe
325 330 335

Glu Thr Gln Glu Leu Cys Gly Leu Thr Leu Glu Tyr Arg Arg Glu Cys
340 345 350

Gly Gly Asp Ser Val Leu Glu Ser Val Thr Ala Met Asp Pro Ser Lys

```
        355                 360                 365

Glu Gly Asp Arg Ser Leu Tyr Gln His Leu Leu Arg Leu Glu Asp Gly
    370                 375                 380

Ala Asp Ile Ala Lys Gly Arg Thr Lys Trp Arg Pro Lys Asn Ala Gly
385                 390                 395                 400

Thr Asn Gly Ala Ile Ser Thr Gly Lys Thr Ser Asn Gly Asn Ser Ile
                405                 410                 415

Ser


<210> SEQ ID NO 113
<211> LENGTH: 409
<212> TYPE: PRT
<213> ORGANISM: Cuphea hyssopifolia

<400> SEQUENCE: 113

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Pro Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Ile Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Phe His
225                 230                 235                 240

Thr Gly Asp Ile Leu Ile Arg Ala Thr Ser Val Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
```

305 310 315 320

Val Lys Tyr Ile Gly Trp Ile Leu Glu Ser Val Pro Thr Glu Val Phe
325 330 335

Glu Thr Gln Glu Leu Cys Gly Leu Thr Leu Glu Tyr Arg Gln Glu Cys
340 345 350

Gly Arg Asp Ser Val Leu Glu Ser Val Thr Ala Met Asp Pro Ser Lys
355 360 365

Glu Gly Asp Arg Ser Leu Tyr Gln His Leu Leu Arg Leu Glu Asp Gly
370 375 380

Thr Asp Ile Ala Lys Gly Arg Thr Lys Trp Arg Pro Lys Asn Ala Gly
385 390 395 400

Lys Thr Ser Asn Gly Asn Ser Ile Ser
405

<210> SEQ ID NO 114
<211> LENGTH: 6541
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 114
gctcttcgcc gccgccactc ctgctcgagc gcgcccgcgc gtgcgccgcc agcgccttgg 60
ccttttcgcc gcgctcgtgc gcgtcgctga tgtccatcac caggtccatg aggtctgcct 120
tgcgccggct gagccactgc ttcgtccggg cggccaagag gagcatgagg gaggactcct 180
ggtccagggt cctgacgtgg tcgcggctct gggagcgggc cagcatcatc tggctctgcc 240
gcaccgaggc cgcctccaac tggtcctcca gcagccgcag tcgccgccga ccctggcaga 300
ggaagacagg tgaggggggt atgaattgta cagaacaacc acgagccttg tctaggcaga 360
atccctacca gtcatggctt tacctggatg acggcctgcg aacagctgtc cagcgaccct 420
cgctgccgcc gcttctcccg cacgcttctt tccagcaccg tgatggcgcg agccagcgcc 480
gcacgctggc gctgcgcttc gccgatctga ggacagtcgg ggaactctga tcagtctaaa 540 ccccccttgcg cgttagtgtt gccatccttt gcagaccggt gagagccgac ttgttgtgcg 600 ccaccccccca caccacctcc tcccagacca attctgtcac ctttttggcg aaggcatcgg 660
cctcggcctg cagagaggac agcagtgccc agccgctggg ggttggcgga tgcacgctca 720
ggtacccttt cttgcgctat gacacttcca gcaaaaggta gggcgggctg cgagacggct 780
tcccggcgct gcatgcaaca ccgatgatgc ttcgaccccc cgaagctcct tcggggctgc 840
atgggcgctc cgatgccgct ccagggcgag cgctgtttaa atagccaggc ccccgattgc 900
aaagacatta tagcgagcta ccaaagccat attcaaacac ctagatcact accacttcta 960
cacaggccac tcgagcttgt gatcgcactc cgctaagggg gcgcctcttc ctcttcgttt 1020
cagtcacaac ccgcaaacgg cgcgccatgc tgctgcaggc cttcctgttc ctgctggccg 1080
gcttcgccgc caagatcagc gcctccatga cgaacgagac gtccgaccgc cccctggtgc 1140
acttcacccc caacaagggc tggatgaacg accccaacgg cctgtggtac gacgagaagg 1200
acgccaagtg gcacctgtac ttccagtaca acccgaacga caccgtctgg gggacgccct 1260
tgttctgggg ccacgccacg tccgacgacc tgaccaactg ggaggaccag cccatcgcca 1320
tcgccccgaa gcgcaacgac tccggcgcct tctccggctc catggtggtg gactacaaca 1380
acacctccgg cttcttcaac gacaccatcg acccgcgcca gcgctgcgtg gccatctgga 1440
cctacaacac cccggagtcc gaggagcagt acatctccta cagcctggac ggcggctaca 1500
ccttcaccga gtaccagaag aaccccgtgc tggccgccaa ctccacccag ttccgcgacc 1560
cgaaggtctt ctggtacgag ccctcccaga agtggatcat gaccgcggcc aagtcccagg 1620
actacaagat cgagatctac tcctccgacg acctgaagtc ctggaagctg gagtccgcgt 1680
tcgccaacga gggcttcctc ggctaccagt acgagtgccc cggcctgatc gaggtcccca 1740
ccgagcagga ccccagcaag tcctactggg tgatgttcat ctccatcaac cccggcgccc 1800
cggccggcgg ctccttcaac cagtacttcg tcggcagctt caacggcacc cacttcgagg 1860
ccttcgacaa ccagtcccgc gtggtggact tcggcaagga ctactacgcc ctgcagacct 1920
tcttcaacac cgacccgacc tacgggagcg ccctgggcat cgcgtgggcc tccaactggg 1980
agtactccgc cttcgtgccc accaacccct ggcgctcctc catgtccctc gtgcgcaagt 2040
tctccctcaa caccgagtac caggccaacc cggagacgga gctgatcaac ctgaaggccg 2100
agccgatcct gaacatcagc aacgccggcc cctggagccg gttcgccacc aacaccacgt 2160
tgacgaaggc caacagctac aacgtcgacc tgtccaacag caccggcacc ctggagttcg 2220
agctggtgta cgccgtcaac accacccaga cgatctccaa gtccgtgttc gcggacctct 2280
ccctctggtt caagggcctg gaggaccccg aggagtacct ccgcatgggc ttcgaggtgt 2340
ccgcgtcctc cttcttcctg gaccgcggga acagcaaggt gaagttcgtg aaggagaacc 2400
cctacttcac caaccgcatg agcgtgaaca accagccctt caagagcgag aacgacctgt 2460
cctactacaa ggtgtacggc ttgctggacc agaacatcct ggagctgtac ttcaacgacg 2520
gcgacgtcgt gtccaccaac acctacttca tgaccaccgg gaacgccctg ggctccgtga 2580
acatgacgac gggggtggac aacctgttct acatcgacaa gttccaggtg cgcgaggtca 2640
agtgacaatt ggcagcagca gctcggatag tatcgacaca ctctggacgc tggtcgtgtg 2700
atggactgtt gccgccacac ttgctgcctt gacctgtgaa tatccctgcc gcttttatca 2760
aacagcctca gtgtgtttga tcttgtgtgt acgcgctttt gcgagttgct agctgcttgt 2820
gctatttgcg aataccaccc ccagcatccc cttccctcgt ttcatatcgc ttgcatccca 2880
accgcaactt atctacgctg tcctgctatc cctcagcgct gctcctgctc ctgctcactg 2940
cccctcgcac agccttggtt tgggctccgc ctgtattctc ctggtactgc aacctgtaaa 3000
ccagcactgc aatgctgatg cacgggaagt agtgggatgg gaacacaaat ggaaagctgt 3060
atagggataa gaattcggcc gacaggacgc gcgtcaaagg tgctggtcgt gtatgccctg 3120
gccggcaggt cgttgctgct gctggttagt gattccgcaa ccctgatttt ggcgtcttat 3180
tttggcgtgg caaacgctgg cgcccgcgag ccgggccggc ggcgatgcgg tgccccacgg 3240
ctgccggaat ccaagggagg caagagcgcc cgggtcagtt gaagggcttt acgcgcaagg 3300
tacagccgct cctgcaaggc tgcgtggtgg aattggacgt gcaggtcctg ctgaagttcc 3360
tccaccgcct caccagcgga caaagcaccg gtgtatcagg tccgtgtcat ccactctaaa 3420
gaactcgact acgacctact gatggcccta gattcttcat caaaaacgcc tgagacactt 3480
gcccaggatt gaaactccct gaagggacca ccaggggccc tgagttgttc cttccccccg 3540
tggcgagctg ccagccaggc tgtacctgtg atcgaggctg gcgggaaaat aggcttcgtg 3600
tgctcaggtc atgggaggtg caggacagct catgaaacgc caacaatcgc acaattcatg 3660
tcaagctaat cagctatttc ctcttcacga gctgtaattg tcccaaaatt ctggtctacc 3720
gggggtgatc cttcgtgtac gggcccttcc ctcaacccta ggtatgcgcg catgcggtcg 3780
ccgcgcaact cgcgcgaggg ccgagggttt gggacgggcc gtcccgaaat gcagttgcac 3840

-continued

```
ccggatgcgt ggcacctttt ttgcgataat ttatgcaatg gactgctctg caaaattctg   3900
gctctgtcgc caaccctagg atcagcggcg taggatttcg taatcattcg tcctgatggg   3960
gagctaccga ctaccctaat atcagcccga ctgcctgacg ccagcgtcca cttttgtgca   4020
cacattccat tcgtgcccaa gacatttcat tgtggtgcga agcgtcccca gttacgctca   4080
cctgtttccc gacctcctta ctgttctgtc gacagagcgg gcccacaggc cggtcgcagc   4140
cactagtatg gccaccacct ccctggcctc cgccttctgc tccatgaagg ccgtgatgct   4200
ggcccgcgac ggccgcggcc tgaagccccg ctcctccgac ctgcagctgc gcgccggcaa   4260
cgcccagacc tccctgaaga tgatcaacgg caccaagttc tcctacaccg agtccctgaa   4320
gaagctgccc gactggtcca tgctgttcgc cgtgatcacc accatcttct ccgccgccga   4380
gaagcagtgg accaacctgg agtggaagcc caagcccaac cccccccagc tgctggacga   4440
ccacttcggc ccccacggcc tggtgttccg ccgcaccttc gccatccgct cctacgaggt   4500
gggcccccgac cgctccacct ccatcgtggc cgtgatgaac cacctgcagg aggccgccct   4560
gaaccacgcc aagtccgtgg gcatcctggg cgacggcttc ggcaccaccc tggagatgtc   4620
caagcgcgac ctgatctggg tggtgaagcg cacccacgtg gccgtggagc gctaccccgc   4680
ctggggcgac accgtggagg tggagtgctg ggtgggcgcc tccggcaaca acggccgccg   4740
ccacgacttc ctggtgcgcg actgcaagac cggcgagatc ctgacccgct gcacctccct   4800
gtccgtgatg atgaacaccc gcacccgccg cctgtccaag atccccgagg aggtgcgcgg   4860
cgagatcggc cccgccttca tcgacaacgt ggccgtgaag gacgaggaga tcaagaagcc   4920
ccagaagctg aacgactcca ccgccgacta catccagggc ggcctgaccc cccgctggaa   4980
cgacctggac atcaaccagc acgtgaacaa catcaagtac gtggactgga tcctggagac   5040
cgtgcccgac tccatcttcg agtcccacca catctcctcc ttcaccatcg agtaccgccg   5100
cgagtgcacc cgcgactccg tgctgcagtc cctgaccacc gtgtccggcg gctcctccga   5160
ggccggcctg gtgtgcgagc acctgctgca gctggagggc ggctccgagg tgctgcgcgc   5220
caagaccgag tggcgcccca agctgtcctt ccgcggcatc tccgtgatcc ccgccgagtc   5280
ctccgtgatg gactacaagg accacgacgg cgactacaag gaccacgaca tcgactacaa   5340
ggacgacgac gacaagtgac tcgaggcagc agcagctcgg atagtatcga cacactctgg   5400
acgctggtcg tgtgatggac tgttgccgcc acacttgctg ccttgacctg tgaatatccc   5460
tgccgctttt atcaaacagc ctcagtgtgt ttgatcttgt gtgtacgcgc ttttgcgagt   5520
tgctagctgc ttgtgctatt tgcgaatacc acccccagca tccccttccc tcgtttcata   5580
tcgcttgcat cccaaccgca acttatctac gctgtcctgc tatccctcag cgctgctcct   5640
gctcctgctc actgcccctc gcacagcctt ggtttgggct ccgcctgtat tctcctggta   5700
ctgcaacctg taaaccagca ctgcaatgct gatgcacggg aagtagtggg atgggaacac   5760
aaatggaaag ctgtataggg ataacagggt aatgagctct tgttttccag aaggagttgc   5820
tccttgagcc tttcattctc agcctcgata acctccaaag ccgctctaat tgtggagggg   5880
gttcgaattt aaaagcttgg aatgttggtt cgtgcgtctg gaacaagccc agacttgttg   5940
ctcactggga aaaggaccat cagctccaaa aaacttgccg ctcaaaccgc gtacctctgc   6000
tttcgcgcaa tctgccctgt tgaaatcgcc accacattca tattgtgacg cttgagcagt   6060
ctgtaattgc ctcagaatgt ggaatcatct gccccctgtg cgagcccatg ccaggcatgt   6120
cgcgggcgag gacacccgcc actcgtacag cagaccatta tgctacctca caatagttca   6180
```

-continued

```
taacagtgac catatttctc gaagctcccc aacgagcacc tccatgctct gagtggccac   6240

cccccggccc tggtgcttgc ggagggcagg tcaaccggca tggggctacc gaaatccccg   6300

accggatccc accacccccg cgatgggaag aatctctccc cgggatgtgg gcccaccacc   6360

agcacaacct gctggcccag gcgagcgtca aaccatacca cacaaatatc cttggcatcg   6420

gccctgaatt ccttctgccg ctctgctacc cggtgcttct gtccgaagca ggggttgcta   6480

gggatcgctc cgagtccgca aacccttgtc gcgtggcggg gcttgttcga gcttgaagag   6540

c                                                                   6541


<210> SEQ ID NO 115
<211> LENGTH: 4
<212> TYPE: PRT
<213> ORGANISM: Unknown
<220> FEATURE:
<223> OTHER INFORMATION: Description of Unknown: N-terminal hydrophobic
      domain peptide

<400> SEQUENCE: 115

Leu Pro Asp Trp
1
```